(12) United States Patent
Chaput et al.

(10) Patent No.: US 11,858,953 B2
(45) Date of Patent: *Jan. 2, 2024

(54) COMPOSITIONS AND METHODS FOR SYNTHESIS OF PHOSPHORYLATED MOLECULES

(71) Applicant: THE REGENTS OF THE UNIVERSITY OF CALIFORNIA, Oakland, CA (US)

(72) Inventors: John Chaput, Irvine, CA (US); Jen-Yu Liao, Irvine, CA (US); Saikat Bala, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 133 days.

This patent is subject to a terminal disclaimer.

(21) Appl. No.: 17/307,567

(22) Filed: May 4, 2021

(65) Prior Publication Data

US 2021/0332070 A1 Oct. 28, 2021

Related U.S. Application Data

(63) Continuation of application No. 16/374,795, filed on Apr. 4, 2019, now Pat. No. 11,021,497.

(60) Provisional application No. 62/652,475, filed on Apr. 4, 2018.

(51) Int. Cl.
*C07F 9/09* (2006.01)
*B01J 27/138* (2006.01)
*C07H 21/04* (2006.01)
*A61K 31/711* (2006.01)

(52) U.S. Cl.
CPC ............ *C07F 9/091* (2013.01); *B01J 27/138* (2013.01); *C07H 21/04* (2013.01); *A61K 31/711* (2013.01)

(58) Field of Classification Search
None
See application file for complete search history.

(56) References Cited

FOREIGN PATENT DOCUMENTS

WO WO-2005080406 A2 * 9/2005 ............... C07F 9/091

OTHER PUBLICATIONS

Taktakishvili et al. J. Am. Chem. Soc. (2000), vol. 122, pp. 5671-5677.*
Bala et al., "Synthesis of α-I-Threofuranosyl Nucleoside 3'-Monophosphates, 3'-Phosphoro(2-Methyl)imidazolides, and 3'-Triphosphates," Jul. 2019, Journal of Organic Chemistry, 82, 5910-5916.
Burgess and Cook, 2000, "Syntheses of Nucleoside Triphosphates", Chem. Rev. 100, 2047-2060.
Chen and Romesberg, 2014, "Directed polymerase evolution", FEBS Lett. 588, 219-229.
Chim et al., 2017, "Structural basis for TNA synthesis by an engineered TNA polymerase", Nat Commun 8, 1810, 11 pages.
Cremosnik et al., 2014, "Iterative Synthesis of Nucleoside Oligophosphates with Phosphoramidites," Angew. Chem. Int. Ed. 53, 286-289.
De et al., 2014, Tailoring New Peptide-Nucleotide Conjugates (PNCs) for Nucleotide Delivery in Bacterial Cells, Eur. J. Org. Chem., 2322-2348.
Debarge et al., 2011, Design and Synthesis of a-Carboxy Phosphononucleosides. J. Org. Chem. 76, 105-126.
Erlich and Zielinski, 2017, "DNA Fountain enables a robust and efficient storage architecture", Science 355, 950-954.
Goodwin et al., 2016, "Coming of age: ten years of next-generation sequencing technologies", Nat. Rev. Genet. 17, 333-351.
Hoard and Ott, 1965, "Conversion of Mono- and Oligodeoxyribonucleotides to 5-Triphosphates", J. Am. Chem. Soc., 87, 1785-1788.
Hofer et al, 2015, "A Modular Synthesis of Modified Phosphoanhydrides", Chemistry 21, 10116-10122.
Hollenstein, 2012, "Nucleoside triphosphates—building blocks for the modification of nucleic acids", Molecules 17, 13569-13591.
Hulett, 1970, "Non-enzymatic hydrolysis of adenosine phosphates", Nature 225, 1248-1249.
International Search Report for PCT/US2019/025696 dated Jun. 25, 2019, 3 pages.
Kathayat et al., 2013, "Sulfoxides as Response Elements for Fluorescent Chemosensors", J. Am. Chem. Soc. 135, 12612-12614.
Kore and Srinivasan, 2013, "Recent Advances in the Synthesis of Nucleoside Triphosphates", Curr. Org. Syn. 10, 903-934.
Larsen et al., 2016, "A general strategy for expanding polymerase function by droplet microfluidics", Nat. Commun., 7, 11235, 9 pages.
Loakes and Holliger, 2009, "Polymerase engineering: towards the encoded synthesis of unnatural polymers", Chem. Commun., 4619-4631.
Loeb et al., 2008, "DNA polymerases and human diseas", Nat. Rev. Genet. 9, 594-604.
Ludwig and Eckstein, 1989, "Rapid and efficient synthesis of nucleoside 5'-0-( 1-thiotriphosphates), 5'-triphosphates and 2',3'-cyclophosphorothioates using 2-chloro-4H-1,3,2-benzodioxaphosphorin-4-one", J. Org. Chem., 54, 631-635.
Office Action dated Jun. 18, 2020 for U.S. Appl. No. 16/374,795 (pp. 1-12).
Pinheiro et al., 2012, "Synthetic genetic polymers capable of heredity and evolution", Science 336, 341-344.
Sau and Chaput, 2017, "A Gram-Scale HPLC-Free Synthesis of TNA Triphosphates Using an Iterative Phosphorylation Strategy", Org. Lett. 19, 4379-4382.
Sau et al., 2016, A Scalable Synthesis of a-L-Threose Nucleic Acid. J. Org. Chem. 81, 2302-2307.
Schoning et al., 2000, "Chemical etiology of nucleic acid structure: the a-threofuranosyl-(3'->2') oligonucleotide system.", Science, 290, 1347-1351.

(Continued)

*Primary Examiner* — Patrick T Lewis
(74) *Attorney, Agent, or Firm* — Riverside Law LLP

(57) ABSTRACT

The invention provides compositions and methods for synthesis of phosphorylated organic compounds, including nucleoside triphosphates.

23 Claims, 140 Drawing Sheets

Specification includes a Sequence Listing.

(56) References Cited

OTHER PUBLICATIONS

Sherstyuk et al., "How to Form a Phosphate Anhydride Linkage in Nucleotide Derivatives," Sep. 2015, ChemBioChem, 16, 2562-2570.
Steitz et al., 1994, "A unified polymerase mechanism for nonhomologous DNA and RNA polymerases", Science 266, 2022-2025.
Taktakishvili etal. J. Am. Chem. Soc. (2002), vol. 122, pp. 5671-5677.
Taylor et al., 2015, "Catalysts from synthetic genetic polymers", Nature 518, 427-430.
Wang et al., 2016, "A synthetic molecular system capable of mirror-image genetic replication and transcription", Nat. Chem., 8, 698-704.
Wang et al., 2018, "Evolution of a general RNA-cleaving FANA enzyme", Nat. Commun., 9:5067, 10 pages.
Written Opinion of the International Searching Authority for PCT/US2019/025696 dated Jun. 25, 2019, 3 pages.
Wu et al., 2017, "How DNA polymerases catalyse replication and repair with contrasting fidelity", Nat. Rev. Chem. 1, 0068, 16 pages.
Yoshikawa et al., 1967, "A novel method for phosphorylation of nucleosides to 5'-nucleotides", Tetrahedron Lett. 8, 5065-5068.
Yu et al., 2012, "Darwinian evolution of an alternative genetic system provides support for TNA as an RNA progenitor", Nat. Chem. 4, 183-187.

\* cited by examiner

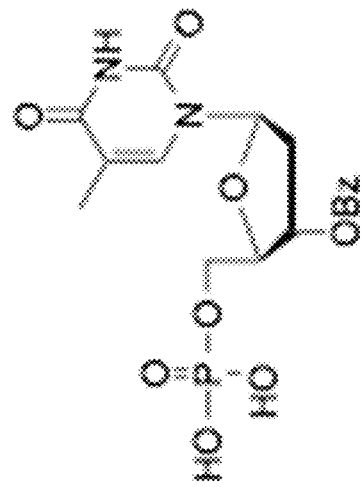
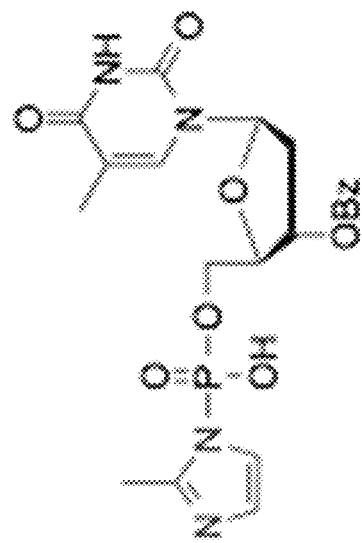
Fig. 3

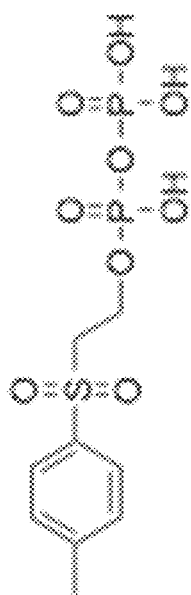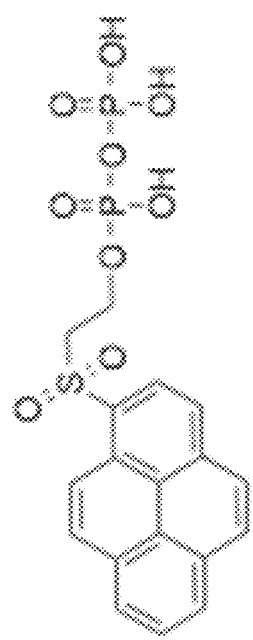
Fig. 5

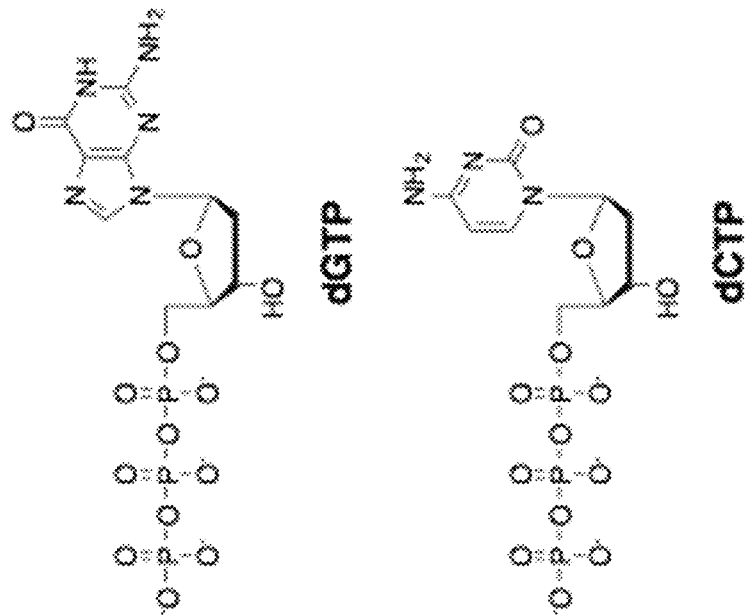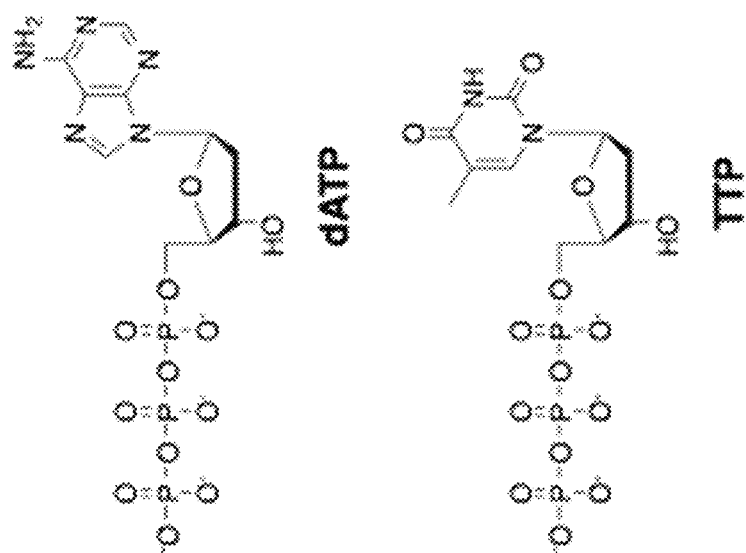
Fig. 7

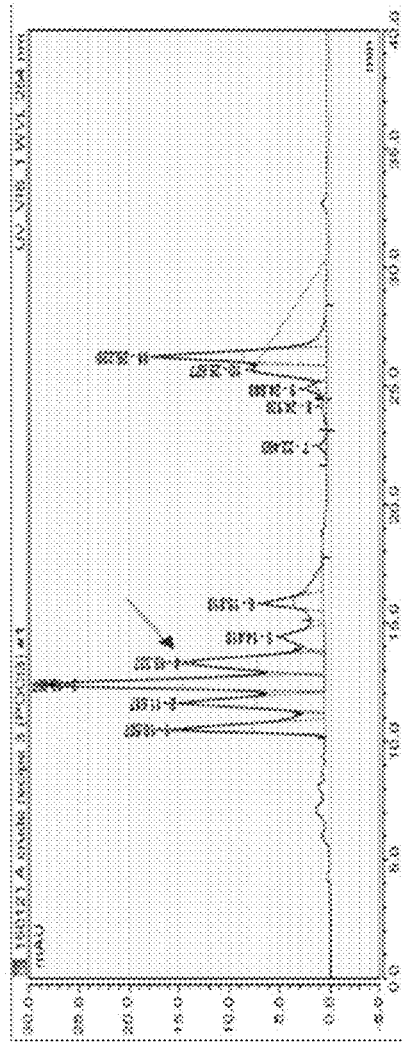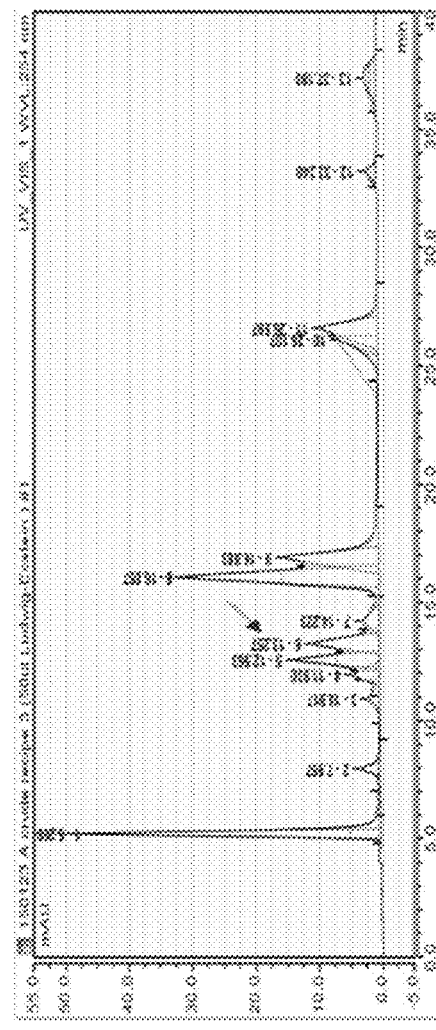
Fig. 11

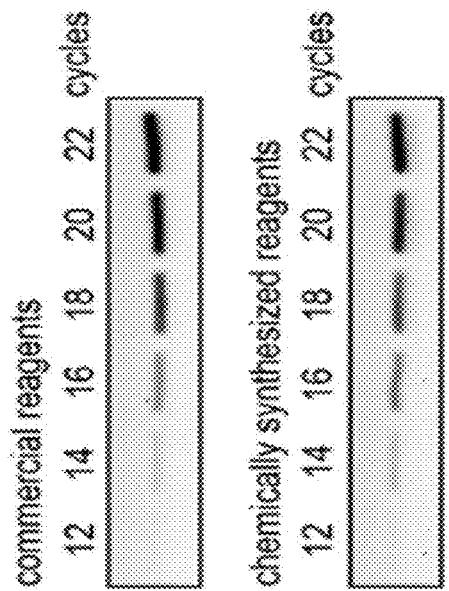
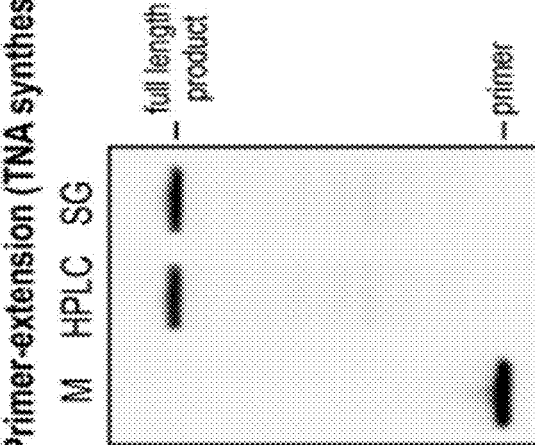
Fig. 16A
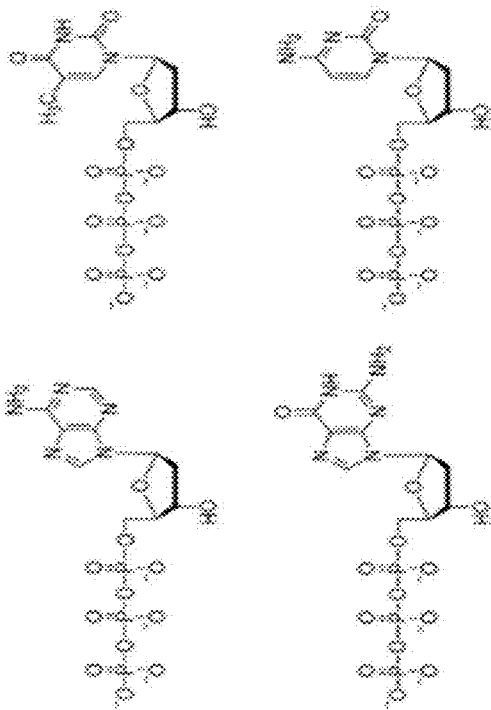
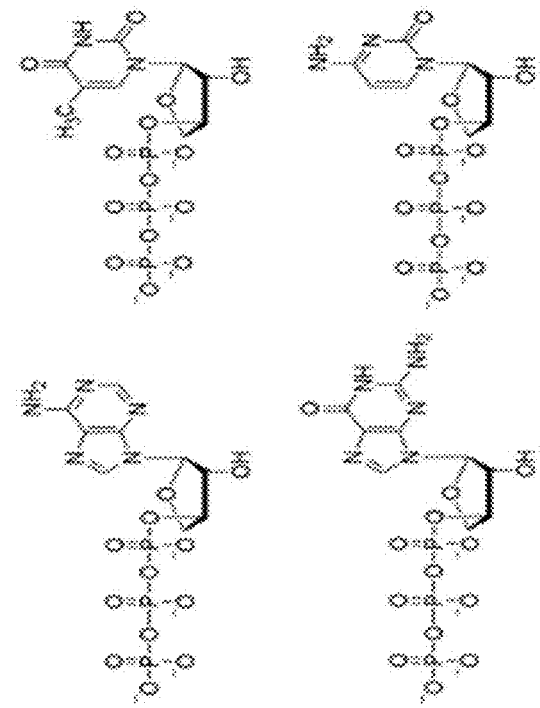
Fig. 16B

Fig. 31 31P NMR spectrum of compound 7 (162 MHz, D2O)

31P NMR spectrum of compound 13b (162 MHz, D2O)

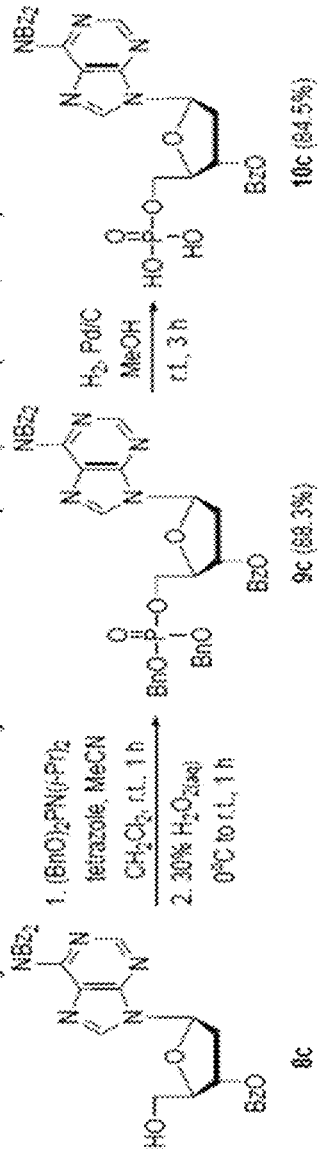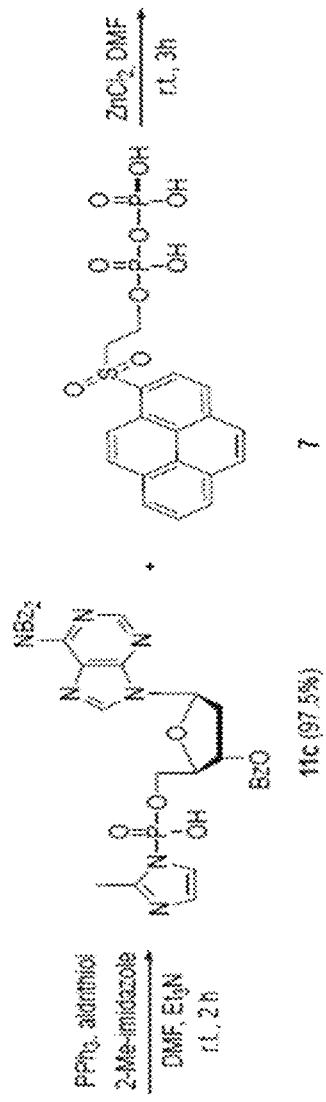
Fig. 56

¹H NMR spectrum of compound 13c (400 MHz, CDCl₃)

31P NMR spectrum of compound 13c (162 MHz, CDCl3)

31P NMR spectrum of compound 13xl (162 MHz, CDCl3)

31P NMR spectrum of compound 10 (162 MHz, D2O)

Fig. 100 $^{31}$P NMR spectrum of compound 25a (400 MHz, D$_2$O)

Fig. 117 1H NMR spectrum of compound 25c (400 MHz, D2O)

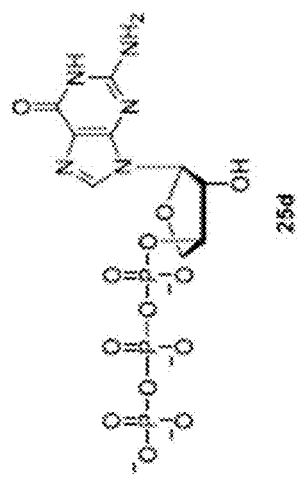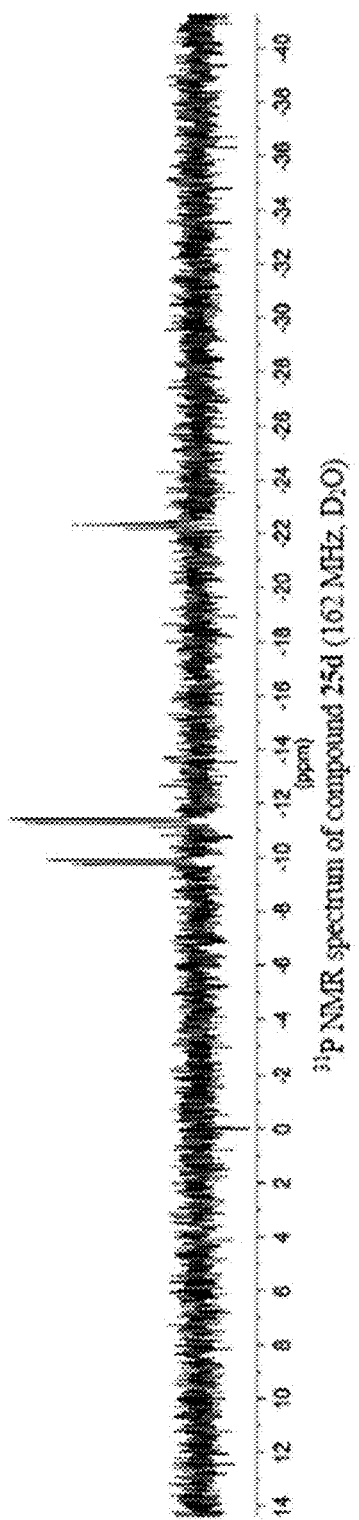
Fig. 127

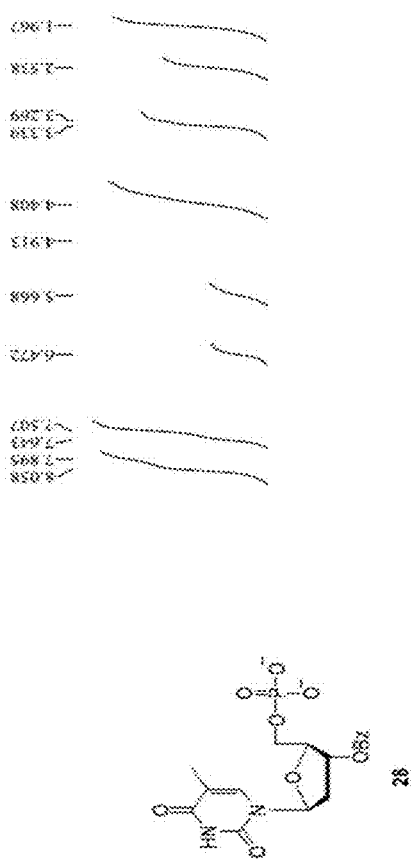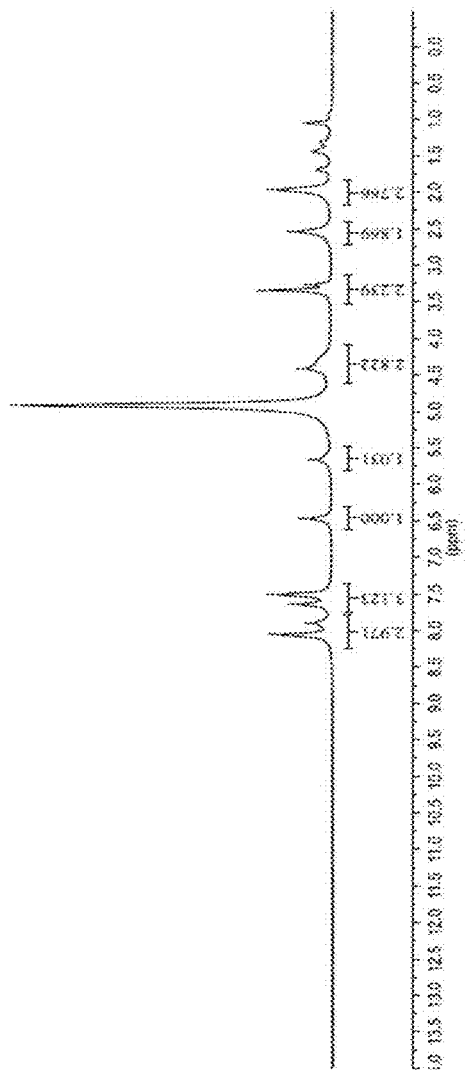
Fig. 132

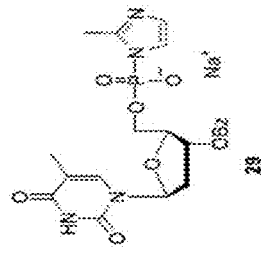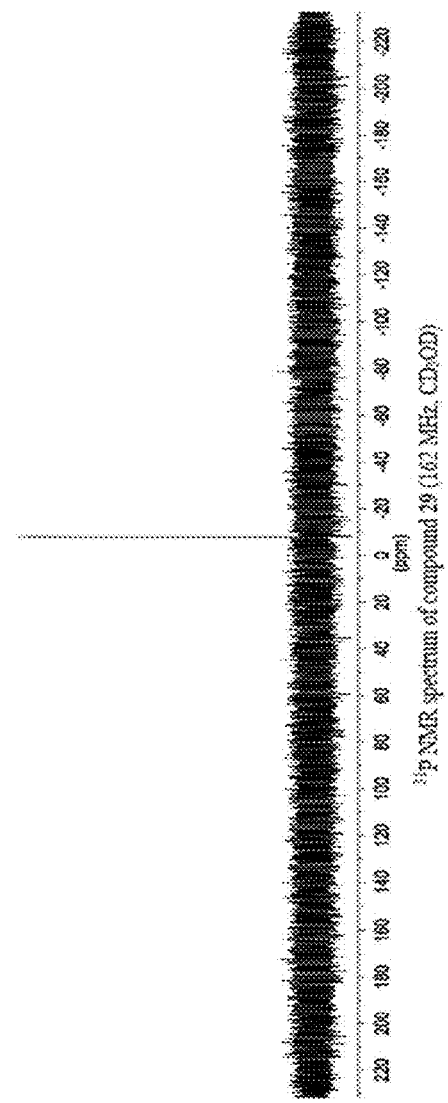
Fig. 135

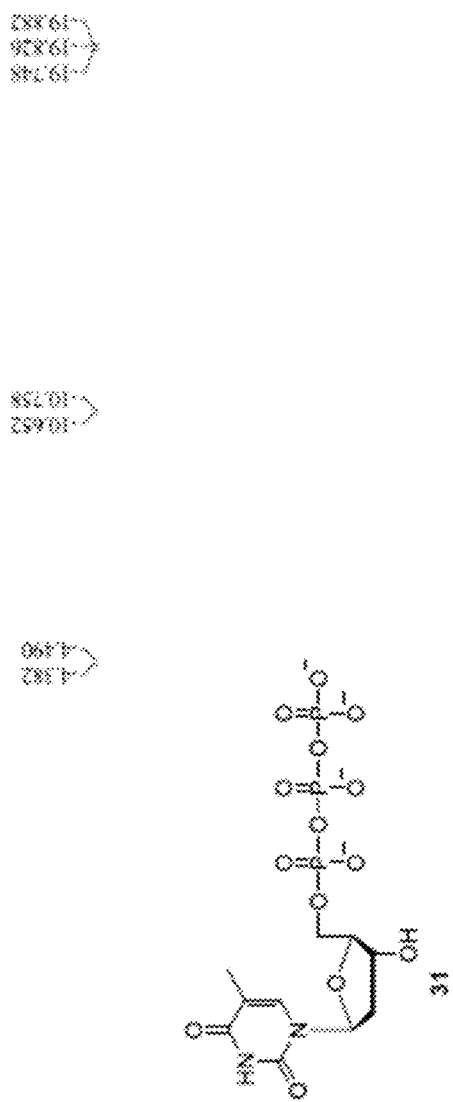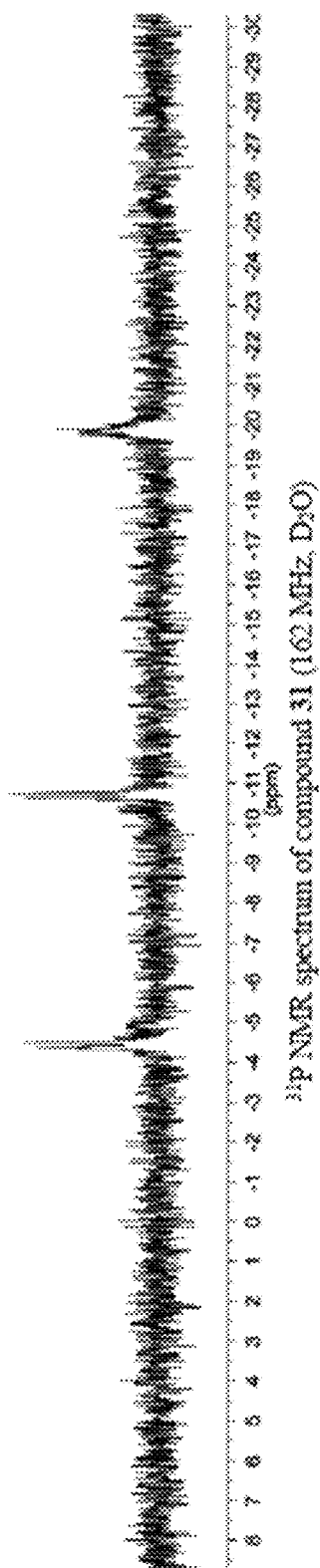
Fig. 139

COMPOSITIONS AND METHODS FOR SYNTHESIS OF PHOSPHORYLATED MOLECULES

CROSS-REFERENCE TO RELATED APPLICATIONS

This application is a continuation of U.S. patent application Ser. No. 16/374,795, filed on Apr. 4, 2019, which claims priority to U.S. Provisional Application No. 62/652,475, filed Apr. 4, 2018, the disclosures of which are hereby incorporated by reference herein in their entireties.

STATEMENT REGARDING FEDERALLY SPONSORED RESEARCH OR DEVELOPMENT

This invention was made with Government support under Grant No. N66001-16-2-4061, awarded by the Defense Advanced Research Projects Agency (DARPA). The Government has certain rights in the invention.

BACKGROUND OF THE INVENTION

Polymerases are among the most powerful tools in the molecular biology arsenal, permitting researchers to precisely synthesize the DNA sequences of genes, gene clusters, and entire genomes for diverse applications ranging from basic research to biotechnology and medicine (Loeb et al, 2008, Nat. Rev. Genet. 9, 594-604; Wu et al., 2017, Nat. Rev. Chem. 1, 0068). Polymerase-mediated DNA synthesis has reduced the cost of DNA sequencing by allowing next-generation sequencing (NGS) platforms to read massive numbers of amplicons and has enabled digital archiving by compressing information into strands of DNA sequences that can be read by NGS analysis and decoded by bioinformatic assembly (Goodwin et al., 2016, Nat. Rev. Genet. 17, 333-351; Erlich and Zielinski, 2017, Science 355, 950-954). Engineered polymerases, developed by directed evolution, have also grown in demand by enabling the synthesis of artificial genetic polymers with backbone structures that are distinct from those found in nature (Chen and Romesberg, 2014, FEBS Lett. 588, 219-229; Loakes and Holliger, 2009, Chem. Commun., 4619-4631). Such enzymes are now used to support the evolution of affinity reagents (aptamers) and catalysts with molecular compositions that are better equipped to function in harsh biological environments (Pinheiro et al., 2012, Science 336, 341-344; Yu et al., 2012, Nat. Chem. 4, 183-187; Taylor et al., 2015, Nature 518, 427-430; Wang et at, 2018, Nat. Commun., in press).

Today, no single strategy has been developed that can be applied universally to the synthesis of all nucleoside triphosphates. Natural DNA triphosphates (dNTPs) used to support traditional DNA synthesis applications are manufactured using enzymatic methods, while modified nucleoside triphosphates developed for biotechnology and medicinal purposes are produced by chemical synthesis (Burgess and Cook, 2000, Chem. Rev. 100, 2047-2060; Kore and Srinivasan, 2013, Curr. Org. Syn. 10, 903-934; Hollenstein, 2012, Molecules 17, 13569-13591). In general, enzymatic strategies suffer from high substrate specificity (low tolerance for analogs), while synthetic routes struggle with functional group compatibility, difficult reaction conditions, and yield.

Even more problematic is the requirement for both strategies to separate highly polar nucleoside triphosphates from polar side products using high performance liquid chromatography (HPLC), In academic environments, HPLC purification is a tedious process that limits the scale of nucleoside triphosphate synthesis to a few tens of milligrams of compound per week and requires subsequent freeze-drying steps that can lead to compound degradation.

Efforts to synthesize nucleoside triphosphates independent of HPLC purification first appeared in 2014 with a phosphorylation strategy that involves iterative cycles of coupling, oxidation, and deprotection (Cremosnik et al., 2014, Angew. Chem. Int. Ed. 53, 286-289; Hofer et al, 2015, Chemistry 21, 10116-10122; Sau and Chaput, 2017, Org, Lett, 19, 4379-4382), This is a P(III)-based reagent method that relies on derivatized phosphoramidite reagents to facilitate P—O bond formation. Free nucleosides are converted to nucleoside triphosphates through the production of P(III)-P(V) anhydride intermediates that are oxidized and deprotected during each cycle of P(V) phosphate generation (Cremosnik et al., 2014, Angew. Chem. Int. Ed. 53, 286-289), The iterative strategy benefits from high yields, rapid coupling rates, and convenient (non-dry) reaction conditions but is marked by several disadvantages that include: (1) the need for quantitative functional group transformations, which are necessary to avoid the accumulation of unwanted side products; (2) prolonged deprotection conditions due to slow removal of the second P—O protecting group on the phosphorylating reagent; (3) incompatibility with certain chemical reagents and nucleoside protecting groups; and (4) a lengthy pathway that involves 9 functional group transformations to convert each nucleoside to its corresponding triphosphate (Cremosnik et al., 2014, Angew. Chem. Int. Ed. 53, 286-289; Hofer et al, 2015, Chemistry 21, 10116-10122; Sau and Chaput, 2017, Org. Lett. 19, 4379-4382).

Thus, there is a need in the art for novel compositions and methods for synthesis of phosphorylated molecules. The present invention satisfies this unmet need.

SUMMARY OF THE INVENTION

In one embodiment, the invention relates to a composition comprising an organic molecule comprising a phosphate moiety of formula (1):

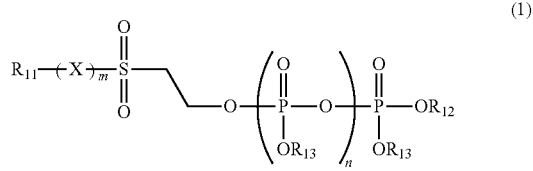

wherein:
m is an integer from 0 to 5;
n is an integer from 0 to 5;
X is O or $CH_2$;
$R_{11}$ is an aryl, a heteroaryl, an alkyl, a cycloalkyl, an alkenyl, an alkynyl, an alkyl-aryl, an aryl-alkyl, or a silyl group;
$R_{12}$ is hydrogen, null, a substituted tetahydrofuranyl group, or an alkyl-substituted tetahydrofuranyl group; and
each occurrence of $R_{13}$ is independently hydrogen or null.

In one embodiment, $R_{11}$ is substituted. In one embodiment, lei is substituted with an alkyl, alkenyl, alkynyl, aryl, cycloalkyl, heteroaryl, halogen, —CN, —$OR_{14}$, or —$N(R_{14})_2$ group, Wherein each occurrence of $R_{14}$ is independently selected from hydrogen, alkyl, alkenyl, alkynyl, aryl, cycloalkyl, heteroaryl, and halogen.

In one embodiment, $R_{11}$ is

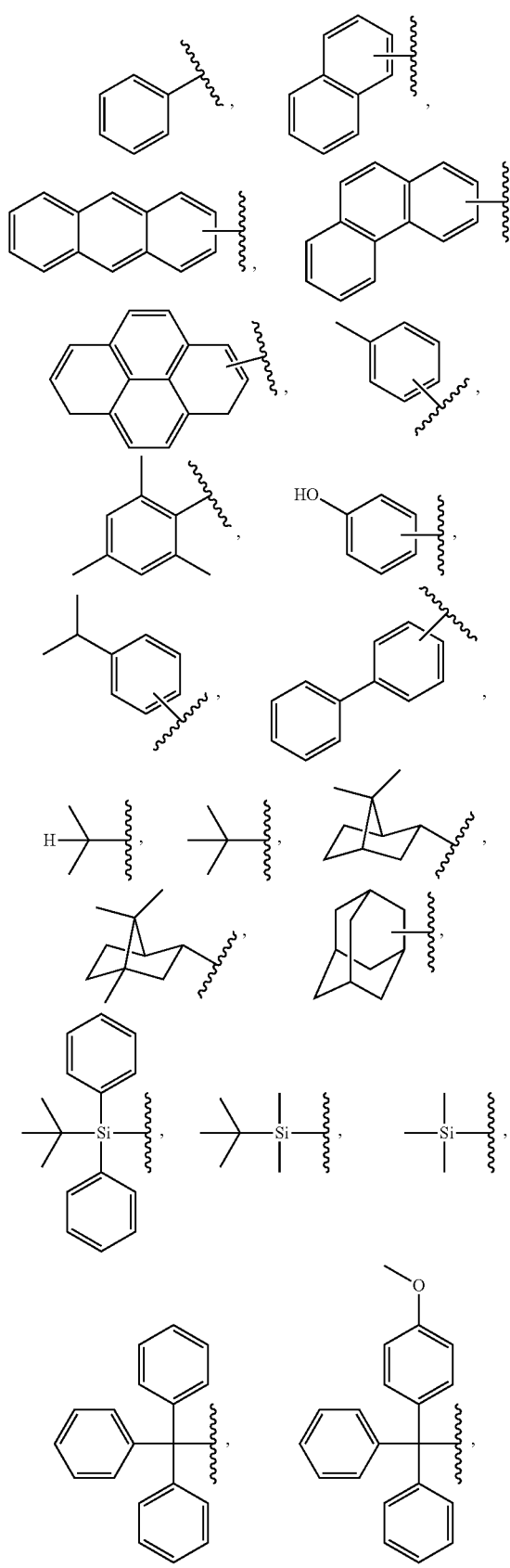

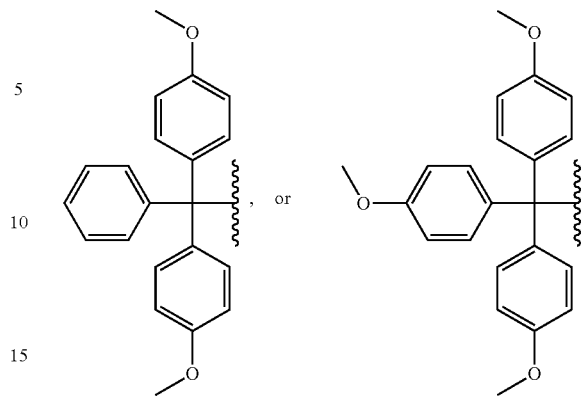

In one embodiment, the compound of formula (1) is a compound of formula (1a):

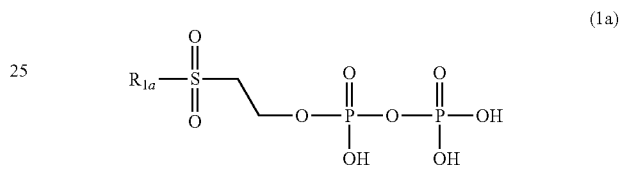

(1a)

wherein:

$R_{1a}$ is an aryl, a heteroaryl, an alkyl, a cycloalkyl, an alkenyl, an alkynyl, an alkyl-aryl, or an aryl-alkyl. In one embodiment, $R_{1a}$ is substituted. In one embodiment, $R_{1a}$ is substituted with an alkyl, alkenyl, alkynyl, aryl, cycloalkyl, heteroaryl, halogen, —CN, —OR$_{11a}$, or —N(R$_{11a}$)$_2$ group, wherein each occurrence of $R_{11a}$ is independently selected from hydrogen, alkyl, alkenyl, alkenyl, aryl, cycloalkyl, heteroaryl, and halogen.

In one embodiment, $R_{1a}$ is:

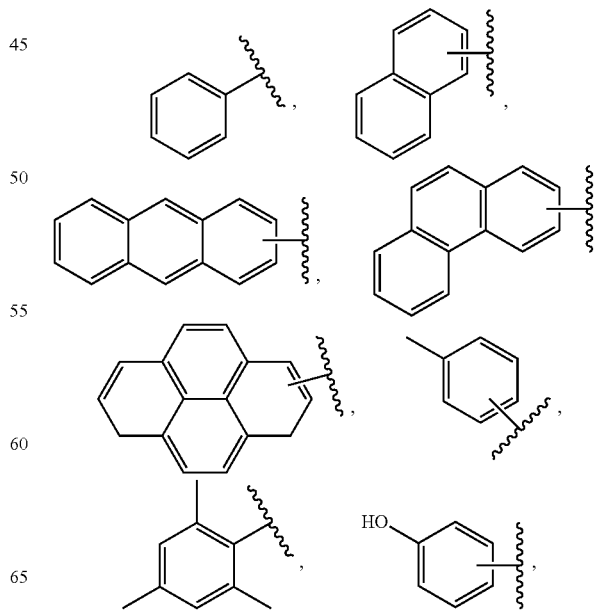

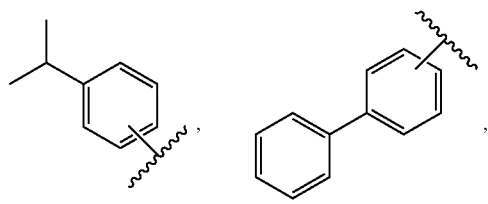
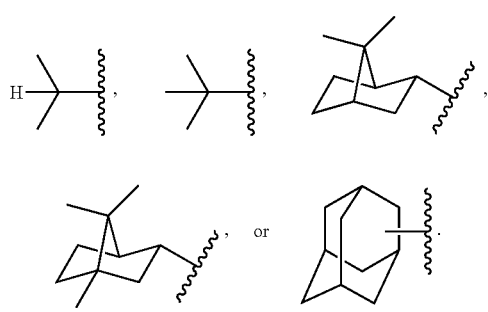
In one embodiment, the compound of formula (1a) is:
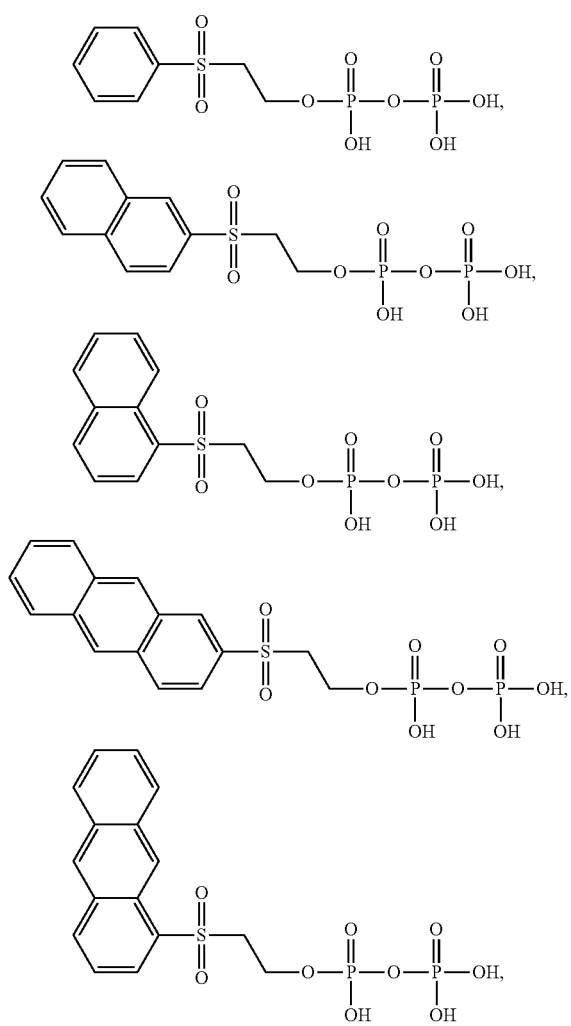
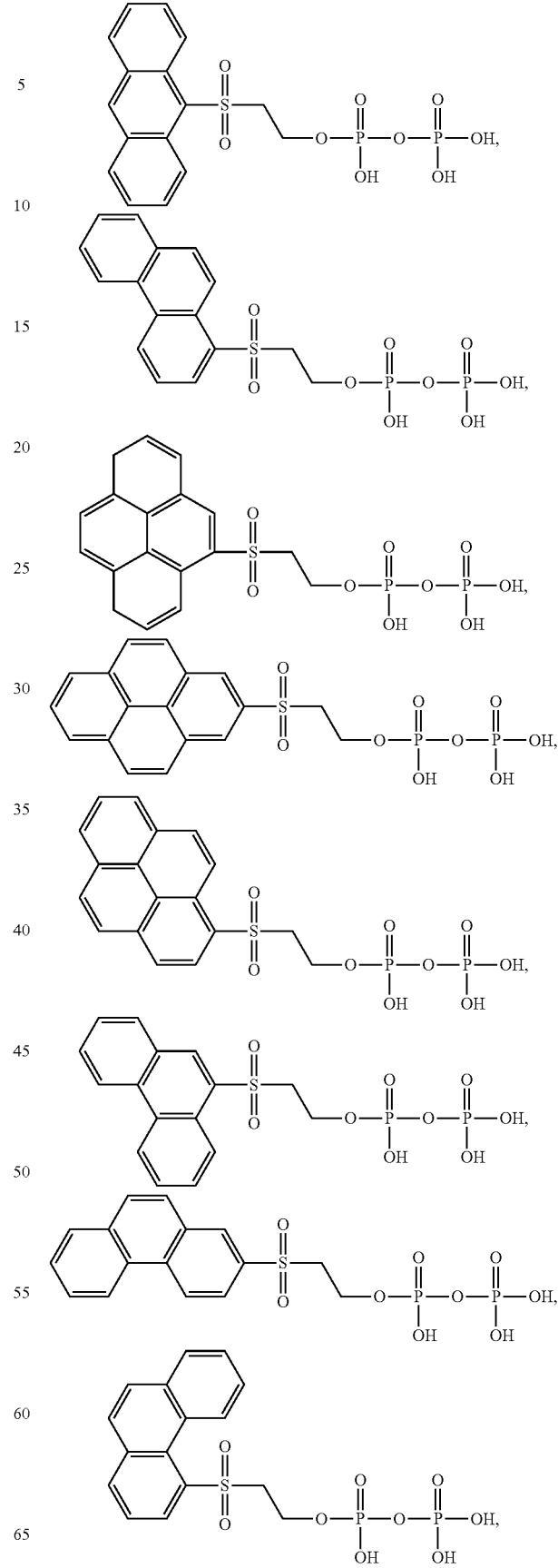

-continued

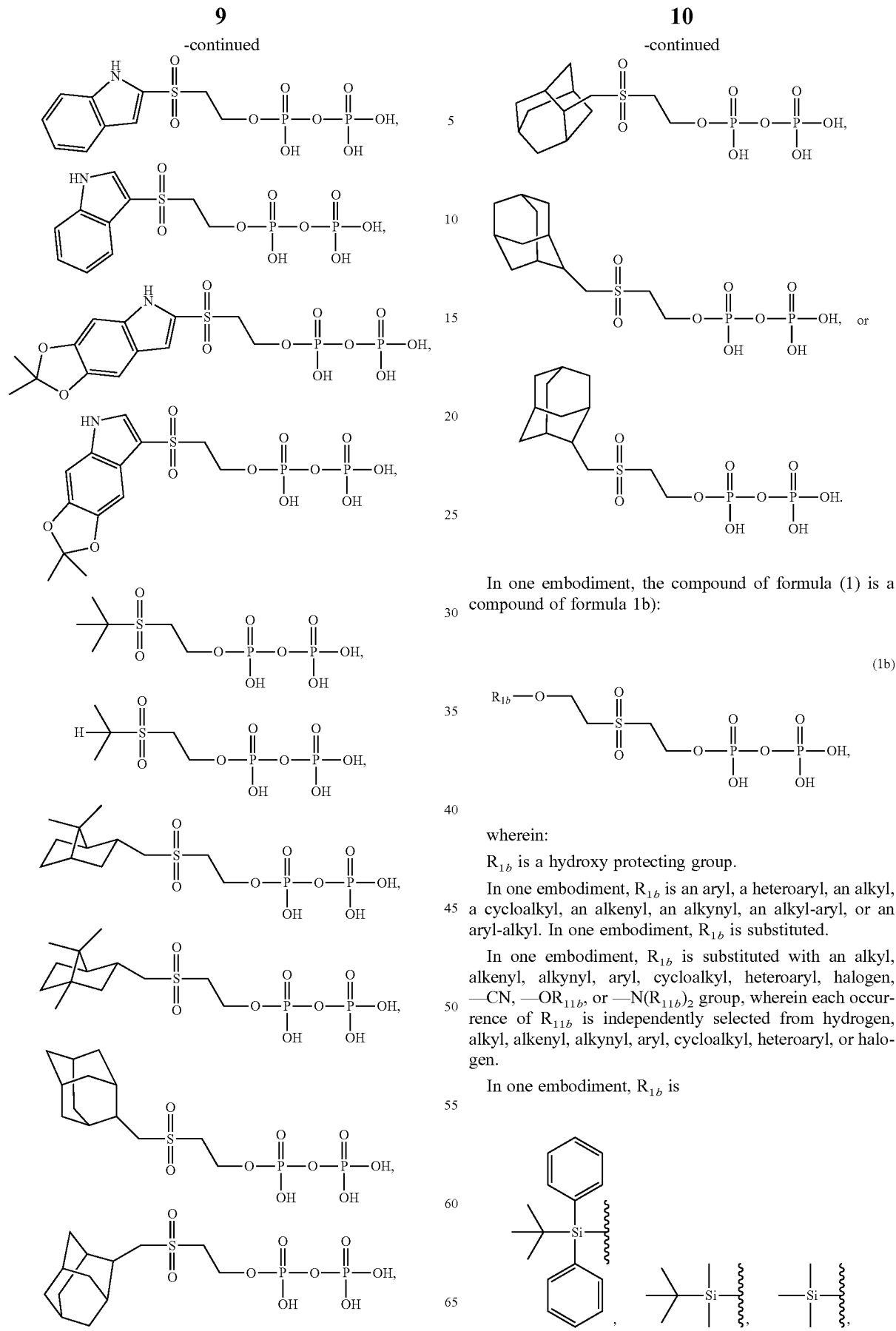

In one embodiment, the compound of formula (1) is a compound of formula 1b):

(1b)

wherein:

$R_{1b}$ is a hydroxy protecting group.

In one embodiment, $R_{1b}$ is an aryl, a heteroaryl, an alkyl, a cycloalkyl, an alkenyl, an alkynyl, an alkyl-aryl, or an aryl-alkyl. In one embodiment, $R_{1b}$ is substituted.

In one embodiment, $R_{1b}$ is substituted with an alkyl, alkenyl, alkynyl, aryl, cycloalkyl, heteroaryl, halogen, —CN, —$OR_{11b}$, or —$N(R_{11b})_2$ group, wherein each occurrence of $R_{11b}$ is independently selected from hydrogen, alkyl, alkenyl, alkynyl, aryl, cycloalkyl, heteroaryl, or halogen.

In one embodiment, $R_{1b}$ is

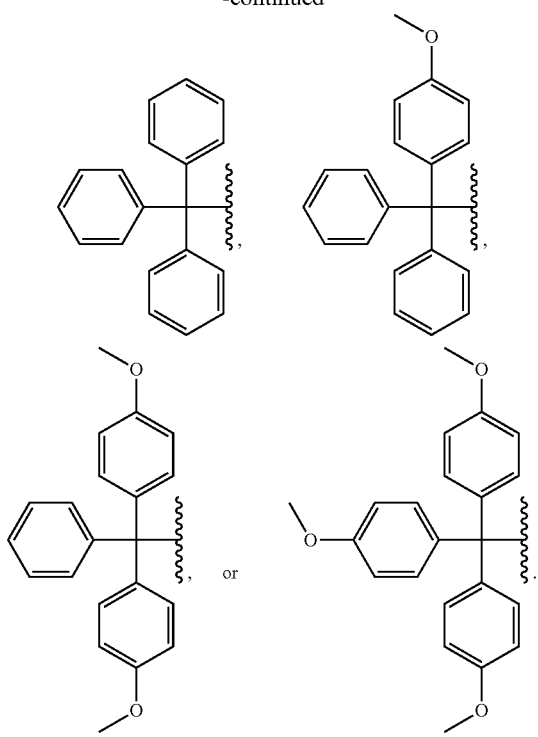
In one embodiment, the compound of formula (1b) is:
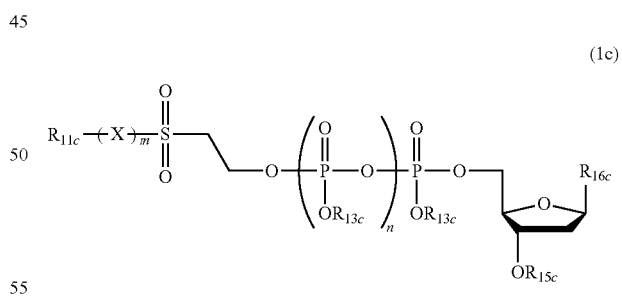
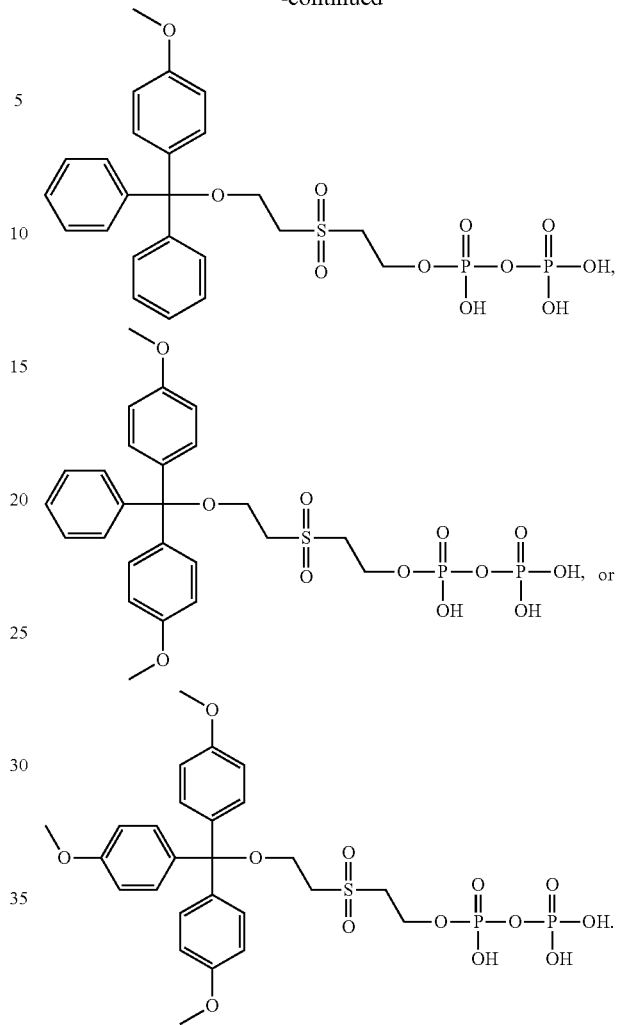
In one embodiment, the compound of formula (1) is a compound of formula (1c);
$$(1c)$$
wherein:
m is an integer from 0 to
n is an integer from 0 to 5;
X is O or $CH_2$;
$R_{11c}$ is an aryl, a heteroaryl, an alkyl, a cycloalkyl, air alkenyl, an alkynyl, an alkyl-aryl, an aryl-alkyl, or a silyl group;
each occurrence of $R_{13c}$ is independently hydrogen or null;

$R_{15c}$ is hydrogen, aryl, or heteroaryl; and
$R_{16c}$ is a nitrogenous base, wherein the nitrogenous base is a natural nitrogenous base or artificial nitrogenous base.
In one embodiment, $R_{11c}$ is
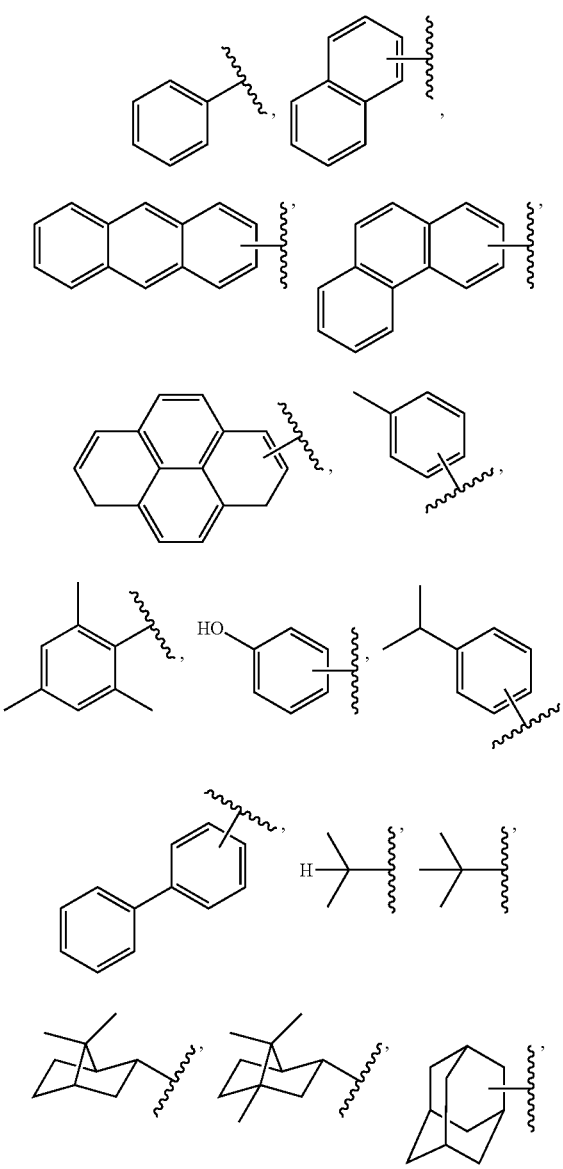
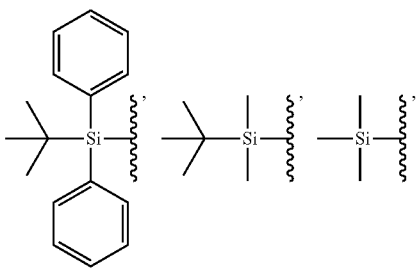
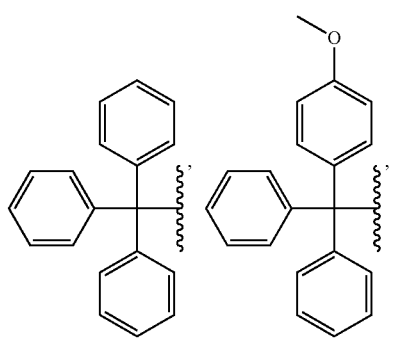
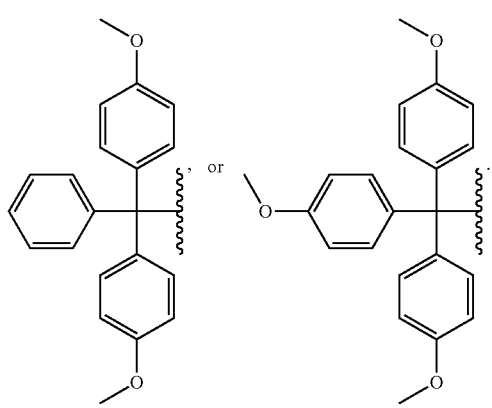
In one embodiment, $R_{15c}$ is phenyl.
In one embodiment the compound of formula (1c) is:
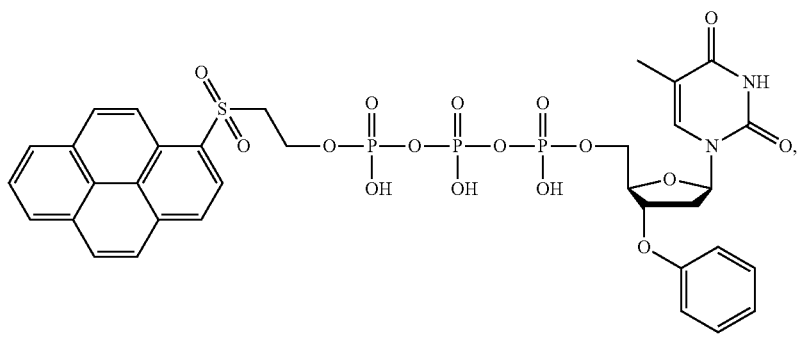

-continued

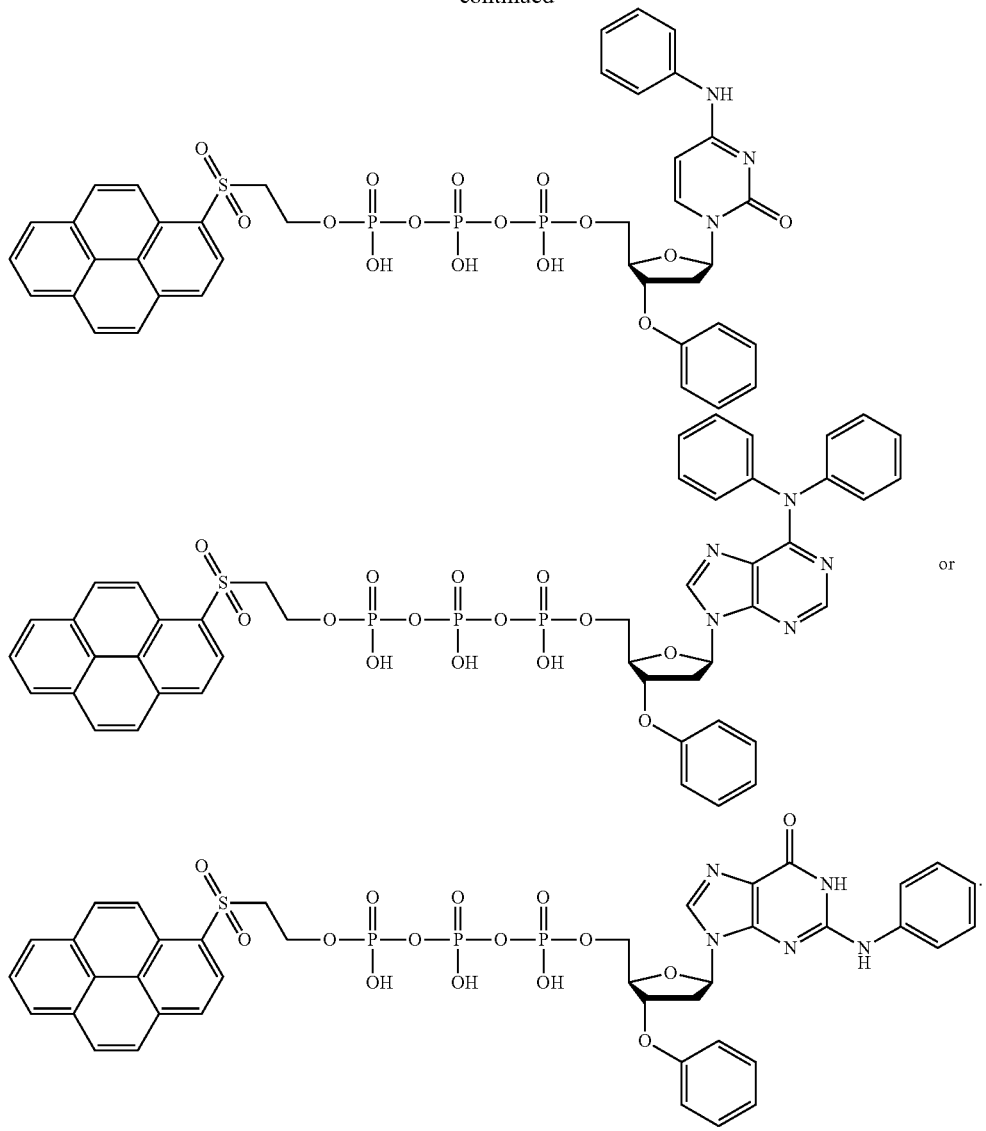

In one embodiment, the compound of formula (1) is a compound of formula (1d):

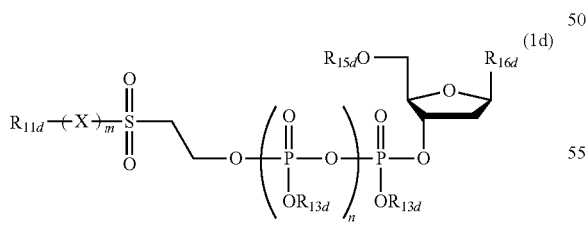

wherein:
m is an integer from 0 to 5;
n is an integer from 0 to 5;
X is O or $CH_2$;
$R_{11d}$ is an aryl, a heteroaryl, an alkyl, a cycloalkyl, an alkenyl, an alkenyl, an alkyl-acyl, an aryl-alkyl, or a silyl group;

each occurrence of $R_{13d}$ is independently hydrogen or null;

$R_{15d}$ is hydrogen, aryl, or heteroaryl; and $R_{16d}$ is a nitrogenous base, wherein the nitrogenous base is a natural nitrogenous base or artificial nitrogenous base.

In one embodiment, $R_{11d}$ is

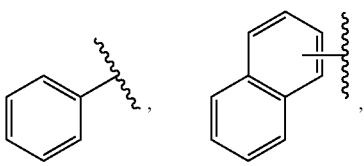

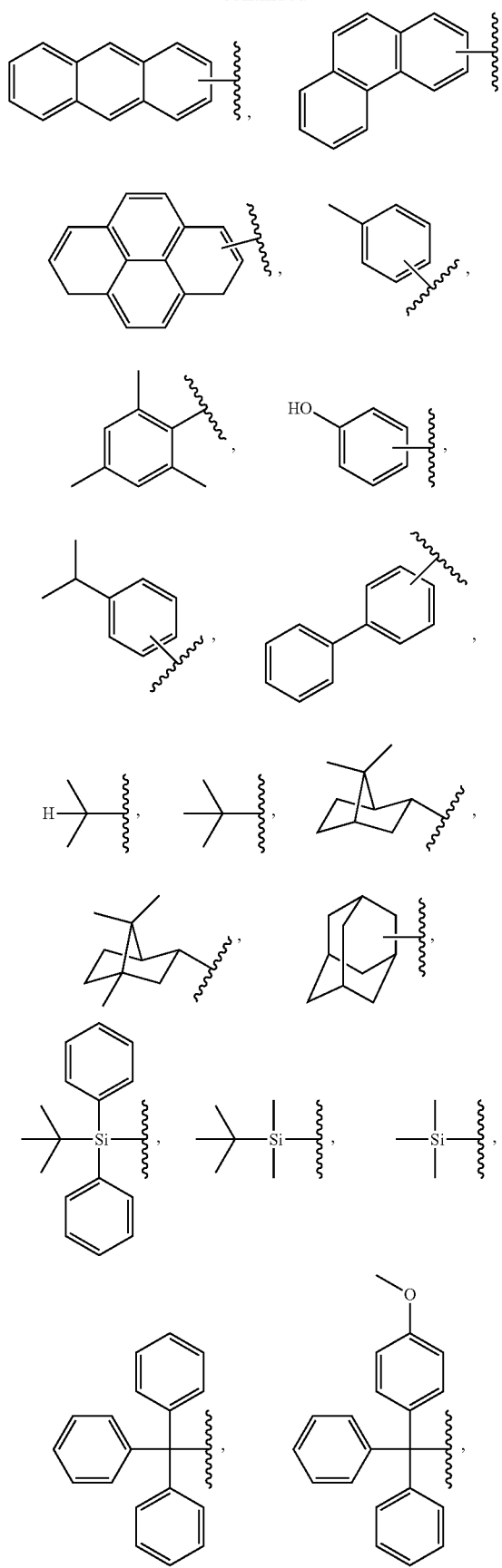

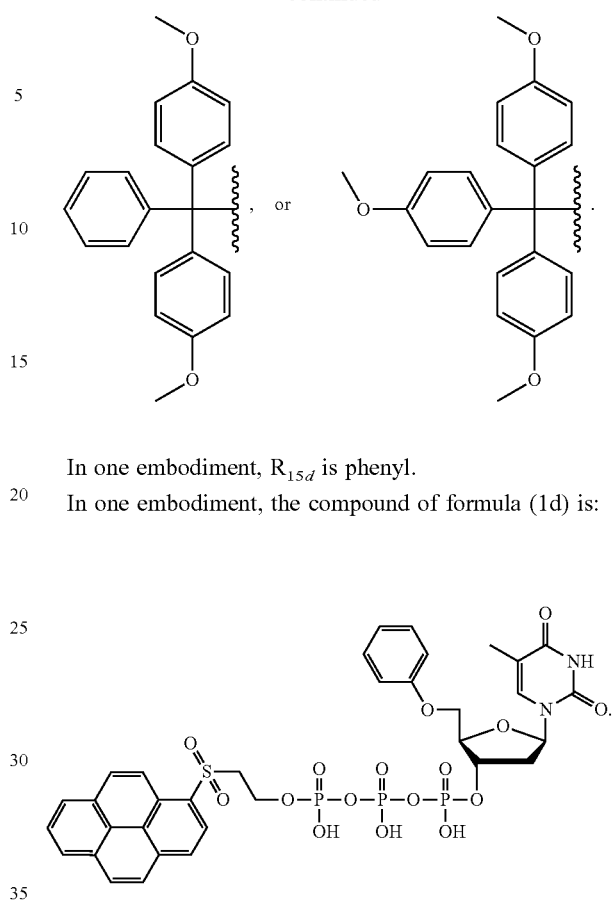

In one embodiment, $R_{15d}$ is phenyl.

In one embodiment, the compound of formula (1d) is:

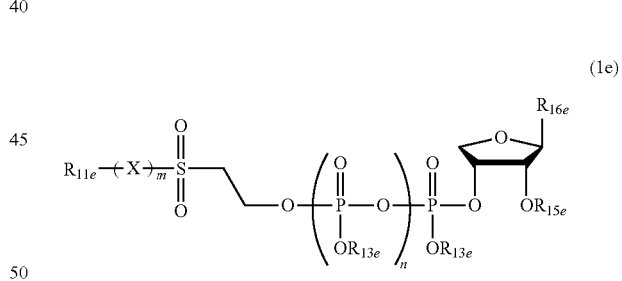

In one embodiment, the compound of formula (1) is a compound of formula (1e):

$$\text{(1e)}$$

wherein:

m is an integer from 0 to 5;

n is an integer from 0 to 5;

X is O or $CH_2$;

$R_{11e}$ is an aryl, a heteroaryl, an alkyl, a cycloalkyl, an alkenyl, an alkynyl, an alkyl-aryl, an aryl-alkyl, or a silyl group;

each occurrence of $R_{13e}$ is independently hydrogen or null;

$R_{15e}$ is hydrogen, aryl, acetyl, or heteroaryl; and $R_{16e}$ is a nitrogenous base, wherein the nitrogenous base is a natural nitrogenous base or artificial nitrogenous base.

In one embodiment, $R_{11e}$ is
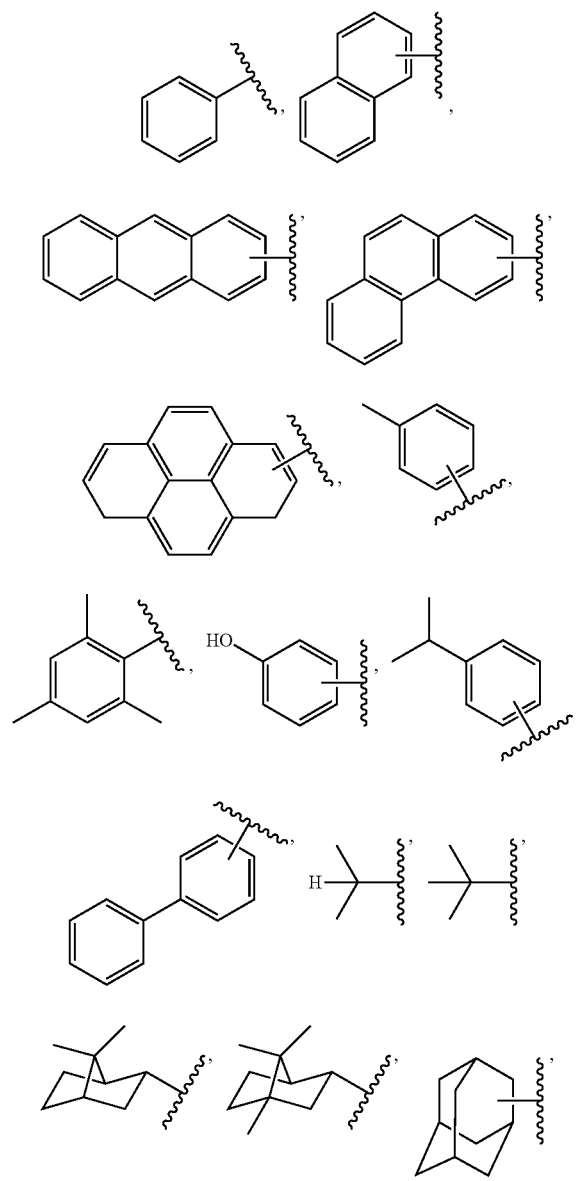
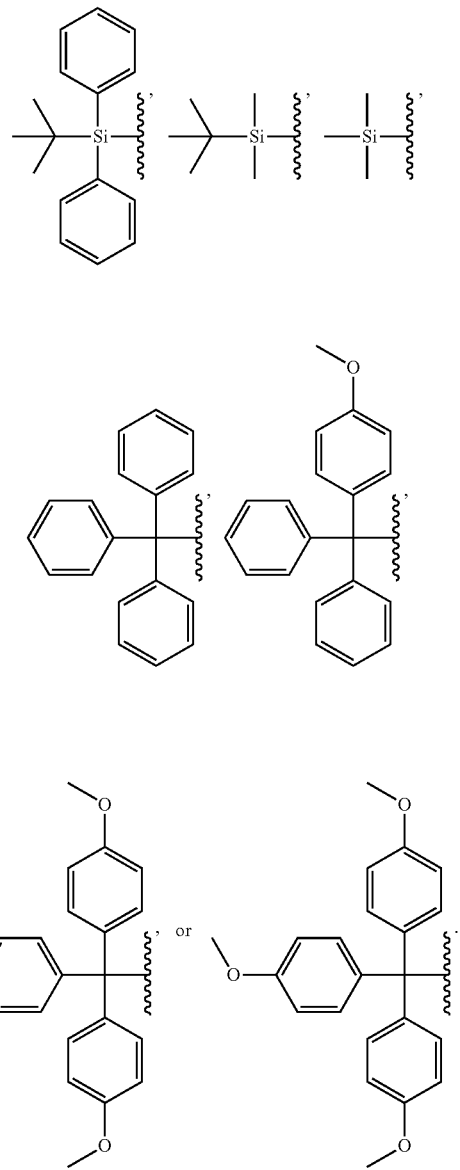
In one embodiment, $R_{15e}$ is phenyl.
In one embodiment, the compound of Formula (1e) is:
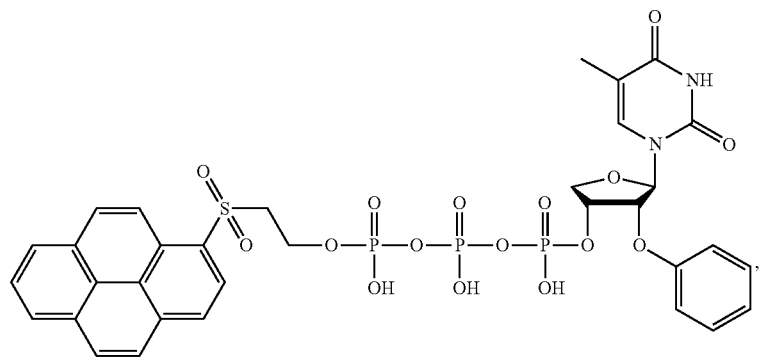

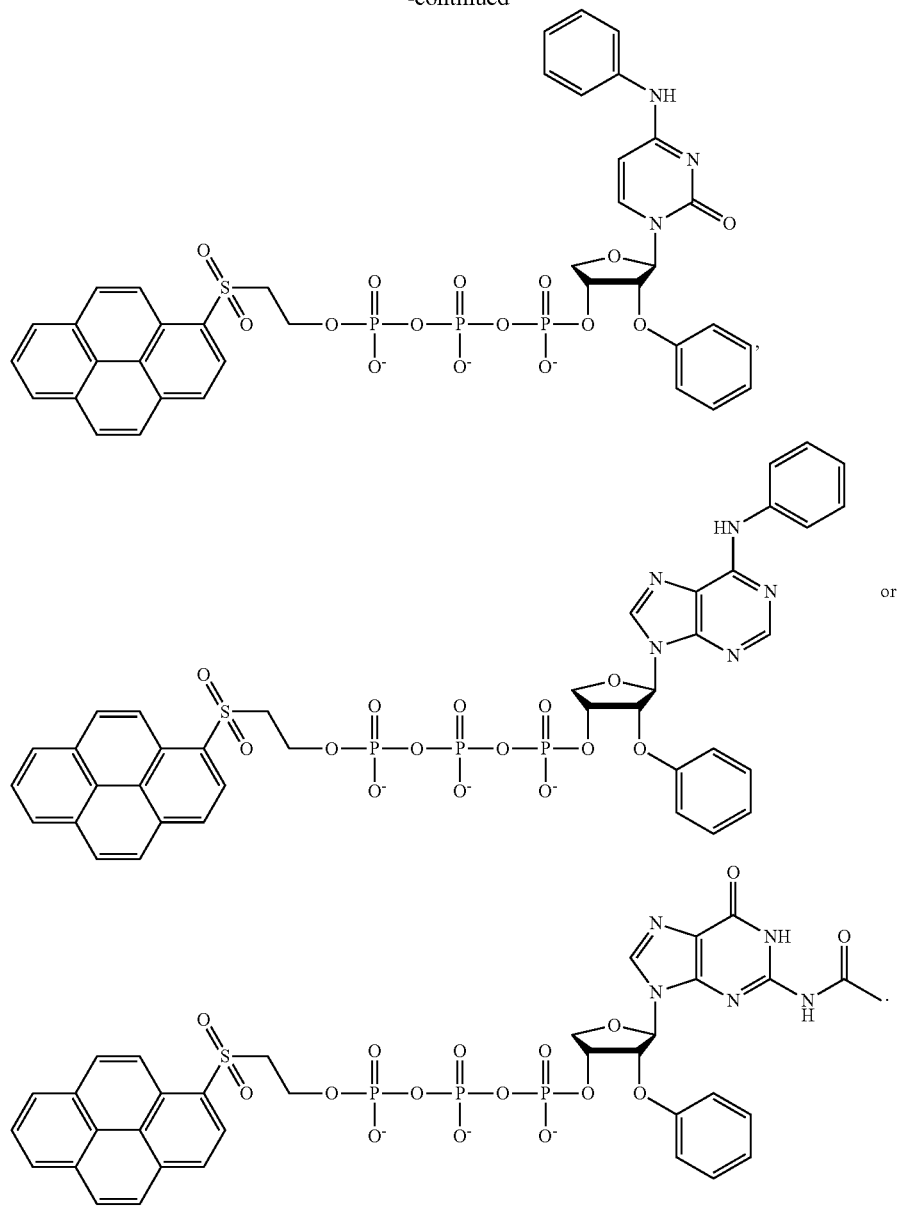
In one embodiment, the invention relates to a compound represented by formula (2):
In one embodiment, the invention relates to a compound represented by formula (3):
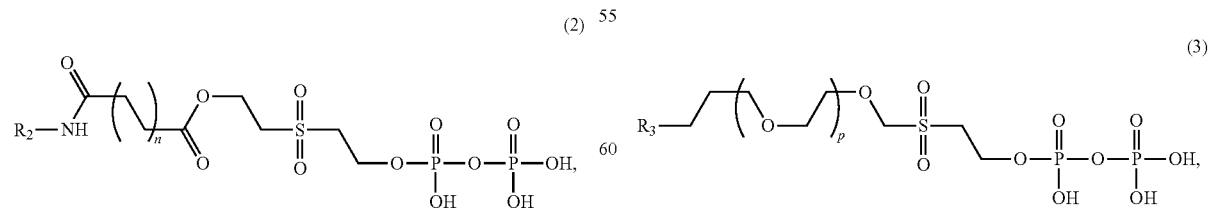
wherein n is an integer from 1 to 10, and wherein $R_2$ is a support.
wherein p is an integer from 0 to 10, and $R_3$ is a support.

In one embodiment, the invention relates to a compound represented by formula (4):

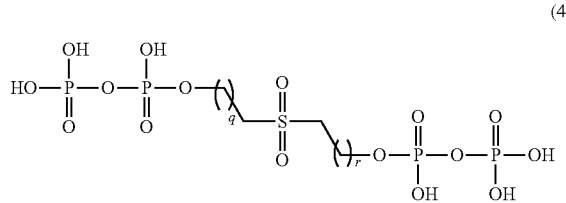
(4)

wherein q is an integer from 0 to 10, and
r is an integer from 0 to 10. In one embodiment, q is 1. In one embodiment, r is 1.

In one embodiment, the compound of formula (4) is

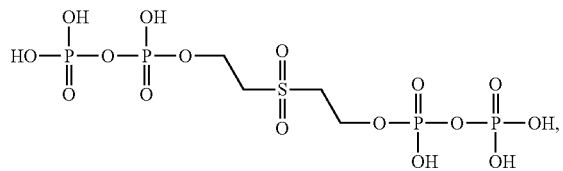

In one embodiment, the invention relates to a method of synthesizing a nucleoside (n)phosphate, wherein (n) is: di, tri, tetra, penta, or hexa, comprising a) contacting an activated nucleoside monophosphate with a compound represented by formula (1), a compound represented by formula (1a), a compound represented by formula (1b), a compound represented by formula (1a), a compound represented by formula (2), a compound represented by formula (3) or a compound represented by formula (4), and an acid catalyst to catalyze the formation of a reaction intermediate, and b) contacting the reaction intermediate with a base to induce formation of a nucleoside (n)phosphate.

In one embodiment, the acid catalyst is $ZnCl_2$.

In one embodiment, the activated nucleoside monophosphate is represented by formula (5)

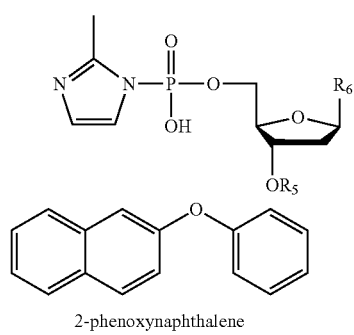
(5)

2-phenoxynaphthalene wherein $R_5$ is hydrogen, aryl, or heteroaryl; and $R_6$ is a nitrogenous base, wherein the nitrogenous base is a natural nitrogenous base or artificial nitrogenous base.

In one embodiment, the activated nucleoside monophosphate is an activated monophosphate of adenosine, cytidine, guanosine, uridine, 2'-deoxyadenosine, 2'-deoxycytidine, 2'-deoxyguanosine, thymidine, inosine, 9-β-D-arabinofuranosyl)adenine, 1-(β-D-arabinofuranosyl)cytosine, 9-(β-D-arabinofuranosyl)guanine, 1-(β-D-arabinofuranosyl)uracil, 9-(β-D-arabinofuranosyl)hypoxanthine, 1-(β-D-arabinofuranosyl)thymine, 3'-azido-3'-deoxythymidine, 3'-azido-2', 3'-dideoxyuridine, 3'-azido-2', 3'-dideoxycytidine, 3'-azido-2', 3'-dideoxyadenosine, 3'-azido-2', 3'-dideoxyguanosine, 3'-azido-2', 3'-dideoxyinosine, 3'-deoxythymidine, 2', 3'-dideoxyuridine, 2', 3'-dideoxyinosine, 2', 3'-dideoxyadenosine, 2', 3'-dideoxycytidine, 2', 3'-dideoxyguanosine, 9-(2, 3-dideoxy-1-β-D-ribofuranosyl)-2, 6-diaminopurine, 3'-deoxy-2', 3'-didehydrothymidine, 2', 3'-didehydro-2', 3'-dideoxyuridine, 2', 3'-didehydro-2', 3'-dideoxycytidine, 2', 3'-didehydro-2', 3'-dideoxyadenosine, 2', 3'-didehydro-2', 3'-dideoxyguanosine, 2', 3'-didehydro-2', 3'-dideoxyinosine, 3-deazaadenosine, 3-deazaguanosine, 3-deazainosine, 7-deazaadenosine, 7-deazaguanosine, 7-deazainosine, 6-azauridine, 6-azathymidine, 6-azacytidine, 5-azacytidine, 9-(β-D-ribofuranosyl)-6-thiopurine, 6-methylthio-9-(β-D-ribofuranosyl)purine, 2-amino-9-(β-D-arabinofuranosyl)-6-thiopurine, 2-amino-6-methylthio-9-(β-D-ribofuranosyl)purine, 5-fluorocytidine, 5-iodocytidine, 5-bromocytidine, 5-chlorocytidine, 5-fluorouridine, 5-iodouridine, 5-bromouridine, 5-chlorouridine, 2'-C-methyladenosine, 2'-C-methylcytidine, 2'-C-methylguanosine, 2'-C-methylinosine, 2'-C-methyluridine, 2'-C-methylthymidine, 2'-deoxy-2'-fluoroadenosine, 2'-deoxy-2'-fluorocytidine, 2'-deoxy-2'-fluoroguanosine, 2'-deoxy-2'-fluorouridine, 2'-deoxy-2'-fluoroinosine, 2'-α-fluorothymidine, 2'-deoxy-2'-fluoroarabinoadenosine, 2'-deoxy-2'-fluoroarabinocytidine, 2'-deoxy-2'-fluoroarabinoguanosine, 2'-deoxy-2'-fluoroarabinouridine, 2'-deoxy-2'-fluoroarabinoinosine, 2'-4-fluorothymidine, 2'40-methyladenosine, 2'-O-methylcytidine, 2'-O-methylguanosine, 2'-O-methylinosine, 2'-O-5-dimethyluridine, 2'-C-ethynylcytosine, 2'-C-ethynylguanosine, 2'-C-ethynyluridine, 2'-C-ethynylinosine, 2'-C-ethynyl-5-methyluridine, 3'-C-ethynyladenosine, 3'-C-ethynylpyridine, 3'-C-ethynylguanosine, 3'-C-ethynyluridine, 3'-C-ethynylinosine, ethynyl-5-methyluridine, 3'-deoxyadenosine, 3'-deoxycytidine, 3'-deoxyguanosine, 3'-deoxyuridine, 3'-deoxyinosine, 4'-C-ethynyladenosine, 4'-C-ethynylpyridine, 4'-C-ethynylguanosine, 4'-C-ethynyluridine, 4'-C-ethynylinosine, 4'-C-ethynylthymidine, 4'-C-methyladenosine, 4'-C-methylcytidine, 4'-C-methylguanosine, 4'-C-methyluridine, 4'-C-methylinosine, T-C-methyl-7-deazaadenosine, 2'-C-methyl-7-deazaguanosine, 2'-C-methyl-3-deazaadenosine, 2'-C-methyl-3-deazaguanosine, methyl-7-deazaadenosine, 2'-O-methyl-7-deazaguanosine, 2'-O-methyl-3-deazaadenosine, 2'-O-methyl-3-deazaguanosine, 2'-C-methyl-6-azauridine, 2'-C-methyl-5-fluorouridine, 2'-C-methyl-5-fluorocytidine, 2'-C-methyl-2-chloroadenosine, 2'-deoxy-7-deazaadenosine, 2'-deoxy-3-deazaadenosine, 2'-deoxy-7-deazaguanosine, 2'-deoxy-3-deazaguanosine, 2'-deoxy-6-azauridine, 2'-deoxy-5-fluorouridine, 2'-deoxy-5-fluorocytidine, 2'-deoxy-5-iodouridine, 2'-deoxy-5-iodocytidine, 2'-deoxy-2-chloroadenosine, 2'-deoxy-2-fluoroadenosine, 3'-deoxy-7-deazaadenosine, 3'-deoxy-7-deazaguanosine, 3'-deoxy-3-deazaadenosine, 3'-deoxy-3-deazaguanosine, 3'-deoxy-6-azauridine, 3'-deoxy-5-fluorouridine, 3'-deoxy-5-iodouridine, 3'-deoxy-5-fluorocytidine, 3'-deoxy-2-chloroadenosine, 2', 3'-dideoxy-7-deazaadenosine, 2', 3'-dideoxy-7-deazaguanosine, 2', 3'-dideoxy-3-deazaadenosine, 2', 3'-dideoxy-3-deazaguanosine, 2', 3'-dideoxy-6-azauridine, 2', 3'-dideoxy-5-fluorouridine, 2', 3'-dideoxy-5-fluorocytidine, 2', 3'-dideoxy-5-iodocytidine, 2', 3'-dideoxy-2-chloroadenosine, 2', 3'-dideoxy-β-L-cytidine, 2', 3'-dideoxy-β-L-adenosine, 2', 3'-dideoxy-β-L-guanosine, 3'-deoxy-β-L-thymidine, 2', 3'-dideoxy-5-fluoro-β-L-cytidine, 3-L-thymidine, 2'-deoxy-β-L-cytidine, 2'-deoxy-β-L-adenosine, 2'-deoxy-β-L-guanosine, 2'-deoxy-β-L-inosine, β-L-cytidine, β-L-adenosine, β-L-guanosine, β-L-uridine, β-L-inosine, 2', 3'-didehydro-2', 3'-dideoxy-β-L-cytidine, 3'-didehydro-3'-dideoxy-β-L-thymidine, 2', 3'-didehydro-2', 3'-dideoxy-β-L-adenosine, 2', 3'-didehydro-2', 3'-dideoxy-β-L-guanosine, 2', 3'-didehydro-2', 3'-dideoxy-β-L-5-fluoro-cytidine, 2'-deoxy-2', 2'-di fluorocytidine, 9-(β-D-arabino-furanosyl)-2-fluoroadenine, 2'-deoxy-2'(E)-fluoromethyl-enecytidine, 2'-deoxy-2' (Z)-fluoromethylenecytidine, (−)-2', 3'-dideoxy-3'-thiacytidine, (+)-2', 3'-dideoxy-3'-thiacyti-dine, 1-β-D-ribofuranosyl-1, 2, 4-triazole-3-carboxamide, 1-β-L-ribofuranosyl-1, 2, 4-triazole-3-carboxamide, 1-β-D-ribofuranosyl-1, 3-imidazolium-5-olate, 1-β-L-ribofurano-syl-1, 3-imidazolium-5-olate, 1-β-D-ribofuranosyl-5-ethy-nylimidazole-4-carboxamide, 1-β-L-ribofuranosyl-5-ethynylimidazole-4-carboxamide, 1-(2-deoxy-2-fluoro-β-D-arabinofuranosyl)-5-iodouracil, 1-(2-deoxy-2-fluoro-β-D-arabinofuranosyl)-5-iodocytosine, 1-(2-deoxy-2-fluoro-β-L-arabinofuranosyl)-5-methyluracil, 1-β-D-arabino-furanosyl)-5-(2-bromovinyl)uracil, E-5-(2-bromovinyl)-2'-deoxyuridine, 5-trifluoromethylthymidine, 1-β-D-arabino-furanosyl-5-propynyluracil, 1-(2-deoxy-2-fluoro-1-β-D-ara-binofuranosyl)-5-ethyluracil, 2', 3'-dideoxy-3'-fluoro-guanosine, 3'-deoxy-3'-fluorothymidine, (±)-(1α, 2β, 3α)-9-[2, 3-bis(hydroxymethyl)-1-cyclobutyl]adenine, (±)-(1α, 2β, 3α)-9-[2, 3-bis(hydroxymethyl)-1-cyclobutyl]guanine, (±)-(1β, 2α, 3β)-9-[2, 3-bis(hydroxymethyl)-1-cyclobutyl]guanine, (±)-(1β, 2α, 3β)-9-[2, 3-bis(hydroxymethyl)-1-cyclobutyl]adenine, (1R, 3S, 4R)-9-(3-hydroxy-4-hydroxymethylcyclopent-1-yl)guanine, (1S, 2R, 4R)-9-(1-hydroxy-2-hydroxymethylcyclopent-4-yl)guanine, (2R, 4R)-9-(2-hydroxymethyl-1, 3-dioxolan-4-yl)-2, 6-diaminopurine, (2R, 4R)-1-(2-hydroxymethyl-1, 3-dioxolan-4-yl)cytosine, (2R, 4R)-9-(2-hydroxymethyl-1, 3-dioxolan-4-yl)guanine, (2R, 4R)-1-(2-hydroxymethyl-1, 3-dioxolan-4-yl)-5-fluoro-cytosine, (1R, 2S, 4S)-9-(4-hydroxy-3-hydroxymethyl-2-methylenecyclopent-4-yl]guanine, or (1S, 3R, 4S)-9-(3-hydroxy-4-hydroxymethyl-5-methylenecyclopent-1-yl] guanine.

In one embodiment, the invention relates to a composition comprising at least one nucleoside (n)phosphate synthesized according to the method of a) contacting an activated nucleoside monophosphate with a compound represented by formula (1), a compound represented by formula (1a), a compound represented by formula (1b), a compound represented by formula (1a), a compound represented by formula (2), a compound represented by formula (3) or a compound represented by formula (4), and an acid catalyst to catalyze the formation of a reaction intermediate, and b) contacting the reaction intermediate with a base to induce formation of a nucleoside (n)phosphate.

In one embodiment, the composition comprises at least four nucleoside triphosphates. In one embodiment, at least four nucleoside triphosphates are deoxyadenosine triphosphate (dATP), deoxyguanosine triphosphate (dGTP), deoxycytidine triphosphate (dCTP), and deoxythymidine triphosphate (dTTP).

In one embodiment, the composition is a pharmaceutical composition.

In one embodiment, the invention relates to a method of treating a disease of disorder in a subject in need thereof, the method comprising administering to the subject a pharmaceutical composition comprising at least one nucleoside (n)phosphate synthesized according to the method of a) contacting an activated nucleoside monophosphate with a compound represented by formula (1), a compound represented by formula (1a), a compound represented by formula (1b), a compound represented by formula (1a), a compound represented by formula (2), a compound represented by formula (3) or a compound represented by formula (4), and an acid catalyst to catalyze the formation of a reaction intermediate, and b) contacting the reaction intermediate with a base to induce formation of a nucleoside (n)phosphate.

In one embodiment, the invention relates to a kit comprising at least one nucleoside (n)phosphate synthesized according to the method of a) contacting an activated nucleoside monophosphate with a compound represented by formula (1), a compound represented by formula (1a), a compound represented by formula (1b), a compound represented by formula (1a), a compound represented by formula (2), a compound represented by formula (3) or a compound represented by formula (4), and an acid catalyst to catalyze the formation of a reaction intermediate, and b) contacting the reaction intermediate with a base to induce formation of a nucleoside (n)phosphate.

In one embodiment, the composition comprises at least four nucleoside triphosphates. In one embodiment, at least four nucleoside triphosphates are deoxyadenosine triphosphate (dATP), deoxyguanosine triphosphate (dGTP), deoxycytidine triphosphate (dCTP), and deoxythymidine triphosphate (dTTP).

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2A depicts the chemical structure of the p-toluene pyrophosphate reagent (1). FIG. 2B depicts a diagram of the synthesis of 5'-thymidine triphosphate from the reaction of activated thymidine monophosphate with the p-toluene pyrophosphate reagent of FIG. 2A. FIG. 2C depicts the chemical structure of an intermediate formed following step 1 of the reaction of FIG. 2B.

FIG. 3 depicts the chemical structures of an exemplary activated monophosphate (left) and monophosphate (right).

FIG. 5 depicts chemical structure of pyrene pyrophosphate (left) and p-toluene pyrophosphate (right).

FIG. 7 depicts the chemical structures of four naturally occurring nucleoside triphosphates which have been synthesized using the methods of the invention.

FIG. 11 depicts HPLC analysis of a-L-threofuranosyl adenosine triphosphate using the traditional Yoshikawa or Ludwig-Eckstein methods. Arrows indicate the location of the desired peak in the crude reaction mixture.

FIG. 14A depicts an application of the organopyrophosphate reagent to the synthesis of natural thymidine-5'-triphosphate. FIG. 14B depicts HPLC traces provided for the activated monophosphate, fully protected triphosphate intermediate after silica gel purification, and thymidine triphosphate after precipitation as the sodium salt, FIG. 14C depicts a comparison of chemically synthesized thymidine 3'-triphosphate (dTTP) with a commercial standard. HPLC gradients are provided in the supplementary information.

FIG. 16A and FIG. 16B depict polymerase activity assay of chemically synthesized DNA and TNA nucleoside triphosphates. All four DNA and TNA nucleoside triphosphates were constructed using the organic pyrophosphate method. (a) Chemically synthesized dNTPs were evaluated against commercial reagents in a standard PCR reaction. (b) Chemically synthesized tNTPs purified by silica get chromatography (SG) were evaluated against HPLC purified tNTPs (HPLC) in a polymerase-mediated primer-extension reaction using Kod-RI TNA polymerase.

FIG. 34 depicts a $^{13}$C NMR spectrum of synthesized compound 9a.

FIG. 35 depicts an $^{31}$P NMR spectrum of synthesized compound 9a.

FIG. 37 depicts a $^{13}$C NMR spectrum of synthesized compound 10a.

FIG. 38 depicts an $^{31}$P NMR spectrum of synthesized compound 10a.

FIG. 41 depicts an $^{31}$P NMR spectrum of synthesized compound 12a.

FIG. 43 depicts a $^{31}$P NMR spectrum of synthesized compound 13a.

FIG. 56 depicts a synthesis scheme for 2'-deoxyadenosine-5'-triphosphate (dATP, compound 13c).

FIG. 94 depicts a $^{13}$C NMR spectrum of synthesized compound 22a,

FIG. 95 depicts an $^{31}$P NMR spectrum of synthesized compound 22a.

FIG. 98 depicts an $^{31}$P NMR spectrum of synthesized compound 24a,

FIG. 99 depicts an $^1$H NMR spectrum of synthesized compound 25a.

FIG. 100 depicts a $^{31}$P NMR spectrum of synthesized compound 25a.

FIG. 123 depicts an $^{31}$P NMR spectrum of synthesized N$^2$-Acetyl-9-(2'-O-benzoyl-α-L-threofuranosyl)guanosine-3'-monophosphor-2-methylimidazolide (compound 23d).

Figure 124:
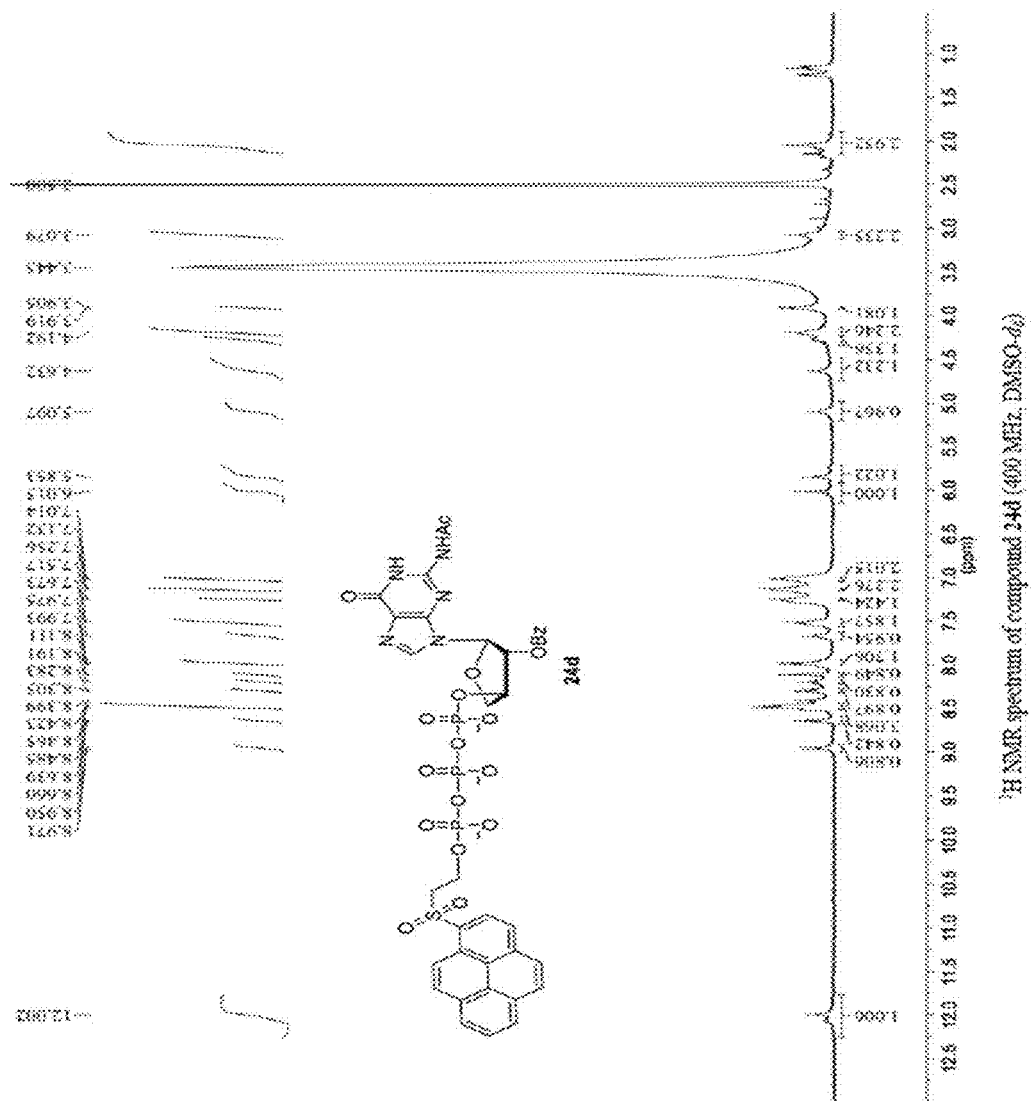
Figure 125:
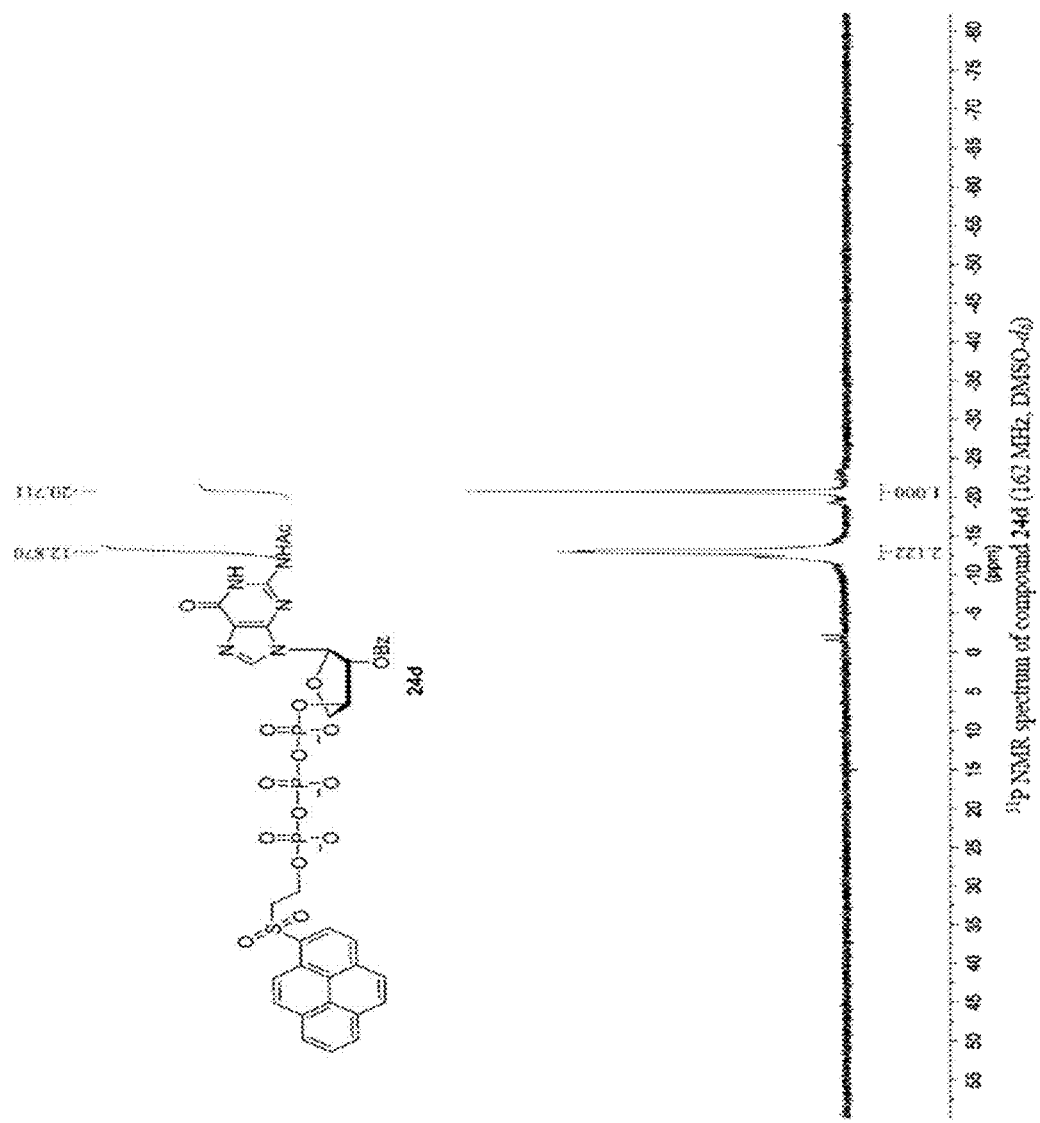
Figure 126:
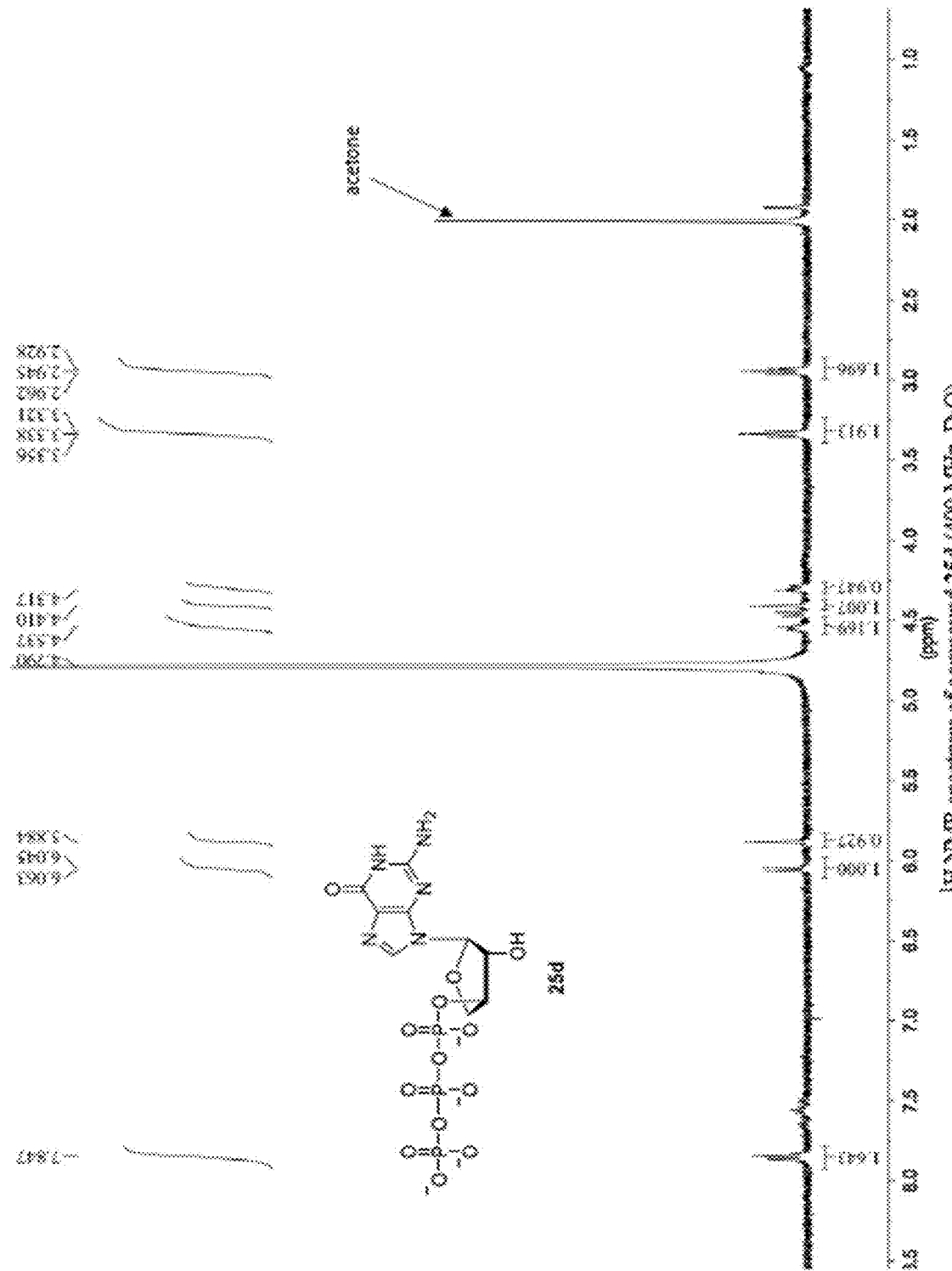

FIG. 124 depicts an $^1$H NMR spectrum of synthesized N$^2$-Acetyl-9-(2'-O-benzoyl-α-L-threofuranosyl)guanosine-3'-(γ-(2-(pyrenesulfonyl)ethyl)) triphosphate (compound 24d), FIG. 125 depicts an $^{31}$P NMR spectrum of synthesized compound 24d, FIG. 126 depicts an $^1$H NMR spectrum of synthesized compound 25d, FIG. 127 depicts a $^{31}$P NMR spectrum of synthesized compound 25d.

Figure 128:
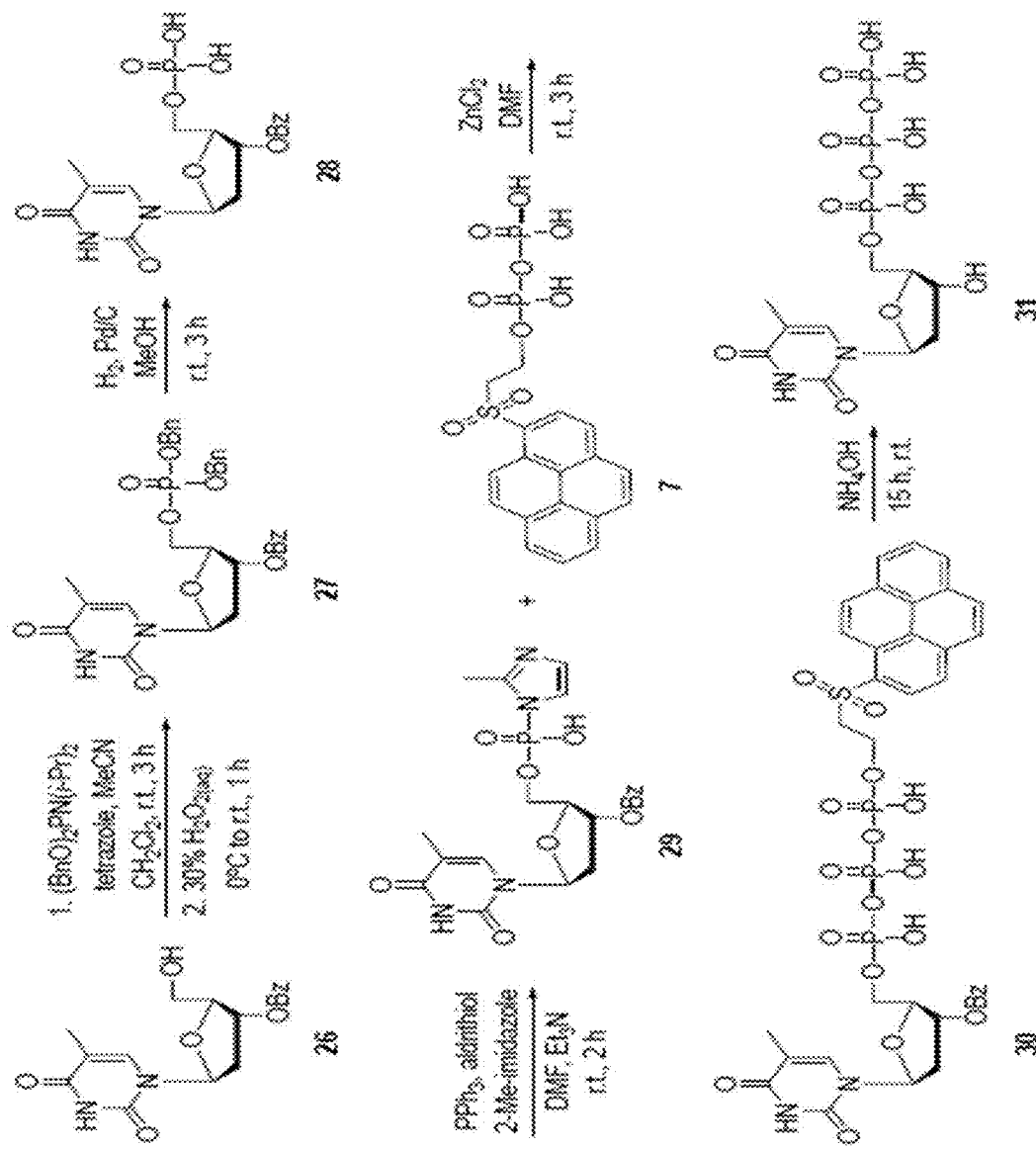

FIG. 128 depicts a synthesis scheme for 1,2'-deoxythymidine-5'-triphosphate (L-dTTP, compound 31).

Figure 129:
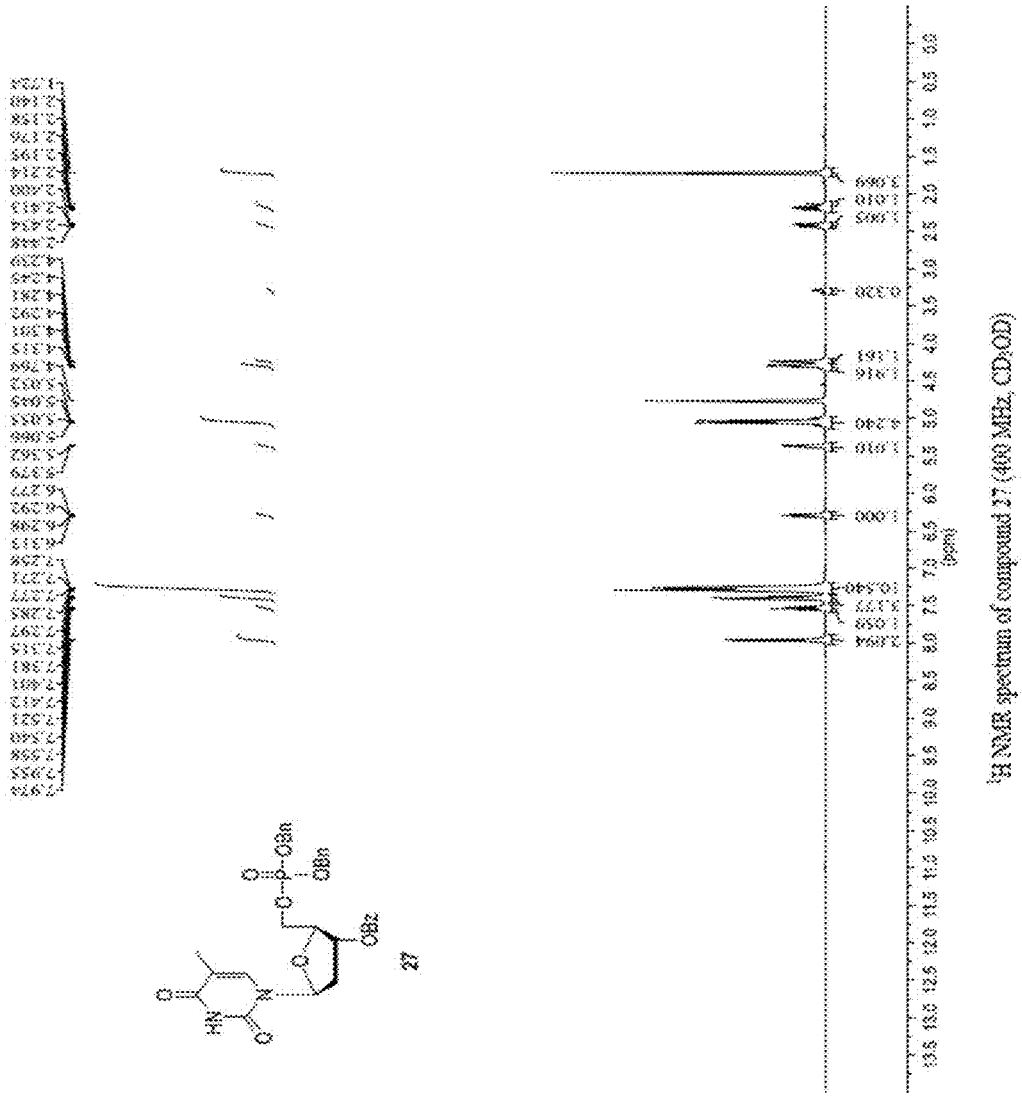

FIG. 129 depicts an NMR spectrum of synthesized 3'-Benzoyl-2'-deoxy-L-thymidine-5'-dibenzylmonophosphate (compound 27).

Figure 130:
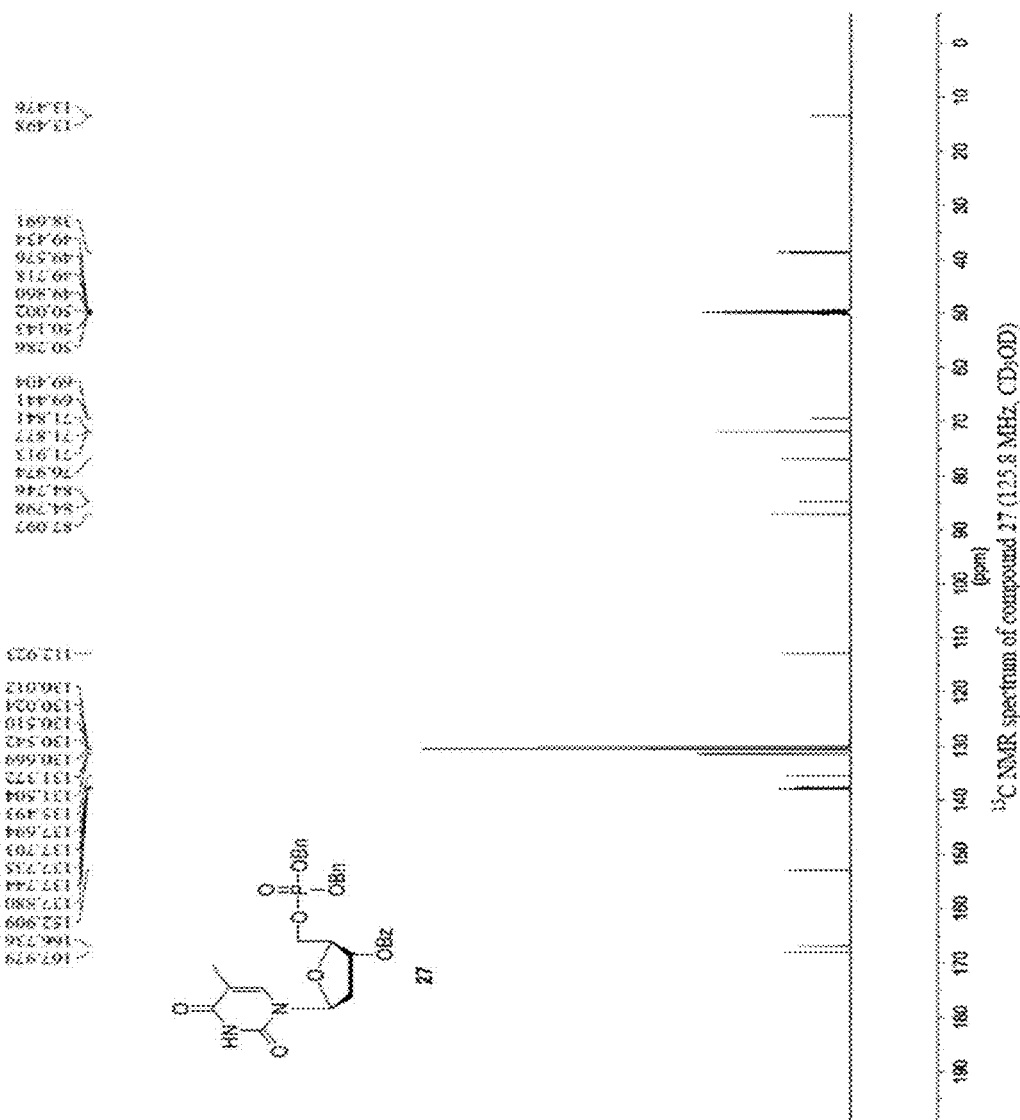

FIG. 130 depicts a $^{13}$C NMR spectrum of synthesized compound 27.

Figure 131:
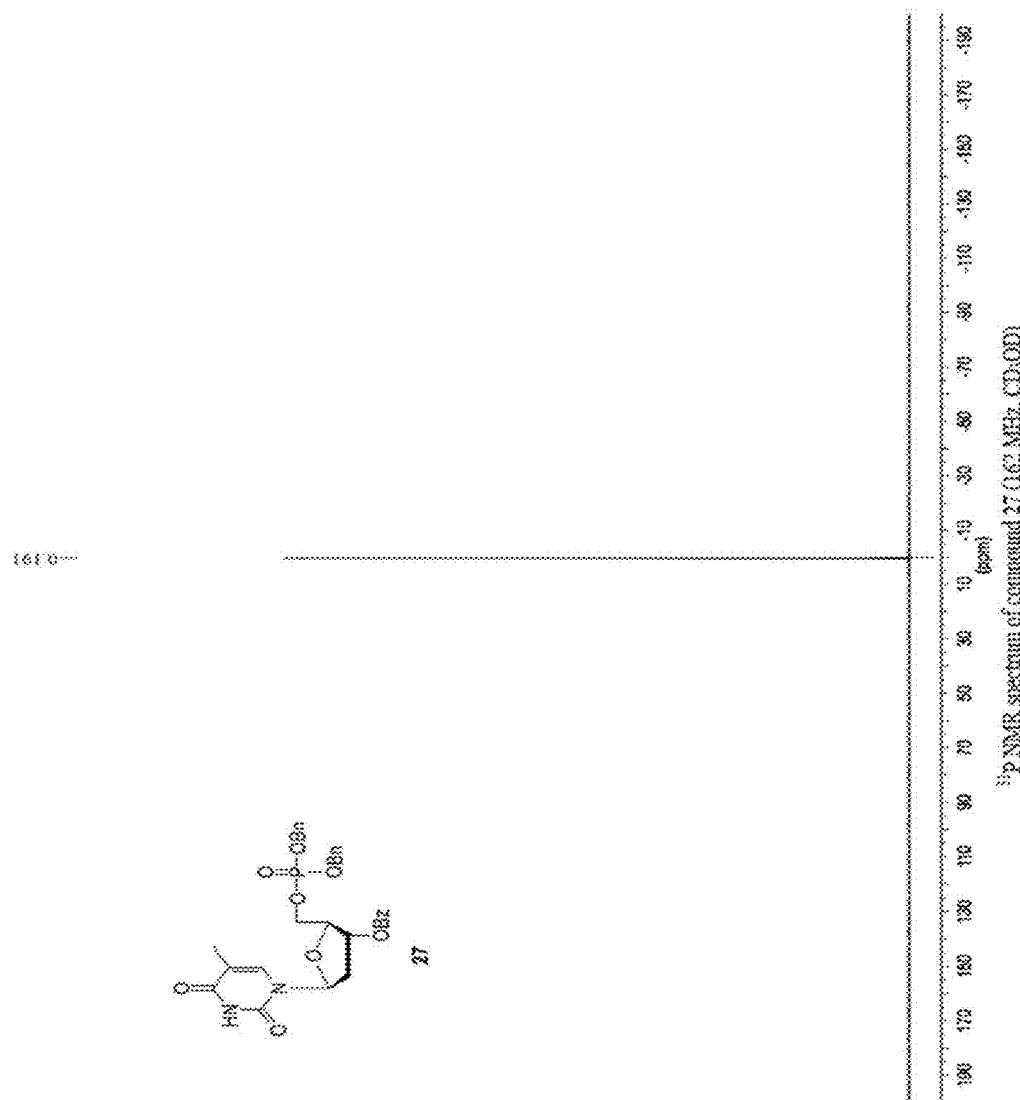

FIG. 131 depicts an $^{31}$P NMR spectrum of synthesized compound 27.

Figure 133:
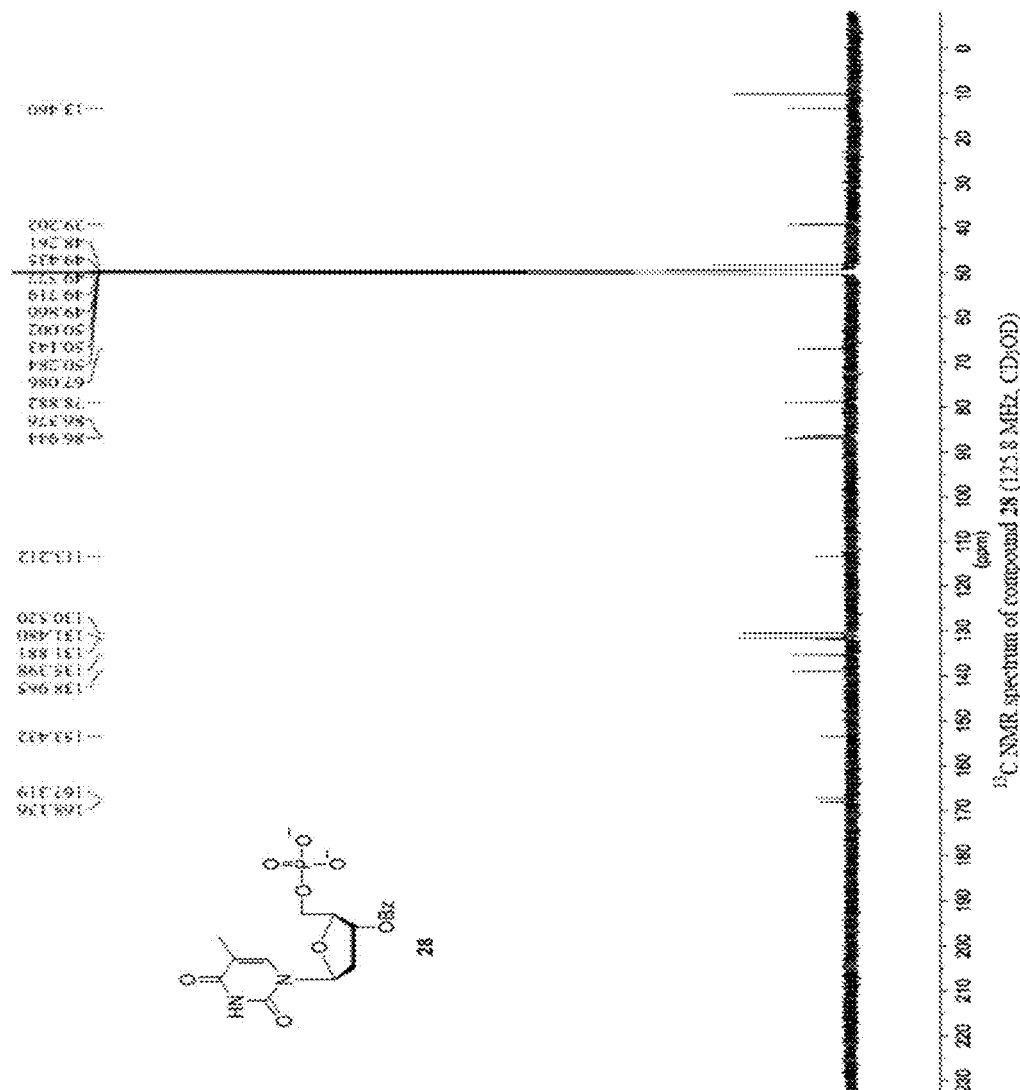

FIG. 132 depicts an $^1$H NMR spectrum of synthesized 3'-Benzoyl-2'-deoxy-L-thymidine-5'-monophosphate (compound 28), FIG. 133 depicts a $^{13}$C NMR spectrum of synthesized compound 28.

Figure 134:
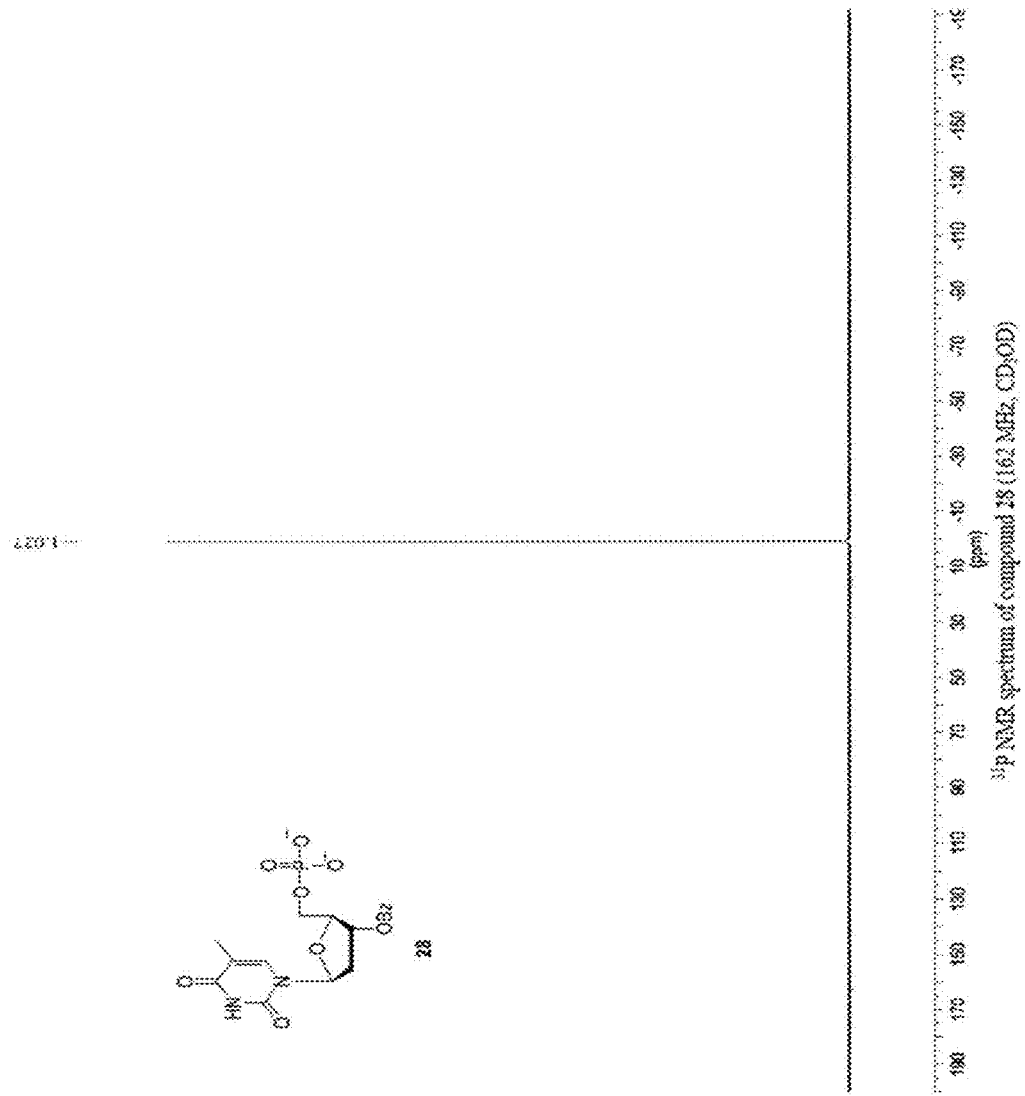

FIG. 134 depicts an $^{31}$P NMR spectrum of synthesized compound 28.

FIG. 135 depicts an $^{31}$P NMR spectrum of synthesized 3'-Benzoyl-2'-deoxy-L-thymidine-5'-phosphor-2-methylimidazolide (compound 29).

Figure 136:
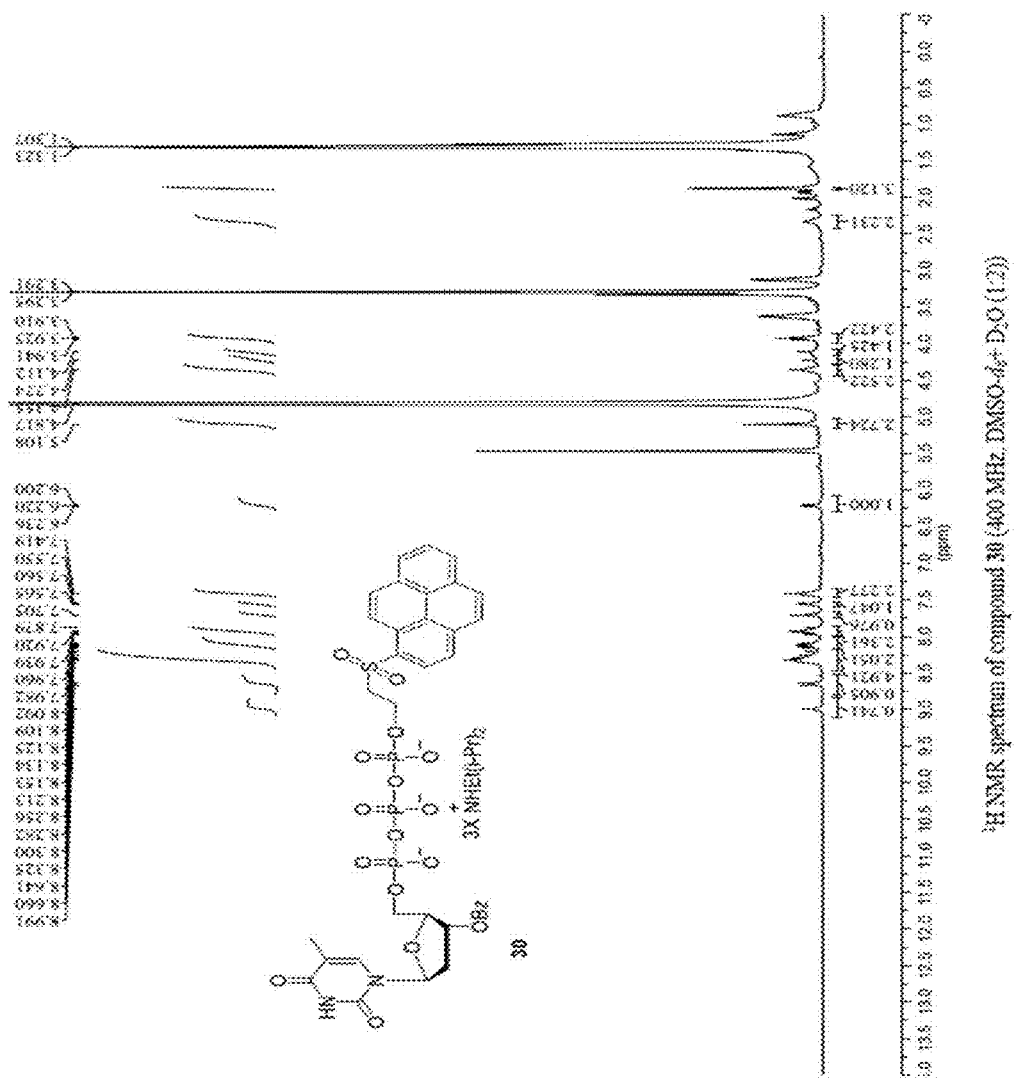

FIG. 136 depicts an $^1$H NMR spectrum of synthesized 3'-Benzoyl-2'-deoxy-L-thymidine-5'-(γ-(2-(pyrenesulfonyl)ethyl))triphosphate (compound 30).

Figure 137:
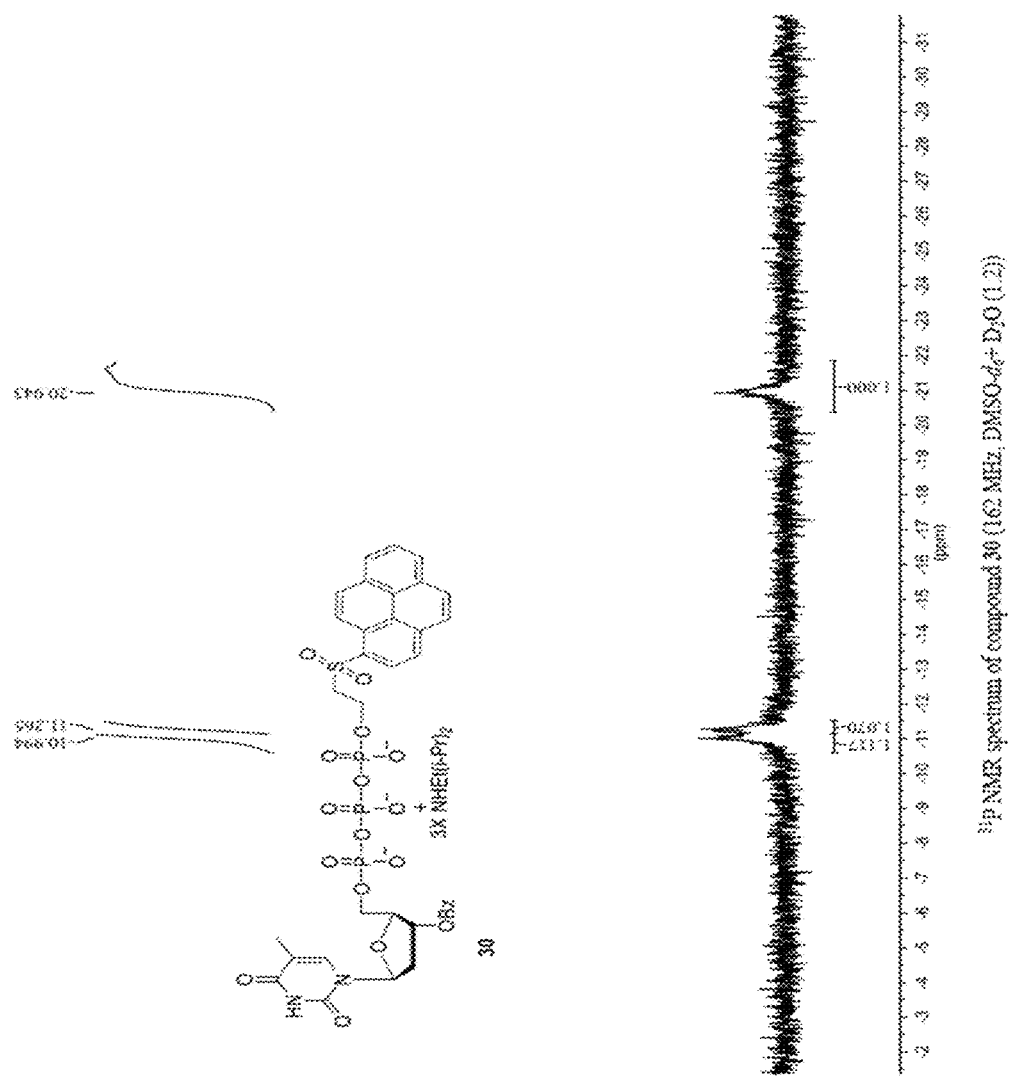

FIG. 137 depicts an $^{31}$P NMR spectrum of synthesized compound 30.

Figure 138:
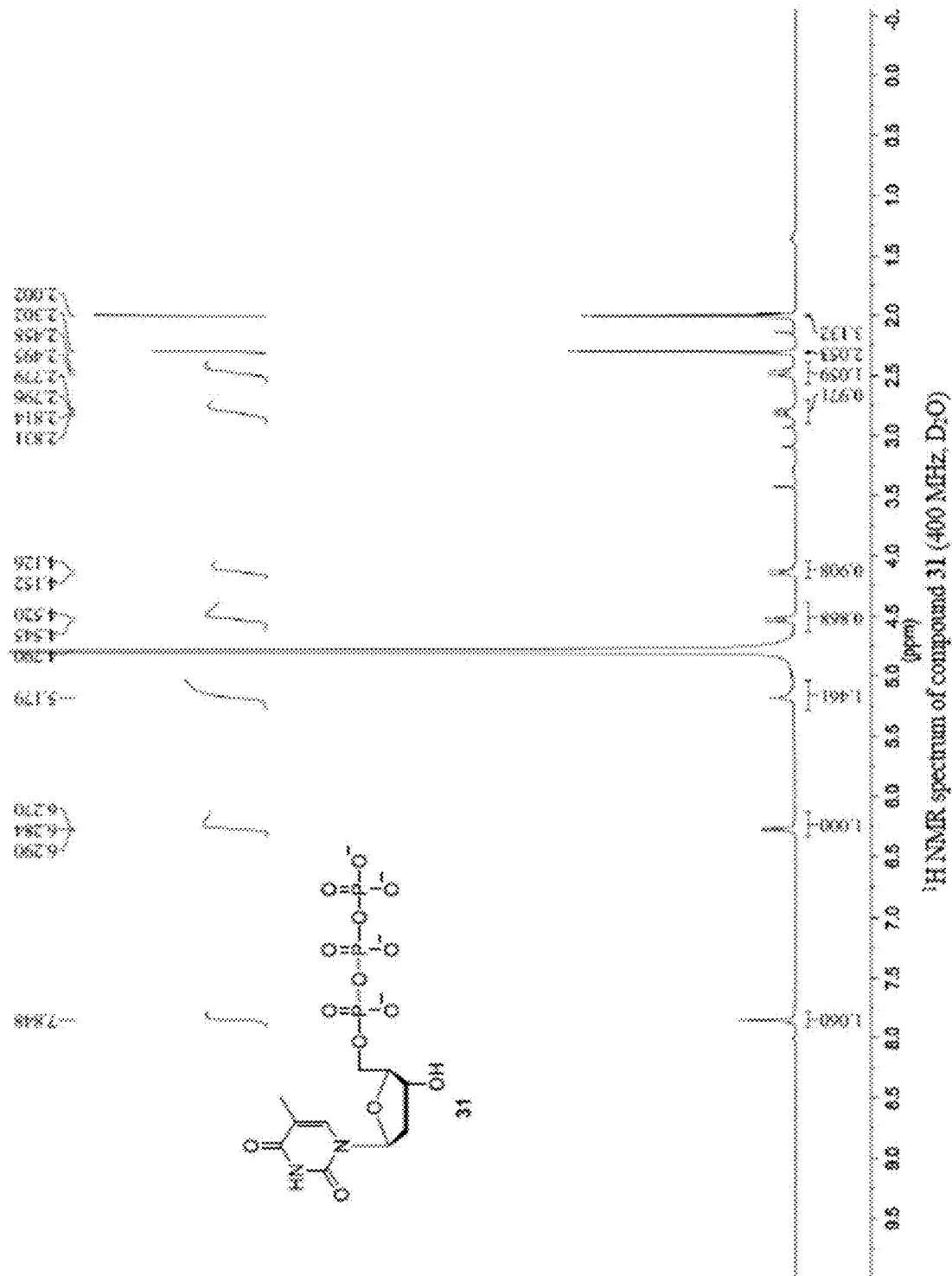

FIG. 138 depicts an $^1$H NMR spectrum of synthesized compound 31,

FIG. 139 depicts a $^{31}$P NMR spectrum of synthesized compound 31.

DETAILED DESCRIPTION

The present invention is based, in part, on the discovery that an organic molecule comprising at least one phosphate moiety can be used as a phosphorylation reagent. In one embodiment, the organic molecule comprising at least one phosphate moiety can be used as a phosphorylation reagent to synthesize a phosphorylated molecule through a reaction of the organic molecule comprising at least one phosphate moiety with an activated precursor molecule. The compositions and methods disclosed herein can be used to synthesize phosphorylated sugar molecules, phosphorylated proteins or peptides, phosphorylated lipids, or phosphorylated nucleic acid molecules. Thus, in various aspects the invention provides compositions and methods for synthesizing natural and modified phosphorylated molecules.

The compositions and methods disclosed herein can be used to synthesize phosphorylated nucleosides. In one embodiment, the organic phosphate molecule of the invention can be an organic pyrophosphate molecule for use in the synthesis of nucleoside triphosphates from an activated nucleoside monophosphate molecule. In one embodiment, the organic phosphate molecule of the invention can be an organic monophosphate molecule for use in the synthesis of nucleoside diphosphates from an activated nucleoside monophosphate molecule. In one embodiment, the organic phosphate molecule of the invention can be an organic triphosphate molecule for use in the synthesis of nucleoside tetraphosphates from an activated nucleoside monophosphate molecule, in one embodiment, the organic phosphate molecule of the invention can be an organic tetraphosphate molecule for use in the synthesis of nucleoside pentaphosphates from an activated nucleoside monophosphate molecule. In one embodiment, the organic phosphate molecule of the invention can be an organic pentaphosphate molecule for use in the synthesis of nucleoside hexaphosphates from an activated nucleoside monophosphate molecule.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass non-limiting variations of ±40% or ±20% or ±10%, ±5%, ±1%, or ±0.1% from the specified value, as such variations are appropriate.

"Acid catalyst," as used herein, refers to any acidic compounds including the so-called Lewis acids, which catalyze the reaction between an activated nucleoside monophosphate and a pyrophosphate containing compound. Examples of acids used for this purpose include $ZnCl_2$, $H_2SO_4$, HCl, $H_3PO_4$ or $BF_3$, or sulfonic acids or their salts.

Examples of sulfonic acids comprise ortho-, meta- and para-toluenesulfonic acids, alkylbenzenesulfonic acids, secondary alkyl-sulfonic acids, sulfonic resins, alkylsulfates, alkylbenzenesulfonates, alkyl-sulfonates and sulfosuccinic acid.

As used herein, the term "purified" or "to purify" refers to the removal of components (e.g., contaminants) from a sample. For example, nucleic acids are purified by removal of contaminating cellular proteins or other undesired nucleic acid species. The removal of contaminants results in an increase in the percentage of a desired compound in the sample.

A "natural" nucleoside is one that occurs in nature. For the purposes of this invention the following nucleosides are defined as the natural nucleosides: adenosine, cytidine, guanosine, uridine, 2'-deoxyadenosine, 2'-deoxycytidine, T-deoxyguanosine, thymidine, and inosine.

The term base, unless otherwise specified, refers to the base moiety of a nucleoside or nucleotide (a nucleobases). The base moiety is the heterocycle portion of a nucleoside or nucleotide. The base moiety may be a pyrimidine derivative or analog, a purine derivative or analog, or other heterocycle. The nucleoside base may contain two or more nitrogen atoms and may contain one or more peripheral substitutents. The nucleoside base is attached to the sugar moiety of the nucleotide mimic in such ways that both β-D- and β-L-nucleoside and nucleotide can be produced.

The term sugar refers to the ribofuranose of deoxyribofuranose portion of a nucleoside or nucleotide. The sugar moiety may contain one or more substitutents at the C1-, C2-, C3-, C4-, and C5-position of the ribofuranose. Substituents may direct to either the α- or β-face of the ribofuranose. The nucleoside base that can be considered as a substitutent at the C-1 position of the ribofuranose directs to the β-face of the sugar. The β-face is the side of a ribofuranose on which a purine or pyrimidine base of natural β-D-nucleosides is present. The α-face is the side of the sugar opposite to the β-face. The sugar moiety of the present invention is not limited to a ribofuranose and its derivatives, instead, it may be a carbohydrate, a carbohydrate analog, a carbocyclic ring, or other ribofuranose analog.

The term sugar-modified nucleoside refers to a nucleoside containing a modified sugar moiety.

The term base-modified nucleoside refers to a nucleoside containing a modified base moiety, relative to a base moiety found in a natural nucleoside.

As used herein, the term "nucleic acid" refers to both naturally-occurring molecules such as DNA and RNA, but also various derivatives and analogs. Generally, the probes, hairpin linkers, and target polynucleotides of the present teachings are nucleic acids, and typically comprise DNA. Additional derivatives and analogs can be employed as will be appreciated by one having ordinary skill in the art.

The term "nucleotide base", as used herein, refers to a substituted or unsubstituted aromatic ring or rings in certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, naturally occurring nucleotide bases adenine, guanine, cytosine, 6 methyl-cytosine, uracil, thymine, and analogs of the naturally occurring nucleotide bases, e.g., 7-deazaadenine, 7-deazaguanine, 7-deaza-8-azaguanine, 7-deaza-8-azaadenine, N6 delta 2-isopentenyladenine (6iA), N6-delta 2-isopentenyl-2-methylthioadenine (2 ms6iA), N2-dimethylguanine (dmG), 7methylguanine (7mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, 06-methylguanine, N6-methyladenine, 04-methylthymine, 5,6-dihydrothymine, 5,6-dihydrouracil, pyrazolo[3,4-D]pyrimidines (see, e.g., U.S. Pat. Nos. 6,143,877 and 6,127,121 and PCT published application WO 01/38584), ethenoadenine, indoles such as nitroindole and 4-methylindole, and pyrroles such as nitropyrrole. Certain exemplary nucleotide bases can be found, e.g., in Fasman, 1989, Practical Handbook of Biochemistry and Molecular Biology, pp. 385-394, CRC Press, Boca. Raton, Fla., and the references cited therein.

The term "nucleotide", as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR2 or halogen groups, where each R is independently H, C1-C6 alkyl or C5-C14 aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-anomeric nucleotides, 1'-anomeric nucleotides, 2'-4'- and 3'-4'-linked and other "locked" or "LNA", bicyclic sugar modifications (see, e.g., PCT published application nos. WO 98/22489, WO 98/39352; and WO 99/14226). The term "nucleic acid" typically refers to large polynucleotides.

The term "nucleotide analogs" as used herein refers to modified or non-naturally occurring nucleotides including, but not limited to, analogs that have altered stacking interactions such as 7-deaza purines 7-deaza-dATP and 7-deaza-dGTP); base analogs with alternative hydrogen bonding configurations such as Iso-C and iso-G and other nonstandard base pairs described in U.S. Pat. No. 6,001,983 to S. Benner and herein incorporated by reference); non-hydrogen bonding analogs non-polar, aromatic nucleoside analogs such as 2,4-difluorotoluene, described by B. A. Schweitzer and E. T. Kool, Org, Chem., 1994, 59, 7238-7242; B. A. Schweitzer and E. T. Kool, J. Am. Chem. Soc., 1995, 117, 1863-1872); "universal" bases such as 5-nitroindole and 3-nitropyrrole; and universal purines and pyrimidines (such as "K" and "P" nucleotides, respectively; Kong, et al., Nucleic Acids Res., 1989, 17, 10373-10383, P. Kong et al., Nucleic Acids Res., 1992, 20, 5149-5152). Nucleotide analogs include nucleotides having modification on the sugar moiety, such as dideoxy nucleotides and 2'-O-methyl nucleotides. Nucleoside analogue examples wherein the natural sugar moiety is modified include but are not limited to hexitol nucleic acid (HNA), cyclohexene nucleic acids (CeNA), locked nucleic acids (LNA), altritol nucleic acids (ANA) and peptide nucleic acids (PNA). Nucleotide analogs include modified forms of deoxyribo-nucleotides as well as ribonucleotides.

The term "oligonucleotide" typically refers to short polynucleotides, generally, no greater than about 50 nucleotides.

It will be understood that when a nucleotide sequence is represented by a DNA sequence (i.e., A, T, G, C), this also includes an RNA sequence (i.e., A, U, G, C) in which "U" replaces "T."

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides," The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning and amplification technology, and the like, and by synthetic means. An "oligonucleotide" as used herein refers to a short polynucleotide, typically less than 100 bases in length.

As used herein, the term "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a sign or symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the terms "effective amount," "pharmaceutically effective amount" and "therapeutically effective amount" refer to a nontoxic but sufficient amount of an agent to provide the desired biological result. That result may be reduction and/or alleviation of a sign, a symptom, or a cause of a disease or disorder, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing an undesirable biological effect or interacting in a deleterious manner with any of the components of the composition in which it is contained.

As used herein, the language "pharmaceutically acceptable salt" refers to a salt of the administered compound prepared from pharmaceutically acceptable non-toxic acids, including inorganic acids, organic acids, solvates, hydrates, or clathrates thereof. Examples of such inorganic acids are hydrochloric, hydrobromic, hydroiodic, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent; diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ; or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), Which is incorporated herein by reference.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl.

As used herein, the term "substituted alkyl" means alkyl as defined above, substituted by one, two or three substituents selected from the group consisting of halogen, —OH, alkoxy, —NH$_2$, amino, azido, —N(CH$_3$)$_2$, —C(=O)OH, trifluoromethyl, —C≡N, —C(=O)O(C$_1$-C$_4$)alkyl, —C(=O)NH$_2$, —SO$_2$NH$_2$, —C(=NH)NH$_2$, and —NO$_2$. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy(isopropoxy) and the higher homologs and isomers.

As used herein, the term "halo" or "halogen" alone or as part of another substituent means, unless otherwise stated, a fluorine, chlorine, bromine, or iodine atom.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

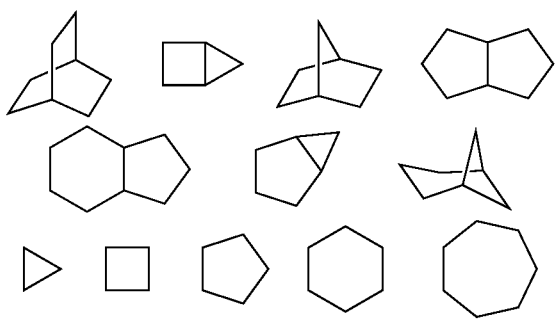

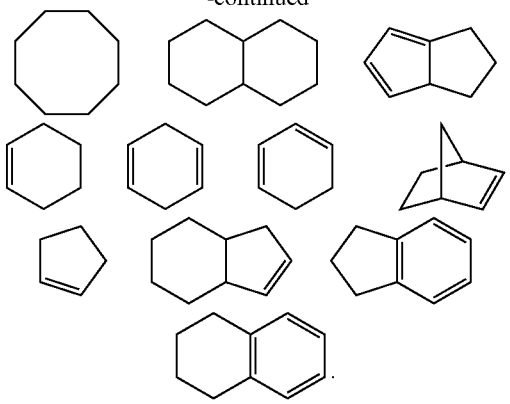

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene, Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon double bond or one carbon triple bond.

As used herein, the term "heterocycloalkyl" or "heterocyclyl." refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure, A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

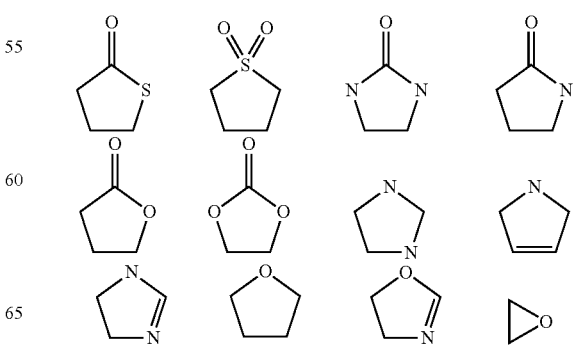

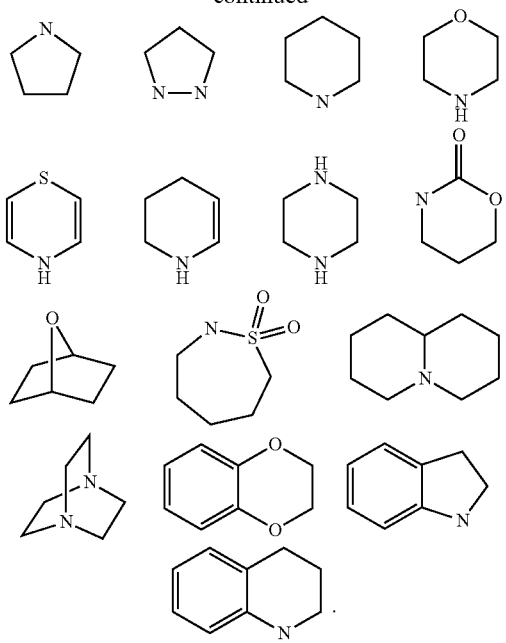
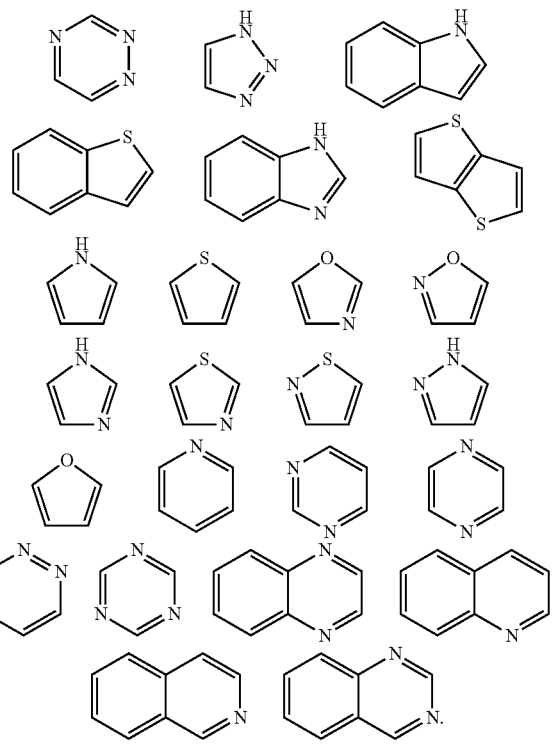

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocatized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl.

As used herein, the term "aryl-($C_1$-$C_3$)alkyl" means a functional group wherein a one- to three-carbon alkylene chain is attached to an aryl group, e.g., —$CH_2CH_2$-phenyl. In one embodiment, aryl-($C_1$-$C_3$)alkyl is aryl-$CH_2$— or aryl-($CH(CH_3)$)—. The term "substituted aryl-($C_1$-$C_3$)alkyl" means an aryl-($C_1$-$C_3$)alkyl functional group in which the aryl group is substituted. Similarly, the term "heteroaryl-($C_1$-$C_3$)alkyl" means a functional group wherein a one to three carbon alkylene chain is attached to a heteroaryl group, e.g., —$CH_2CH_2$-pyridyl. The term "substituted heteroaryl-(C1-C3)alkyl" means a heteroaryl-(C1-C3)alkyl functional group in which the heteroaryl group is substituted.

As used herein, the term "heteroaryl" or "heteroaromatic" refers to a heterocycle having aromatic character. A polycyclic heteroaryl may include one or more rings that are partially saturated. Examples include the following moieties:

Examples of heteroaryl groups also include pyridyl, pyrazinyl, pyrimidinyl (particularly 2- and 4-pyrimidinyl), pyridazinyl, thienyl, furyl, pyrrolyl (particularly pyrrolyl), imidazolyl, oxazolyl, pyrazolyl (particularly 3- and 5-pyrazolyl), isothiazoyl, 1,2,3-triazolyl, 1,2,4-triazolyl, 1,3,4-triazolyl, tetrazolyl, 1,2,3-thiadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl quinoxalinyl (particularly 2- and 5-quinoxalinyl), quinazolinyl, phthalazinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthenyl, carbazolyl, carbolinyl, acridinyl, pyrrolizidinyl, and quinolizidine.

As used herein, the term "substituted" means that an atom or group of atoms has replaced hydrogen as the substituent attached to another group. The term "substituted" further refers to any level of substitution, namely mono-, di-, tri-, tetra-, or Penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]2, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(O)[substituted or unsubstituted alkyl], —C(OH)[substituted or unsubstituted alkyl]$_2$, and —C(NH$_2$)[substituted or unsubstituted alkyl]$_2$. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, —ON(O)$_2$, and —C(=O)OH. In yet one embodiment, the substituents are independently selected from the group consisting of C$_{1-6}$alkyl, —OH, C$_{1-6}$ alkoxy, halo, amino, acetamido, oxo and nitro. In yet another embodiment, the substituents are independently selected from the group consisting of C$_{1-6}$alkyl, C$_{1-6}$ alkoxy, halo, acetamido, and nitro. As used herein, where a substituent is an alkyl or alkoxy group, the carbon chain may be branched, straight or cyclic.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

In one embodiment, the invention provides organic molecules comprising at least one phosphate moiety, and methods of use for the synthesis of phosphorylated molecules. The phosphorylated molecule generated using the compositions and methods of the invention may be a phosphorylated protein, a phosphorylated sugar, a phosphorylated lipid, or a phosphorylated nucleoside molecule. Phosphorylated nucleosides that can be synthesized using the methods of the invention include, but are not limited to, natural or modified nucleoside hexaphosphates (e.g., 5' nucleoside hexaphosphate (Np$_6$) and 2'-deoxynucleoside-5'-hexaphosphates (dNp$_6$)), nucleoside hexaphosphate analogs, natural or modified nucleoside pentaphosphates (e.g., pppGpp, dinucleoside pentaphosphate (e.g., diadenosine pentaphosphate), 5' nucleoside pentaphosphate (Np$_5$) and 2'-deoxynucleoside-5'-pentaphosphates (dNp$_5$)), nucleoside pentaphosphate analogs, natural or modified nucleoside tetraphosphates (e.g., ppGpp, dinucleoside tetraphosphate (e.g., diadenosine tetraphosphate), 5' nucleoside tetraphosphate (Np$_4$) and 2'-deoxynucleoside-5'-tetraphosphates (dNp$_4$)), nucleoside tetraphosphate analogs, natural or modified nucleoside triphosphates 5' nucleoside triphosphate (NTPs), 5' nucleoside triphosphate (NTPs) and 2'-deoxynucleoside-5'-triphosphates (dNTPs)), nucleoside triphosphate analogs, natural or modified nucleoside diphosphates (e.g., 5' nucleoside triphosphate. (NDPs) and 2'-deoxynucleoside-5'-diphosphates (dNDPs)), nucleoside diphosphate analogs, natural or modified nucleoside monophosphates (e.g., 5' nucleoside monophosphate (NMPs) and 2'-deoxynucleoside-5'-monophosphates (dNMPs)), and nucleoside monophosphate analogs.

Compounds of the Invention

The compounds of the present invention may be synthesized using techniques well-known in the art of organic synthesis. The starting materials and intermediates required for the synthesis may be obtained from commercial sources or synthesized according to methods known to those skilled in the art.

In one embodiment, the invention relates to a compound represented by formula (1):

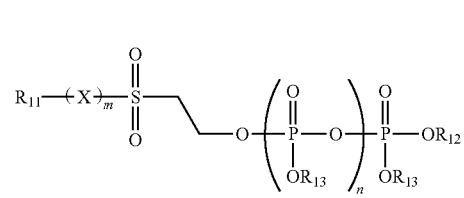

(1)

wherein, m is an integer from 0 to 5;

n is an integer from 0 to 5;

X is O or C1'12;

R$_{11}$ is an aryl, a heteroaryl, an alkyl, a cycloakyl, an alkenyl, an alkynyl, an alkyl-aryl-alkyl, or a silyl group;

R$_{12}$ is hydrogen, null, a substituted tetahydrofuranyl group, or an alkyl-substituted tetahydrofuranyl group; and each occurrence of R$_{13}$ is independently hydrogen or null.

In one embodiment, R$_{11}$ is substituted with a group selected from the group consisting of alkyl, alkenyl, alkynyl, aryl, cycloalkyl, heteroaryl, halogen, —CN, —OR$_{14}$, and —N(R$_{14}$)$_2$, wherein each occurrence of R$_{14}$ is independently selected from the group consisting hydrogen, alkyl, alkenyl, alkynyl, aryl, cycloalkyl, heteroaryl, and halogen.

In one embodiment, R$_{11}$ is selected from the group consisting of

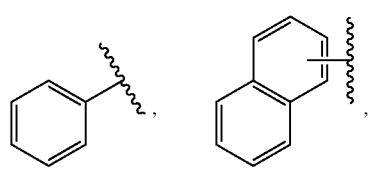

In one embodiment, $R_{12}$ is hydrogen. In one embodiment, $R_{12}$ is null. In one embodiment, when $R_{12}$ is null there is an anion. In one embodiment, $R_{12}$ is a methyl-tetrahydrofuranyl group wherein the tetrahydrofuranyl group is substituted. In one embodiment, $R_{12}$ is tetrahydrofuranyl group wherein the tetrahydrofuranyl group is substituted. In one embodiment, the tetrahydrofuranyl group is substituted with a oxy-phenyl. In one embodiment, the tetrahydrofuranyl group is substituted with a nitrogenous base.

In one embodiment, each occurrence of $R_{13}$ is hydrogen. In one embodiment occurrence of $R_{13}$ is null. In one embodiment, when $R_{13}$ is null there is an anion.

In one embodiment, m is 0.
In one embodiment m is 1.
In one embodiment, m is 2.
In one embodiment, m is 3.
In one embodiment, n is 0.
In one embodiment, n is 1.
In one embodiment, n is 2.
In one embodiment, n is 3.
In one embodiment, n is 4.
In one embodiment, n is 5.
In one embodiment X is O.
In one embodiment, X is $CH_2$.

In one embodiment, the compound of formula (1) is a compound of formula (1a):

$$R_{1a}-S(=O)_2-CH_2CH_2-O-P(=O)(OH)-O-P(=O)(OH)-OH \quad (1a)$$

wherein $R_{11}$ is selected from the group consisting of an aryl, a heteroaryl, an alkyl, a cycloalkyl, an alkenyl, an alkynyl, an alkyl-aryl, and an aryl-alkyl, wherein $R_{1a}$ is optionally substituted.

In one embodiment, $R_{1a}$ is substituted with a group selected from the group consisting of alkyl, alkenyl, alkynyl, aryl, cycloalkyl; heteroaryl, halogen, —CN, and —N$(R_{11a})_2$, wherein each occurrence of Riva is independently selected from the group consisting hydrogen, alkyl, alkenyl, alkynyl, aryl, cycloalkyl, heteroaryl, and halogen.

In one embodiment, $R_{1a}$ is selected from the group consisting of
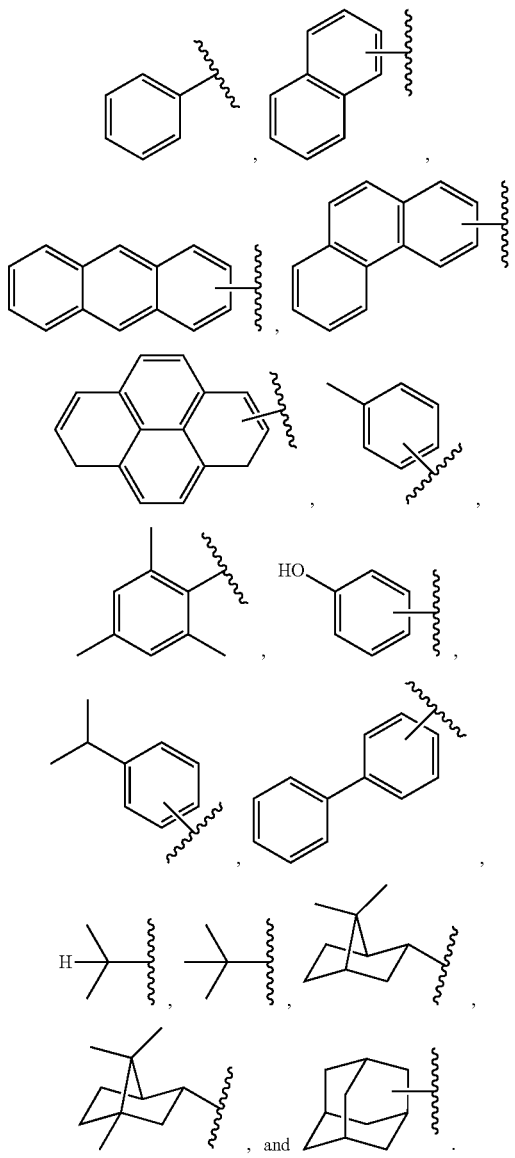
In one embodiment, the compound of formula (1a) is selected from the group consisting of
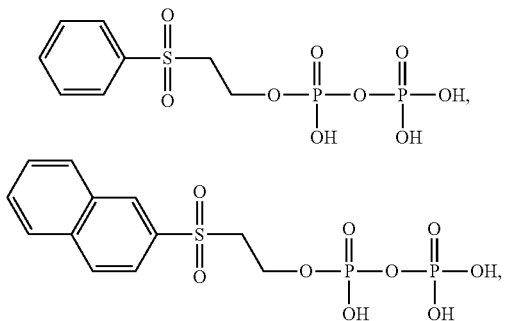
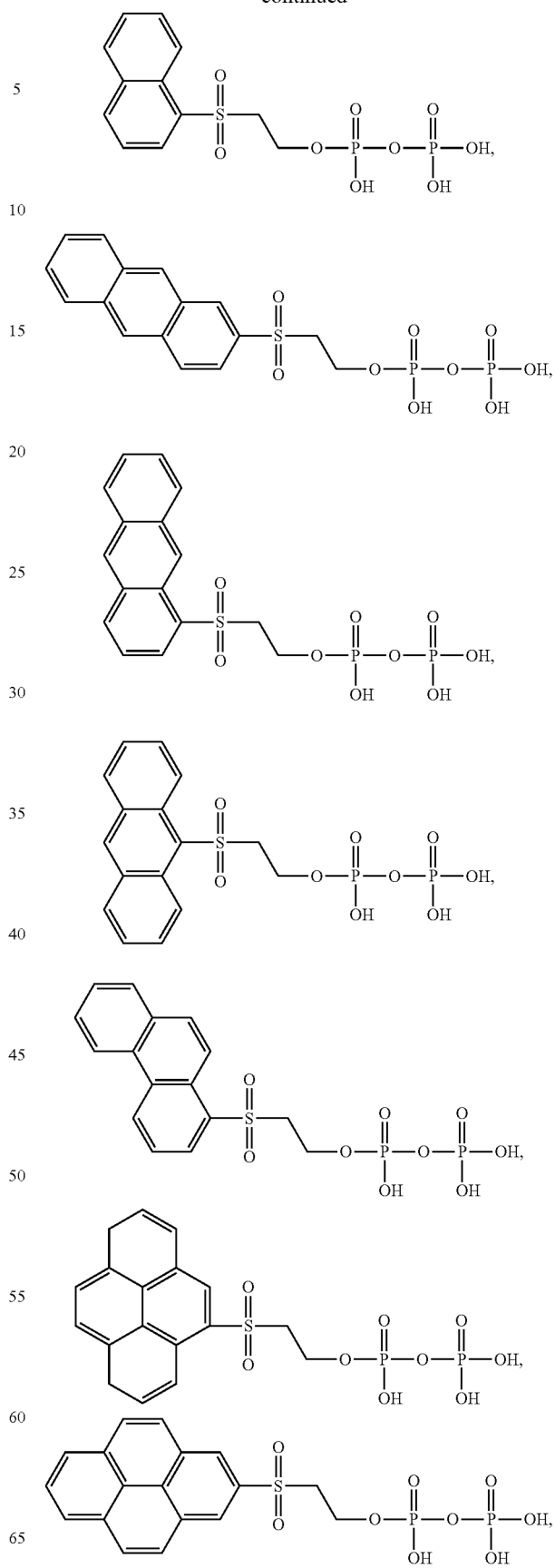

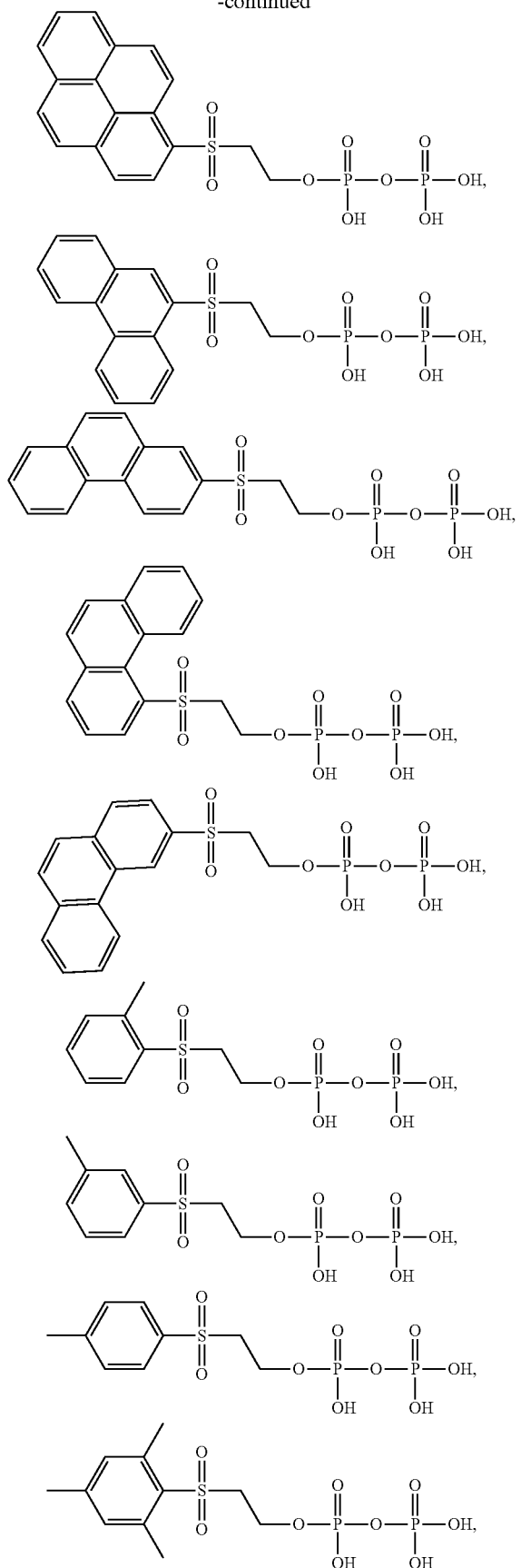
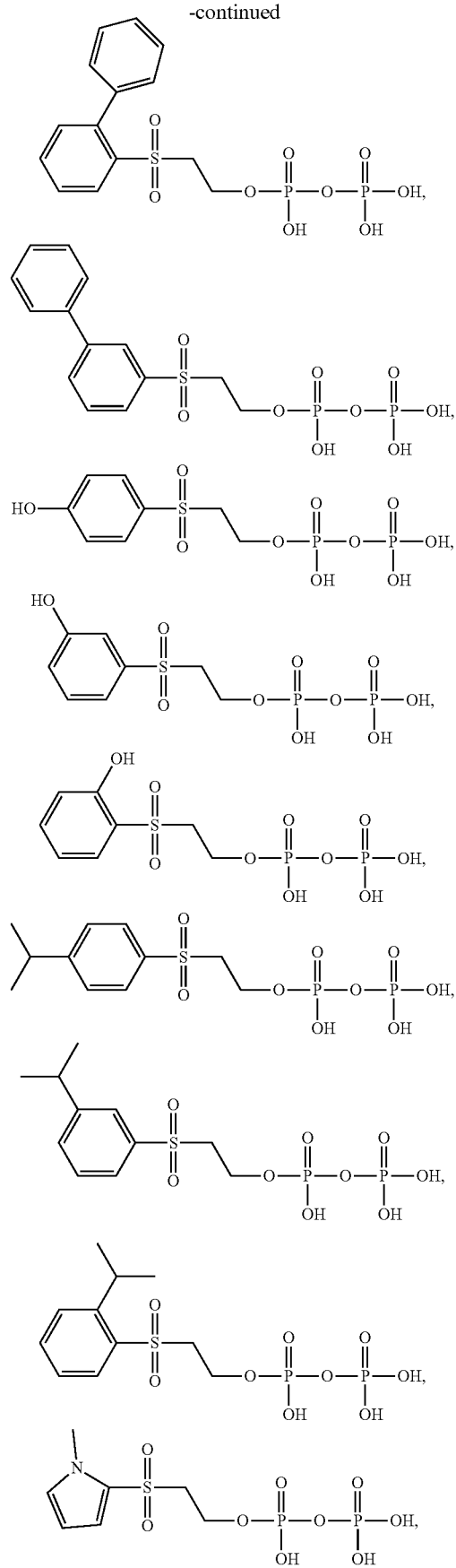

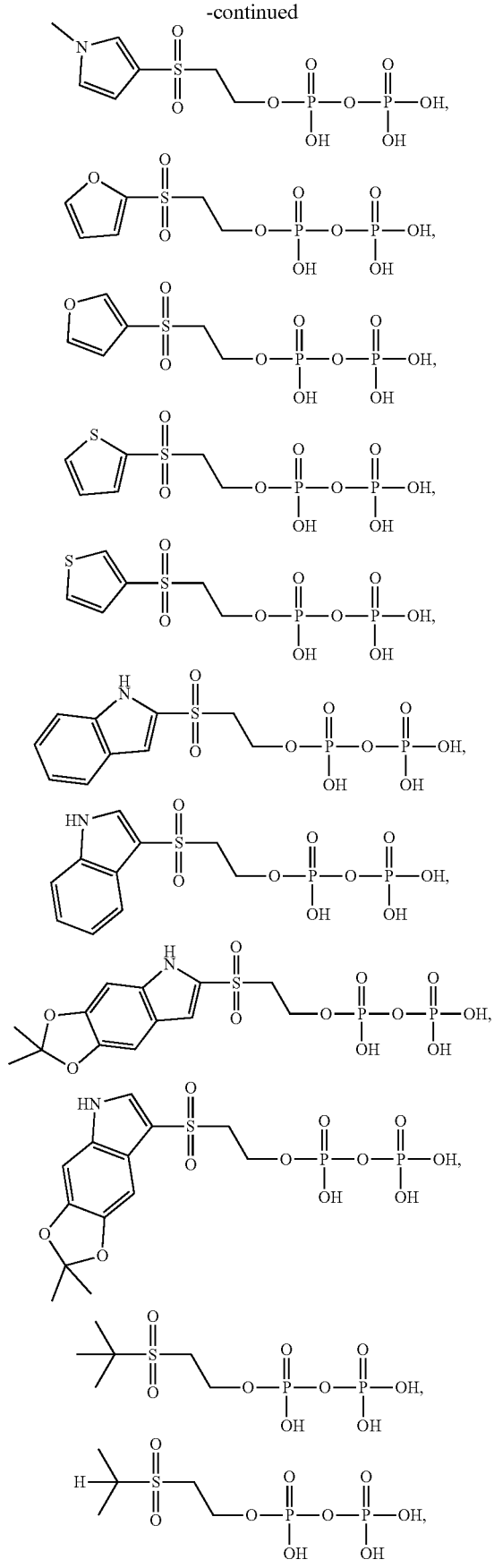
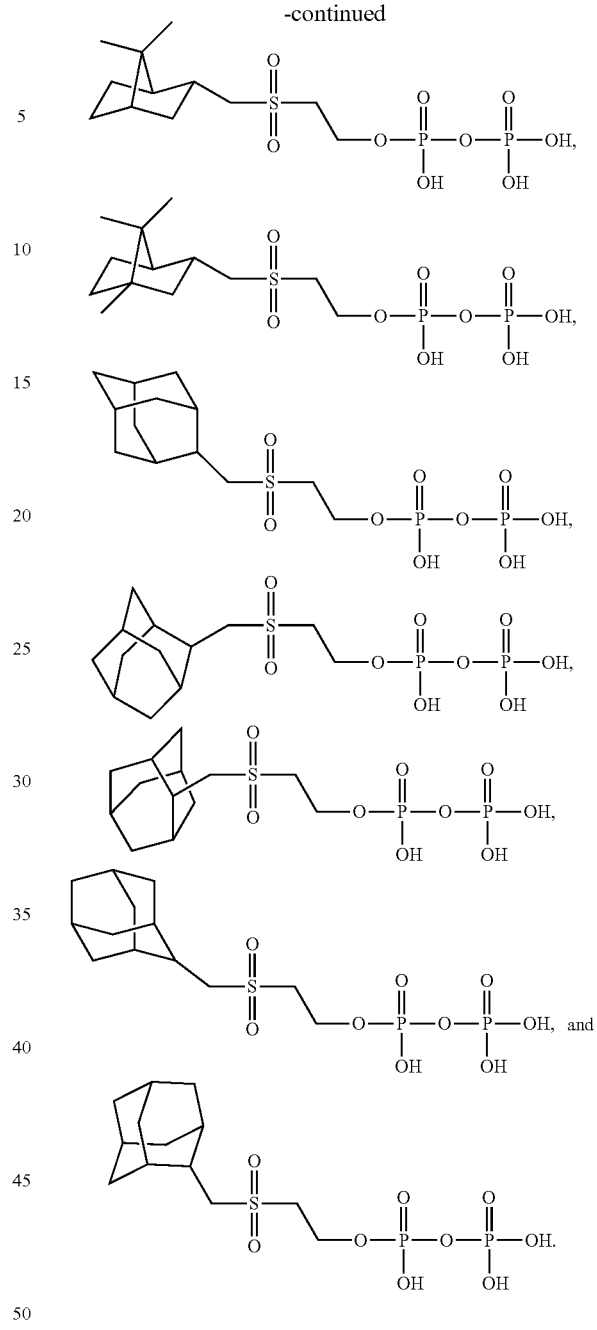
In one embodiment, the compound of formula (1) is a compound of formula (1b):
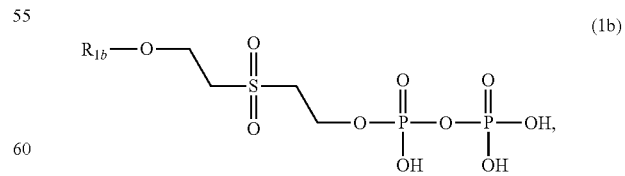
wherein $R_{1b}$ is a hydroxy protecting group.
In one embodiment, $R_{1b}$ is selected from the group consisting of an aryl, a heteroaryl, an alkyl, a cycloalkyl, an alkenyl, an alkynyl, an alkyl-aryl, and an aryl-alkyl, wherein $R_{1b}$ is optionally substituted.

In one embodiment, $R_{1b}$ is substituted with a group selected from the group consisting of alkyl, alkenyl, alkynyl, aryl, cycloalkyl, heteroaryl, halogen, —CN, —OR$_{11b}$, and —N(R$_{11b}$)$_2$, wherein each occurrence of Rub is independently selected from the group consisting hydrogen, alkyl, alkenyl, alkynyl, aryl, cycloalkyl, heteroaryl, and halogen.

In one embodiment, $R_{1b}$ is selected from the group consisting of

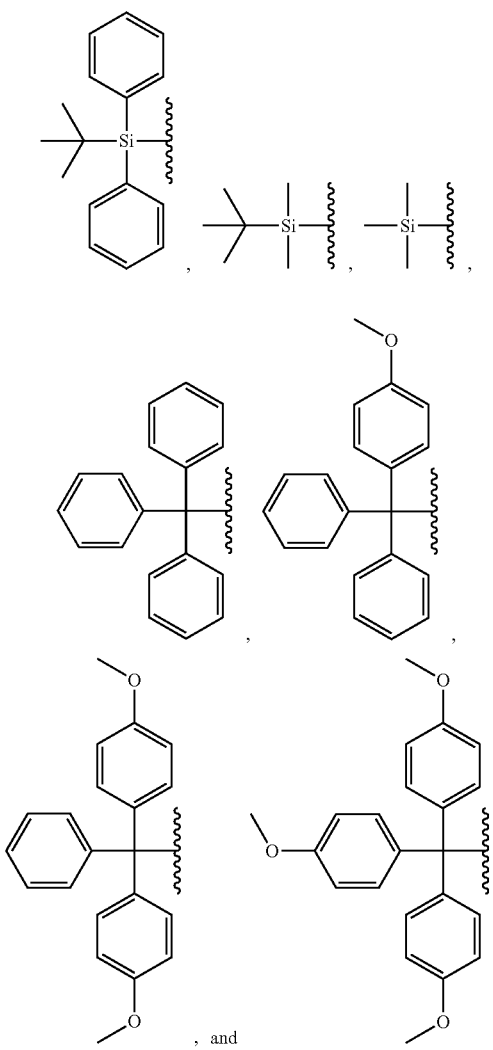

, and

In one embodiment, the compound of formula (1b) is selected from the group consisting of

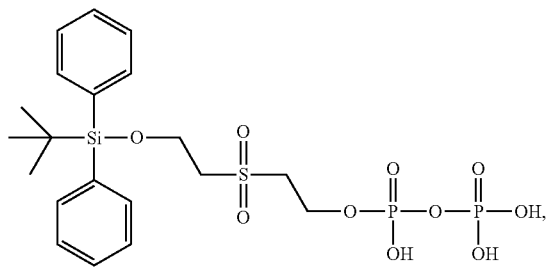

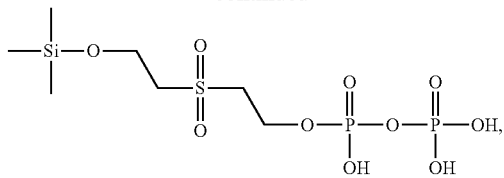

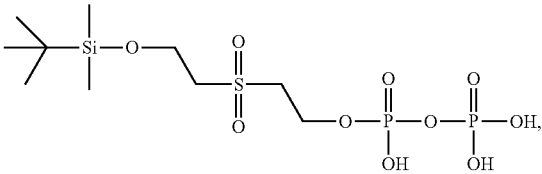

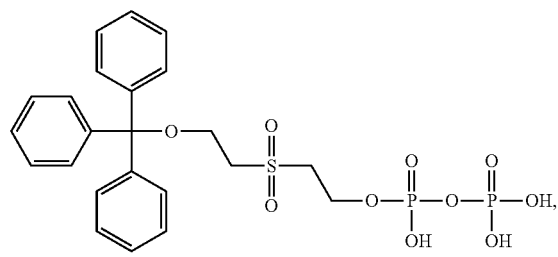

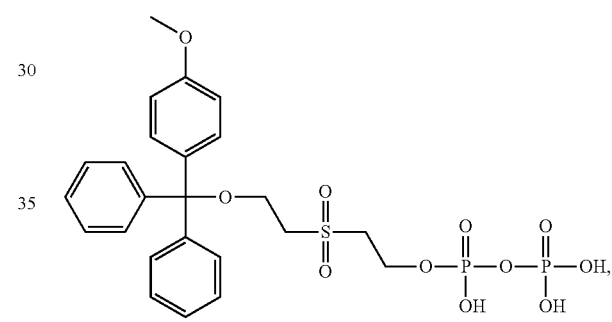

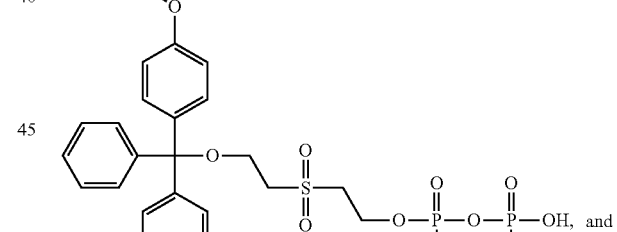

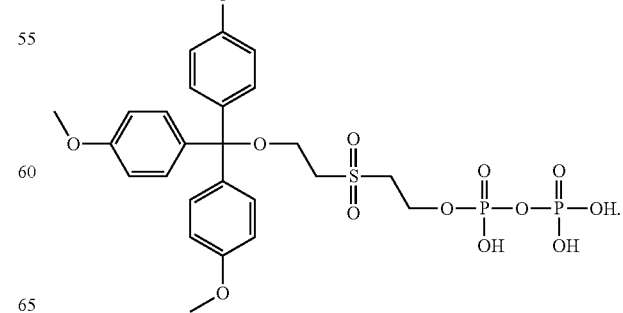

In one embodiment, the compound of formula (1) is a compound of formula (1c):

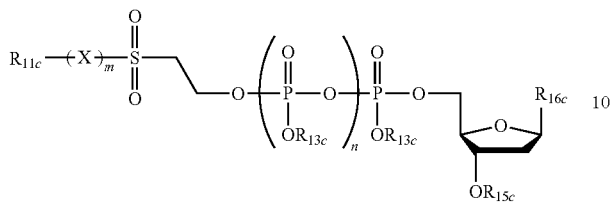

(1c)

wherein:

m is an integer from 0 to 5;

n is an integer from 0 to 5;

X is O or $CH_2$;

$R_{11c}$ is an aryl, a heteroaryl, an alkyl, a cycloakyl, an alkenyl, an alkynyl, an alkyl-aryl, an aryl-alkyl, or a silyl group;

each occurrence of $R_{13c}$ is independently hydrogen or null;

$R_{15c}$ is hydrogen, aryl, or heteroaryl; and $R_{16c}$ is a nitrogenous base, wherein the nitrogenous base is a natural nitrogenous base or artificial nitrogenous base.

In one embodiment, $R_{11c}$ is

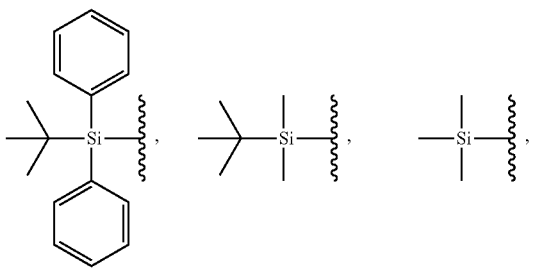

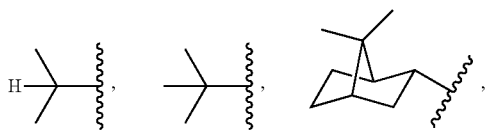

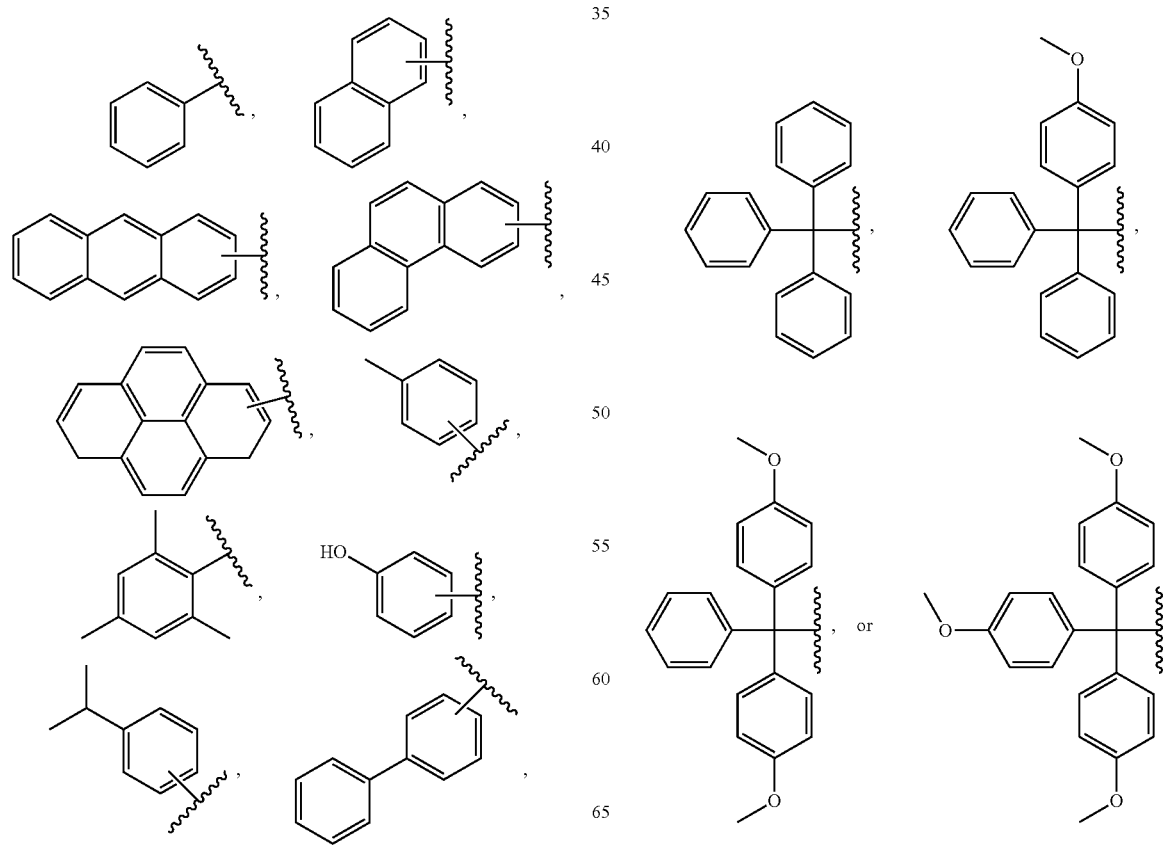

In one embodiment, $R_{15c}$ is phenyl.
In one embodiment the compound of formula (1c) is:
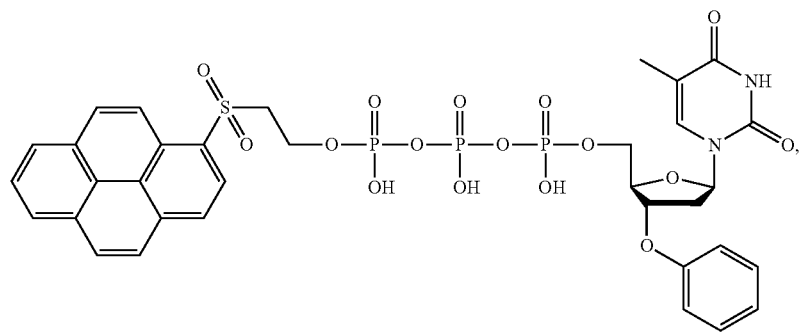
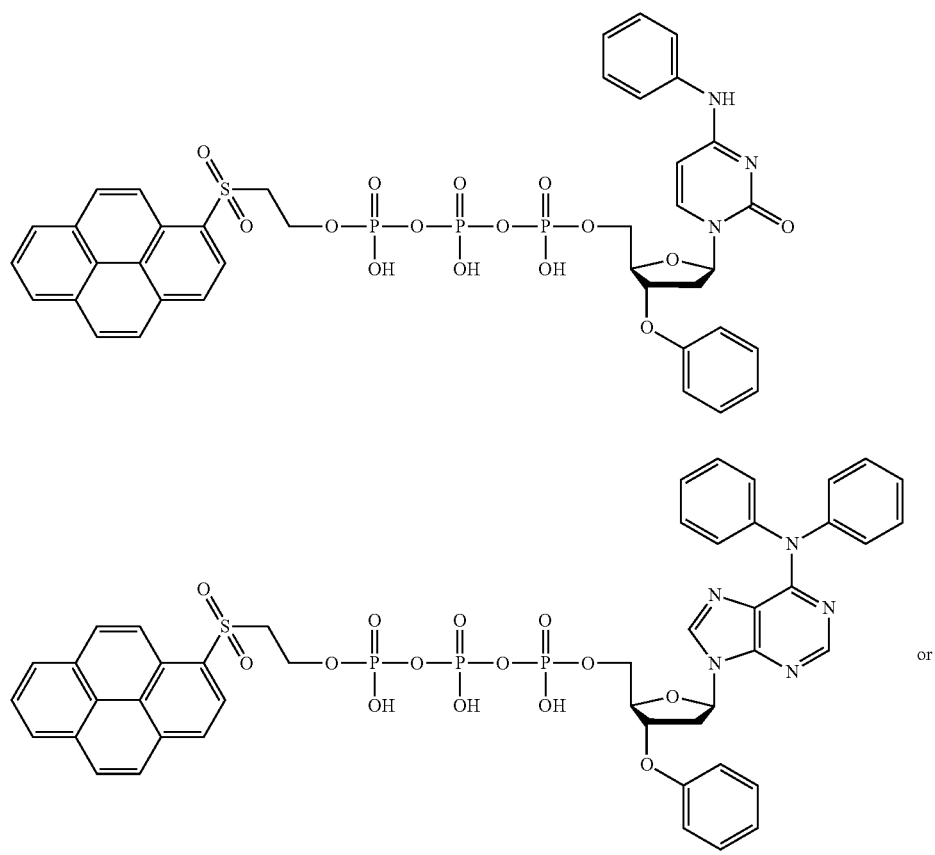
or
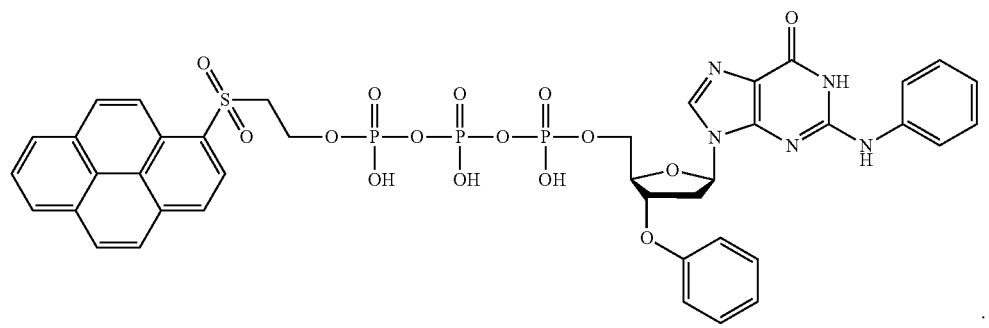

In one embodiment, the compound of formula (1) is a compound of formula (1d):

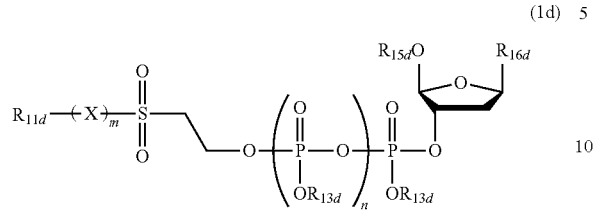

(1d)

wherein:
m is an integer from 0 to 5;
n is an integer from 0 to 5;
X is O or CH$_2$;
R$_{11d}$ is an aryl, a heteroaryl, an alkyl, a cycloalkyl, an alkenyl, an alkynyl, an alkyl-aryl, an aryl-alkyl, or a silyl group;
each occurrence of R$_{13d}$ is independently hydrogen or null;
R$_{15d}$ is hydrogen, aryl, or heteroaryl; and
R$_{16d}$ is a nitrogenous base, wherein the nitrogenous base is a natural nitrogenous base or artificial nitrogenous base.

In one embodiment, R$_{11d}$ is

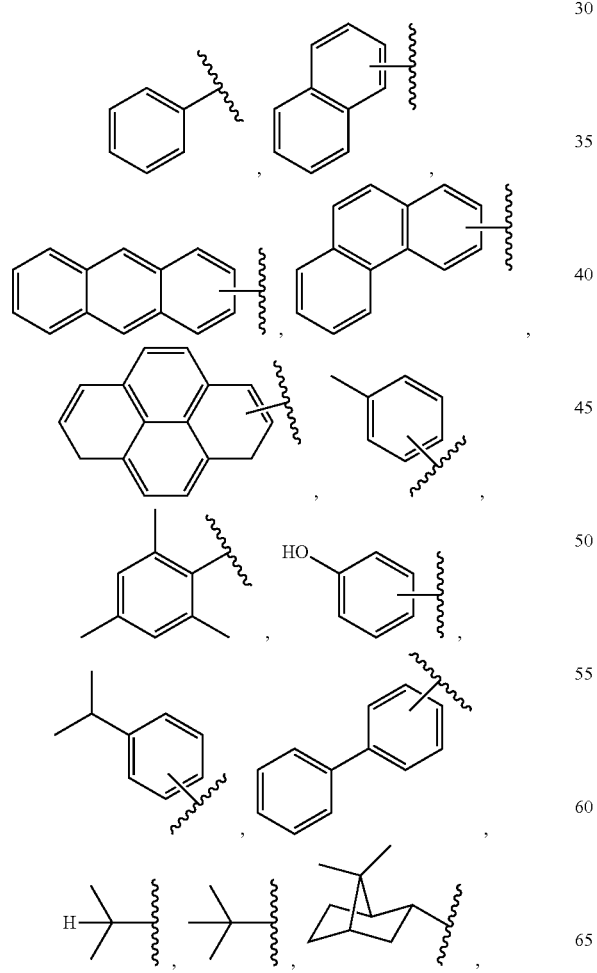

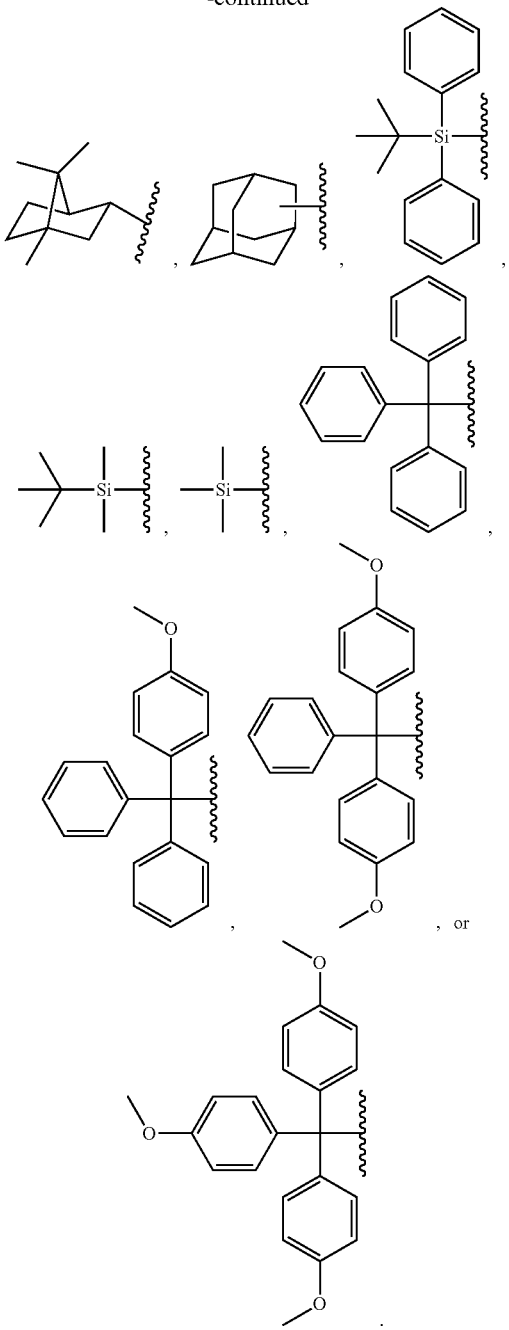

, or

In one embodiment, R$_{15d}$ is phenyl.
In one embodiment, the compound of formula (1d) is:

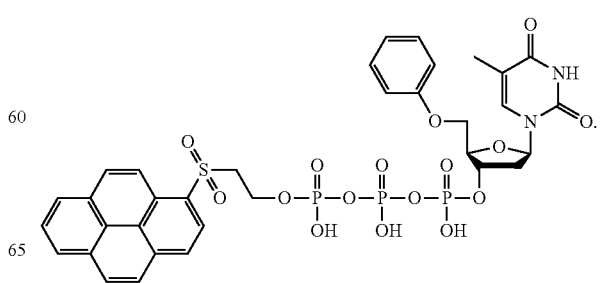

In one embodiment, the compound of formula (1) is a compound of formula (13):

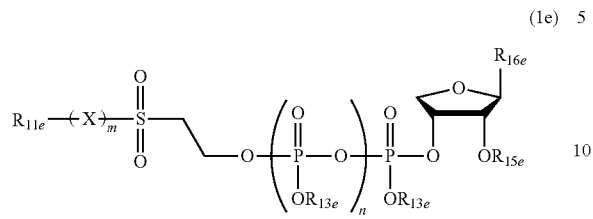

(1e)

wherein:
m is an integer from 0 to 5;
n is an integer from 0 to 5;
X is O or $CH_2$;
$R_{11e}$ is an aryl, a heteroaryl, an alkyl, a cycloalkyl, an alkenyl, an alkynyl, an alkyl-aryl, an aryl-alkyl, or a silyl group;
each occurrence of $R_{13e}$ is independently hydrogen or null;
$R_{15e}$ is hydrogen, aryl, acetyl, or heteroaryl; and
$R_{16e}$ is a nitrogenous base, wherein the nitrogenous base is a natural nitrogenous base or artificial nitrogenous base.

In one embodiment, $R_{11e}$ is

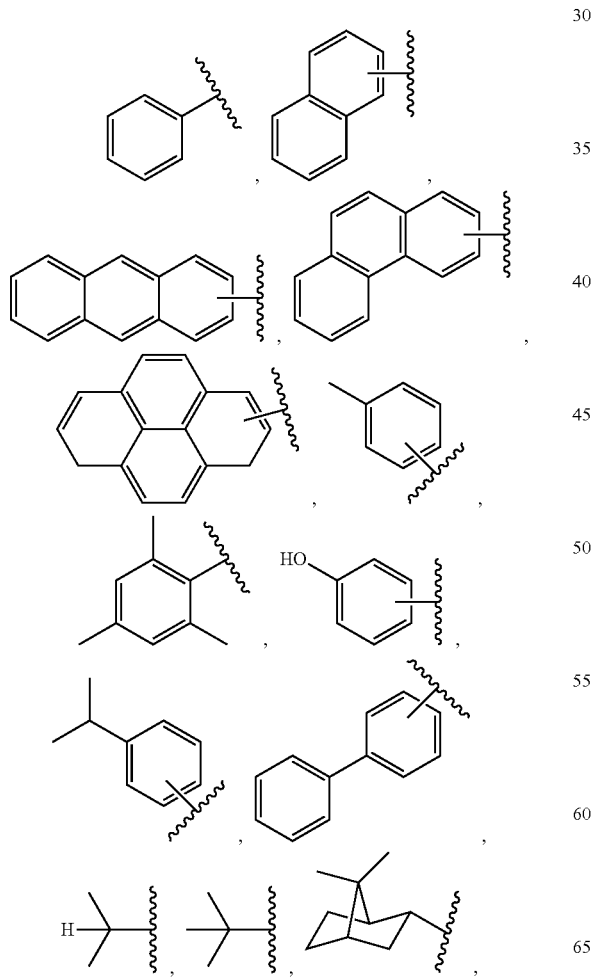

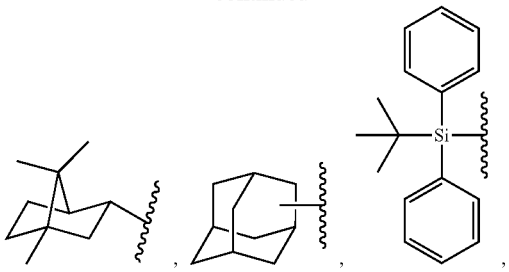

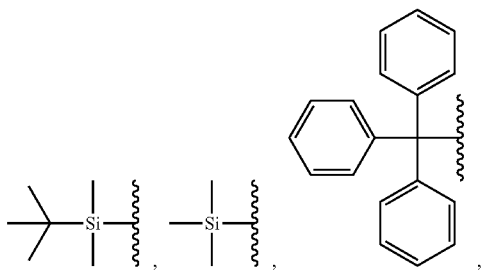

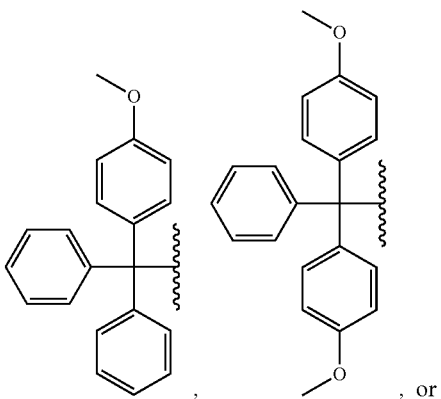

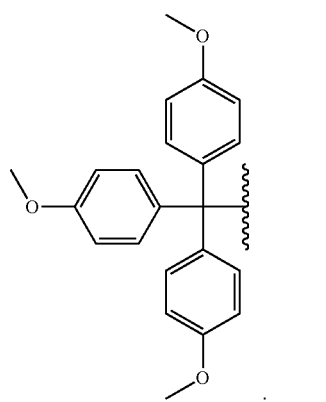

, or

.

In one embodiment, R$_{15e}$ is phenyl.
In one embodiment, the compound of formula (1e) is:
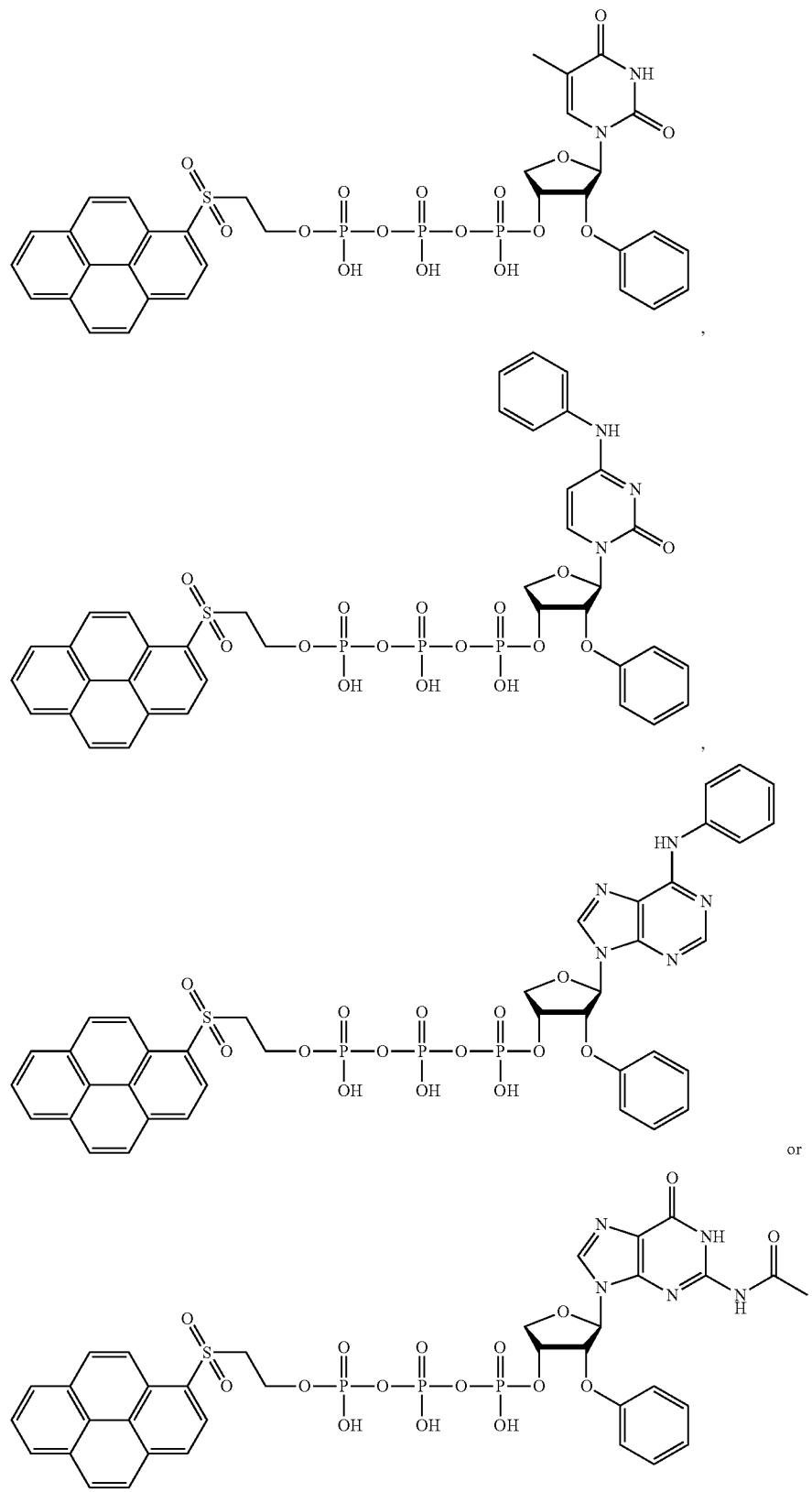

In one embodiment, the invention relates to a compound represented by formula (2):

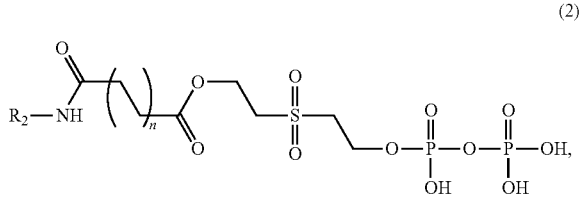

wherein n is an integer from 1 to 10, and
R$_2$ is a support.

In one embodiment, the invention relates to a compound represented by formula (3):

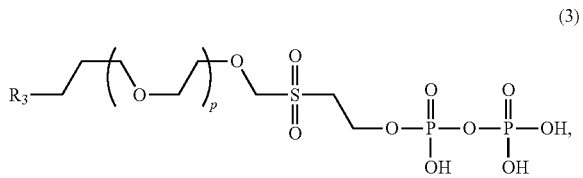

wherein p is an integer from 0 to 10, and
R$_3$ is a support.

In one embodiment, the invention relates to a compound represented by formula (4):

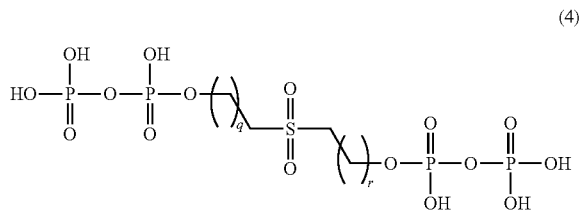

wherein q is an integer from 0 to 10, and
r is an integer from 0 to 10.
In one embodiment q is 1. In one embodiment r is 1.
In one embodiment, the compound of formula (4) is

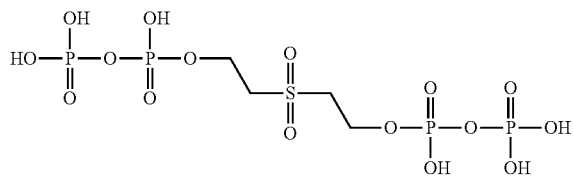

Supports

The attachment of useful materials such as catalysts, reagents, chelating or complexing agents, and proteins to insoluble supports is well-known. With the attending advantages of ease of removal and recovery from the system, e.g., by simple filtration, regeneration (if necessary), and recycling coupled with the increased utilization of continuous flow systems in both general chemical processing and diagnostic monitoring procedures, supported materials and methods of generating polymer supported reaction reagents are well known in the art.

In one embodiment, the invention relates to a compound represented by formula (2) or formula (3) attached to an inorganic polymer support. Inorganic polymer supports include, but are not limited to, silica gel and alumina.

In one embodiment, the invention relates to a compound represented by formula (2) or formula (3) attached to an organic polymer support. Organic polymer supports include, but are not limited to, polystyrene.

In one embodiment, the invention relates to a compound represented by formula (2) or formula (3) attached to solid support (e.g., controlled pore glass).

Nucleoside Triphosphates and Nucleic Acids

In one embodiment, the compounds and methods of the invention are used to synthesize a naturally occurring nucleoside triphosphate. Naturally occurring nucleoside triphosphates include, but are not limited to, adenosine triphosphate (ATP), guanosine triphosphate (GTP), cytidine triphosphate (CTP), 5-methyluridine triphosphate (m$^5$UTP), and uridine triphosphate (UTP), The terms ATP, GTP, CTP, and UTP refer to those nucleoside triphosphates that contain ribose. The nucleoside triphosphates containing deoxyribose are called dNTPs, and include deoxyadenosine triphosphate (dATP), deoxyguanosine triphosphate (dGTP), deoxycytidine triphosphate (dCTP), deoxythymidine triphosphate (dTTP) and deoxyuridine triphosphate (dUTP).

In one embodiment, the compounds and methods of the invention are used to synthesize isomers or analogs of nucleoside triphosphates. Exemplary nucleoside triphosphate analogs or isomers include, but are not limited to, 2'-deoxythymidine-3'-triphosphate (3'-TTP), 1-(α-L-threofuranosyl)thymidine-3'-triphosphate (tTTP), 1-(α-L-threofuranosyl)cytidine-3'-triphosphate (tCTP), 9-(1-L-threofuranosyl)adenosine-3'-triphosphate (tATP), 9-(α-L-threofuranosyl)guanosine-3'-triphosphate (tGTP), and L-2'-deoxythymidine-5'-triphosphate (L-dTTP).

In some embodiments, the nucleoside triphosphate can be labeled. Examples of possible labels include, but are not limited to a radioisotope, an enzyme, an enzyme cofactor, an enzyme substrate, an enzyme inhibitor, a dye, a hapten, chemiluminescent molecule, a fluorescent molecule, a phosphorescent molecule, an electrochemiluminescent molecule, a chromophore, a magnetic particle, an affinity label, a chromogenic agent, an azide group or other groups used for click chemistry, and other moieties known in the art.

In one aspect, the nucleoside triphosphates synthesized according to the methods of the invention can be used for synthesizing nucleic acid molecules. Nucleic acid in the context of the present invention includes but is not limited to deoxyribonucleic acid (DNA), ribonucleic acid (RNA) and peptide nucleic acid (PNA). A nucleic acid of the invention also includes artificial genetic polymers, commonly referred to as XNAs or 'xeno-nucleic acids' where the backbone structure contains a sugar other than ribose or deoxyribose. While some of these molecules can be considered natural derivatives of RNA, like arabino nucleic acid (ANA), threose nucleic acid (TNA), and glycerol nucleic acid (GNA), others are completely unnatural, like locked nucleic acid (INA), cyclohexene nucleic acid (CeNA), and hexitol nucleic acid (HNA).

Therefore in one embodiment, the invention provides artificial or synthetic nucleic acid molecules which incorporate one or more natural or modified nucleoside triphosphate of the invention. The length of the nucleic acids may vary. The nucleic acids may be modified, e.g. may comprise one or more modified nucleobases or modified sugar moieties (e.g., comprising methoxy groups). The backbone of the nucleic acid may comprise one or more peptide bonds as in peptide nucleic acid (PNA). The nucleic acid may comprise a base analog such as non-purine or non-pyrimidine analog or nucleotide analog. It may also comprise additional attachments such as proteins, peptides and/or or amino acids.

Activated Nucleoside Monophosphates

In one embodiment, the invention relates to the synthesis of activated nucleoside monophosphates for use in synthesizing a nucleoside triphosphate of the invention. An activated nucleoside monophosphates for use in the methods of the invention can be synthesized from any nucleoside monophosphate. In various embodiments, a nucleoside monophosphate is a naturally occurring nucleoside monophosphate, an unnatural nucleoside monophosphate or a modified nucleoside monophosphate.

In one embodiment, the activated nucleoside monophosphate comprises 2-methylimidazole linked to a phosphate group. In one embodiment, the phosphate group is linked to a sugar moiety which is attached to a nitrogenous base. In one embodiment, the sugar of the activated nucleoside monophosphate comprises ribose. In one embodiment, the sugar of the activated nucleoside monophosphate comprises deoxyribose.

In one embodiment, the activated nucleoside monophosphate is represented by formula (5)

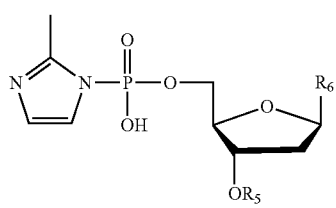

(5)

wherein $R_5$ is selected from the group of hydrogen, aryl, and heteroaryl; and $R_6$ is a nitrogenous base. In one embodiment, the nitrogenous base is a natural nitrogenous base or artificial nitrogenous base. In one embodiment, $R_5$ is phenyl.

A variety of purities, purine analogs, pyrimidines, pyrimidine analogs, and other heterocycles as nitrogenous bases have been well documented (Chemistry of Nucleosides and Nucleotides Vol 1, 2, 3, edited by Townsend, Plenum Press, 1988, 1991, 1994). The condensations of sugars with nitrogenous bases to yield nucleosides are frequently used reactions in nucleoside chemistry. Well-established procedures and methodologies can be found in the literature (Vorbruggen et al., Chem. Ber. 1981, 114, 1234-1268, 1279-1286; Wilson et al., Synthesis, 1995, 1465-1479).

A large number of known nucleosides are prepared from the modifications of purine and pyrimidine nucleosides. The modifications can be done on the sugars and/or nucleoside bases. A simple, widely-used reaction is the nucleophilic substitution of halopurine or halopyrimidine base by a variety of nucleophiles such as hydroxide, ammonia, hydrogen sulfide, alkoxides, amities, alkylthiol, hydrazine, hydroxyamines, azide, cyanide, and hydride. This type of reactions can be very useful for preparation of 2-substituted purine nucleoside, 6-substituted purine nucleosides, 8-substituted purine nucleosides, 2,6-disubstituted purine nucleosides, 2,8-disubstituted purine nucleosides, 6,8-disubstituted purine nucleosides, 2,6,8-trisubstituted purine nucleosides (Halbfinger et al., J. Med. Chem. 1999, 42, 5323-5337, Lin et al., J. Med. Chem. 1985, 28, 1481-1485; Bressi et al., J. Med. Chem. 2000, 43, 4135-4150). These substitution reactions are readily extended to purine nucleoside analogs such as 7-deazapurine nucleosides, 7-deaza-8-azapurine nucleosides, 8-azapurine nucleosides, 3-deazapurine nucleosides, 3-deaza-8-azapurine nucleosides, and 3,8-dideazapurine nucleosides. For instance, a number of 7-deaza-7-substituted purine nucleoside have been prepared through such substitutions (Ugarkar et al., J. Med. Chem. 2000, 43, 2894-2905), The same methodologies can be used for the preparation of 4-substituted pyrimidine nucleosides, 5-substituted pyrimidine nucleosides, 4,5-disubstituted pyrimidine nucleosides, 5-substituted 6-azapyrimidine nucleosides, 5-substituted 6-azapyrimidine nucleosides, and 4,5-disubstituted 6-azapyrimidine nucleosides.

The sugar moieties of synthesized nucleosides can be further modified. There are a variety of reactions which can be used to modify the sugar moiety of nucleosides. The reactions frequently used include deoxygenation, oxidation/addition, substitution, and halogenation. The deoxygenations are useful for the preparation of 2'-deoxy-, 3'-deoxy-, and 2',3'-dideoxy-nucleosides. A widely-used reagent is phenyl chlorothionoformate, which reacts with the hydroxy of nucleosides to yield a thionocarbonate. The treatment of the thionocarbonate with tributyltin hydride and AIBN yields deoxygenated nucleosides. The oxidation/addition includes the conversion of a hydroxy group to a carbonyl group, followed by a nucleophilic addition, resulting in C-alkylated nucleosides and C-substituted nucleosides. The substitution may be just a simple displacement of a hydroxyl proton by alkyl, or may be a conversion of a hydroxyl to a leaving group, followed by a nucleophilic substitution. The leaving group is usually a halogen, mesylate, tosylate, nisylate, or a triflate. A variety of nucleophiles can be used, resulting in 2-, or 3-substituted nucleosides. Halogenation can be used to prepare 2'-halo 3'-halo-, or 4'-halonucleosides, Chlorination and fluorination are commonly used and result in important fluoro-sugar and chloro-sugar nucleosides.

Nucleosides that can be included in an activated nucleoside monophosphate according to the methods of the invention include, but are not limited to, adenosine, cytidine, guanosine, uridine, 2'-deoxyadenosine, 2'-deoxycytidine, 2'-deoxyguanosine, thymidine, inosine, 9-(β-D-arabinofuranosyl)adenine, 10-D-arabinofuranosyl)cytosine, 9-(β-D-arabinofuranosyl)guanine, 1-(β-D-arabinofuranosyl)uracil, 9-(β-D-arabinofuranosyl)hypoxanthine, 1-(β-D-arabinofuranosyl)thymine, 3'-azido-3'-deoxythymidine, 3'-azido-2', 3'-dideoxyuridine, 3'-azido-2', 3'-dideoxycytidine, 3'-azido-2', 3'-dideoxyadenosine, 3'-azido-2', 3'-dideoxyguanosine, 3'-azido-2', 3'-dideoxyinosine, 3'-deoxythymidine, 2', 3'-dideoxyuridine, 2', 3'-dideoxyinosine, 2', 3'-dideoxyadenosine, 2', 3'-dideoxycytidine, 2', 3'-dideoxyguanosine, 9-(2, 3-dideoxy-1-β-D-ribofuranosyl)-2, 6-diaminopurine, 3'-deoxy-2', 3'-didehydrothymidine, 2', 3'-didehydro-2', 3'-dideoxyuridine, 2', 3'-didehydro-2', 3'-dideoxycytidine, 2', 3'-didehydro-2', 3'-dideoxyadenosine, 2', 3'-didehydro-2', 3'-dideoxyguanosine, 2', 3'-didehydro-2', 3'-dideoxyinosine, 3-deazaadenosine, 3-deazaguanosine, 3-deazainosine, 7-deazaadenosine, 7-deazaguanosine, 7-deazainosine, 6-azauridine, 6-azathymidine, 6-azacytidine, 5-azacytidine, 9-(β-D-ribofuranosyl)-6-thiopurine, 6-methylthio-9-(β-D-ribofuranosyl)purine, 2-amino-9-(β-D-ribofuranosyl)-6-thiopurine, 2-amino-6-methylthio-9-(β-D-ribofuranosyl)purine, 5-fluorocytidine, 5-iodocytidine, 5-bromocytidine, 5-chlorocytidine, 5-fluorouridine, 5-iodouridine, 5-bromouridine, 5-chlorouridine, 2'-C-methyladenosine, 2'-C-methylcytidine, 2'-C-methylguanosine, 2'-C-methylinosine, 2'-C-methyluridine, 2'-C-methylthymidine, 2'-deoxy-2'- fluoroadenosine, 2'-deoxy-2'-fluorocytidine, 2'-deoxy-2'-fluoroguanosine, 2'-deoxy-2'-fluorouridine, 2'-deoxy-2'-fluoroinosine, 2'-α-fluorothymidine, 2'-deoxy-2'-fluoroarabinoadenosine, 2'-deoxy-2'-fluoroarabinocytidine, 2'-deoxy-2'-fluoroarabinoguanosine, 2'-deoxy-2'-fluoroarabinouridine, 2'-deoxy-2'-fluoroarabinoinosine, 2'-β-fluorothymidine, 2'-O-methyladenosine, 2'-O-methylcytidine, 2'-O-methylguanosine, 2'-O-methylinosine, 2'-O-5-dimethyluridine, 2'-C-ethynylcytidine, 2'-C-ethynylguanosine, 2'-C-ethynyluridine, 2'-C-ethynylinosine, 2'-C-ethynyl-5-methyluridine, 3'-C-ethynyladenosine, 3'-C-ethynylcytidine, 3'-C-ethynylguanosine, 3'-C-ethynyluridine, 3'-C-ethynylinosine, 3'-C-ethynyl-5-methyluridine, 3'-deoxyadenosine, 3'-deoxycytidine, 3'-deoxyguanosine, 3'-deoxyuridine, 3'-deoxyinosine, 4'-C-ethynyladenosine, 4'-C-ethynylpyridine, 4'-C-ethynylguanosine, 4'-C-ethynyluridine, 4'-C-ethynylinosine, 4'-C-ethynylthymidine, 4'-C-methyladenosine, 4'-C-methylcytidine, 4'-C-methylguanosine, 4'-C-methyluridine, 4'-C-methylthymidine, 2'-C-methyl-7-deazaadenosine, 2'-C-methyl-7-deazaguanosine, 2'-C-methyl-3-deazaadenosine, 2'-C-methyl-3-deazaguanosine, deazaadenosine, 2'-O-methyl-7-deazaguanosine, 2'-O-methyl-3-deazaadenosine, 2'-O-methyl-3-deazaguanosine, 2'-C-methyl-6-azauridine, 2'-C-methyl-5-fluorouridine, 2'-C-methyl-5-fluorocytidine, 2'-C-methyl-2-chloroadenosine, 2'-deoxy-7-deazaadenosine, 2'-deoxy-3-deazaadenosine, 2'-deoxy-7-deazaguanosine, 2'-deoxy-3-deazaguanosine, 2'-deoxy-6-azauridine, 2'-deoxy-5-fluorouridine, 2'-deoxy-5-fluorocytidine, 2'-deoxy-5-iodouridine, 2'-deoxy-5-iodocytidine, 2'-deoxy-2-chloroadenosine, 2'-deoxy-2-fluoroadenosine, 3'-deoxy-7-deazaadenosine, 3'-deoxy-7-deazaguanosine, 3'-deoxy-3-deazaadenosine, 3'-deoxy-3-deazaguanosine, 3'-deoxy-6-azauridine, 3'-deoxy-5-fluorouridine, 3'-deoxy-5-iodouridine, 3'-deoxy-5-fluorocytidine, 3'-deoxy-2-chloroadenosine, 2', 3'-dideoxy-7-deazaadenosine, 2', 3'-dideoxy-7-deazaguanosine, 2', 3'-dideoxy-3-deazaadenosine, 2', 3'-dideoxy-3-deazaguanosine, 2', 3'-dideoxy-6-azauridine, 2', 3'-dideoxy-5-fluorouridine, 2', 3'-dideoxy-5-fluorouridine, 2', 3'-dideoxy-5-iodocytidine, 2', 3'-dideoxy-2-chloroadenosine, 3'-dideoxy-β-L-cytidine, 2', 3'-dideoxy-β-L-adenosine, 2', 3'-dideoxy-β-L-guanosine, 3'-deoxy-L-thymidine, 2', 3'-dideoxy-5-fluoro-β-L-cytidine, β-L-thymidine, 2'-deoxy-β-L-cytidine, 2'-deoxy-β-L adenosine, 2'-deoxy-β-L-guanosine, 2'-deoxy-β-L-inosine, 13-L-cytidine, β-L-adenosine, β-L-guano sine, β-L-uridine, β-L-inosine, 2', 3'-didehydro-2', 3'-dideoxy-β-L-cytidine, 2', 3'-didehydro-3'-dideoxy-β-L-thymidine, 2', 3'-didehydro-2', 3'-dideoxy-β-L-adenosine, 2', 3'-didehydro-2', 3'-dideoxy-β-L-guanosine, 2', 3'-didehydro-2', 3'-dideoxy-β-L-5-fluorocytidine, 2'-deoxy-2', 2'-di fluorocytidine, 9-(β-D-arabinofuranosyl)-2-fluoroadenine, 2'-deoxy-2'(E)-fluoromethylenecytidine, 2'-deoxy-2' (Z)-fluoromethylenecytidine, (−)-2', 3'-dideoxy-3'-thiacytidine, (+)-2', 3'-dideoxy-3'-thiacytidine, 1-β-D-ribofuranosy-1, 2, 4-triazole-3-carboxamide, 1-β-L-ribofuranosyl-1, 2, 4-triazole-3-carboxamide, 1-β-D-ribofuranosyl-1, 3-imidazolium-5-olate, 1-β-L-ribofuranosyl-1, 1-β-D-ribofuranosyl-5-ethynylimidazole-4-carboxamide, 1-β-L-ribofuranosyl-5-ethynylimidazole-4-carboxamide, 1-(2-deoxy-2-fluoro-3-D-arabinofuranosyl)-5-iodouracil, 1-(2-deoxy-2-fluoro-β-D-arabinofuranosyl)-5-iodocytosine, 1-(2-deoxy-2-fluoro-β-L-arabinofuranosyl)-5-methyluracil, arabinofuranosyl)-5-(2-bromovinyl)uracil, E-5-(2-bromovinyl)-2'-deoxyuridine, 5-trifluoromethylthymidine, 1-β-D-arabinofuranosyl-5-propynyluracil, 1-(2-deoxy-2-fluoro-β-D-arabinofuranosyl)-5-ethyluracil, 2', 3'-dideoxy-3'-fluoroguanosine, 3'-deoxy-3'-fluorothymidine, (±)-(1α, 2β, 3α)-9-[2, 3-bis(hydroxymethyl)-1-cyclobutyl]adenine, (±)-(1α, 2β, 3α)-9-[2, 3-bis(hydroxymethyl)-1-cyclobutyl]guanine, (±)-(1β, 2α, 3β)-9-[2, 3-bis(hydroxymethyl)-1-cyclobutyl]guanine, (±)-(1β, 2α, 3β)-9-[2, 3-bis(hydroxymethyl)-1-cyclobutyl]adenine, (1R, 3S, 4R)-9-(3-hydroxy-4-hydroxymethylcyclopent-1-yl)guanine, (1S, 2R, 4R)-9-(1-hydroxy-2-hydroxymethylcyclopent-4-yl)guanine, (2R, 4R)-9-(2-hydroxymethyl-1, 3-dioxolan-4-yl)-2, 6-diaminopurine, (2R, 4R)-1-(2-hydroxymethyl-1, 3-dioxolan-4-yl)cytosine, (2R, 4R)-9-(2-hydroxymethyl-1, 3-dioxolan-4-yl)guanine, (2R, 4R)-1-(2-hydroxymethyl-1, 3-dioxolan-4-yl)-5-fluorocytosine, (1R, 2S, 4S)-9-(4-hydroxy-3-hydroxymethyl-2-methylenecyclopent-4-yl]guanine, and (1S, 3R, 4S)-9-(3-hydroxy-4-hydroxymethyl-5-methylenecyclopent-1-yl]guanine, Methods In one aspect, the invention provides methods of synthesizing phosphorylated molecules. In one aspect, the method comprises forming a mixture comprising an activated precursor molecule and an organic molecule comprising at least one phosphate moiety of the invention and incubating the mixture in the presence of a catalyst to catalyze synthesis of a phosphorylated molecule. In various embodiments, the compositions and methods of the invention can be used to synthesize molecules with mono-, tri-, tetra-, penta- or hexa-peptide moieties. The methods disclosed herein can be used to synthesize phosphorylated sugar molecules, phosphorylated proteins or peptides, phosphorylated lipids, or phosphorylated nucleic acid molecules.

In one aspect, the invention provides methods of synthesizing natural or modified nucleoside monophosphates including, but not limited to, 5' nucleoside monophosphate (NMP), 2'-deoxynucleoside-5'-monophosphate (dNMP), and analogs thereof. In one aspect, the method comprises forming a mixture comprising an activated nucleoside molecule and an organic molecule comprising a monophosphate moiety of the invention and incubating the mixture in the presence of a catalyst to catalyze synthesis of a nucleoside monophosphate.

In one aspect, the invention provides methods of synthesizing natural or modified nucleoside diphosphates including, but not limited to, 5' nucleoside diphosphate (NDP) and 2'-deoxynucleoside-5'-diphosphates (dNDP), and analogs thereof. In one aspect, the method comprises forming a mixture comprising an activated nucleoside monophosphate and an organic molecule comprising a monophosphate moiety of the invention and incubating the mixture in the presence of a catalyst to catalyze synthesis of a nucleoside diphosphate. In one aspect, the method comprises forming a mixture comprising an activated nucleoside molecule and an organic molecule comprising a pyrophosphate moiety of the invention and incubating the mixture in the presence of a catalyst to catalyze synthesis of a nucleoside diphosphate.

In one aspect, the invention provides methods of synthesizing natural or modified nucleoside triphosphates including, but not limited to, 5' nucleoside triphosphate (NTP) and 2'-deoxynucleoside-5'-triphosphates (dNTP), and analogs thereof. In one aspect, the method comprises forming a mixture comprising an activated nucleoside monophosphate and an organic molecule comprising a pyrophosphate moiety of the invention and incubating the mixture in the presence of a catalyst to catalyze synthesis of a nucleoside triphosphate. In one aspect, the method comprises forming a mixture comprising an activated nucleoside molecule and an organic molecule comprising a triphosphate moiety of the invention and incubating the mixture in the presence of a catalyst to catalyze synthesis of a nucleoside triphosphate.

In one aspect, the invention provides methods of synthesizing natural or modified nucleoside tetraphosphates including, but not limited to, 5' nucleoside tetraphosphate ($Np_4$) and 2'-deoxynucleoside-5'-tetraphosphates ($dNp_4$), and analogs thereof. In one aspect, the method comprises forming a mixture comprising an activated nucleoside monophosphate and an organic molecule comprising a triphosphate moiety of the invention and incubating the mixture in the presence of a catalyst to catalyze synthesis of a nucleoside tetraphosphate. In one aspect, the method comprises forming a mixture comprising an activated nucleoside molecule and an organic molecule comprising a tetraphosphate moiety of the invention and incubating the mixture in the presence of a catalyst to catalyze synthesis of a nucleoside tetraphosphate. In one aspect, the method comprises forming a mixture comprising an activated nucleoside diphosphate molecule and an organic molecule comprising a pyrophosphate moiety of the invention and incubating the mixture in the presence of a catalyst to catalyze synthesis of a nucleoside tetraphosphate.

In one aspect, the invention provides methods of synthesizing natural or modified nucleoside pentaphosphates including, but not limited to, 5' nucleoside pentaphosphate ($Np_5$) and 2'-deoxynucleoside-5'-pentaphosphates ($dNp_5$), and analogs thereof. In one aspect, the method comprises forming a mixture comprising an activated nucleoside monophosphate and an organic molecule comprising a pentaphosphate moiety of the invention and incubating the mixture in the presence of a catalyst to catalyze synthesis of a nucleoside pentaphosphate. In one aspect, the method comprises forming a mixture comprising an activated nucleoside molecule and an organic molecule comprising a pentaphosphate moiety of the invention and incubating the mixture in the presence of a catalyst to catalyze synthesis of a nucleoside pentaphosphate, in one aspect, the method comprises forming a mixture comprising an activated nucleoside triphosphate molecule and an organic molecule comprising a pyrophosphate moiety of the invention and incubating the mixture in the presence of a catalyst to catalyze synthesis of a nucleoside pentaphosphate. In one aspect, the method comprises forming a mixture comprising an activated nucleoside diphosphate molecule and an organic molecule comprising a triphosphate moiety of the invention and incubating the mixture in the presence of a catalyst to catalyze synthesis of a nucleoside pentaphosphate.

In one aspect, the invention provides methods of synthesizing natural or modified nucleoside hexaphosphates including, but not limited to, 5' nucleoside hexaphosphate ($Np_6$) and 2'-deoxynucleoside-5'-hexaphosphates ($dNp_6$), and analogs thereof. In one aspect, the method comprises forming a mixture comprising an activated nucleoside monophosphate and an organic molecule comprising a pentaphosphate moiety of the invention and incubating the mixture in the presence of a catalyst to catalyze synthesis of a nucleoside hexaphosphate. In one aspect, the method comprises forming a mixture comprising an activated nucleoside pentaphosphate and an organic molecule comprising a monophosphate moiety of the invention and incubating the mixture in the presence of a catalyst to catalyze synthesis of a nucleoside hexaphosphate. In one aspect, the method comprises forming a mixture comprising an activated nucleoside tetraphosphate molecule and an organic molecule comprising a pyrophosphate moiety f the invention and incubating the mixture in the presence of a catalyst to catalyze synthesis of a nucleoside hexaphosphate. In one aspect, the method comprises forming a mixture comprising an activated nucleoside diphosphate molecule and an organic molecule comprising a tetraphosphate moiety of the invention and incubating the mixture in the presence of a catalyst to catalyze synthesis of a nucleoside hexaphosphate. In one aspect, the method comprises forming a mixture comprising an activated nucleoside triphosphate molecule and an organic molecule comprising a triphosphate moiety of the invention and incubating the mixture in the presence of a catalyst to catalyze synthesis of a nucleoside hexaphosphate.

Similarly, the compositions and methods of the invention can be used to synthesize molecules with heptapeptides, octapeptides, nonapeptides, decapeptides or longer peptide moieties.

Although it is not intended that the method of the invention be limited to a particular set of reaction conditions, in one embodiment, the reaction conditions include a first step of contacting an activated nucleoside monophosphate with an organic molecule comprising a phosphate moiety of the invention in the presence of an acid catalyst at room temperature (rt) to form a reaction intermediate, followed by second step of contacting the reaction intermediate with a base at a temperature of 37° C.

Although it is not intended that the method of the invention be limited to any particular acid catalyst, in one embodiment, any acidic compound (including the so-called Lewis acids) may be used as catalysts. In one embodiment, the acid catalyst is $ZnCl_2$, $H_2SO_4$, HCl, $H_3PO_4$ or $BF_3$. In another embodiment, the acid catalyst is a sulfonic acid or its salt, comprising ortho-toluenesulfonic acid, meta-toluenesulfonic acid, alkylbenzenesulfonic acid, secondary alkyl-sulfonic acid, sulfonic resin, alkylsulfate, alkylbenzenesulfonate, alkyl-sulfonate and sulfosuccinic acid. In a preferred embodiment, the acid catalyst is $ZnCl_2$.

Although it is not intended that the method of the invention be limited to a particular base, in one embodiment, the base is selected from a group of organic or inorganic basic materials comprising the alkali metal bases such as alkali metal hydroxide, carbonates, and bicarbonates. In another embodiment, the base is selected from a group comprising the alkaline earth bases such as calcium oxide and magnesium oxide. In another embodiment, aluminum bases such as aluminum hydroxide or its basic alkali aluminum components are contemplated. In a further embodiment, the base is selected from a group comprising ammonia-based compounds, such as ammonium hydroxide, and amines including, but not limited to, primary, secondary tertiary and heterocyclic amines, Applications The compositions comprising modified nucleotides and methods catalyzing the incorporation of modified nucleotides of the present invention may be used in a wide variety of protocols and technologies. For example, in certain embodiments, the modified nucleotides are used in the fields of molecular biology, genomics, transcriptomics, epigenetics, nucleic acid sequencing, and the like. That is, modified nucleotides may be used in any technology that may require or benefit from specific incorporation of modified nucleotides, Exemplary technologies, include, but are not limited to cDNA library construction; DNA epigenome and RNA methylome assays, high-throughput next generation sequencing technologies including but not limited to Illumina, soLiD, and Ion Torrent sequencing; and single nucleic acid molecule real time sequencing (SMRT) including, but not limited to, technologies from Pacific Bioscience and Oxford Nanopore Technologies such as zero-mode waveguide or nanopore sequencing, respectively.

Pharmaceutical Compositions

In some embodiments, nucleoside triphosphates can function as pharmaceutical agents, e.g. 3'-azido-3'-deoxythymidine (AZT, an anti-HIV drug) triphosphate and arabinosylcytosine (Cytarabine, an anticancer drug) triphosphate. In addition, nucleotides have been considered as antimetabolite drugs, agents for the treatment of diseases and disorders associated with infection (e.g., U.S. Pat. No. 5,763,447). Nucleoside triphosphates or nucleoside triphosphate analogs have also been described for the treatment of diseases and disorders including, but not limited to, sinusitis (e.g., U.S. Pat. No. 5,789,391), ostitis media (e.g., U.S. Pat. No. 6,423,694), inflammatory conditions (e.g., U.S. Patent Application No. 2005/261239), and cancer (e.g., U.S. Pat. No. 5,049,372).

Therefore, in one embodiment, the invention also relates to a pharmaceutical composition comprising a therapeutically effective amount of a synthesized nucleotide of the invention, a pharmaceutically acceptable salt thereof, optionally in combination with one or more other active ingredients and/or with a pharmaceutically acceptable carrier. Moreover, the above any of the compounds may be used in a method for the treatment of a disease or disorder including, but not limited to, a microbial infection or proliferative disorder, comprising administering a therapeutically effective amount of any of the above compounds to a subject in need thereof.

The pharmaceutical composition of the present invention comprises at least one nucleotide triphosphate synthesized according to the methods of the invention, or pharmaceutically acceptable salts, esters or prodrugs thereof as active ingredients. The compositions include those suitable for oral, topical, intravenous, subcutaneous, nasal, ocular, pulmonary, and rectal administration. The compounds of the invention can be administered to mammalian individuals, including humans, as therapeutic agents.

For example, the compounds of the invention are useful as antiviral agents. The present invention provides a method for the treatment of a patient afflicted with a viral infection comprising administering to the patient a therapeutically effective antiviral amount of a compound of the invention. The term "viral infection" as used herein refers to an abnormal state or condition characterized by viral transformation of cells, viral replication and proliferation. Viral infections for which treatment with a compound of the invention will be particularly useful include the viruses mentioned above.

A "therapeutically effective amount" of a compound of the invention refers to an amount which is effective, upon single or multiple dose administration to the patient, in controlling the growth of e.g., the microbe or tumor or in prolonging the survivability of the patient beyond that expected in the absence of such treatment. As used herein, "controlling the growth" refers to slowing, interrupting, arresting or stopping the microbial or proliferative transformation of cells or the replication and proliferation of the microbe and does not necessarily indicate a total elimination of e.g., the microbe or tumor.

Accordingly, the present invention includes pharmaceutical compositions comprising, as an active ingredient, at least one of the compounds of the invention in association with a pharmaceutical carrier. The compounds of this invention can be administered by oral, parenteral (intramuscular, intraperitoneal, intravenous (IV) or subcutaneous injection), topical, transdermal (either passively or using iontophoresis or electroporation), transmucosal (e.g., nasal, vaginal, rectal, or sublingual) or pulmonary (e.g., via dry powder inhalation) routes of administration or using bioerodible inserts and can be formulated in dosage forms appropriate for each route of administration.

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating, agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories Which may contain, in addition to the active substance, excipients such as cocoa butter or a suppository wax. Compositions for nasal or sublingual administration are also prepared with standard excipients well known in the art.

Topical formulations will generally comprise ointments, creams, lotions, gels or solutions. Ointments will contain a conventional ointment base selected from the four recognized classes: oleaginous bases; emulsifiable bases; emulsion bases; and water-soluble bases. Lotions are preparations to be applied to the skin or mucosal surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Creams, as known in the art, are viscous liquid or semisolid emulsions, either oil-in-water or water-in-oil. Topical formulations may also be in the form of a gel, i.e., a semisolid, suspension-type system, or in the form of a solution.

Formulations of these drugs in dry powder form for delivery by a dry powder inhaler offers yet another means of administration. This overcomes many of the disadvantages of the oral and intravenous routes.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment desired.

Generally, dosage levels of between 0.001 to 10 mg/kg of body weight daily are administered to mammals.

Kits

The present invention also relates to a kit for performing any of the above described methods, wherein the kit comprises a synthesized nucleoside triphosphate or a nucleic acid molecule comprising a synthesized nucleoside triphosphate. In one embodiment, the kit may comprise a mixture of synthesized nucleotides. In some embodiments, one or more of the components are premixed in the same reaction container.

In particular embodiments, the kit additionally comprises instructional material.

EXPERIMENTAL EXAMPLES

The invention is further described in detail by reference to the following experimental examples. These examples are provided for purposes of illustration only, and are not intended to be limiting unless so specified. Thus, the invention should in no way be construed as being limited to the following examples, but rather, should be construed to encompass any and all variations which become evident as a result of the teaching provided herein. Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure Example 1: Synthesis of Natural and Modified Nucleoside Triphosphates Examples for the synthesis of the nucleotides of the present invention are given in this section.

Synthesis of Activated Thymidine Monophosphate

Figure 10:
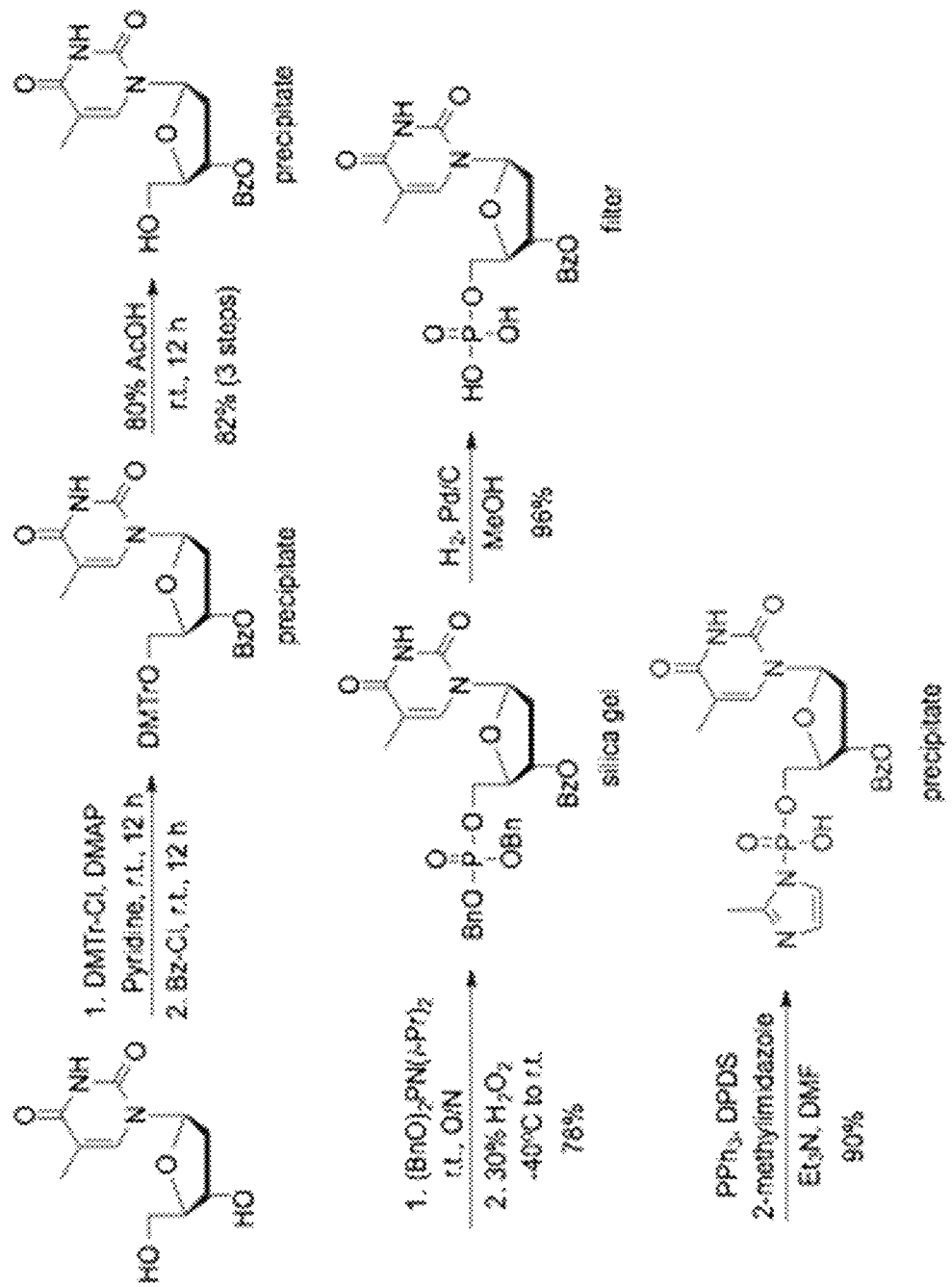
FIG. 10 depicts a diagram of the synthesis of activated thymidine monophosphate.

Activated thymidine monophosphate was synthesized according to the scheme shown in FIG. 10.

Synthesis of p-Toluene Pyrophosphate

Figure 8:
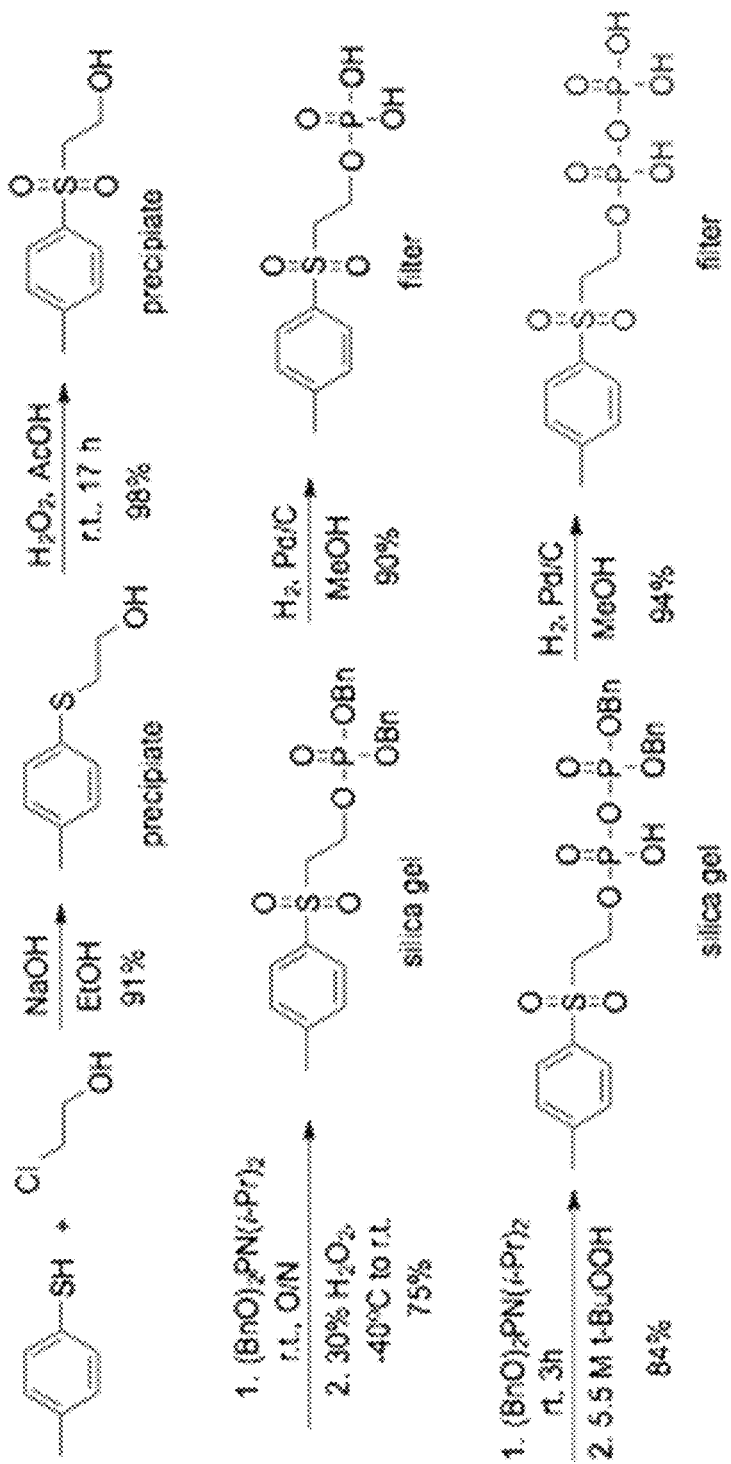
FIG. 8 depicts a diagram of the synthesis of p-toluene pyrophosphate reagent.

A p-toluene pyrophosphate reagent was synthesized according to the scheme shown in FIG. 8.

Synthesis of Pyrene Pyrophosphate

Figure 9:
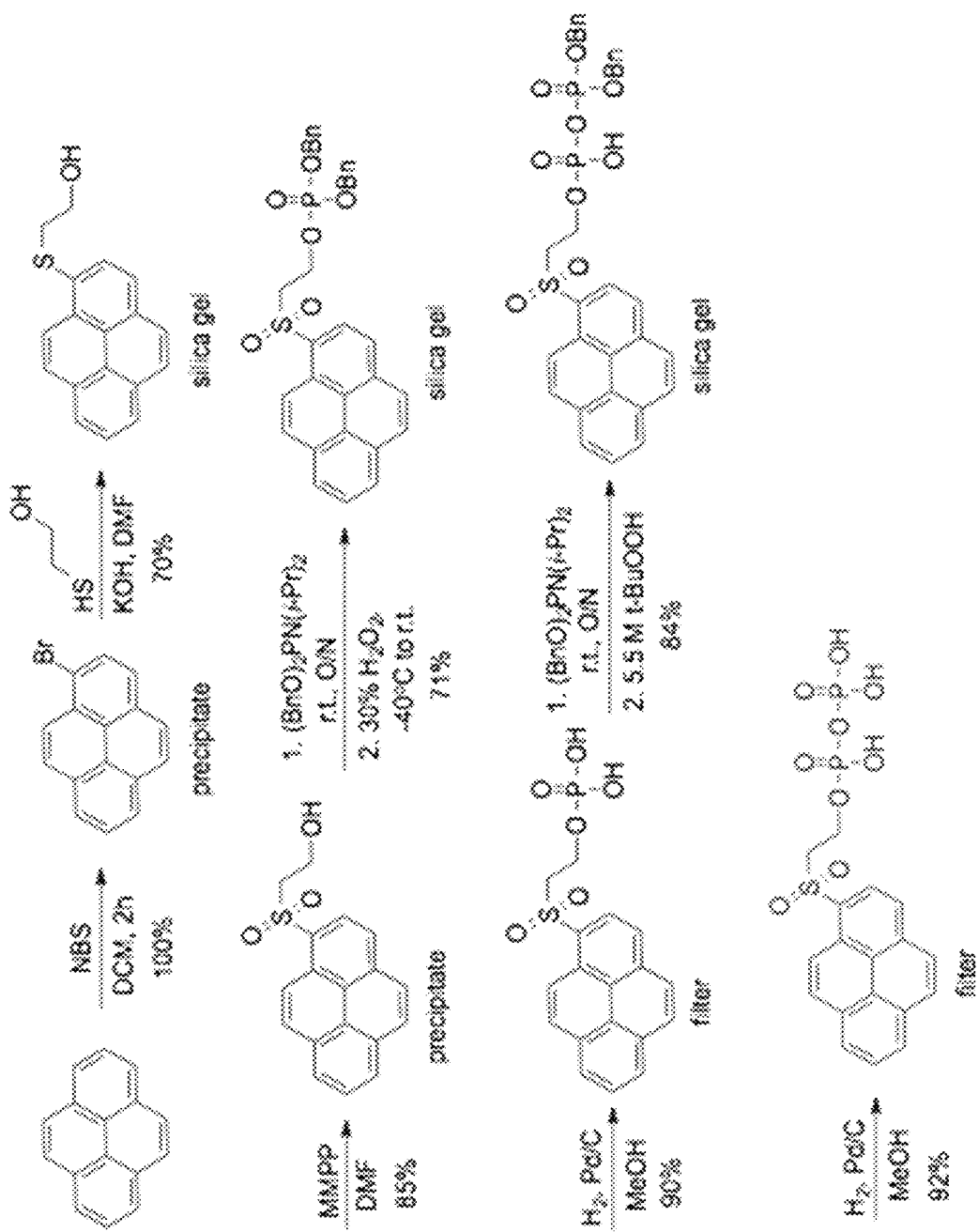
FIG. 9 depicts a diagram of the synthesis of pyrene pyrophosphate reagent.

A pyrene pyrophosphate reagent was synthesized according to the scheme shown in FIG. 9.

Synthesis of Nucleoside Triphosphates

Figure 1:
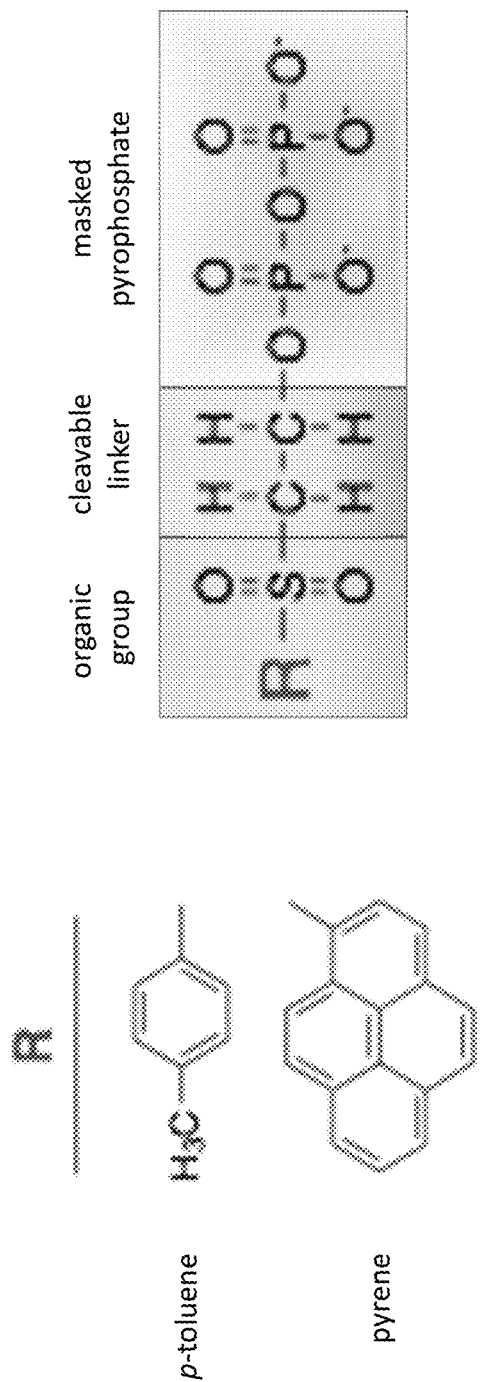
FIG. 1 depicts exemplary structures of organic pyrophosphates, the phosphorylation reagent used in the synthesis of natural and modified nucleoside triphosphates.
Figures 2A, 2B, 2C:
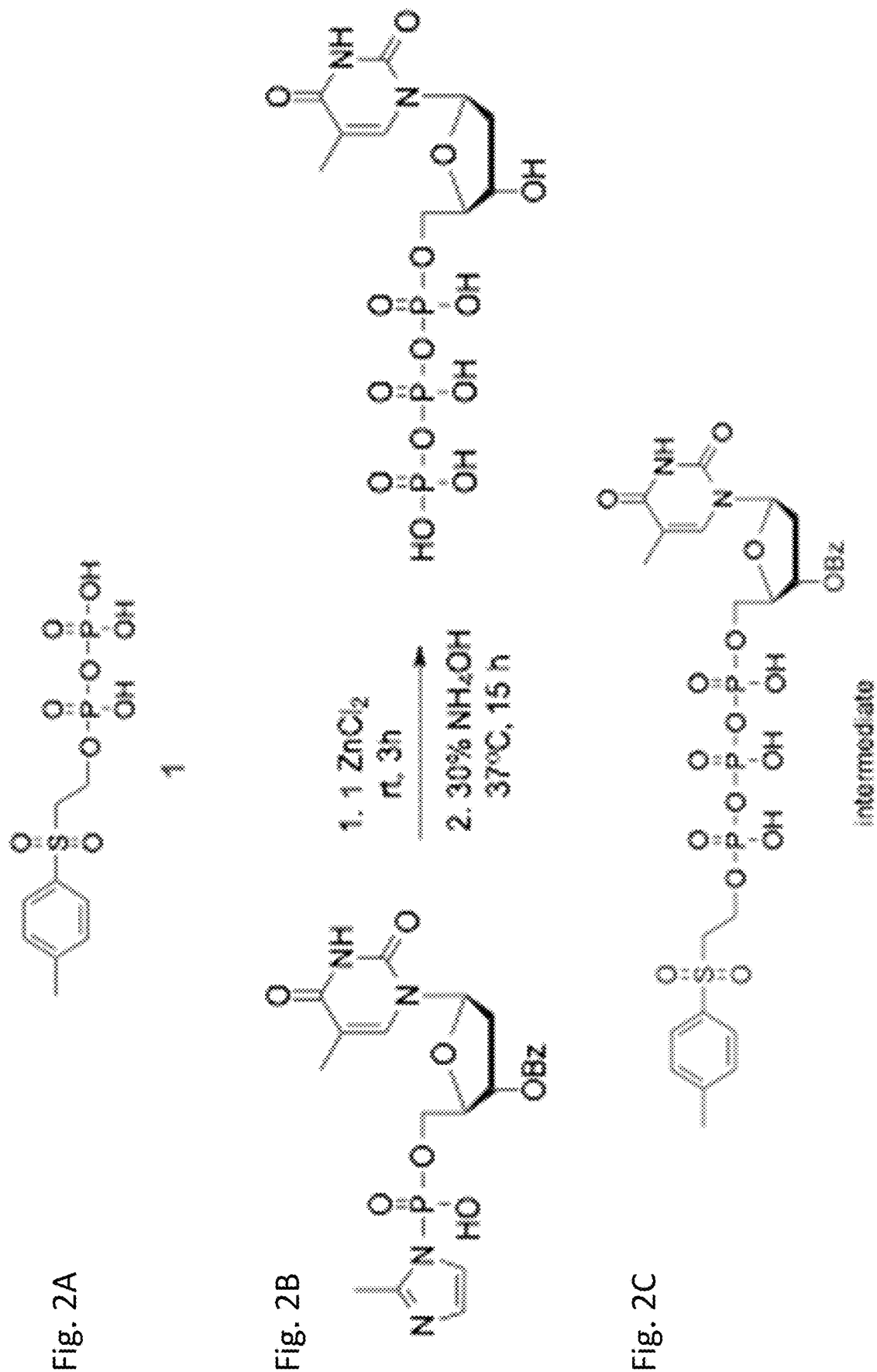
FIG. 2A through FIG. 2C, depicts a model for the synthesis of natural and modified nucleoside triphosphates.

5'-thymidine triphosphate was synthesized according to the scheme shown in FIG. 2B. The activated nucleoside monophosphate is reacted with an organic pyrophosphate reagent (FIG. 1, FIG. 2A, FIG. 5) to form an intermediate product (FIG. 2C) which is then reduced to form a nucleoside triphosphate. The reaction shown in FIG. 2B is catalyzed by $ZnCl_2$.

Figure 4:
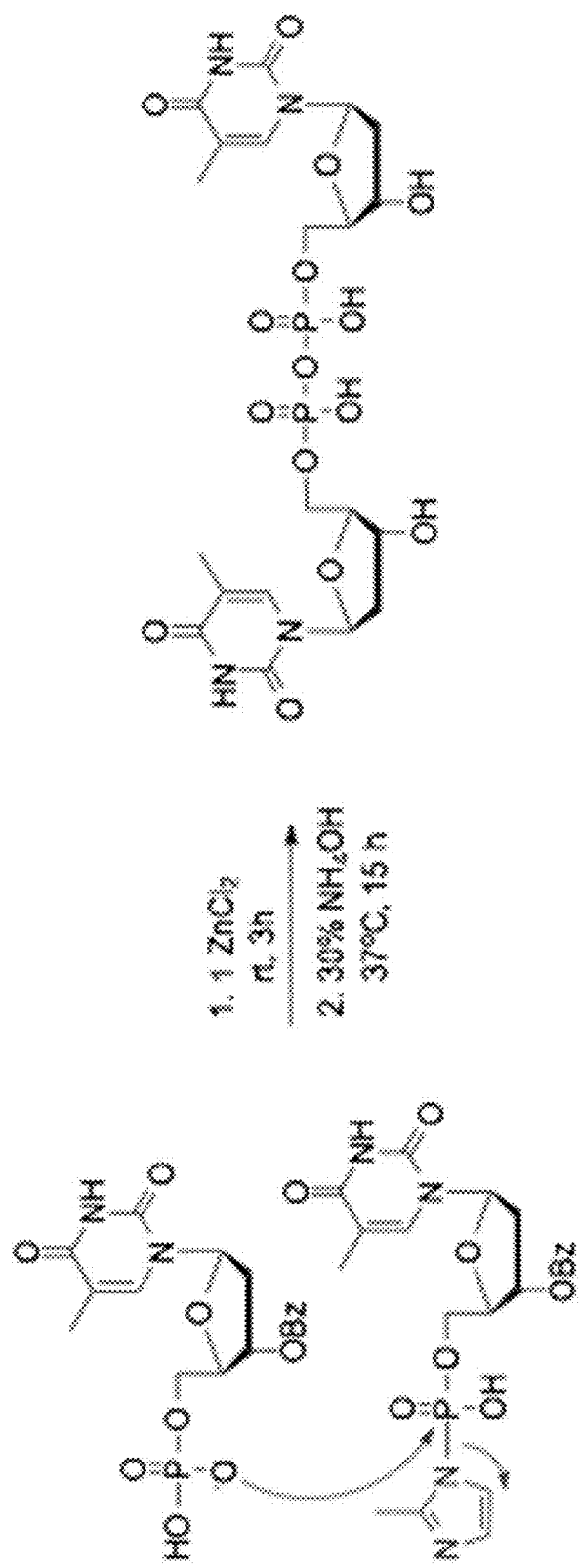
FIG. 4 depicts a model for the formation of dinucleoside diphosphate, a minor contaminant of the reaction of FIG. 2B.

The reaction of FIG. 2B results in the formation of dinucleoside diphosphate, a minor contaminant (FIG. 4).

Figure 6:
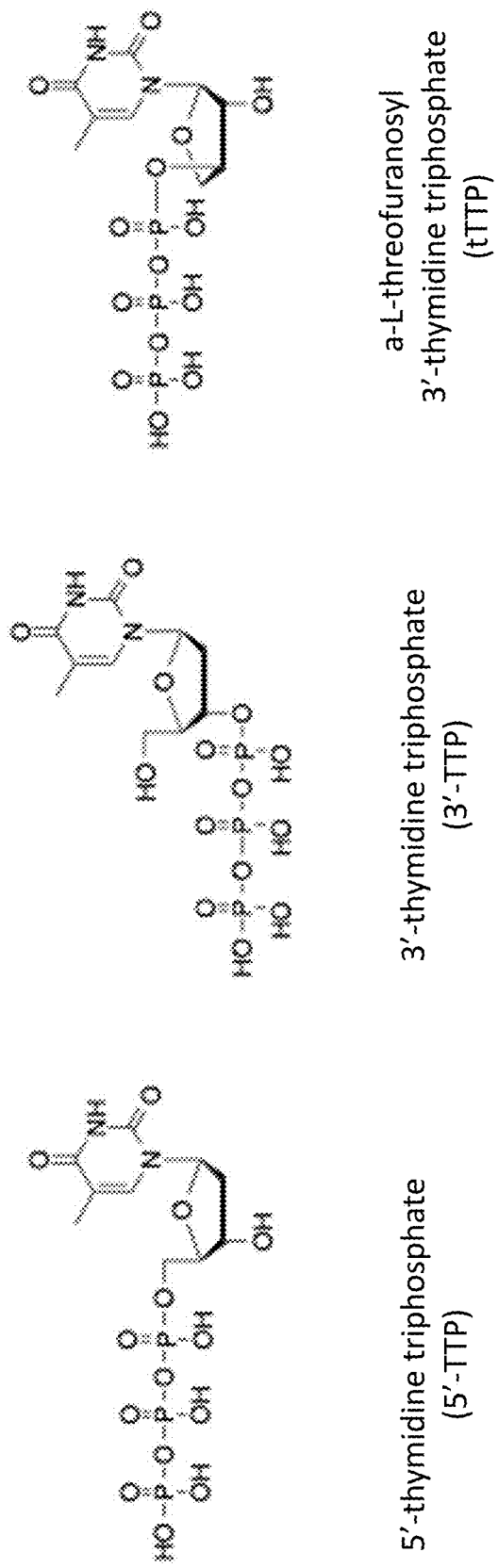
FIG. 6 depicts the chemical structures of exemplary nucleoside triphosphates (from left to right: 5'-thymidine triphosphate (5'-TTP), triphosphate (3'-TTP), and a-L-threo-furanosyl 3'-thymidine triphosphate (tTTP)) which have been synthesized using the methods of the invention.

5'-thymidine triphosphate (5'-TTP), 3'-thymidine triphosphate (3'-TTP), and a-L-threofuranosyl 3'-thymidine triphosphate (tTTP)) as well as four naturally occurring nucleoside triphosphates have all been synthesized using the methods of the invention (FIG. 6 and FIG. 7).

Example 2: P(V) Reagents for the Scalable Synthesis of Natural and Modified Nucleoside Triphosphates Historically, the synthesis of chemically modified nucleoside triphosphates has been limited by such factors as scalability, low yields, difficult reaction conditions, and tedious purifications protocols (Burgess and Cook, 2000, Chem. Rev. 100, 2047-2060; Kore and Srinivasan, 2013, Curr. Org, Syn. 10, 903-934; Hollenstein, 2012, Molecules 17, 13569-13591). Efforts to overcome these problems have resulted in an astonishing number of publications, nearly all of which require HPLC purification (Burgess and Cook, 2000, Chem. Rev, 100, 2047-2060; Kore and Srinivasan, 2013, Curr. Org. Syn. 10, 903-934; Hollenstein, 2012, Molecules 17, 13569-13591). Attempts to synthesize α-L-threofuranosyl adenosine triphosphates using the classic Yoshikawa or Ludwig-Eckstein methods (Yoshikawa et at, 1967, Tetrahedron Lett. 8, 5065-5068; Ludwig and Eckstein, 1989, J. Org. Chem. 54, 631-635) produced complex mixtures of phosphorylated compounds with the desired compound present as a minor product (FIG. 11).

Therefore, a fundamentally different approach was developed for the synthesis of natural and modified nucleoside triphosphates that required invention of a novel P(V)-based organic pyrophosphate reagent to mediate P—O bond formation between the α- and β-phosphate positions, Here, a synthetic route to nucleic acid building blocks is described that (1) is not constrained to natural substrates; (2) is scalable to gram quantities of material; (3) eliminates the requirement for HPLC purification; and (4) avoids the need for freeze drying. The pyrophosphate reagent and activated nucleoside monophosphates described in this study are readily produced on scales of 5-10 grams using synthetic methodology that is inexpensive, straightforward and high yielding. The availability of these reagents makes it possible to generate 1.0 gram of nucleoside triphosphate, which is enough material to perform 5 liters of PCR or 100,000 PCR reactions with a standard 50 μL volume. Unlike conventional tributyl ammonium pyrophosphate, pyrene pyrophosphate is a solid at room temperature and stable to atmospheric conditions, allowing it to be used without specialized equipment and stored for long periods of time without loss of activity. Last, the pyrene pyrophosphate method was found to be superior for synthesizing chemically modified nucleotides that were challenging to synthesize using the classic Yoshikawa or Ludwig-Eckstein methods (14, 15), Based on these considerations, the current approach provides an alternative paradigm for synthesizing large quantities of nucleoside triphosphates for emerging applications in biotechnology and molecular medicine.

Figure 12:
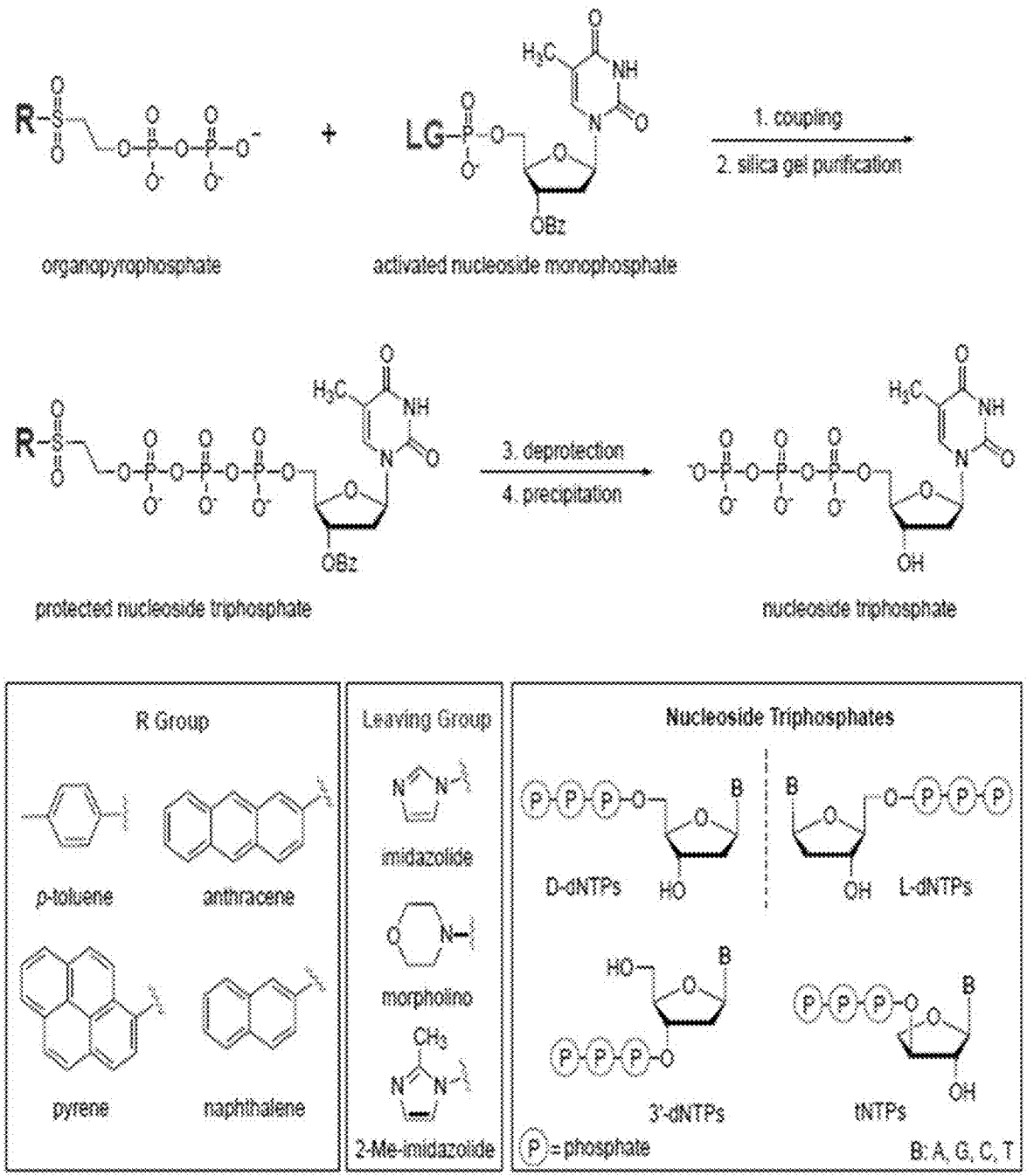
FIG. 12 depicts a diagram of the strategy and methodology development. Shown is a diagram for the scalable synthesis of natural and modified nucleoside triphosphates using a new class of organopyrophosphate reagents. R, the aromatic substitution attached to a cleavable sulfonylethyl linker. LG, leaving group moiety. B, nucleobase moieties: adenine (A), guanine (C), cytosine (C), thymine (T).
Figure 13:
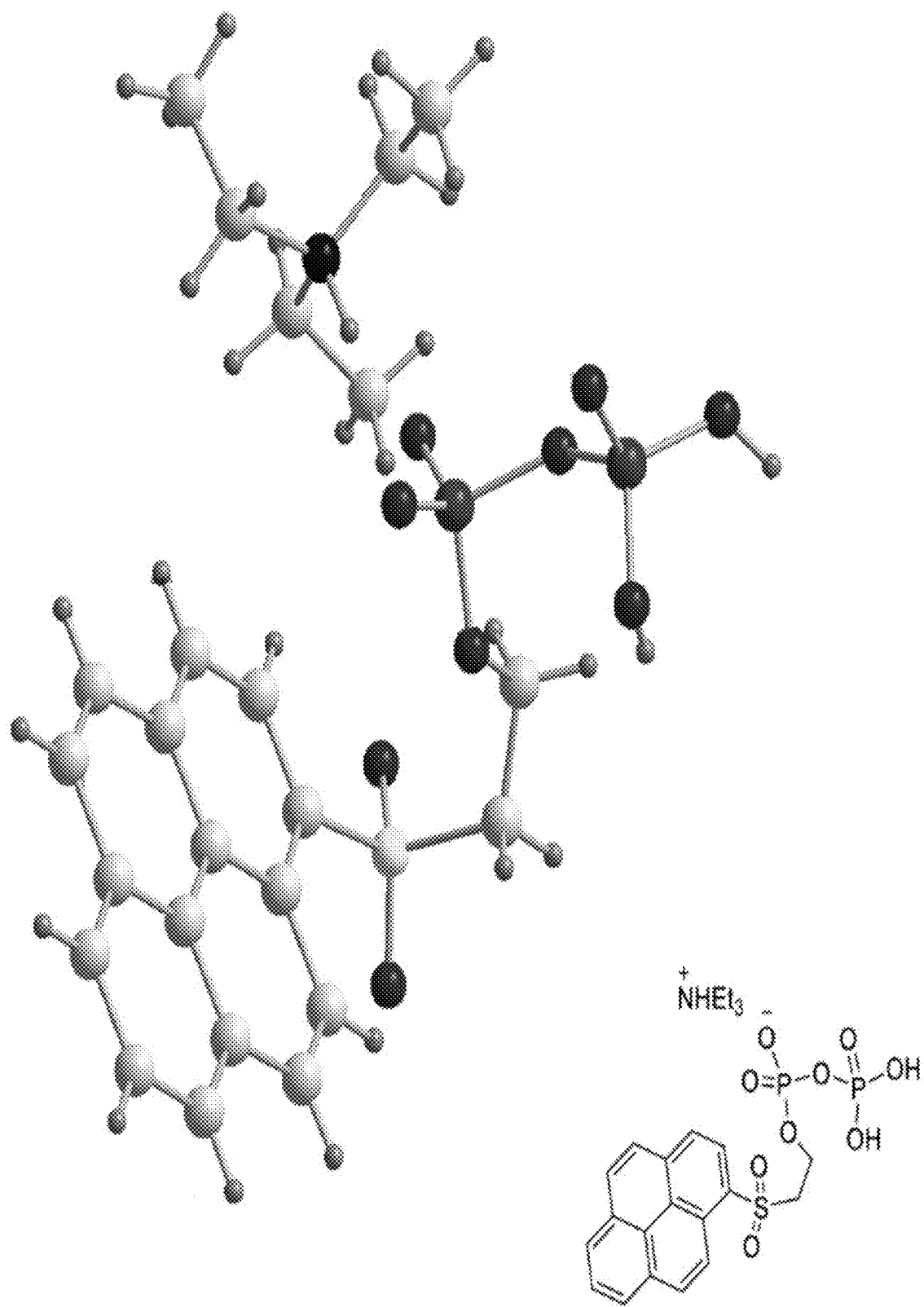
FIG. 13 depicts the organic pyrophosphate reagent as verified by the crystal structure.

The invention establishes an Hoard-Ott-like procedure (FIG. 12) using nucleoside and pyrophosphate reagents that were suitably hydrophobic so as to generate nucleoside triphosphate derivatives that were amenable to purification by silica gel chromatography but could be readily converted to the desired compound using standard deprotection and precipitation conditions (Hoard and Ott, 1965, J. Am. Chem. Soc. 87, 1785-1788). This type of convergent synthesis strategy provides a direct and scalable route to natural and chemically modified nucleoside triphosphates using operationally simple protocols that process and discovery chemists would find appealing. Critical to this effort was the need to establish a new class of organic pyrophosphate reagents that contain a large hydrophobic moiety attached to the pyrophosphate group via a cleavable linker and to demonstrate that these reagents could mediate the synthesis of nucleoside triphosphates. Reducing this concept to practice involved a systematic evaluation of three key components: (1) hydrophobic groups necessary to construct a stable organic pyrophosphate reagent that is a solid compound at room temperature and exhibits minimal hygroscopic properties; (2) a strong leaving group to activate the nucleoside monophosphate for nucleophilic attack by the pyrophosphate reagent; and (3) a suitable Lewis acid to accelerate phosphodiester bond formation (FIG. 12). The goals of this study were ultimately met through a systematic exploration and subsequent optimization of reaction conditions which revealed that pyrene, 2-methylimidazole, and zinc chloride provided the optimal hydrophobic moiety, leaving group, and Lewis acid catalyst, respectively, necessary to mediate the synthesis of nucleoside triphosphates in their fully protected form. The crystal structure of the pyretic pyrophosphate reagent verified correct synthesis of the organic pyrophosphate reagent (FIG. 13).

The materials and methods used are now described.

Analytical Reverse-Phase HPLC Analysis.

2 µL of reaction crude (compounds: 10-11a-d, and 16-17, and 22-23a-d, and 28-29) in DMF or 1 µL of purified pyrene substituted nucleoside triphosphates (compounds: 12a-d, and 18, and 24a-d, and 30) in methanol or 3 of nucleoside triphosphates (compounds: 13a-d, and 19, and 25a-d, and 31) in $H_2O$ was added to 50 µL of 0.1 M triethylammonium acetate (TEAA) buffer pH 7.0. The solution was centrifuged by 4000 rpm for 2 minutes at room temperature and 30 µL of supernatant was injected for HPLC analysis, Reaction progress of the synthesis of nucleoside monophosphates (compounds: 10a-d, and 16, and 22a-d, and 28), nucleoside phosphor-2-methylimidazolides (compounds: 11a-d, and 17, and 23a-d, and 29), pyrene substituted nucleoside triphosphates (compounds: 12a-d, and 18, and 24a-d, and 30) and nucleoside triphosphates (compounds: 13a-d, and 19, and 25a-d, and 31) in FIG. 32, FIG. 44, FIG. 56, FIG. 68, FIG. 80, FIG. 92, FIG. 101, FIG. 110, FIG. 119, and FIG. 128 was monitored by analytical HPLC chromatography with the gradient from 0% to 50% of acetonitrile in 0.1 M triethylammonium acetate buffer pH 7.0 over forty minutes. Purity determination of synthesized 5'-dNTPs (compounds: 13a-d) was monitored by the coinfection with the commercial 5'-dNTPs purchased from Sigma-Aldrich by analytical HPLC chromatography in with the gradient from 0% to 10% of acetonitrile in 0.1 M triethylammonium acetate buffer pH 7.0 over forty minutes of analytical run.

PCR Fidelity Assay,

A 100 µl PCR reaction was performed in 1× ThermoPol buffer (20 mM Tris-HCl, 10 mM $(NH_4)2SO_4$, 10 mM KCl, 2 mM $MgSO_4$, 0.1% Triton X-100, pH 8.8, NEB), 0.5 of Fwd [CAACCGGTCCCCACGTTGCC] (SEQ ID NO:1) and Rev [AACGGCTGGGAGAACCTGGTTCTCA AT GTA] (SEQ ID NO:2) PCR primers, 400 µM dNTPs (Chemically Synthesized vs Life Technologies), 4.4 ng of pGDR11 KOD-RS plasmid [Target sequence: CAACCG GTCCCCACGTTGCCGTTGCCAAGAGGTTGG CCGC GAGAGGAGTC AAAATACGCCCTGGAACGGTGA-TAAGCTACATCGTGCTCAAGGGCTCTGG GAGGA-TAGGCGACAGGGCGATACCGTTCGACGAG TTCG ACCCGACGAAG CACAAGTACGACGCCGAGTACTA-CATTGAGAACCAGGTTCTCCCAGCCGT T] (SEQ ID NO:3) with final concentration of 5 units/100 µL Taq polymerase (NEB). The PCR conditions were: 95° C., 2.5 min (melt), 95° C., 30 sec, 62° C., 45 sec, 72° C., 30 sec for 20 cycles and an additional 72° C., 2 mm. The amplified amplicon (200 bp) was agarose purified, ligated into a TOPO-TA vector, and subsequently cloned into NEB DH5α *E. coli* competent cells following the manufacturer's instructions, Individual colonies were grown in liquid media and sequenced using the M13F primer by Retrogen, San Diego, CA DNA sequences were aligned and analyzed using MEGA7 software. Five sequences clones were analyzed for each condition to give a total of 750 nucleotide positions.

TNA Transcription Assay.

Primer-extension reactions were performed in a final volume of 20 µl. Each reaction contained 10 pmol of primer [IR680-5'-GTCCCCTTGGGGATACCACC-3'] (SEQ ID NO:4) annealed to 10 pmol of template [5'-ATCGAGTA-CAGTCAGATCGATATGATCTATATATTAATTAGGTG-GTATCC CCAAGGGGAC-3'] (SEQ ID NO:5), 1× ThermoPol buffer, 0.5 µM KOD-RS, 100 µM of each tNTP. Reactions were incubated tor 120 min at 55° C., quenched with stop buffer (40% Formamide and 1×TBE buffer, 10 mM EDTA), and analyzed by 10% denaturing urea PAGE.

The results of the experiments are now described.

Figure 14A:
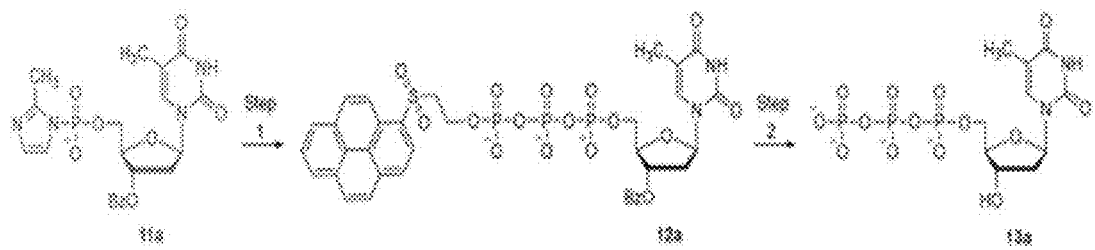
FIG. 14A through FIG. 14C depicts a synthesis and purity comparison of thymidine triphosphate.
Figure 14B:
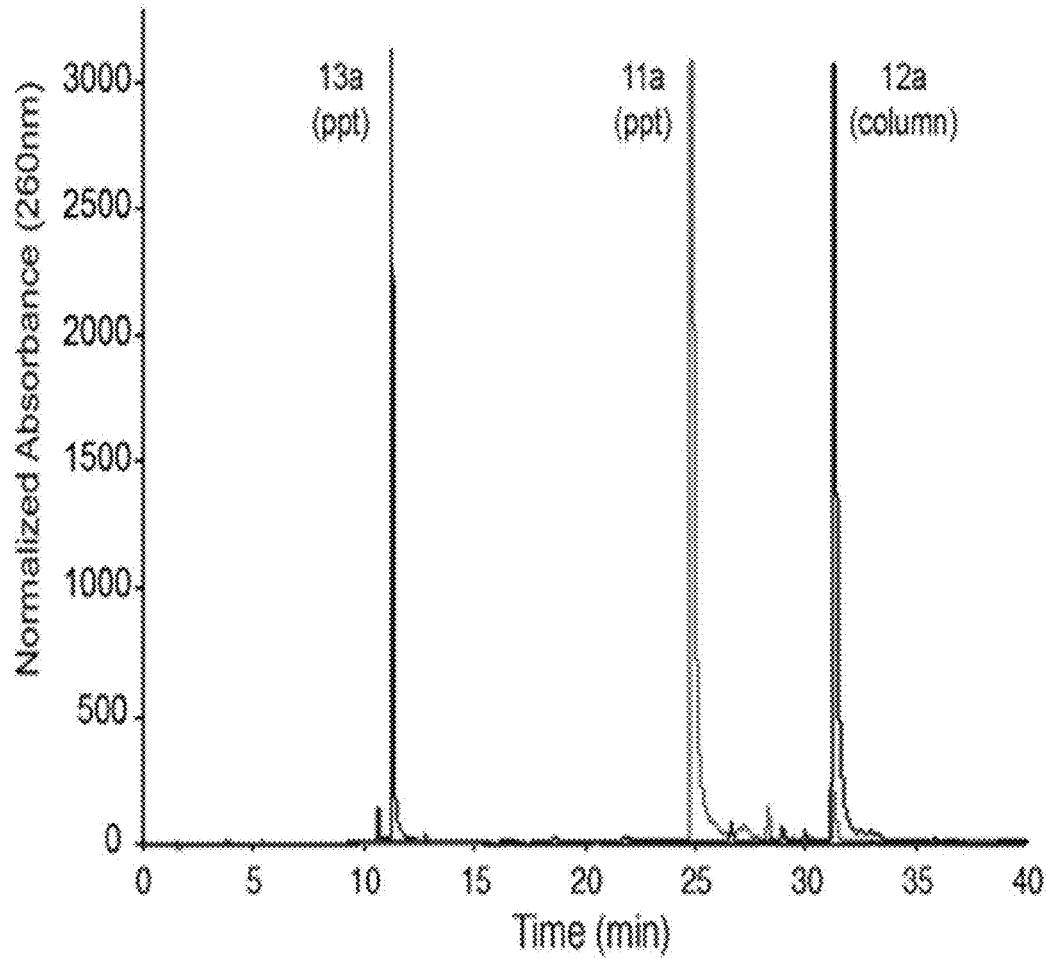
Figure 14C:
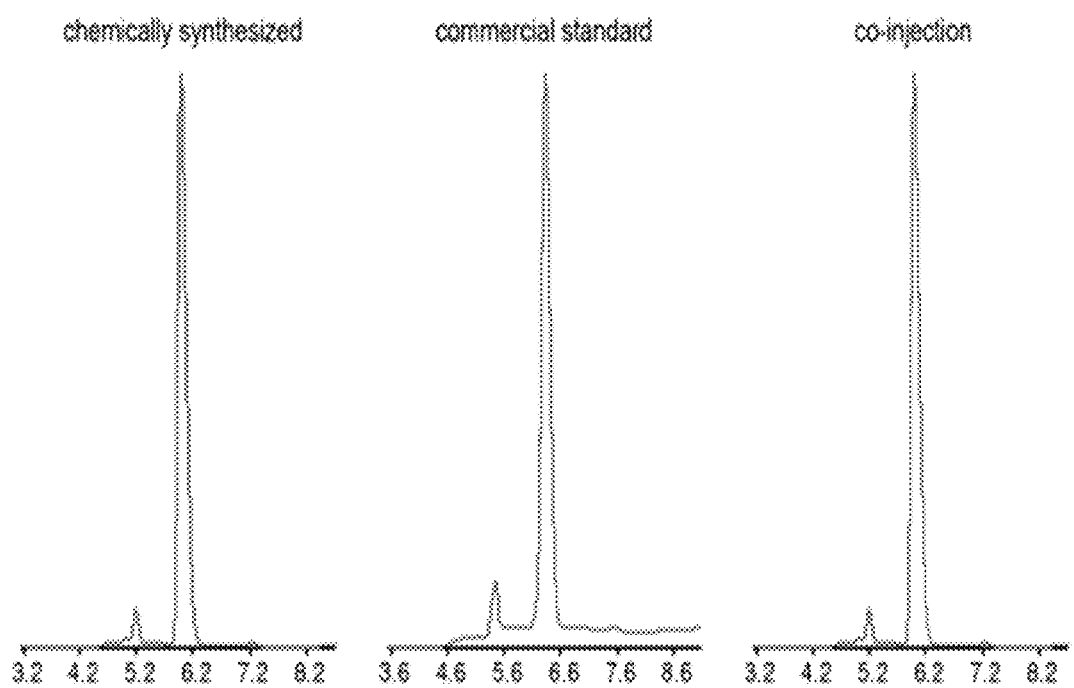

The pyrene pyrophosphate method was applied to the synthesis of natural thymidine-5'-triphosphate (dTTP). As shown in FIG. 14A FIG. 14C, activated thymidine-5'-monophosphate is readily converted to a fully protected thymidine-5'-triphosphate derivative, which was purified by silica gel chromatography, deprotected, and precipitated to obtain the desired product as a highly pure compound in sodium form. In this reaction, 10 molar equivalents of $ZnCl_2$ enabled a near quantitative coupling (>95%) of the pyrene pyrophosphate reagent to the activated nucleoside monophosphate after 3 hours of stirring in DMF at 24° C. The phosphorylation reaction also generated trace amounts (1-2%) of unwanted side products, including dinucleotide diphosphate, that were removed by silica gel purification using a 10% $H_2O$/isopropanol mobile phase containing 1% base [diisopropylethylamine, DIPEA] as an organic counterion. Following purification, the triphosphate intermediate was deprotected with concentrated ammonium hydroxide (33% aq.) and precipitated as the sodium salt using standard conditions. Analytical HPLC analysis reveals that chemically synthesized dTTP was equivalent in purity to a commercial standard (FIG. 14C), demonstrating that the process of the nucleotide triphosphate synthesis is capable of generating material that is identical in purity to commercial compounds obtained by conventional enzymatic synthesis.

Figure 15:
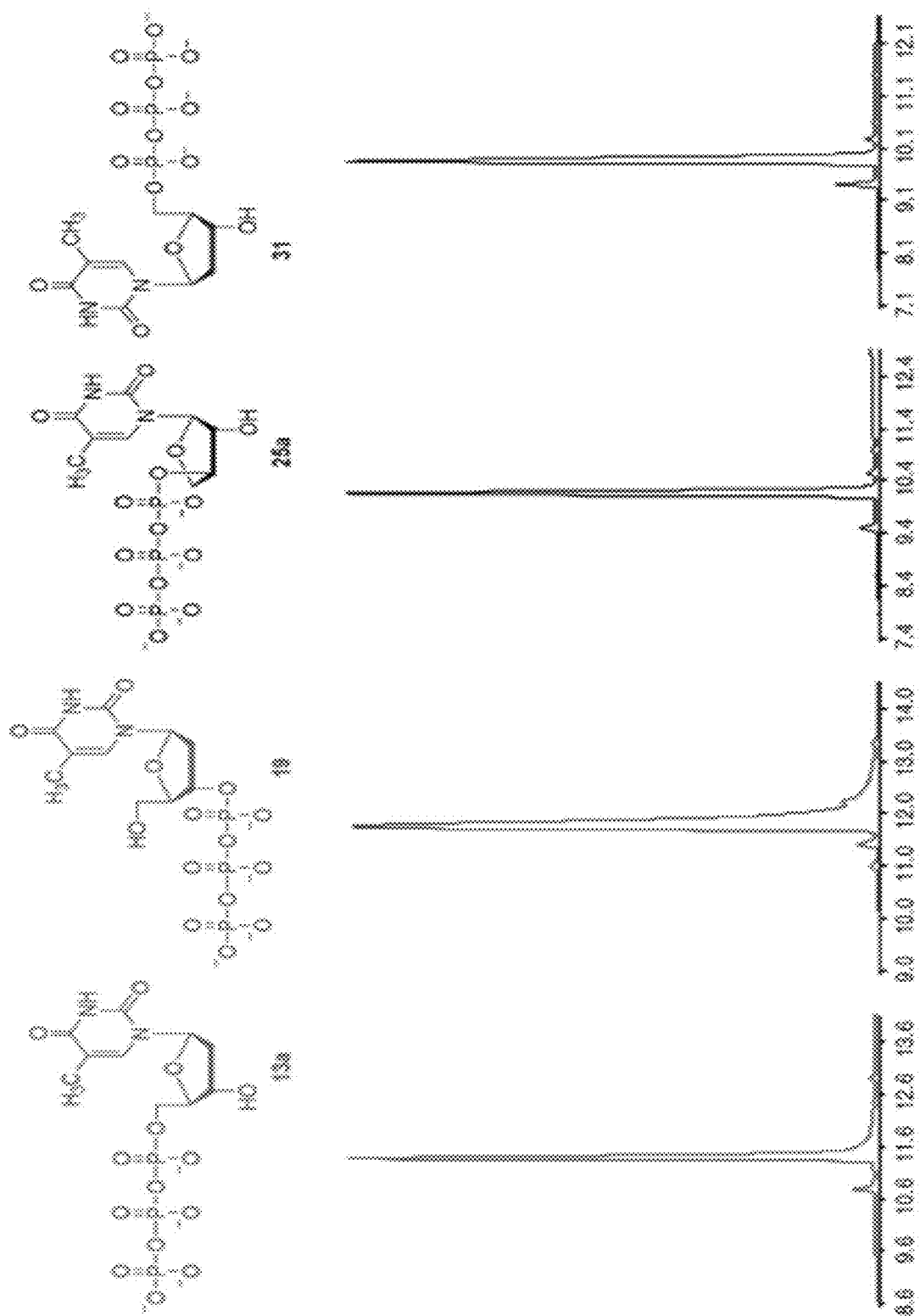
FIG. 15 depicts synthesis of thymidine triphosphate analogs. The organopyrophosphate reagent was applied to the synthesis of thymidine 3'-triphosphate, a-L-threofuranosyl thymidine 3'-triphosphate, and L-thymidine 5'-triphosphate. HPLC traces are provided after precipitation as the sodium salt.

Because enzymatic approaches are not compatible with most nucleic acid analogs, it was decided to broaden the scope of the reaction by applying the pyrene pyrophosphate method to a select panel of thymidine analogs (FIG. 15). The list of target molecules included thymidine-3'-triphosphate (a regioisomer of natural dTTP), L-threofuranosyl thymidine 3'-triphosphate (tTTP, a building block for threose nucleic acid, TNA) (Schoning et al., 2000, Science 290, 1347-1351), and L-thymidine-5'-triphosphate (the mirror image form of natural D-dTTP). The last two examples have become valuable compounds for biomedical research due to recent advances in polymerase engineering that have enabled the synthesis of artificial genetic polymers with non-natural sugar-phosphate backbones (Larsen et at, 2016, Nat. Common. 11235; Wang et al., 2016, Nat. Chem. 8, 698-704), some of which have been used to evolve biologically stable aptamers and catalysts (Pinheiro et al., 2012, Science 336, 341-344; Yu et al., 2012, Nat. Chem. 4, 183-187; Taylor et al., 2015, Nature 518, 427-430; Wang et al., 2018, Nat. Commun., in press). As with natural dTTP, each unnatural thymidine triphosphate was obtained in highly pure form (>95%) as the desired sodium salt. Occasionally, a small amount of nucleoside diphosphate (dNDP) (~1-2%) was observed after deprotection of the protected nucleoside triphosphates. dNDPs are common contaminants of commercial nucleotide triphosphates due to the slow hydrolysis of ATP to ADP (Hulett, 1970, Nature 225, 1248-1249). However, these molecules do not interfere with normal DNA synthesis as natural DNA polymerases are highly specific for dNTP substrates (Steitz al., 1994, Science 266, 2022-2025).

Next, a complete set of DNA nucleoside triphosphates (dNTPs) was prepared using the pyrene pyrophosphate method. Each activated nucleoside monophosphate was converted to the desired nucleoside triphosphate following the standard procedure of pyrene pyrophosphate coupling, purification by silica gel chromatography, deprotection with concentrated ammonium hydroxide, and precipitation as the sodium salt (FIG. 16A). Concurrently, all four TNA nucleoside triphosphates (tNTPs) were synthesized, which are the substrates for engineered TNA polymerases developed by directed evolution (FIG. 16B) (Larsen et al., 2016, Nat. Commun. 7, 11235). In all cases, analytical HPLC chromatograms reveal high conversion (>95%) of activated nucleoside triphosphate into the fully protected nucleoside triphosphate. Following deprotection and precipitation, the desired DNA and TNA nucleoside triphosphates were produced in highly pure form on scales (>500 milligrams) and timeframes (2-3 days) vastly exceeding those of traditional protocols.

Since nucleoside triphosphates would ultimately be used as substrates for oligonucleotide synthesis, the use of these reagents was investigated in a conventional DNA synthesis assay. One critical question that this study aimed to address is whether chemically synthesized DNA triphosphates function with same level of efficiency as enzymatically produced dNTPs obtained from commercial venders. To address this question, the polymerase chain reaction (PCR) was used to amplify an arbitrary DNA sample in reaction mixtures that contained either chemically synthesized or commercial dNTPs. A 200 base pair segment was amplified that defines the finger subdomain of an archaeal DNA polymerase isolated from the thermophilic species *Thermococcus kodakarensis* (Kod) (Chico et al., 2017, Nat Common 8, 1810). Analysis of the resulting PCR amplicons by agarose gel electrophoresis confirmed that chemically synthesized dNTP substrates function identically to commercial dNTPs, as both reactions produce equivalent amounts of DNA at each cycle of PCR amplification (FIG. 16A). Moreover, DNA sequencing of the amplified product failed to identify any instances of insertions, deletions, or mutations, indicating that the reactions proceed with high template-sequence fidelity.

Next, the set of chemically synthesized TNA triphosphates was evaluated as substrates for TNA synthesis using an engineered TNA polymerase (Chim et al., 2017, Nat Common 8, 1810). In this assay, a DNA primer-template complex was extended with TNA using either newly synthesized tNTPs or tNTPs obtained by a traditional Hoard-Ott-like approach that requires HPLC purification (Bala et al, 2017, J. Org. Chem. 82, 5910-5916). Analysis of the resulting primer-extension reactions by denaturing polyacrylamide gel electrophoresis reveals that the two sets of TNA substrates generate equivalent amounts of full-length TNA product after 3 hours of incubation at 55° C. (FIG. 16B), This result, along with the PCR assay, confirms that the pyrene pyrophosphate method produces high quality nucleoside triphosphates that function as substrates for natural and engineered polymerases.

Example 3: Synthesis of 1-(2-(pyrenesulfonyl)ethyl)pyrophosphate

Figure 17:
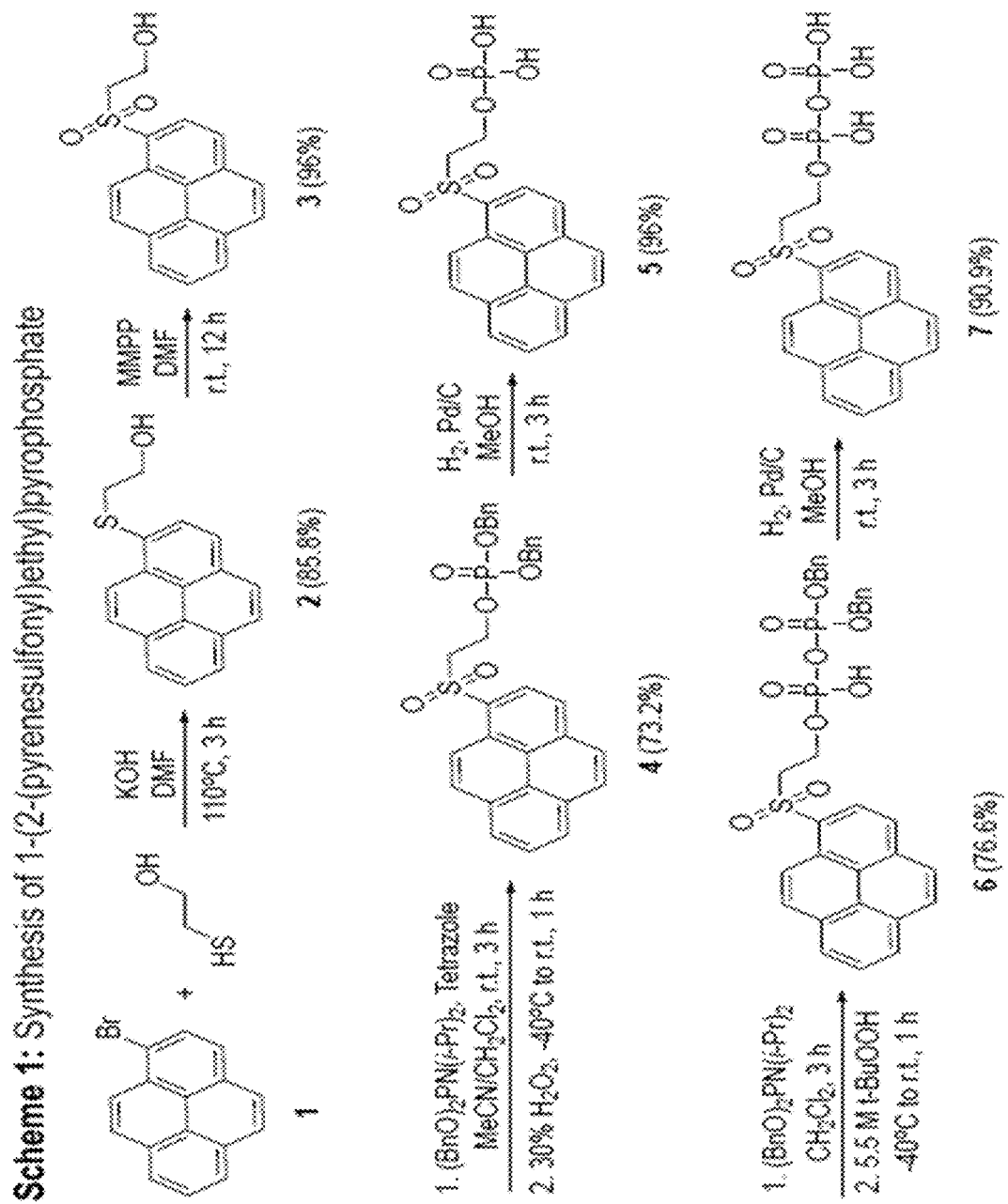
FIG. 17 depicts a synthesis scheme for (pyrenesulfonyl) ethyl)pyrophosphate (compound 7).
Figure 18:
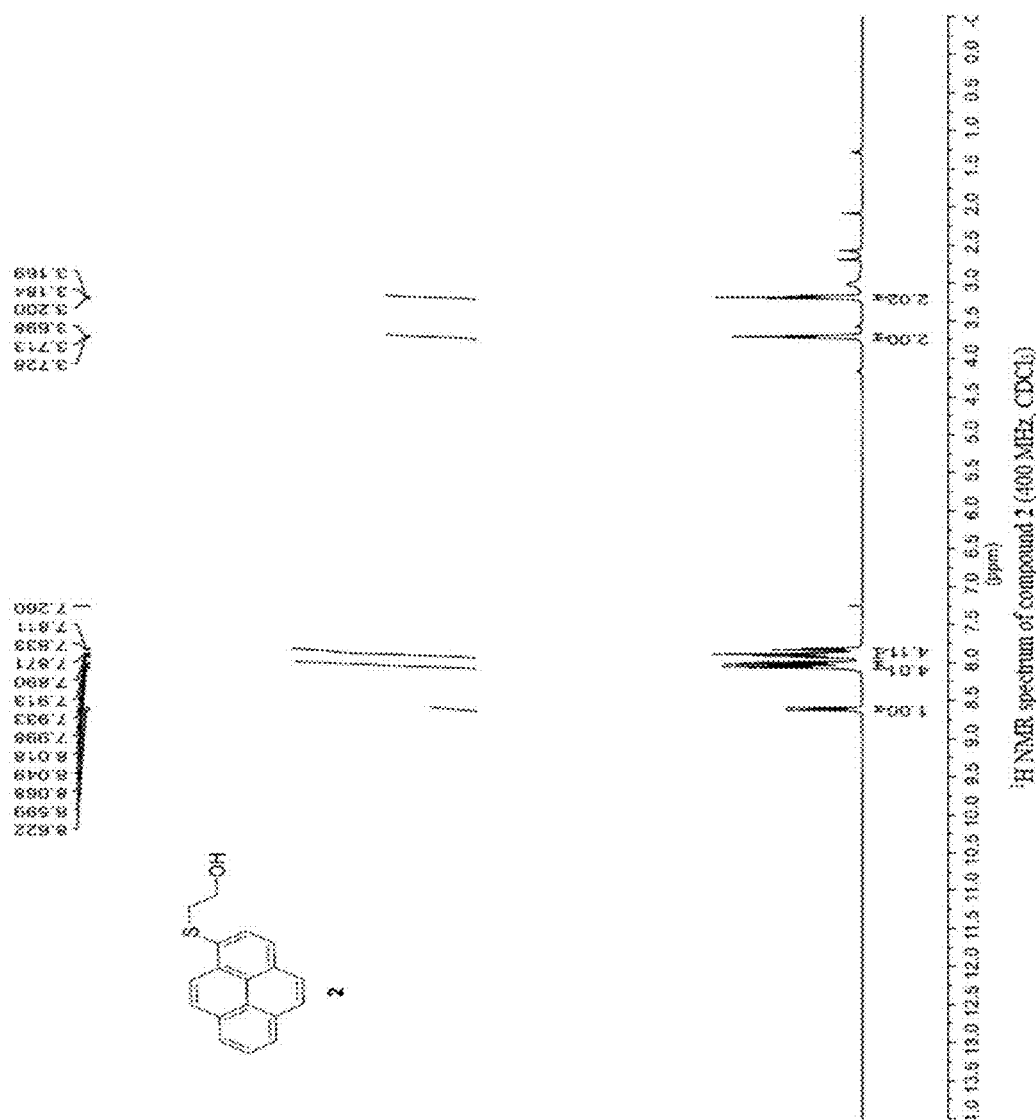
FIG. 18 depicts an $^1$H NMR spectrum of synthesized 2-(Pyrenethio)ethanol (compound 2).
Figure 19:
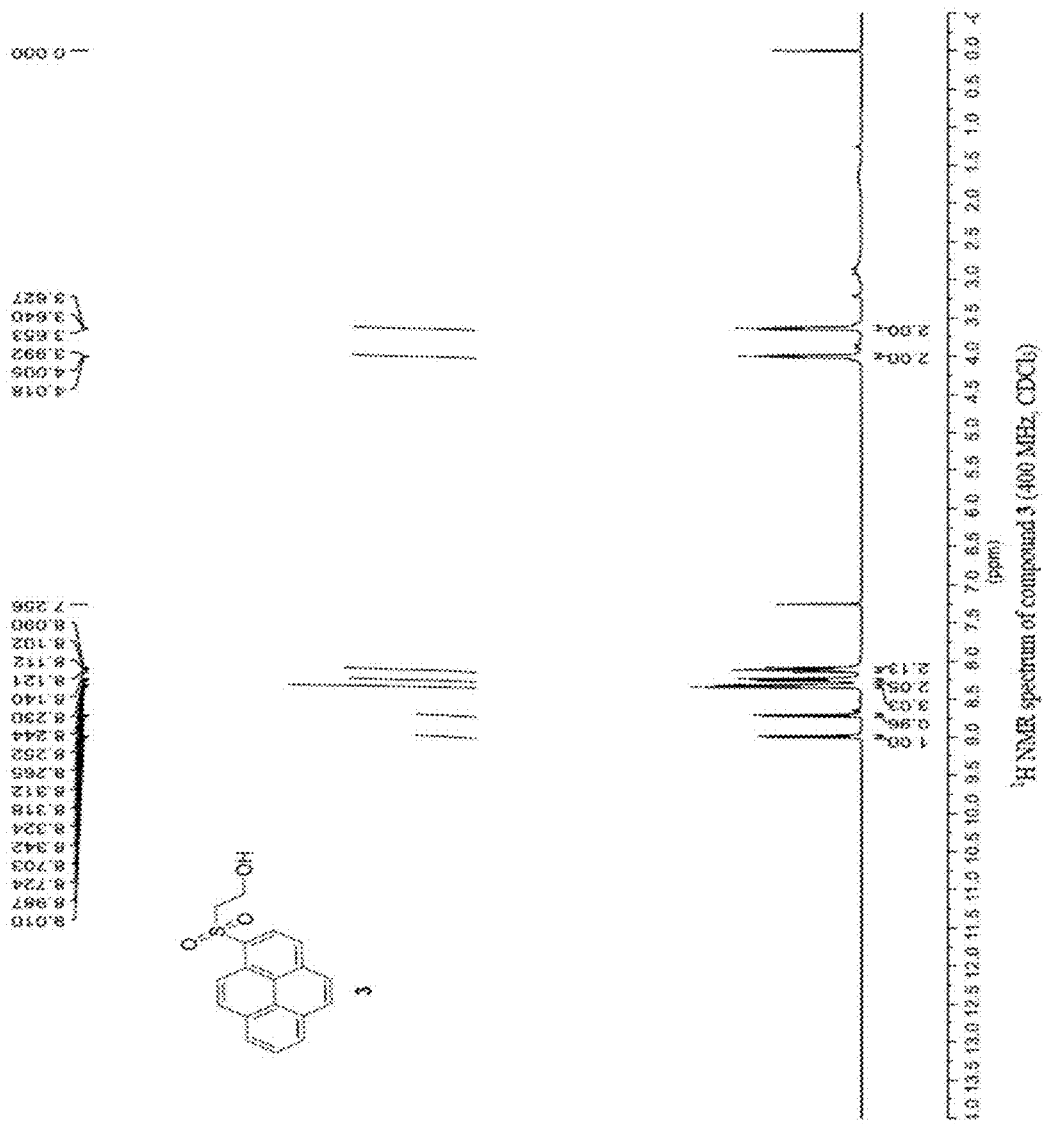
FIG. 19 depicts an $^1$H NMR spectrum of synthesized 2-(Pyrenesulfonyl)ethanol (compound 3).
Figure 20:
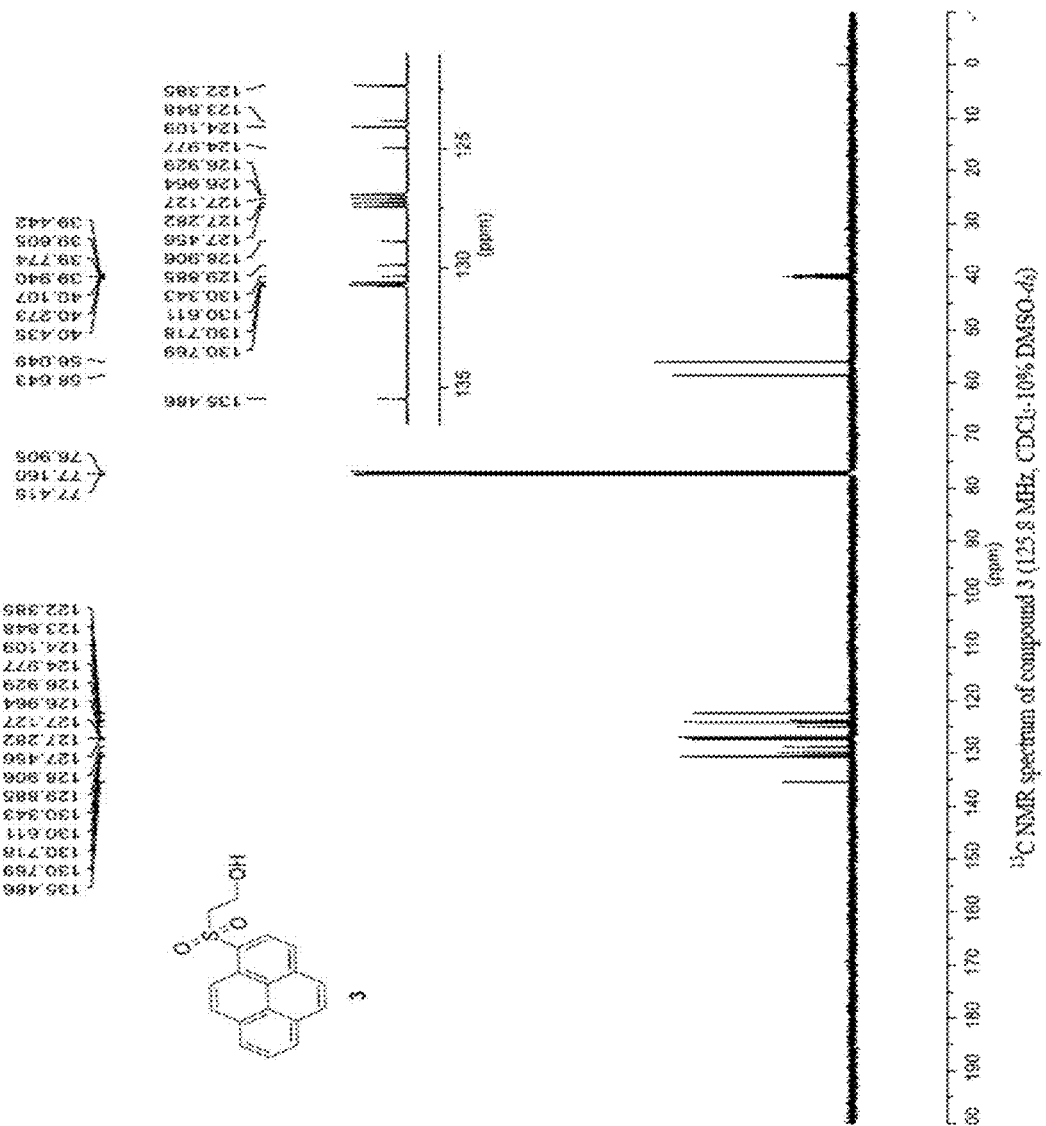
FIG. 20 depicts a $^{13}$C NMR spectrum of synthesized compound 3.
Figure 21:
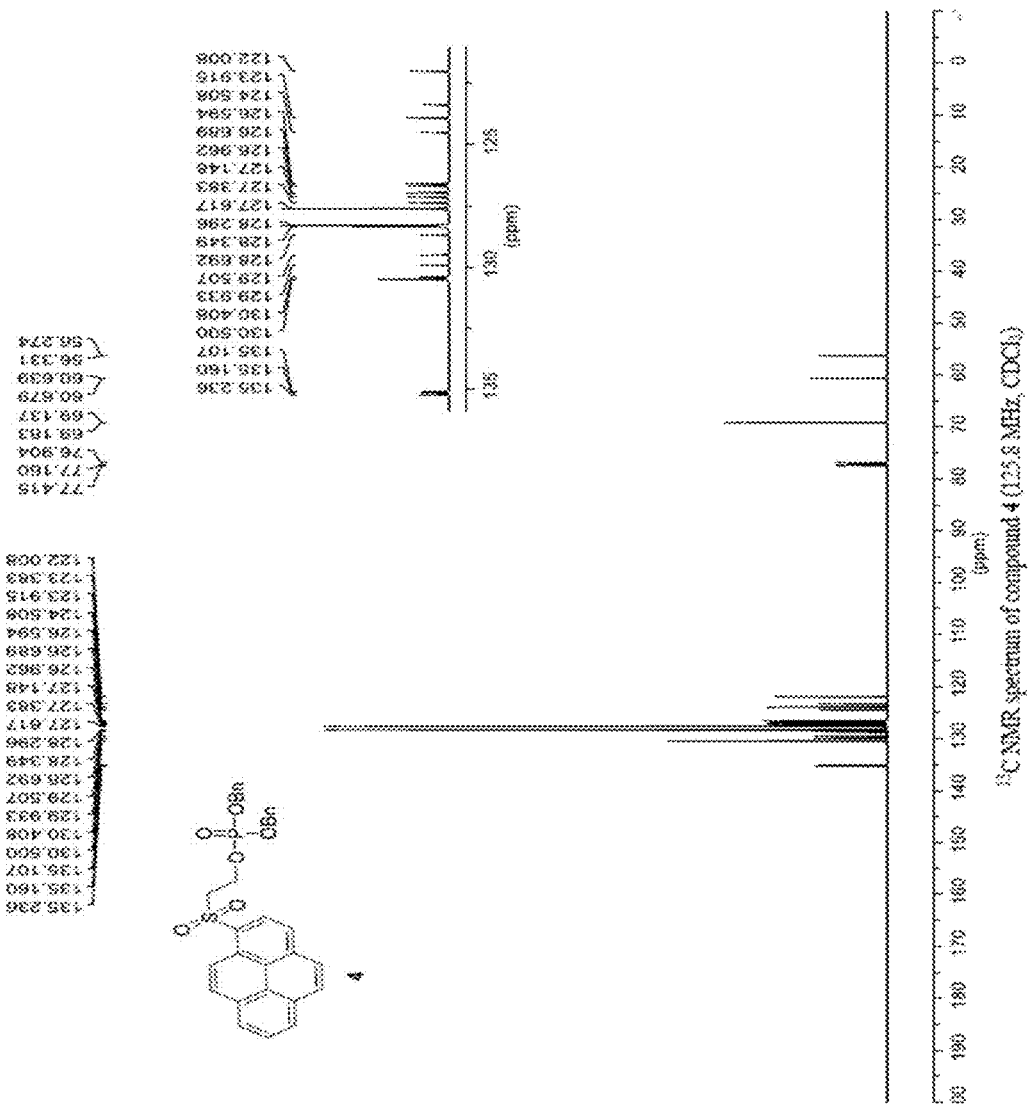
FIG. 21 depicts a $^{13}$C NMR spectrum of synthesized Dibenzyl-1-(2-(pyrenesulfonyl)ethyl) monophosphate (compound 4).
Figure 22:
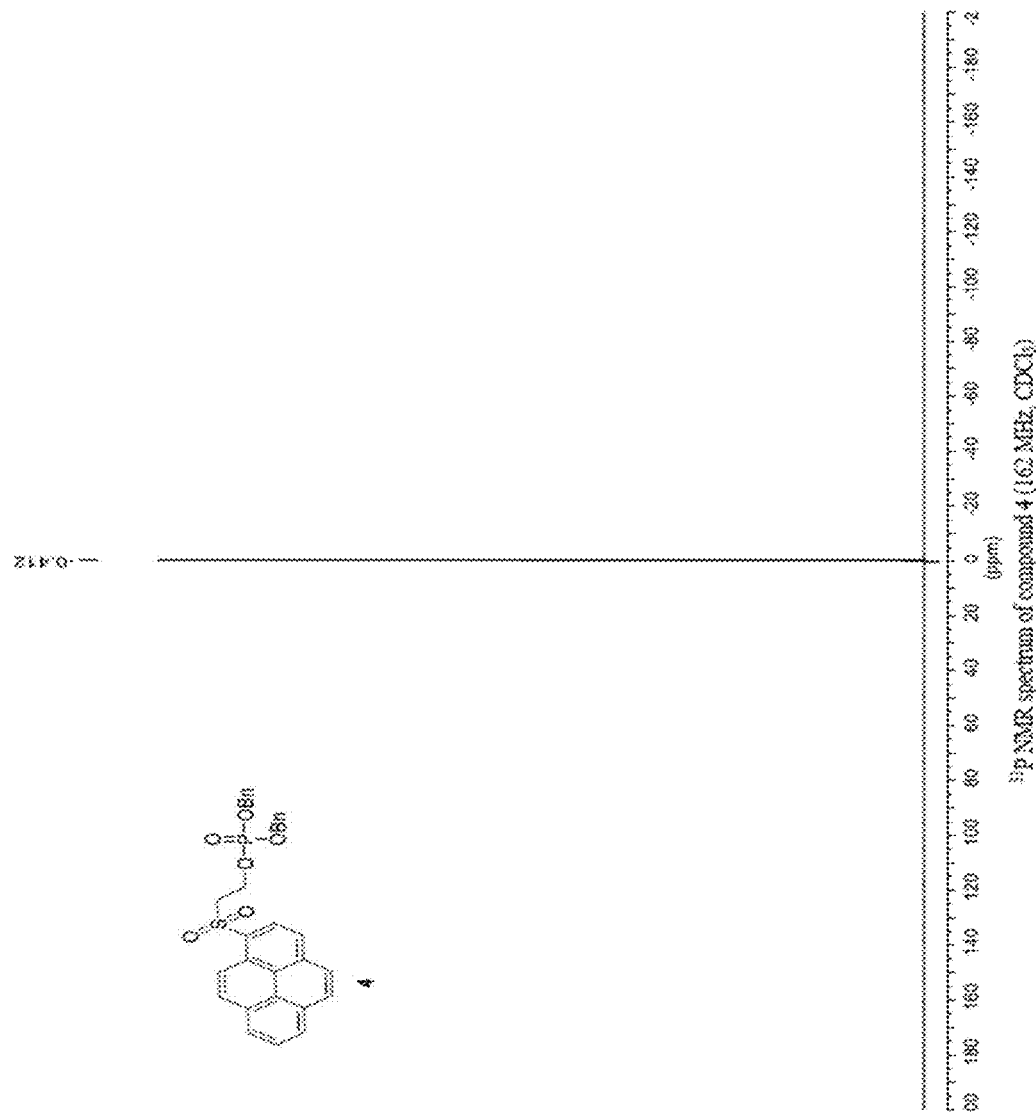
FIG. 22 depicts an $^{31}$P NMR spectrum of synthesized compound 4.
Figure 23:
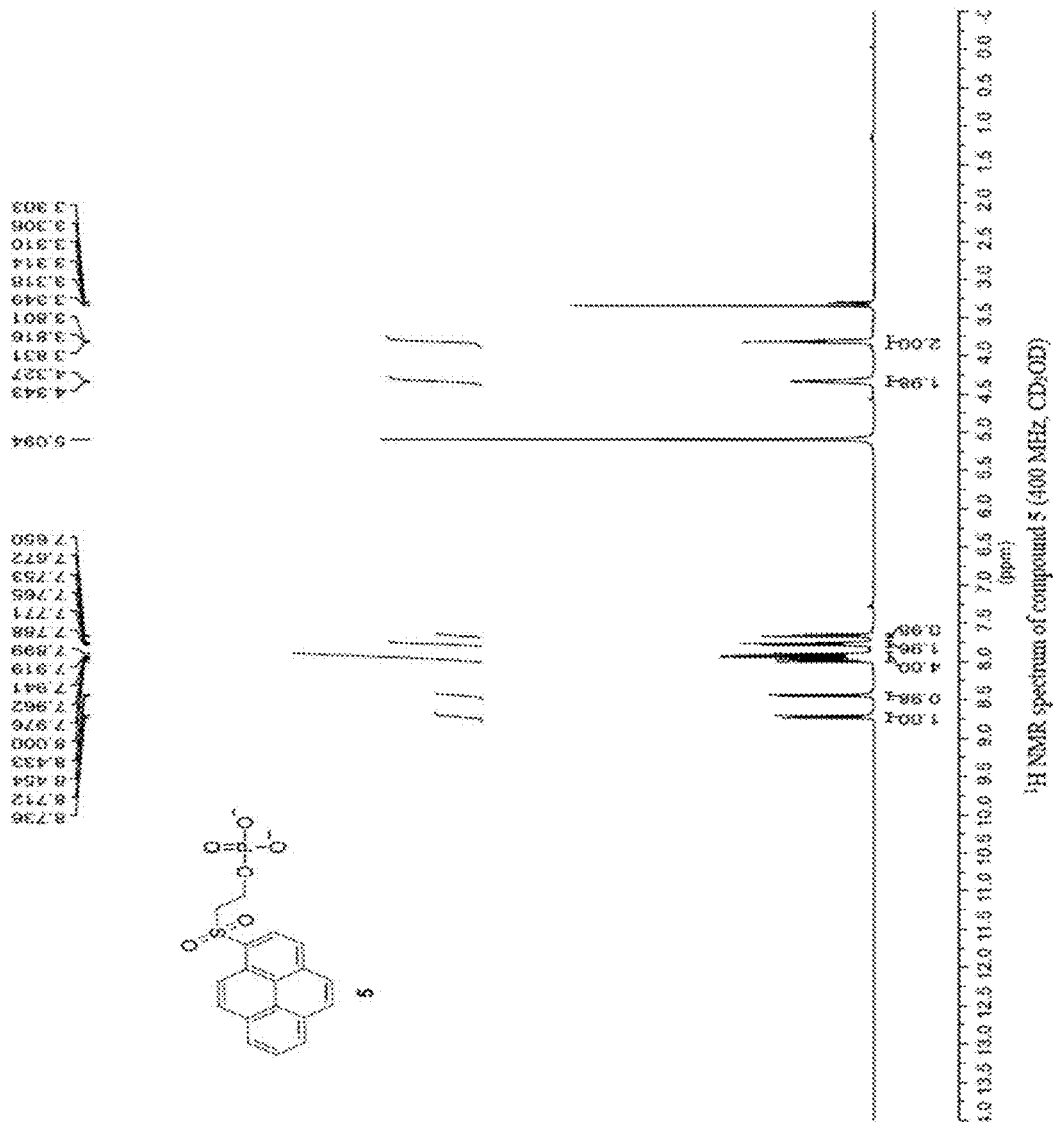
FIG. 23 depicts an $^1$H NMR spectrum of synthesized 1-(2-(Pyrenesulfonyl)ethyl) monophosphate (compound 5).
Figure 24:
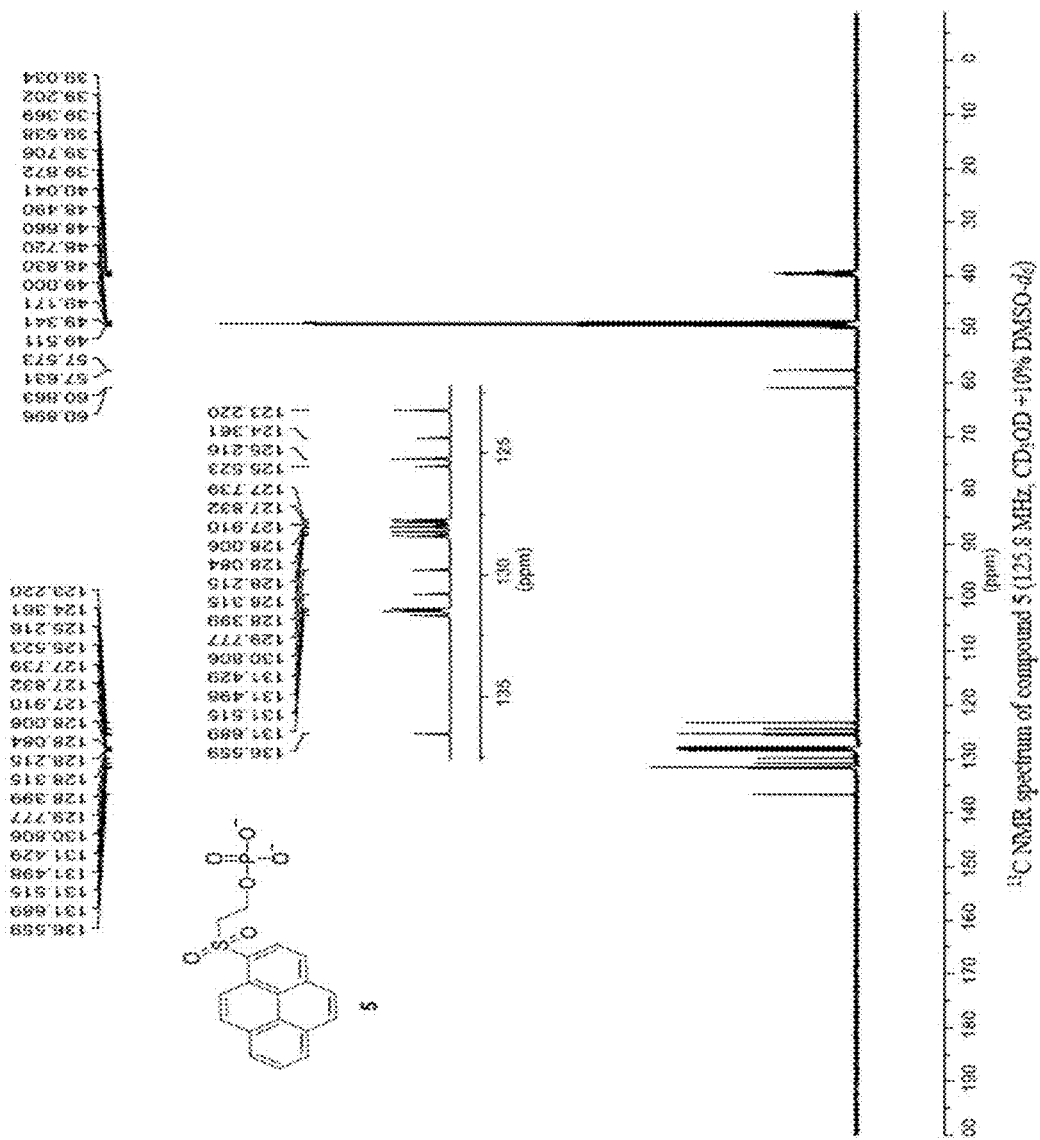
FIG. 24 depicts a $^{13}$C NMR spectrum of synthesized compound 5.
Figure 25:
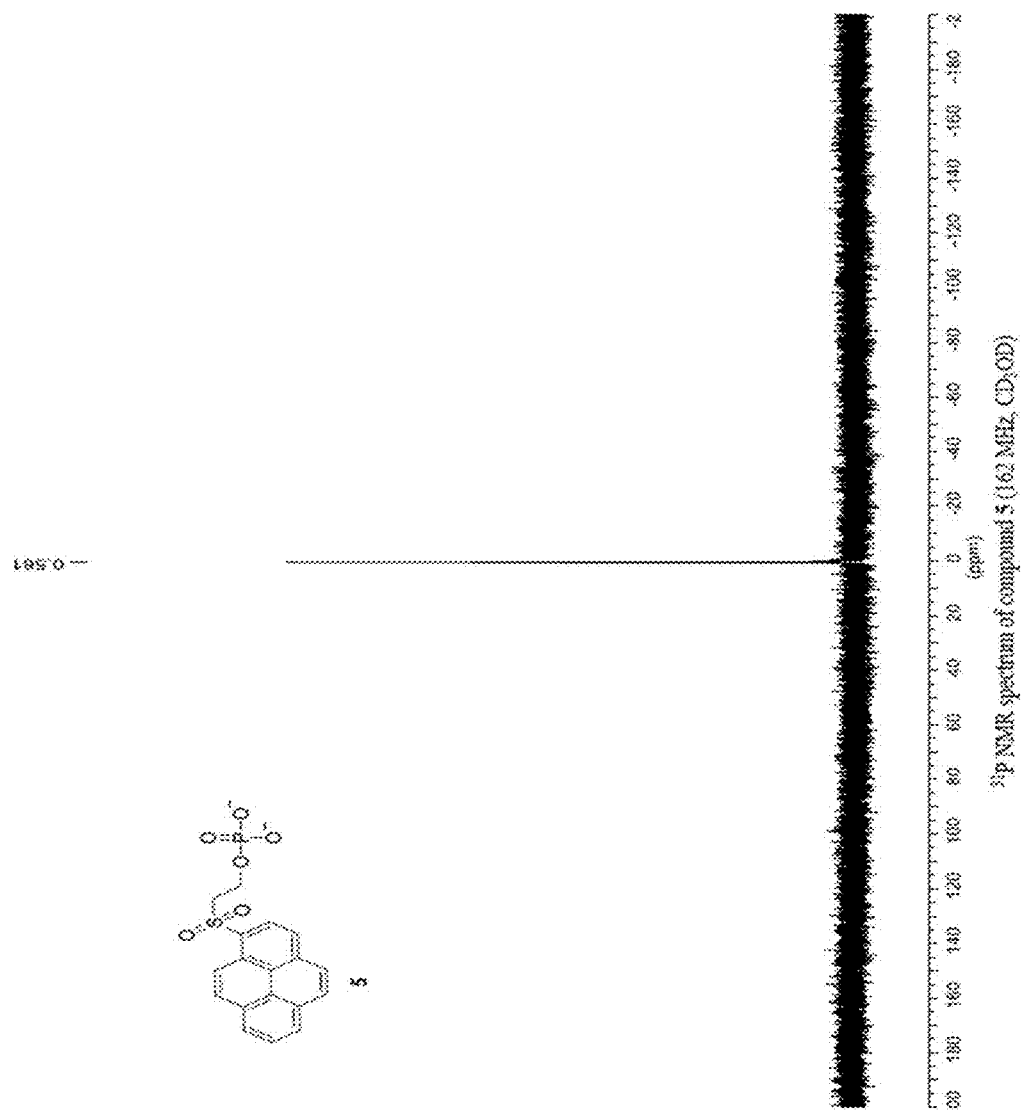
FIG. 25 depicts an $^{31}$P NMR spectrum of synthesized compound 5.
Figure 26:
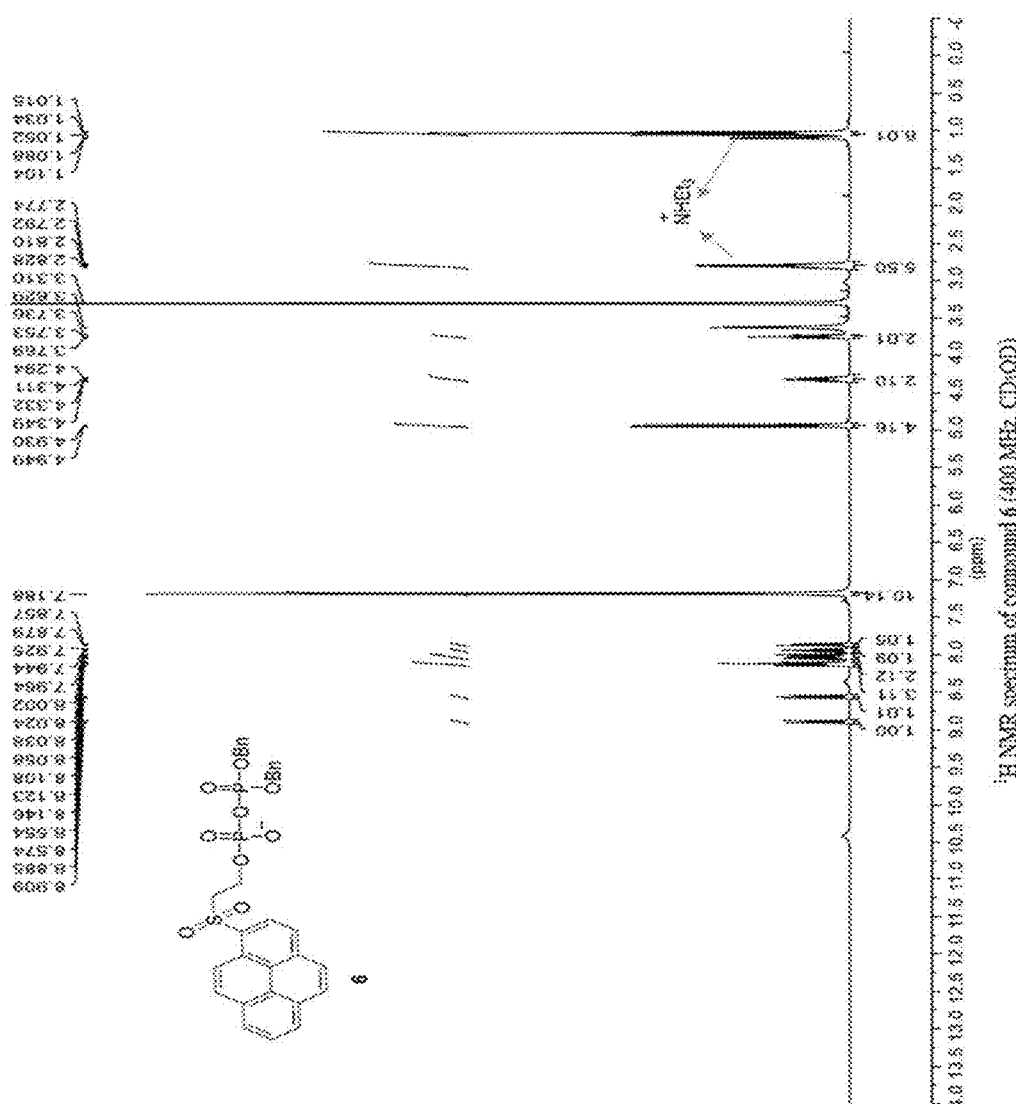
FIG. 26 depicts an $^1$H NMR spectrum of synthesized 1-(2-(Pyrenesulfonyl)ethyl)-(β-dibenzyl)pyrophosphate (compound 6)
Figure 27:
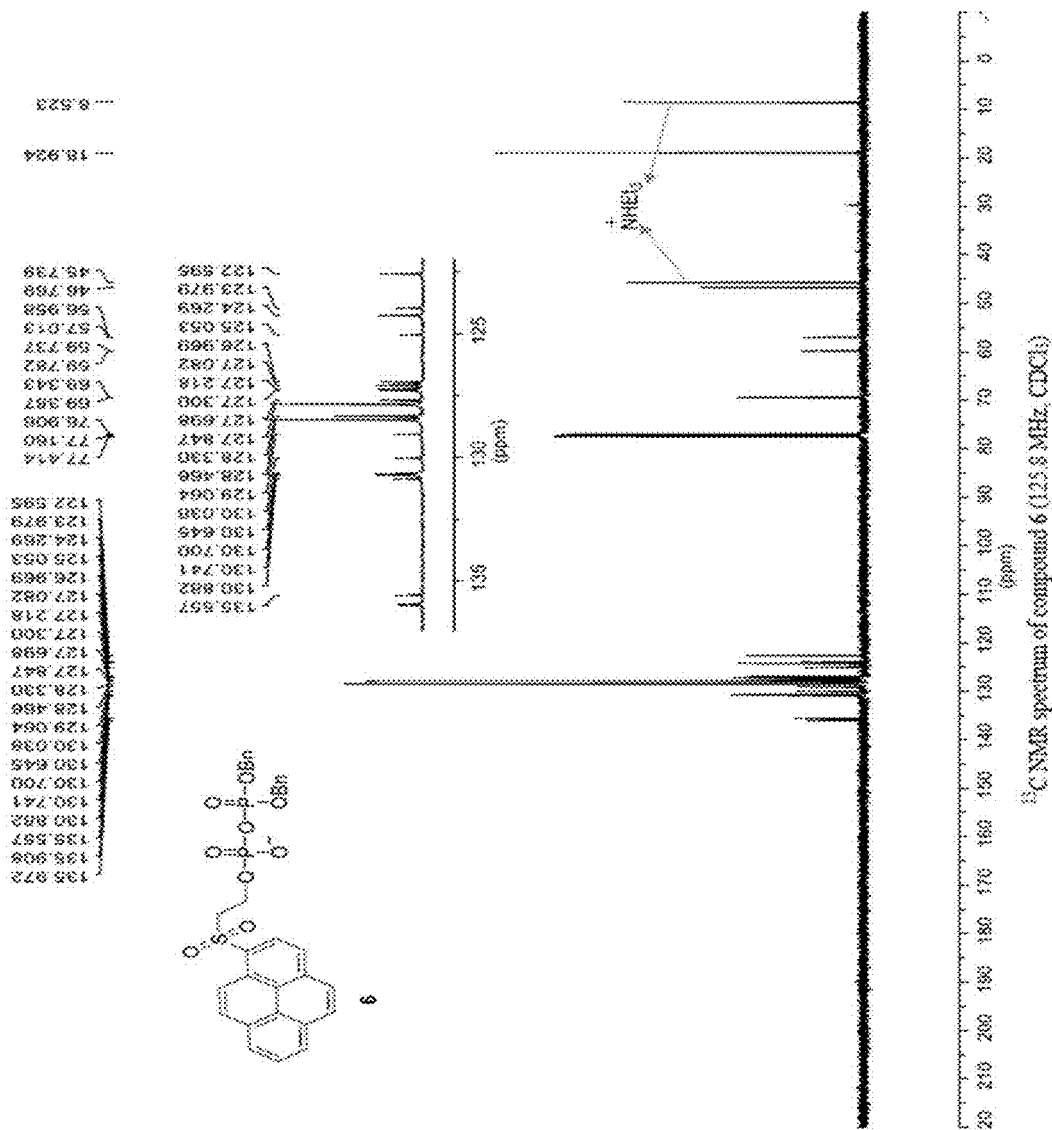
FIG. 27 depicts a $^{13}$C NMR spectrum of synthesized compound 6.
Figure 28:
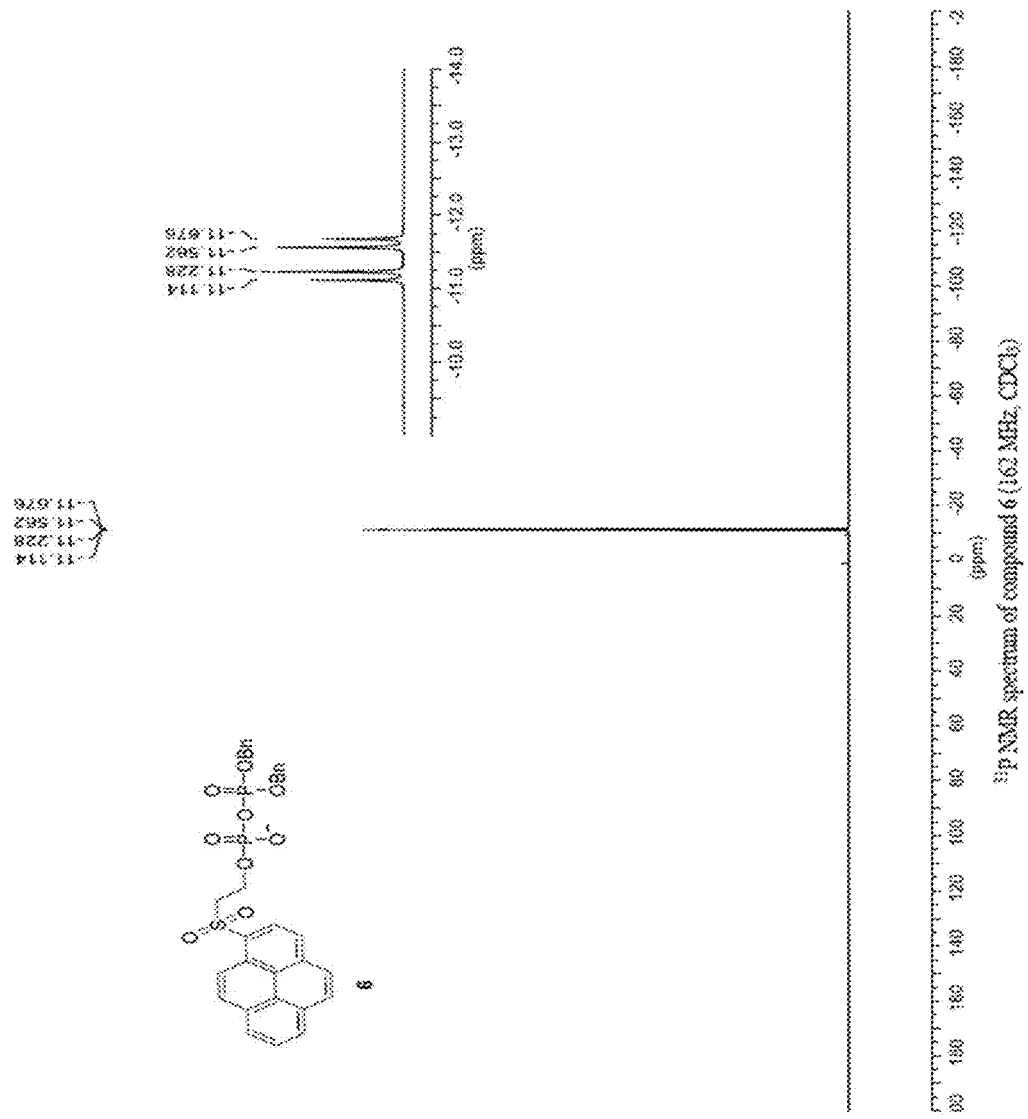
FIG. 28 depicts an $^{31}$P NMR spectrum of synthesized compound 6.
Figure 29:
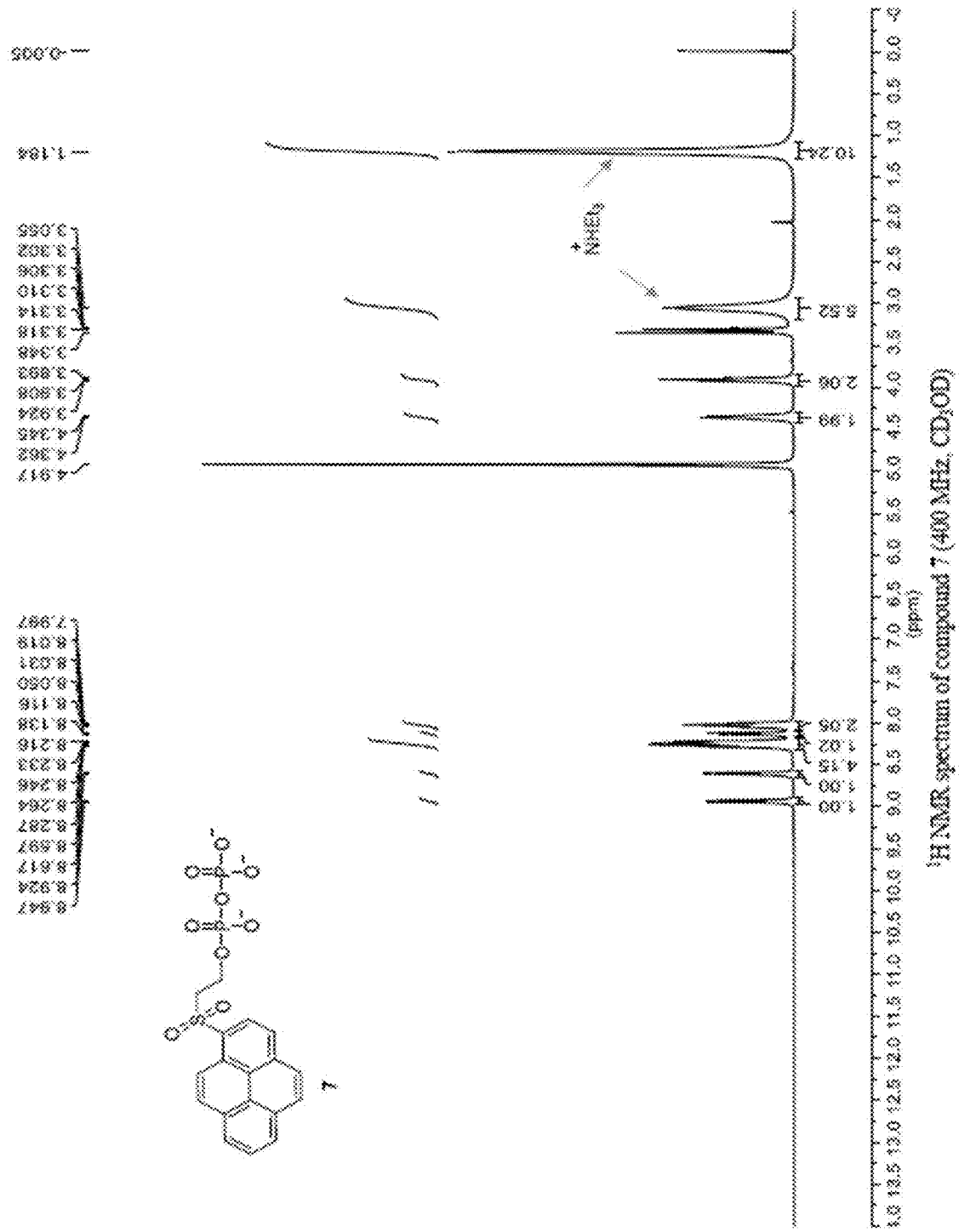
FIG. 29 depicts an $^1$H NMR spectrum of synthesized compound 7.
Figure 30:
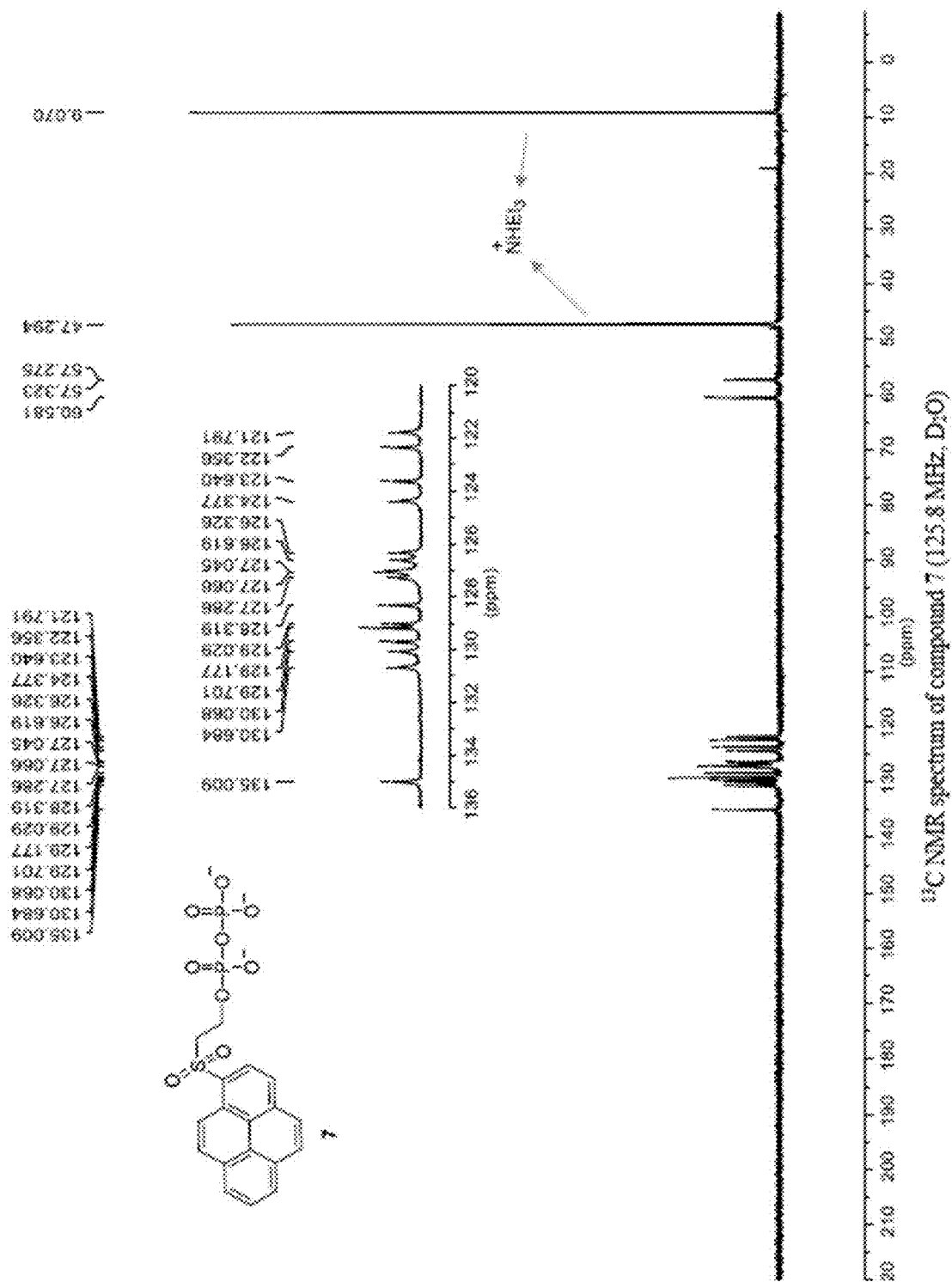
FIG. 30 depicts a $^{13}$C NMR spectrum of synthesized compound 7.
Figure 31:
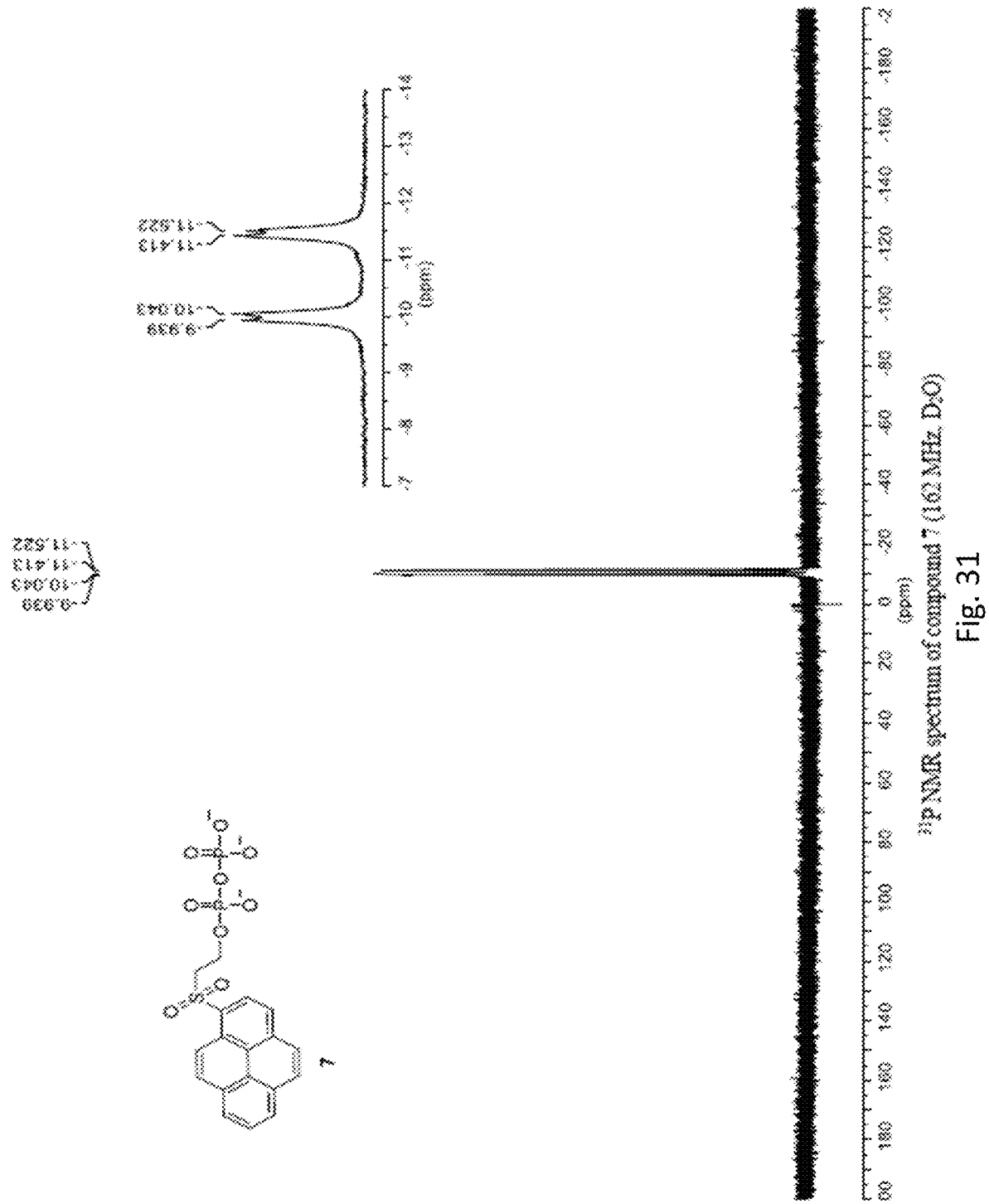
FIG. 31 depicts an $^{31}$P NMR spectrum of synthesized compound 7.

FIG. 17 shows the synthesis scheme for 1-(2-(pyrenesulfonyl)ethyl)pyrophosphate (compound 7), FIG. 18 through FIG. 31 provide spectra of the synthesized intermediates and product.

Methods used for the synthesis are now described.

2-(Pyrenethio)ethanol (Compound 2)

To a solution containing 9.98 g (177.8 mmol) of potassium hydroxide in 250 mL of anhydrous DMF was added 12.5 mL (177.8 mmol) of 2-mercaptoethanol. The reaction mixture was heated to 80° C. with stirring until potassium hydroxide dissolved. A premade solution containing 25 g (88.92 mmol) of 1-bromopyrene (compound 1) in 200 mL of anhydrous DMF was dropwise added to the reaction and stirred at 110° C. for 3 hours. Then, the reaction was cooled to room temperature, condensed to 100 mL of solution under diminished pressure and diluted into 500 mil, of $CH_2Cl_2$. The organic layer was washed with 200 mL of $H_2O$ four times. And the combined aqueous layer was back extracted with 200 mL of $CH_7Cl_2$ two times. The organic layers were combined and evaporated to the dryness under diminished pressure. The crude product was purified by silica column chromatography with eluents ($CH_2Cl_2$/Hexane, 25% to 50%, then EtOAc/$CH_2Cl_2$, from 0% to 2%) to afford the compound 2 as a yellowish solid; yield: 21.3 g (85.8%); silica gel TLC (EtOAc/Hexane, 1:2) $R_f$=0.35; NMR (400 MHz, $CDCl_3$) δ 8.61 (d, 1H, J=9.2 Hz), 8.07-8.00 (m, 4H), 7.93-7.81 (m, 4H), 3.71 (t, 2H, J=6.0 Hz), 3.18 (t 2H, J=6.0 Hz); HRMS (ESI-TOF) calcd. for $C_{18}H_{14}OSNa$ $[M+Na]^+$ 301.0663. found 301.0658. Compound 2 has been reported in Kathayat et al., 2013, J. Am. Chem. Soc. 135, 12612-12614.

2-(Pyrenesulfonyl)ethanol (Compound 3

To a solution containing 71 g (114.9 mmol, 80% technical grade) of magnesium bis(monoperoxyphthalate) hexahydrate in 0.450 mL of anhydrous DMF was slowly added a pre-made solution of 21.3 g (76.6 mmol) of compound (2) in 150 of anhydrous DMF at 0° C. The reaction was stirring at room temperature for 12 hours. At which the TLC showed the reaction was finished, the reaction was dropwise added to a solution containing 2 L of satd. $NaHCO_{3(aq)}$ while stirring. The precipitate was washed with 300 mL of $H_2O$ twice, and dried under high vacuum to afford the compound 3 as a yellowish solid; yield: 22.8 g (96%); silica gel TLC (EtOAc/$CH_2Cl_2$. 1:20) $R_f$=0.22; $^1H$ NMR (400 MHz, $CDCl_3$) δ 9.00 (d, 1H, J=9.2 Hz), 8.71 (d, 1H, J=8.4 Hz), 8.34-8.31 (m, 3H), 8.27-8.23 (m, 2H), 8.14-8.09 (in, 214), 4.00 (t, 21H, J=5.2 Hz), 3.64 (t, 2H, J=5.2 Hz); $^{13}C$ NMR (125.8 MHz, $CDCl_{3-10}$% DMSO-$d_6$) δ 135.5, 130.8, 130.7, 130.6, 130.3, 129.9, 128.9, 127.5, 127.2, 127.1, 127.0, 126.9, 125.0, 124.1, 123.9, 122.4, 58.6, 56.1; HRMS (ESI-TOF) calcd. for $C_{18}H_{14}O_3SNa$ $[M+Na]^+$ 333.0561. found 333.0571.

Dibenzyl-1-(2-(pyrenesulfonyl)ethyl) Monophosphate (Compound 4)

To a mixture containing 5 g (16.13 mmol) of 2-(pyrenesulfonyl)ethanol (compound 3), 2.03 g (29.03 mmol) of tetrazole in 106 mL of anhydrous solution (MeCN/CH$_2$Cl$_2$, 1:1) was slowly added 6.64 mL (20.96 mmol) of (BnO)$_2$PN(i-Pr)$_2$ at room temperature. The reaction was sonicated until the solid disappeared (otherwise add additional 20 mL of anhydrous DMF) and the mixture was stirring at room temperature for 3 hours. Then reaction was cooled to −40° C. followed by adding 15 mL of H$_2$O (33% in 1-120) for additional 1 h stirring at room temperature. The solution was condensed to 20 mL under diminished pressure and poured to 150 mL EtOAc. The organic layer was washed with 100 mL brine, 200 mL satd. NaHCO$_3$, 200 mL H$_2$O, dried over MgSO$_4$ and evaporated under diminished pressure. The crude product was purified by silica column chromatography with eluent (CH$_2$Cl$_2$/Hexane, from 25% to 100%, then MeOH/CH$_2$Cl$_2$, from 1% to 3%) to afford the yellowish solid product, compound 4; yield: 6.73 g (73.2%); TLC (EtOAc/CH$_2$Cl$_2$ 1:20) R$_f$=0.34; $^1$H NMR (400 MHz, CDCl$_3$) δ 8.89 (d, 1H, J=9.2 Hz), 8.60 (d, 1H, J=8.0 Hz), 8.15-8.11 (m, 3H), 8.01-7.94 (m, 3H) 7.82 (d, J 8.8 Hz), 7.20-7.16 (m, 611), 7.06-7.04 (m, 4H), 4.67 (d, 4H, J=8.4 Hz), 4.36 (dd, 2H, J=14, 6.0 Hz), 3.70 (t, 2H, J=6.0 Hz); $^{13}$C NMR (125.8 MHz, CDCl$_3$) δ135.2, 135.2, 135.1, 130.5, 130.4, 129.9, 129.5, 128.7, 128.3, 128.3, 127.6, 127.4, 127.1, 127.0, 126.7, 126.6, 124.5, 123.9, 123.4, 122.0, 69.2 (d, J$_C$, P=5.8 Hz), 60.7 (d, J$_C$, P=5.0 Hz), 56.3 (d, J$_C$, P=7.2 Hz); $^{31}$P NMR (162 MHz, CDCl$_3$) δ −0.41; HRMS (ESI-TOF) calcd. for C$_{32}$H$_{27}$O$_6$PSNa [M+Na]$^+$ 593.1164. found 593.1158.

1-(2-(Pyrenesulfonyl)ethyl) Monophosphate (Compound 5)

To a solution containing 6.73 g (11.8 mmol) of dibenzyl-1-(2-(pyrenesulfonyl)ethyl) monophosphate (compound 4) in 50 mL of MeOH was purged with nitrogen gas. The solution was added to 0.1-0.2 mass equivalent of 10% Pd/C, and repurged with nitrogen gas followed by adding hydrogen gas. The mixture was stirred at room temperature for 3 hours with monitoring by TLC (MeOH/CH$_2$Cl$_2$, 1:10 with 1% Et$_3$N), The resulting suspension was filtered over a pad of celite, washed with 100 mL of MeOH four times, evaporated, and then coevaporated with dry C$_2$H$_1$Cl$_2$ under reduced pressure to afford the product, compound 5, as a yellowish solid; yield 4.42 g (96%); TLC (MeOH/CH$_2$Cl$_2$, 1:10 with 1% triethylamine) R$_f$=0; $^1$H NMR (400 MHz, CD$_3$OD) δ 8.72 (d, 1H, J=9.6 Hz), 8.44 (d, 1H, J=8.4 Hz), 8.00-7.90 (m, 4H), 7.79-7.75 (m, 2H), 7.66 (d, 1H, J=8.8 Hz), 4.34 (dd, 2H, J=12.4, 6.0 Hz), 3.82 (t, 214, J==6.0 Hz); $^{13}$C NMR (125.8 MHz, CD$_3$OD+10% DMSO-d$_6$) δ 136.6, 131.7, 131.5, 131.5, 131.4, 130.8, 129.8, 128.4, 128.2, 128.0, 127.8, 127.7, 125.5, 125.2, 124.4, 123.2, 60.9 (d, J$_C$, P=4.2 Hz), 57.6 (d, J$_C$, P=7.2 Hz); $^{31}$P NMR (162 MHz, CD$_3$OD) δ −0.56. HRMS (ESI-TOF) calcd. for C$_{18}$H$_{14}$O$_6$PS [M−H]$^-$ 389.0249. found 389.0234.

1-(2-(Pyrenesulfonyl)ethyl)-(β-dibenzyl)pyrophosphate (Compound 6)

To the 4.42 g (11.3 mmol) of 1-(2-(pyrenesulfonyl)ethyl) monophosphate (compound 5) in 39.3 mL of anhydrous dichloromethane was added 5.33 mL (15.82 mmol) of (BnO)$_2$PN(i-Pr)$_2$ at room temperature under a nitrogen atmosphere. After two hours stirring, the reaction was slowly added to 6.16 mL (33.9 mmol) of tert-butyl hydrogen peroxide (5.5 Min decane) at −40° C. and stirred for an additional 30 minutes at room temperature. The reaction was evaporated under diminished pressure and the crude product was purified by silica column chromatography with the eluents (MeCN then MeOH/CH$_2$Cl$_2$ from 1% to 3% containing 1% triethylamine) to afford the solid product, compound 6; yield: 6.5 g (76.6%); TLC (2:100 MeOH—CH$_2$Cl$_2$ with 1% triethylamine) 0.26; $^1$H NMR (400 MHz, CD$_3$OD) 8.90 (d, 1H, J=9.6 Hz), 8.56 (d, 1H, J=8.0 Hz), 8.15-8.11 (m, 3H), 8.06-8.00 (m, 211), 7.94 (t, 1H, J=8.0 Hz), 7.87 (d, 1H, J=8.8 Hz), 7.19 (m, 10H), 4.94 (d, 4H, J=7.6 Hz), 4.32 (dd, 2H, J=15.2, 6.8 Hz), 3.75 (t, 2H, J=6.8 Hz); $^{13}$C NMR (125.8 MHz, CDCl$_3$)<136.0, 135.9, 135.6, 130.9, 130.7, 130.7, 130.6, 130.0, 129.1, 128.5, 128.3, 127.8, 127.7, 127.3, 127.2, 127.1, 127.0, 125.1, 124.3, 124.0, 122.6, 69.3 (d, J$_C$, P=5.5 Hz), 59.7 (d, J$_C$, P=5.5 Hz), 57.0 (d, J$_C$, P=6.9 Hz); $^{31}$P NMR (162 MHz, CDCl$_3$) δ −11.2 (d, 18.5 Hz), −11.6 (d, J=18.5 Hz); HRMS (ESI-TOF) calcd. for C$_{32}$H$_{27}$O$_9$P$_2$SNa$_2$ [M−H+2Na]$^+$ 695.0646. found 695.0660.

1-2-(Pyrenesulfonyl)ethyl)pyrophosphate (Compound 7)

To a solution containing 6.5 g of 1-(2-(pyrenesulfonyl) ethyl)-β-dibenzyl)pyrophosphate (compound 6) in 30 mL of MeOH was purged with nitrogen gas. The solution was added to 0.1-0.2 mass equivalent of 10% Pd/C and purged with nitrogen gas followed by adding hydrogen gas. The mixture was stirred at room temperature for 3 h with monitoring by TLC (MeOH/CH$_2$Cl$_2$, 1:10 with 1% Et$_3$N). The resulting suspension was filtered over a pad of celite, washed with 100 mL of MeOH three times, evaporated, and coevaporated with dry C$_2$H$_4$Cl$_2$ under reduced pressure to afford the product as a yellowish solid (compound 7); yield: 4.27 g (90.9%); TLC (MeOH/CH$_2$Cl$_2$, 1:10 with 1% triethylamine) R$_f$=0; $^1$H NMR (400 MHz, CD$_3$OD) 8.93 (d, 1H, J=9.2 Hz), 8.61 (d, 1H, J=8.0 Hz), 8.29-8.22 (m, 4H), 8.13 (d, 8.8 Hz), 8.05-8.00 (m, 2H), 4.35 (m, 2H), 3.91 (t, 2H, J=10.4 Hz); $^{13}$C NMR (125.8 MHz, D$_2$O) δ 135.0, 130.7, 130.1, 129.7, 129.2, 129.0, 128.3, 127.3, 127.1, 127.0, 126.6, 126.3, 124.4, 123.6, 122.4, 121.8, 60.6, 57.3 (d, J$_C$, P=6.0 Hz); $^{31}$P NMR (162 MHz, D$_2$O) δ −10.0 (d, J=16.8 Hz), −11.5 (d, 16.8 Hz); HRMS (ESI-TOF) calcd. for C$_{18}$H$_{14}$O$_9$P$_2$SNa$_3$[M−2H+3Na]$^+$ 536.9527. found 536.9521.

Example 4: Synthesis of Nucleoside Triphosphates

Figure 32:
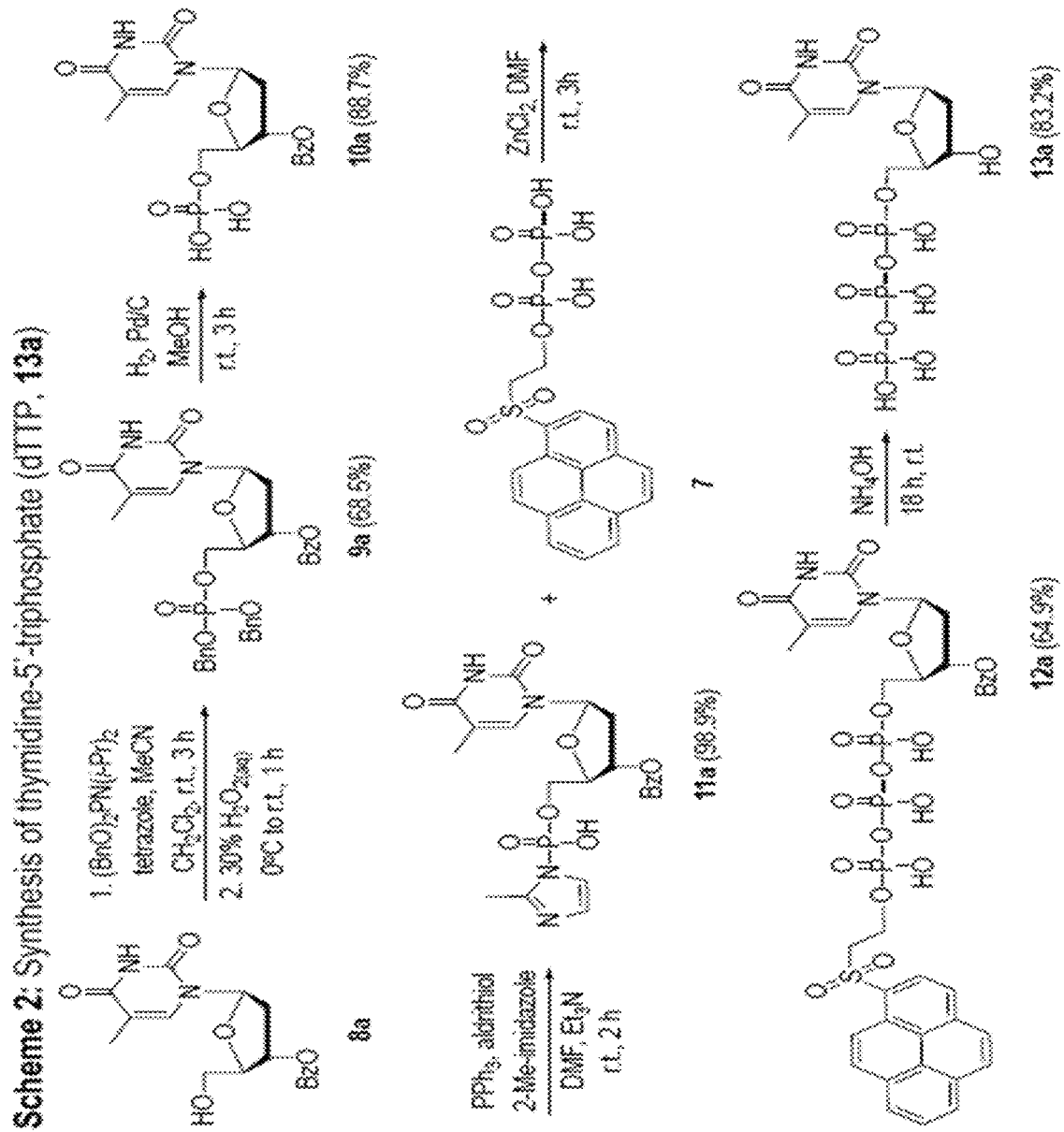
FIG. 32 depicts a synthesis scheme for 1-(2-(pyrenesulfonyl)ethyl)pyrophosphate (dTTP, compound 13a).
Figure 33:
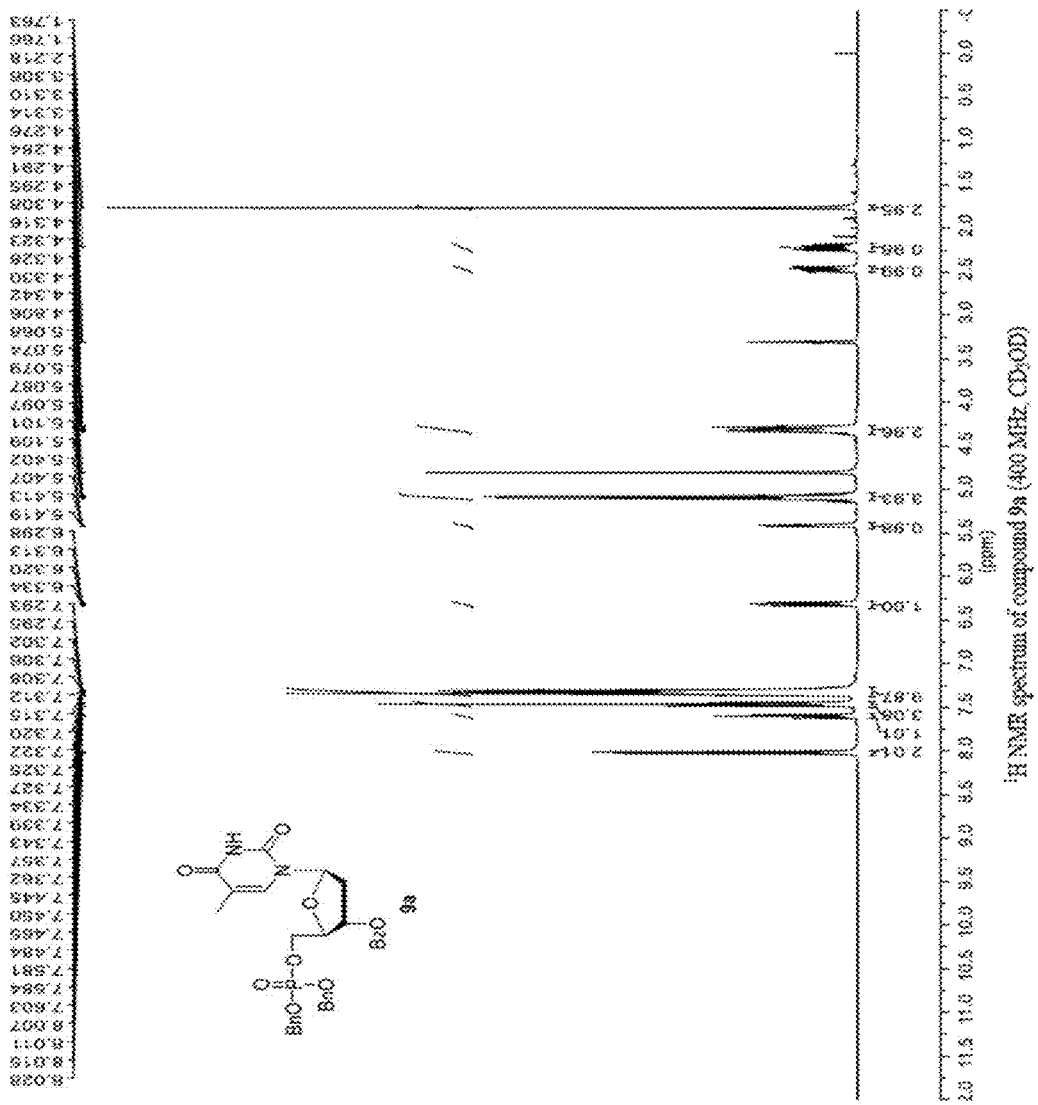
FIG. 33 depicts an $^1$H NMR spectrum of synthesized 3'-O-Benzoyl-2'-deoxythymidine-5'-dibenzylmonophosphate (compound 9a).
Figure 34:
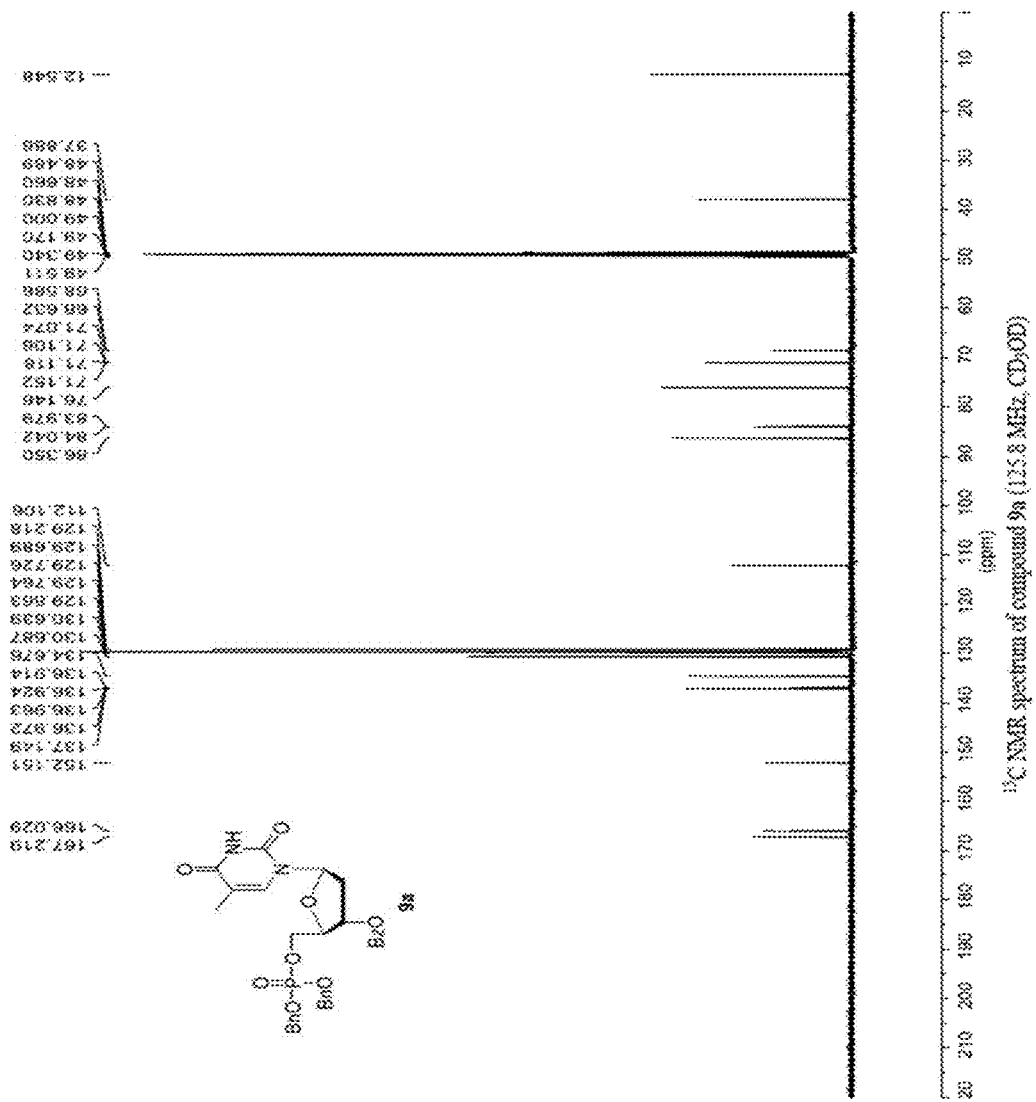
Figure 35:
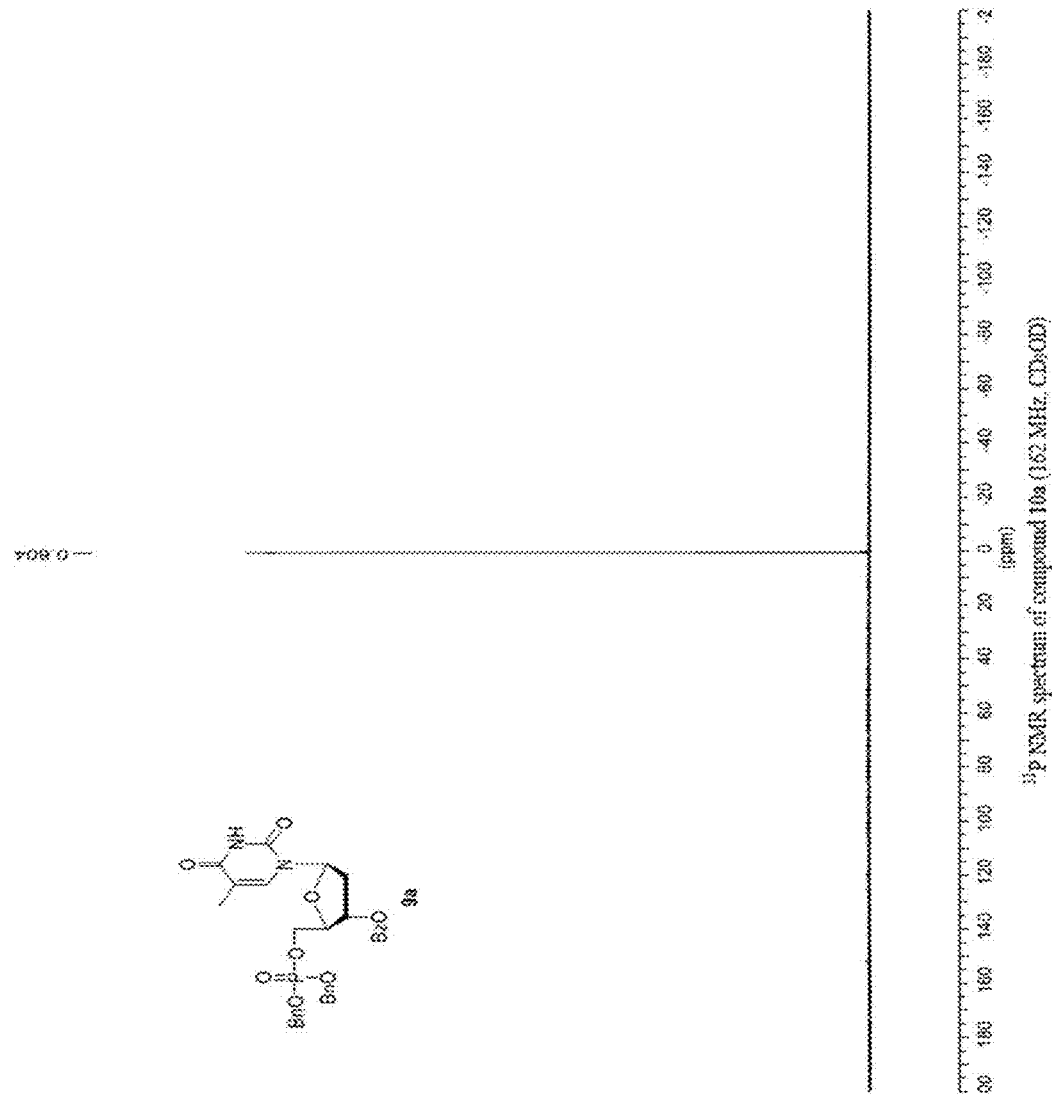
Figure 36:
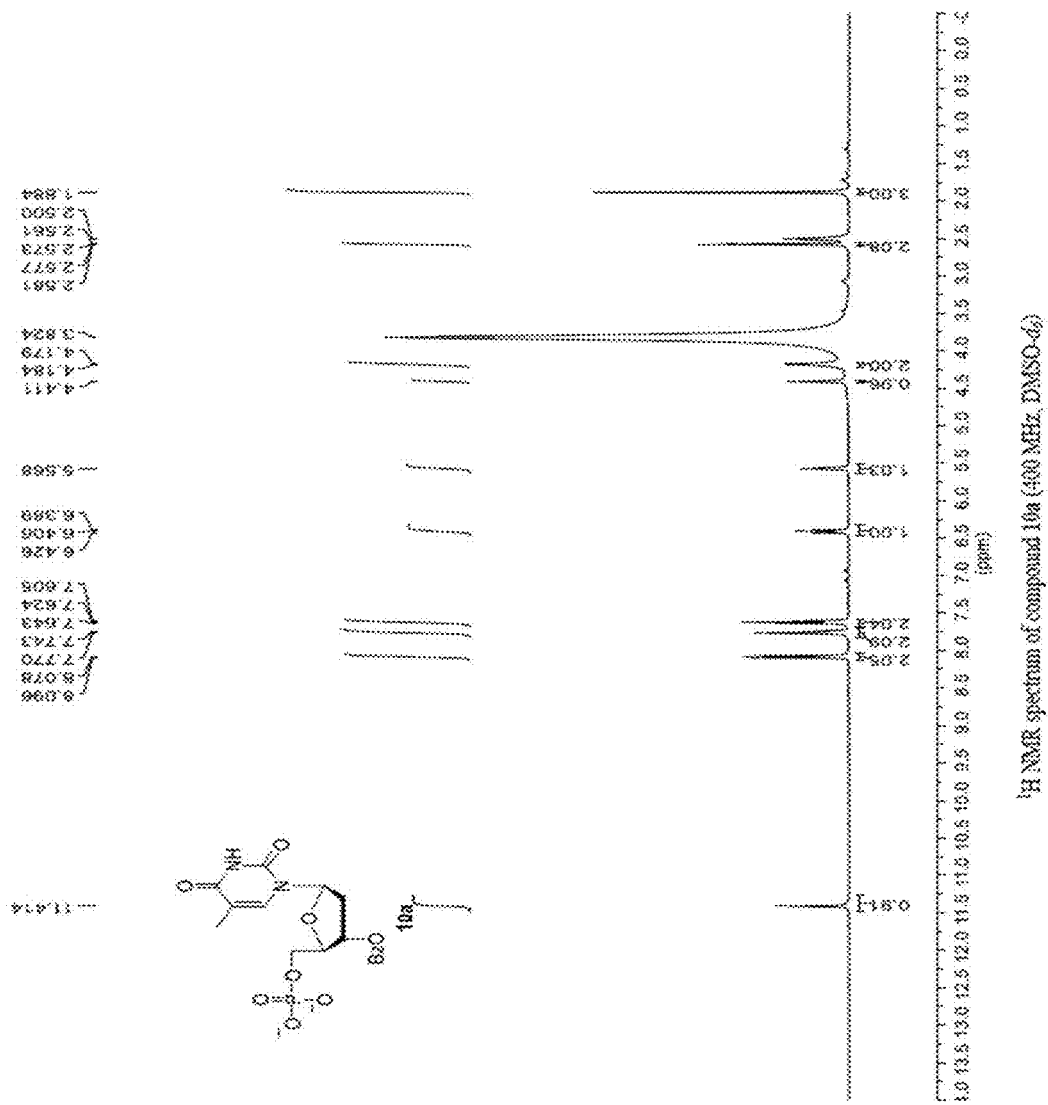
FIG. 36 depicts an $^1$H NMR spectrum of synthesized 3'-O-Benzoyl-2'-deoxythymidine-5'-monophosphate (compound 10a).
Figure 37:
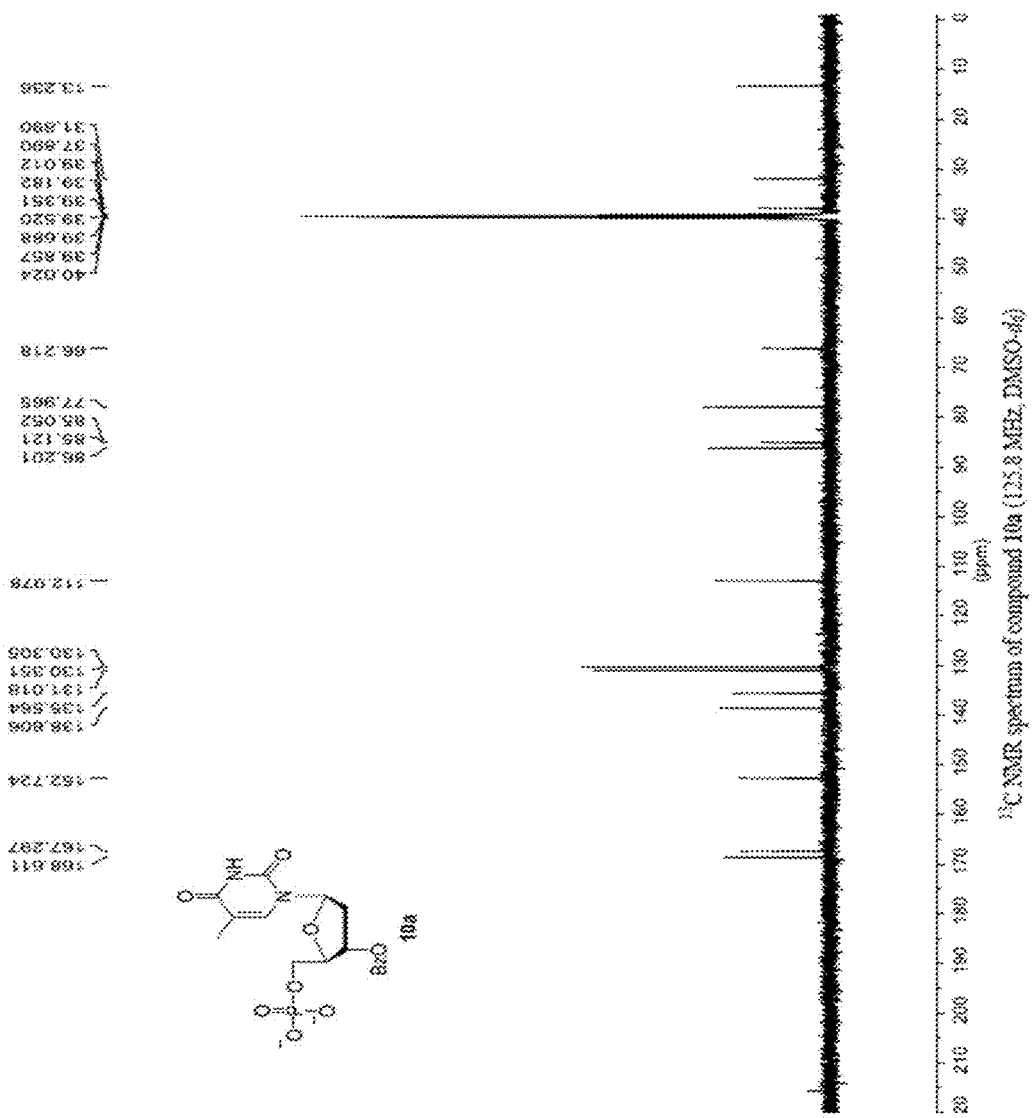
Figure 38:
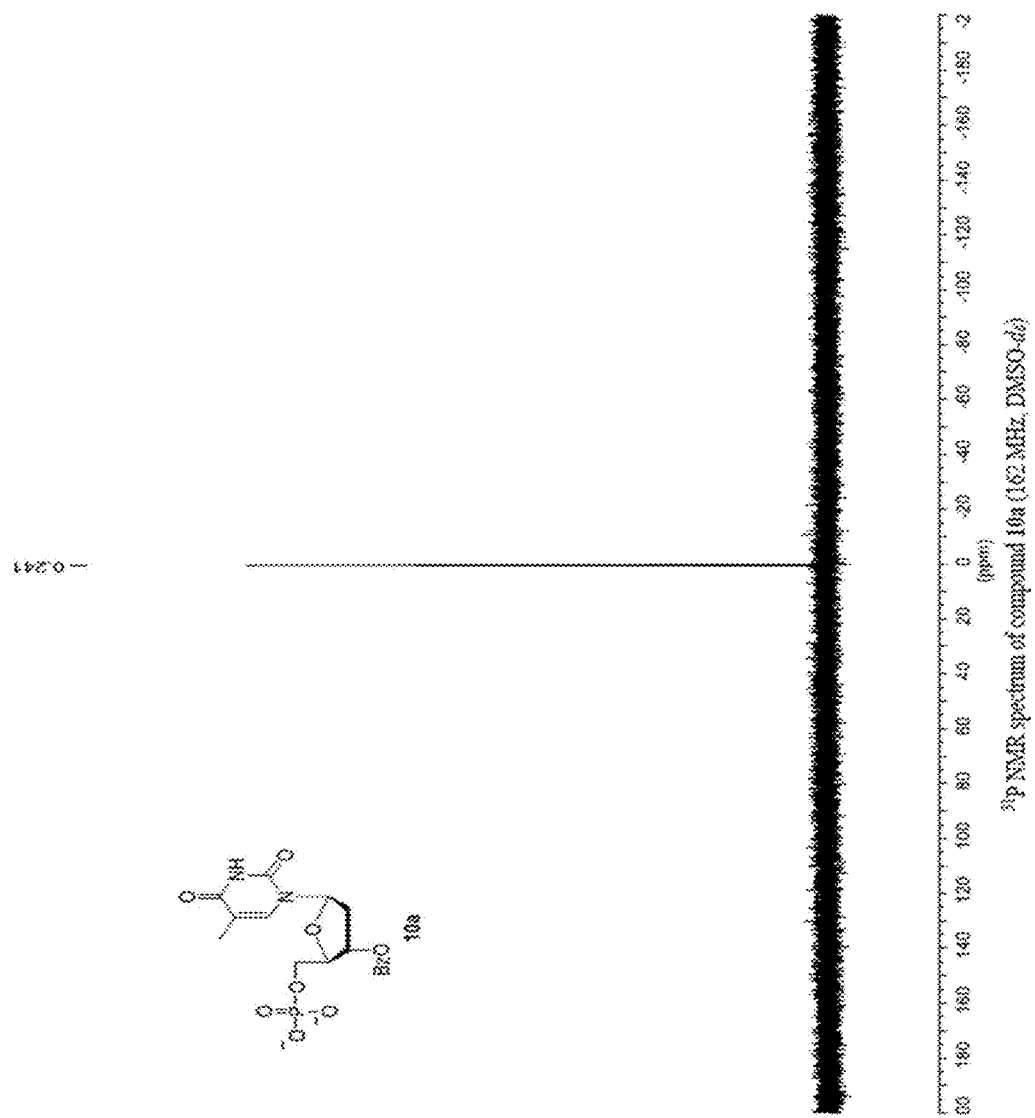
Figure 39:
FIG. 39 depicts an $^{31}$P NMR spectrum of synthesized 3'-O-Benzoyl-2'-deoxythymidine-5'-phosphor-2-methylimidazolide (compound 11a).
Figure 40:
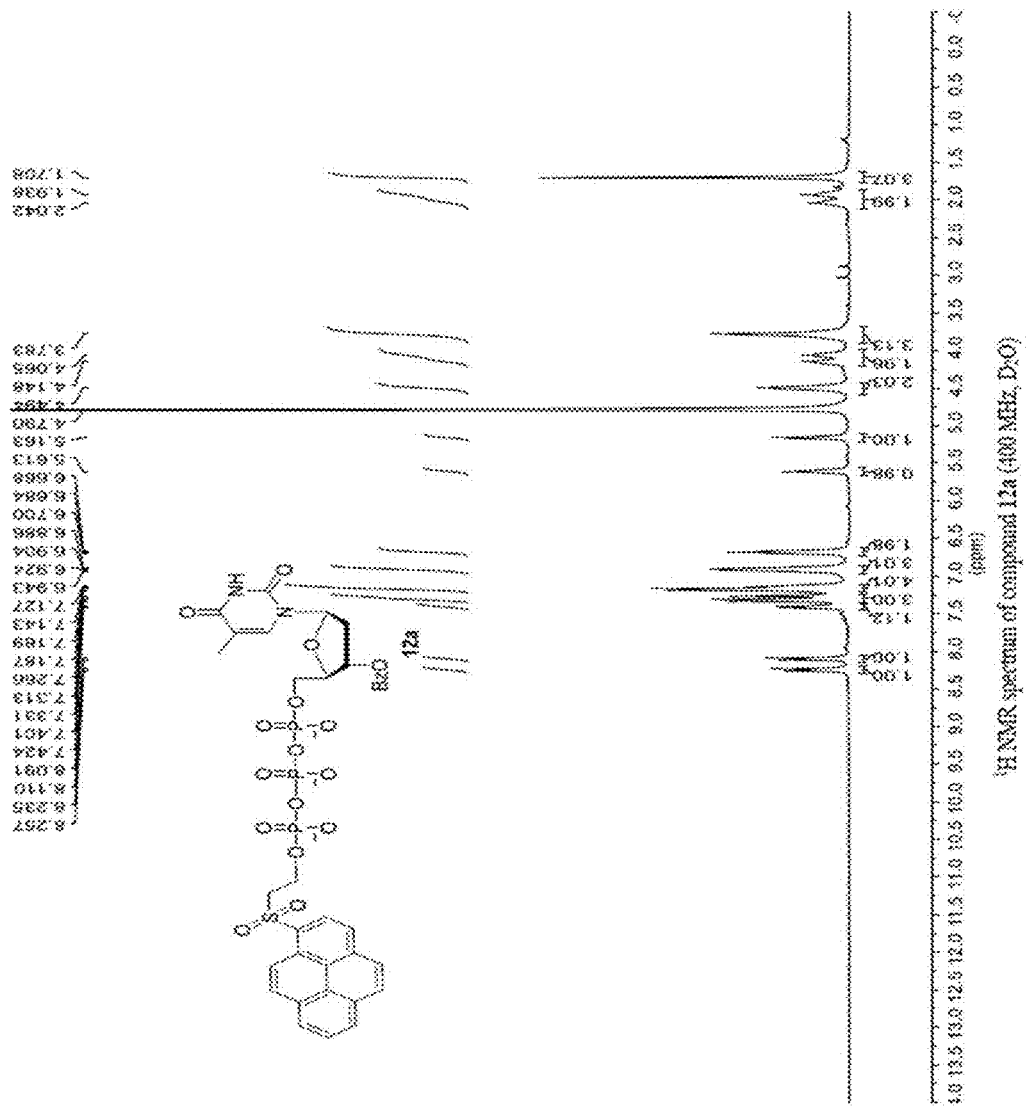
FIG. 40 depicts an $^1$H NMR spectrum of synthesized 3'-O-Benzoyl-2'-deoxythymidine-5'-(γ-(2-(pyrenesulfonyl) ethyl))triphosphate (compound 12a).
Figure 41:
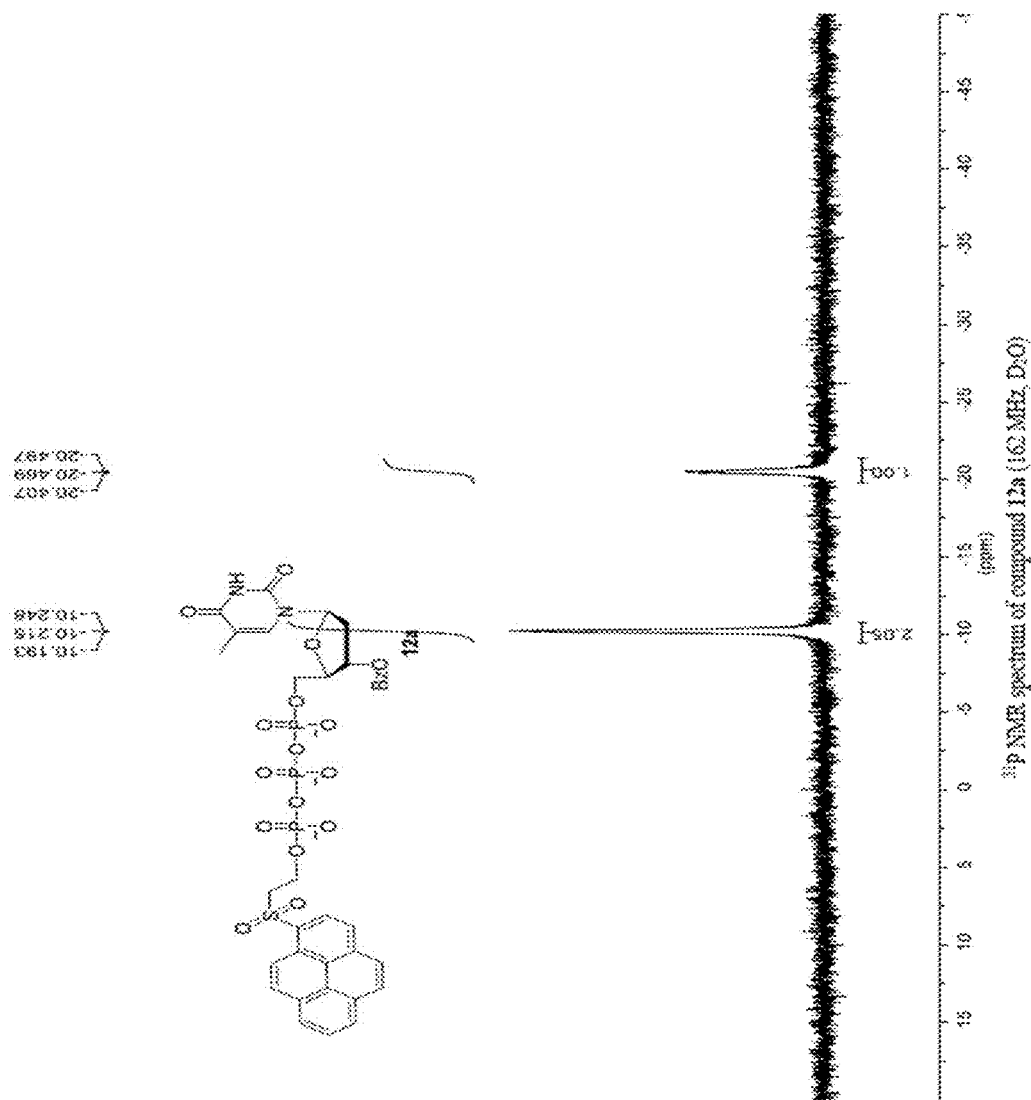
Figure 42:
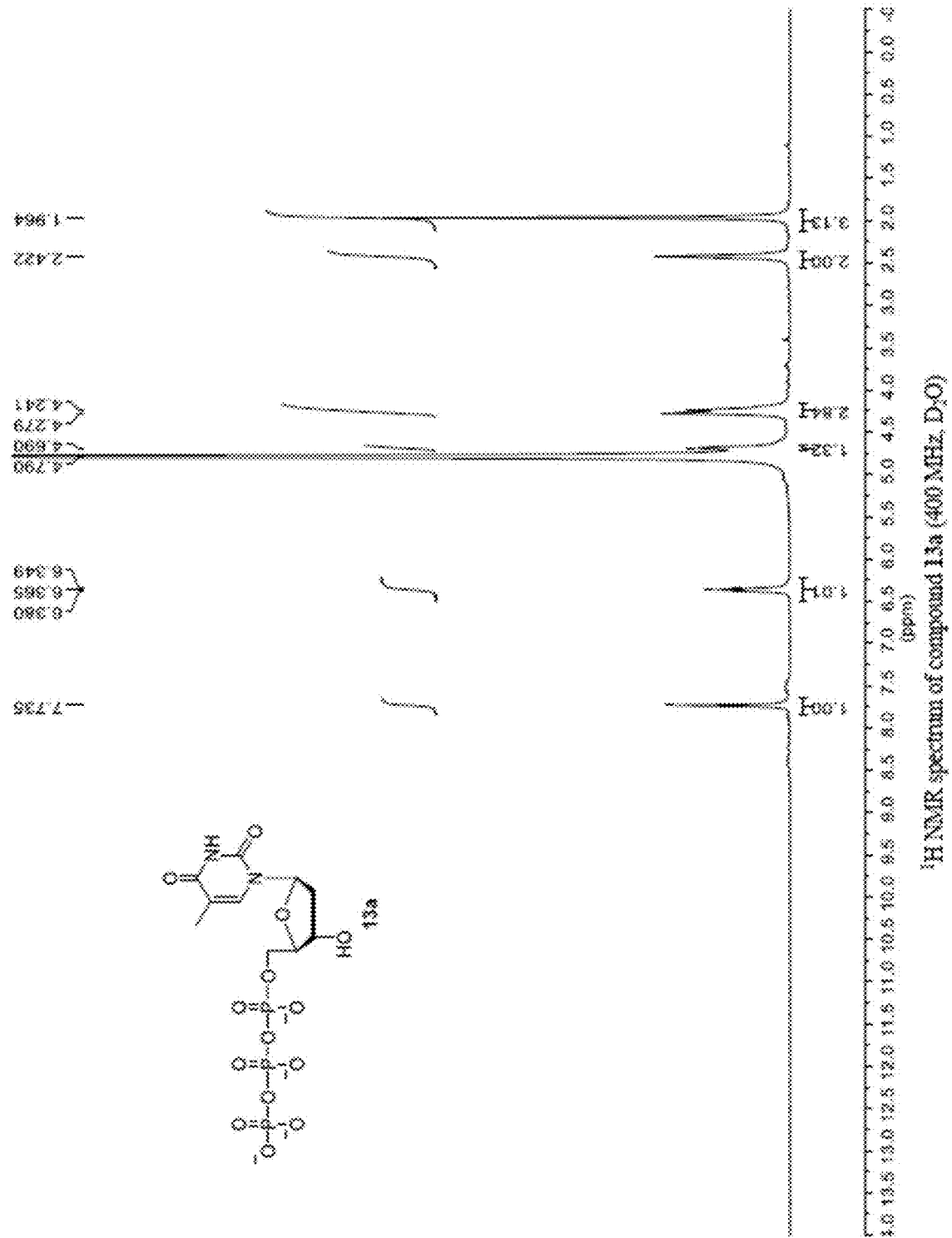
FIG. 42 depicts an NMR spectrum of synthesized compound Da.
Figure 43:
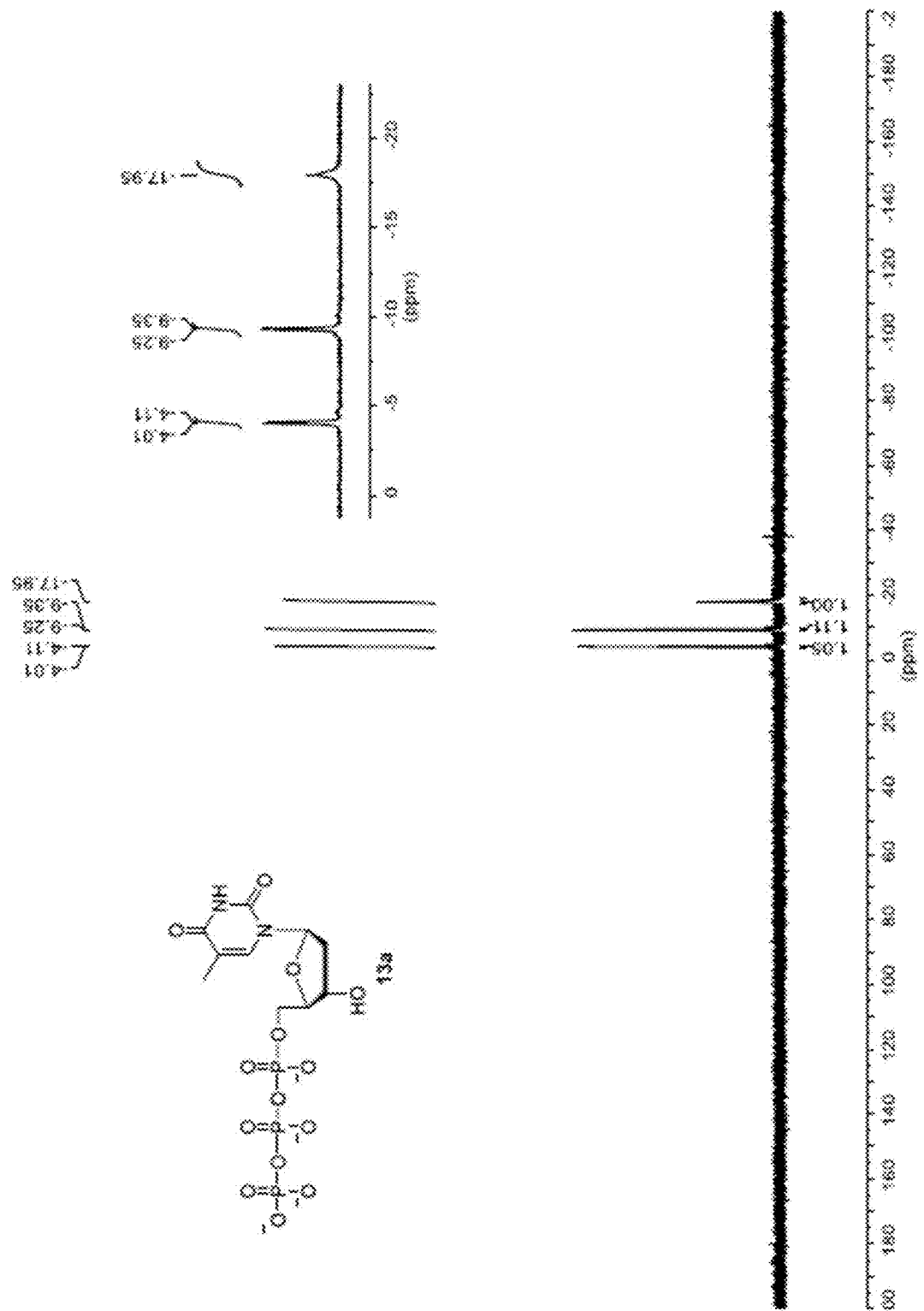

FIG. 32 through FIG. 141 depict schematic diagrams for the synthesis of nucleoside triphosphates and NMR spectra of the synthesized intermediates and products.

Methods used for the synthesis are now described.

General Procedure A: Synthesis of Protected Nucleoside Monophosphates

To a mixture containing suitably protected free nucleoside (compounds: 8a-d, 14, 20a-d, and 1.8 equivalents of tetrazole in an anhydrous solvent (MeCN/CH$_2$Cl$_2$, 1:1) was added to 1.3 equivalents of (BnO)$_2$PN(i-Pr)$_2$ under a nitrogen atmosphere. The mixture was stirred at room temperature for 1-3 hours and the reaction was monitored by TLC. At which the starting material was consumed, the reaction was slowly added excess H$_2$O$_2$ (33% in H$_2$O) at −40° C. and the resulting mixture was stirred at room temperature for 1 hour. The solution was then diluted with 15-20 times volume of CH$_2$Cl$_2$ and the organic layer was sequentially washed with saturated NaHCO$_{3(aq)}$, brine, and water. The organic extracts were combined, dried with MgSO$_4$, and evaporated under diminished pressure. The crude residue was purified by silica gel chromatography and the fractions containing the product were collected and evaporated to afford the product, compounds: 9a-d, 15, 21a-d, or 27.

General Procedure B: Synthesis of Nucleoside Monophosphates

To a solution containing the protected nucleoside monophosphate (compounds 9a-d, 15, 21a-d, and in MeOH was purged with nitrogen gas. The solution was added 0.1-0.2 mass equivalent of 10% Pd/C, and re-purged with nitrogen gas followed by adding hydrogen gas. The mixture was stirred at room temperature for 3-5 hours with monitoring by TLC (MeOH/CH$_2$Cl$_2$, 1:10 with 1% triethylamine). Then the solution was purged with nitrogen, filtered over a pad of celite, and washed with MeOH or MeOH containing 2% triethylamine. The filtrate was collected, evaporated and coevaporated with dry 1, 2-dichloroethane under reduced pressure to afford the product, compounds: 10a-d, 16, 22a-d, or 28.

General Procedure C: Synthesis of Activated Nucleoside Monophosphates

To a solution containing the nucleoside monophosphate (compounds 10a-d, 16, 22a-d and 28) in anhydrous DMF under a nitrogen atmosphere was slowly added 5 equivalents of anhydrous triethylamine at 0° C. After 5 minutes with stirring, 2 equivalents of 2-methylimidazole was added followed by 2 equivalents of triphenylphosphine. After 10 minutes of stirring at room temperature, 2 equivalents of 2, 2'-dipyridyl disulfide was added and stirring was continued for an additional 3 hours at room temperature with monitoring by analytical HPLC (mobile phase: MeCN/0.1 M TEAA buffer, from 0% to 50% over 40 minutes). After consumption of the starting material, the product was precipitated by adding the reaction dropwise with stirring to 300 mL of diethyl ether. The precipitate was collected by centrifuging at 4400 rpm for 15 minutes at room temperature. The supernatant was discarded, and the pellet was resuspended with minimal amount of CH$_2$Cl$_2$ or anhydrous DMF (DMF is used when the nucleoside monophosphate is not soluble in CH$_2$Cl$_2$). The solution was added dropwise to a premade solution of ether/ethyl acetate/triethylamine (5:10:1) containing 8 equivalents of sodium perchlorate for a second precipitation. The suspended solid was centrifuged at 4400 rpm for 15 minutes at room temperature, the supernatant was discarded, and the pellet was washed twice with 40 mL of mixed solvent (ether/ethyl acetate, 1:2), and dried under high vacuum to afford the product, compounds: 11a-d, 17, 23a-d or 29.

General Procedure 1): Synthesis of Fully Protected Nucleoside Triphosphates

To a mixture containing the activated nucleoside monophosphate (compounds 11a-d, 17, 23a-d, and 29) and 1.2 equivalents of 1-(2-(pyrenesulfonyl)ethyl)pyrophosphate (compound 7) was added along with 8-10 equivalents of a premade solution of ZnCl$_2$ (1.0 M in anhydrous DMF) under a nitrogen atmosphere. The mixture was stirred at room temperature for 3-5 hours and the reaction progress was monitored by HPLC (MeCN/0.1 M TEAA buffer, from 0% to 50% over 40 minutes). At which the starting material was consumed, the reaction was dropwise added to ethyl acetate or ether for precipitation. The precipitate was centrifuged and collected at 4400 rpm for 10 minutes at room temperature, and the supernatant was discarded. The pellet was resuspended by 20% H$_2$O in MeCN with 2% Hunig's base and the solid was filtered by pyrex glass funnel with filter paper. The filtrate was collected and evaporated under diminished pressure and dry-packing loaded to silica gel for normal phase silica column chromatography. The fractions containing the product were collected and evaporated under diminished pressure at 30-40° C. The product was resuspended with CH$_2$Cl$_2$ and insoluble silica gel was removed by filtration. The filtrate was collected and evaporated to dryness to afford the product, compounds: 12a-d, 18, 24a-d, or 30.

General Procedure Synthesis of Free Nucleoside Triphosphates

To a solution of fully protected nucleoside triphosphate (compounds: 12a, 18, 24a, and 301 in 50 mL of 33% NH$_4$OH$_{(aq)}$ was stirred for 18 hours at room temperature or (compounds: 12b-d, and 24b-d) was stirred for 3 hours at 37° C. and 15 hours at room temperature in a sealed tube. After the reaction, the solvent was evaporated under diminished pressure. The solid was resuspended with water and the aqueous solution was washed with CH$_2$Cl$_2$ and ethyl acetate. The organic portion was discarded and the aqueous extract was collected, and evaporated under diminished pressure. The crude solid was resuspended with minimal amount of RNAse free water, filtrated by 0.22 um syringe filter and dropwise added to the forty times volume of acetone at room temperature containing 15 equivalents of sodium perchlorate. The resulting suspension was centrifuged at 4400 rpm for 15 minutes at room temperature. The supernatant was discarded and the pellet was washed with organic solution acetone/CH$_2$Cl$_2$, 10:1) twice to afford the product, compounds: 13a-d, 19, 25a-d, or 31.

Synthesis of thymidine-5'-triphosphate

FIG. 32 shows the synthesis scheme for 1-(2-(pyrenesulfonyl)ethyl)pyrophosphate (dTTP, compound 13a). FIG. 33 through FIG. 43 provide spectra of the synthesized intermediates and product.

Methods used for the synthesis are now described.

3'-O-Benzoyl-2'-deoxythymidine-5'-dibenzylmonophosphate (Compound 9a)

General procedure A with 1 g (2.89 mmol) of 3'-O-benzoyl-2'-deoxythymidine compound 8a, 364.4 mg (5.2 mmol) of tetrazole, 28.9 mL of anhydrous solution (MeCN/CH$_2$Cl$_2$, 1:1), 1.3 mL (3.76 mmol) of dibenzyl-N, N-diisopropylphosphoramidite for 3 hours reaction at room temperature. Then, 6 mL of 30% H$_2$O$_{2(aq)}$ for 1 hour oxidation reaction at room temperature. Column chromatography with eluents (MeOH/CH$_2$Cl$_2$, from 1% to 1.4%) to afford the product compound 9a as a white solid; yield: 1.2 g (68.5%); TLC (MeOH/CH$_2$Cl$_2$, 1:40) R$_f$=0.23; $^1$H NMR (400 MHz, CD$_3$OD) δ 8.03-8.00 (m, 2H), 7.62-7.58 (m, 1H), 7.48-7.45 (m, 3H), 7.36-7.29 (m, 10H), 6.32 (dd, 1H, J=8.4, 6.0 Hz), 5.42-5.40 (m, 1H), 5.12-5.07 (m, 4H), 4.34-4.28 (m, 3H), 2.47 (ddd, 1H, J=14.4, 6.0, 2.0 Hz), 2.26-2.18 (m, 1H), 1.77 (d, 3H, J=1.2 Hz); HRMS (ESI-TOF) calcd. for $C_{31}H_{31}N_2O_9PNa$ [M+Na]$^+$ 629.1665. found 629.1664. Compound 9a has been reported in De et al., 2014, Eur. J. Org. Chem. 2322-2348.

3'-O-Benzoyl-2'-deoxythymidine-5'-monophosphate (Compound 10a)

General procedure B with 1.2 g (1.98 mmol) of compound 9a, 50 mL of MeOH, and 200 mg of 10% Pd/C for 3 hours stirring at room temperature. The suspension was filtered over a pad of celite, and washed with 100 mL of MeOH containing 2% triethylamine four times to afford the product compound 10a as a white foam of triethylammonium salt; yield: 1.11 g (88.7%); TLC (MeOH/CH$_2$Cl$_2$, 1:10 with 1% triethylamine) $R_f$=0; $^1$H NMR (400 MHz, DMSO-d$_6$) δ 11.41 (s, 1H), 8.09 (d, 2H, J=8.0 Hz), 7.77-7.74 (m, 2H), 7.62 (t, 2H, J=7.6 Hz), 6.41 (dd, 8.0, 6.8 Hz), 5.57 (s, 1H), 4.41 (s, 1H), 4.18 (m, 2H), 2.58-2.57 (m, 2H), 1.88 (s, 3H); $^{13}$C NMR (125.8 MHz, DMSO-d$_6$) δ 168.6, 167.3, 152.7, 138.6, 135.6, 131.0, 130.4, 130.3, 113.0, 86.2, 85.1 (d, $J_C$, P=8.7 Hz), 78.0, 66.2, 37.9, 31.9, 13.2; $^{31}$P NMR (162 MHz, DMSO-d$_6$) δ 0.24; HRMS (ESI-TOF) calcd. for $C_{17}H_{18}N_2O_9PNa_2$ [M−H+2Na]$^+$ 471.0545. found 471.0539.

3'-O-Benzoyl-2'-deoxythymidine-5'-phosphor-2-methylimidazole (Compound 11a)

General procedure C with 1.11 g (1.76 mmol) of compound 10a, 7.8 mL of anhydrous DMF, 1.63 mL (11.72 mmol) of triethylamine, 385 mg (4.69 mmol) of 2-methylimidazole, 1.23 g (4.69 mmol) of triphenylphosphine, 1.04 g (4.72 mmol) of dipyridyl disulfide for 2 hours reaction at room temperature. First precipitation was achieved with 250 mL of diethyl ether. The product was resuspended with 10 mL of DMF and dropwise added to the solution containing 2.01 g of sodium perchlorate, 15 mL of triethylamine in 300 mL of ethyl acetate for second precipitation. The product was afforded as a white solid compound 11a; yield: 0.89 g (98.9%); $^{31}$P NMR (162 MHz, D$_2$O) δ −6.83; HRMS (ESI-TOF) calcd. for $C_{21}H_{23}N_4O_8PNa$ [M+Na]$^+$ 513.1151. found 513.1141.

3'-O-Benzoyl-2'-deoxythymidine-5'-(γ-(2-(pyrenesulfonyl)ethyl))triphosphate (Compound 12a)

General procedure 1) with 0.89 g (1.74 mmol) of compound 11a, 1.09 g (1.91 mmol) of 1-2-(pyrenesulfonyl)ethyl) pyrophosphate (compound 7) and 13932 mL (13.92 mmol) of ZnCl$_2$ solution (1.0 M in anhydrous DMF) for 3 hours stirring at room temperature. Then crude was precipitated by dropwise adding the solution to the 300 mL of ethyl acetate with stirring, After centrifugation, the pellet was resuspended by 20% H$_2$O/MeCN containing 2% Hunig's base and filtered by pyrex glass funnel. The filtrate was evaporated and the crude material was purified by silica column chromatography with eluents (H$_2$O/(isopropanol-MeCN 1:1) from 2% to 7% containing 1% diisopropylethylamine (DIPEA) to obtain pure compound 12a; yield: 1.43 g (64.9%); TLC (H$_2$O/acetone 1:10 with 2% diisopropylethylamine) Rf=0.29; $^1$H NMR (400 MHz, D$_2$O) δ 8.25 (d, 1H, J=8.8 Hz), 8.10 (d, 1H, J=7.6 Hz), 7.41 (d, 1H, J=9.2 Hz) 7.33-7.27 (m, 3H), 7.19-7.13 (m, 4H), 6.94-6.89 (m, 3H), 6.68 (t, 2H, J=6.4 Hz), 5.61 (s, 1H), 5.16 (s, 1H), 4.49 (s, 2H), 4.15-4.07 (m, 2H), 3.78 (m, 3H) 7.04-1.94 (m, 2H), 1070 (s, 3H); $^{31}$P NMR (162 MHz, D$_2$O) δ −10.22 (brs, 2P), −20.50 (brs, LP); HRMS (ESI-TOF) calcd. for $C_{35}H_{31}N_2O_{17}P_3SNa_3$ [M−2H+3Na]$^+$ 945.0250; found 945.0261.

2'-deoxythymidine-5'-triphosphate (Compound 13a)

General procedure E with 1.43 g (1.13 mmol) of compound 12a, 50 mL of 33% NH$_4$OH$_{(aq)}$ for 18 h stirring at room temperature. The product compound 13a was afforded as a white solid; yield: 453 mg (83.2%, T, $ε_{267}$: 9600 M$^{-1}$ cm$^{-1}$); $^1$H NMR (400 MHz, D$_2$O) δ 7.74 (s, 1H), 6.37 (t, 1H, J=6.0 Hz), 4.69 (s, 1H), 4.28-4.24 (m, 3H), 2.42 (s, 2H), 1.96 (s, 3H); $^{31}$P NMR (162 MHz, D$_2$O) 6-4.06 (d, 16.2 Hz), −9.30 (d, J=16.2 Hz), −17095 (brs).

Synthesis of 2'-deoxycytidine-5'-triphosphate

Figure 44:
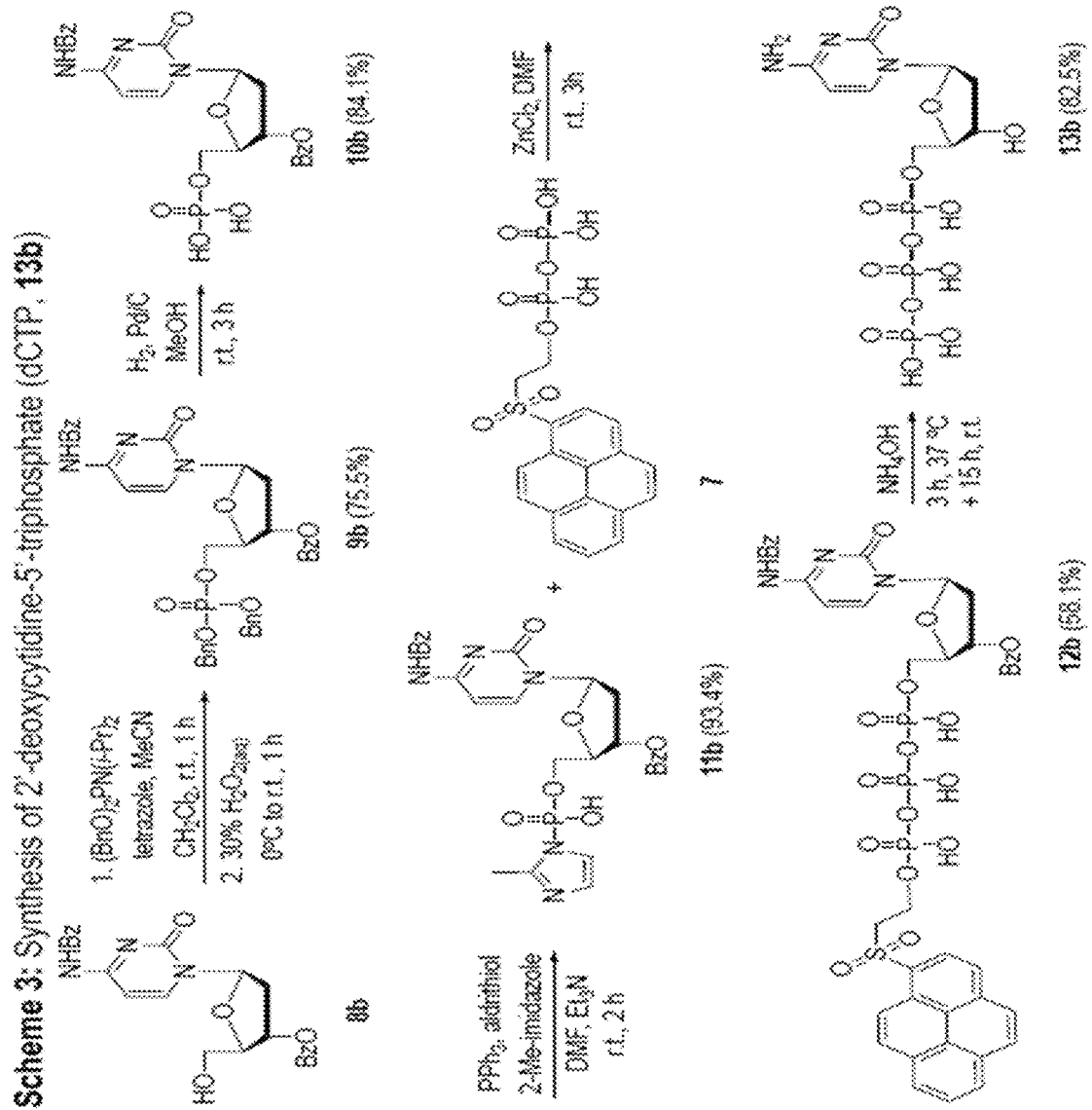
FIG. 44 depicts a synthesis scheme for 2'-deoxycytidine-5'-triphosphate (dCTP, compound 13b).
Figure 45:
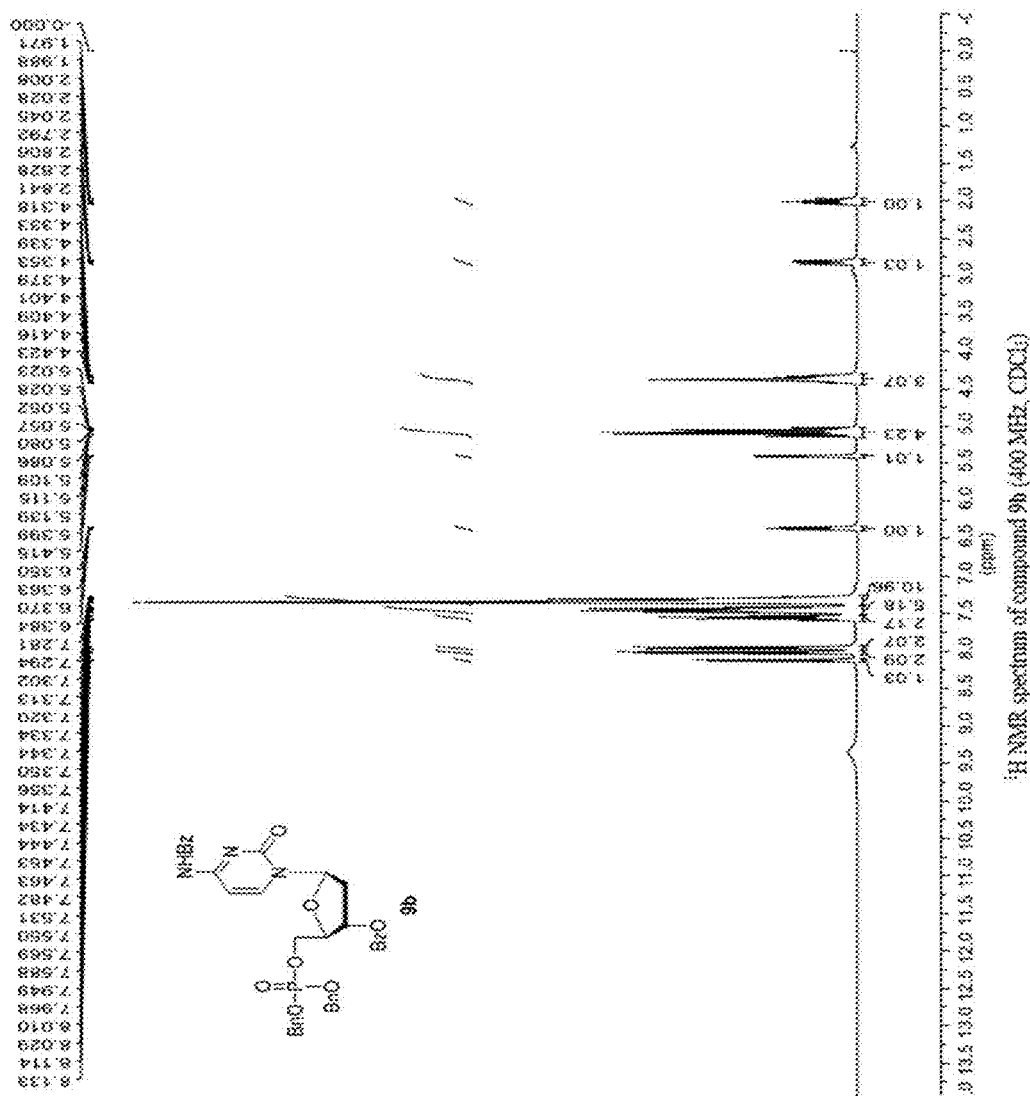
FIG. 45 depicts an $^1$H NMR spectrum of synthesized 3'-O, N4-Dibenzoyl-2'-deoxycytidine-5'-dibenzylmonophosphate (compound 9b).
Figure 46:
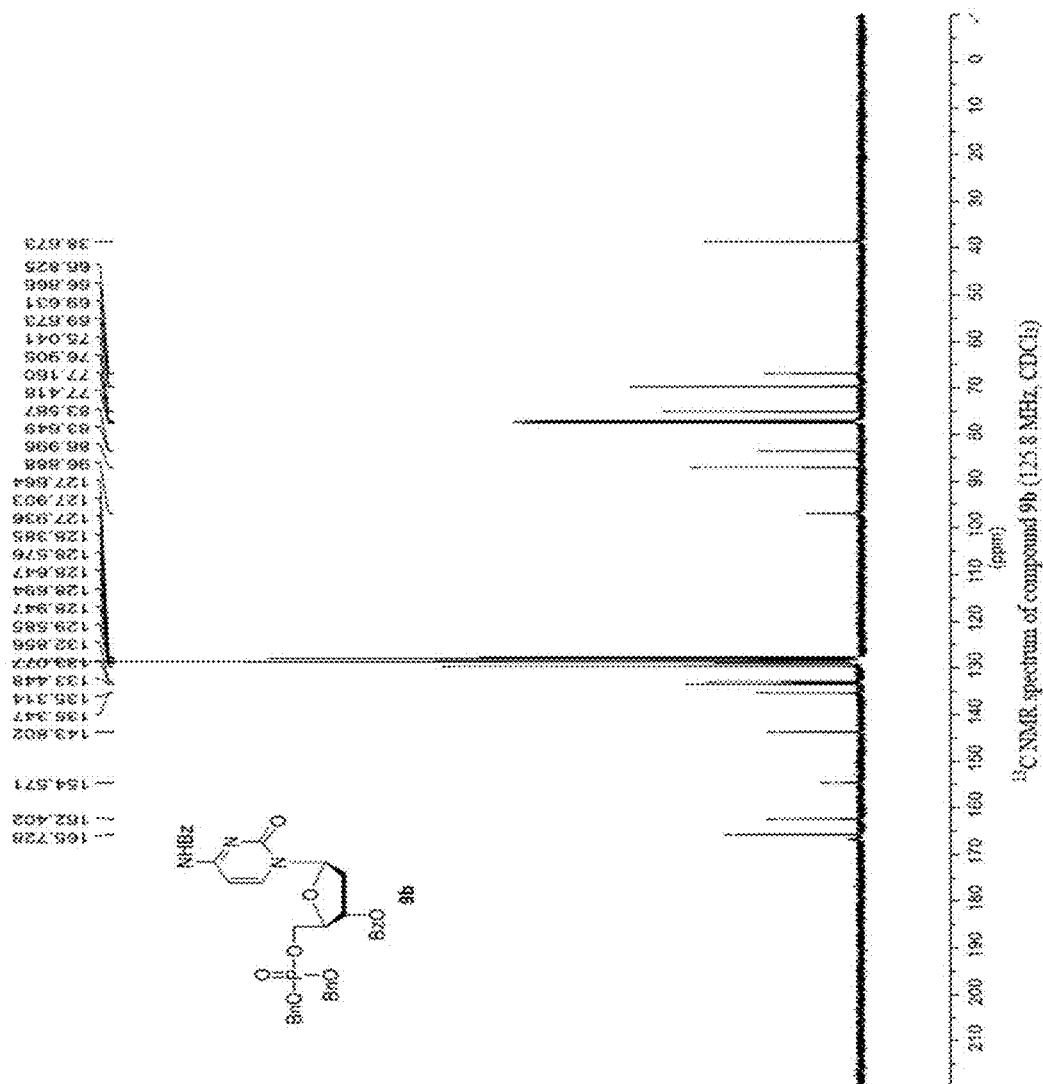
FIG. 46 depicts a $^{13}$C NMR spectrum of synthesized compound 9b.
Figure 47:
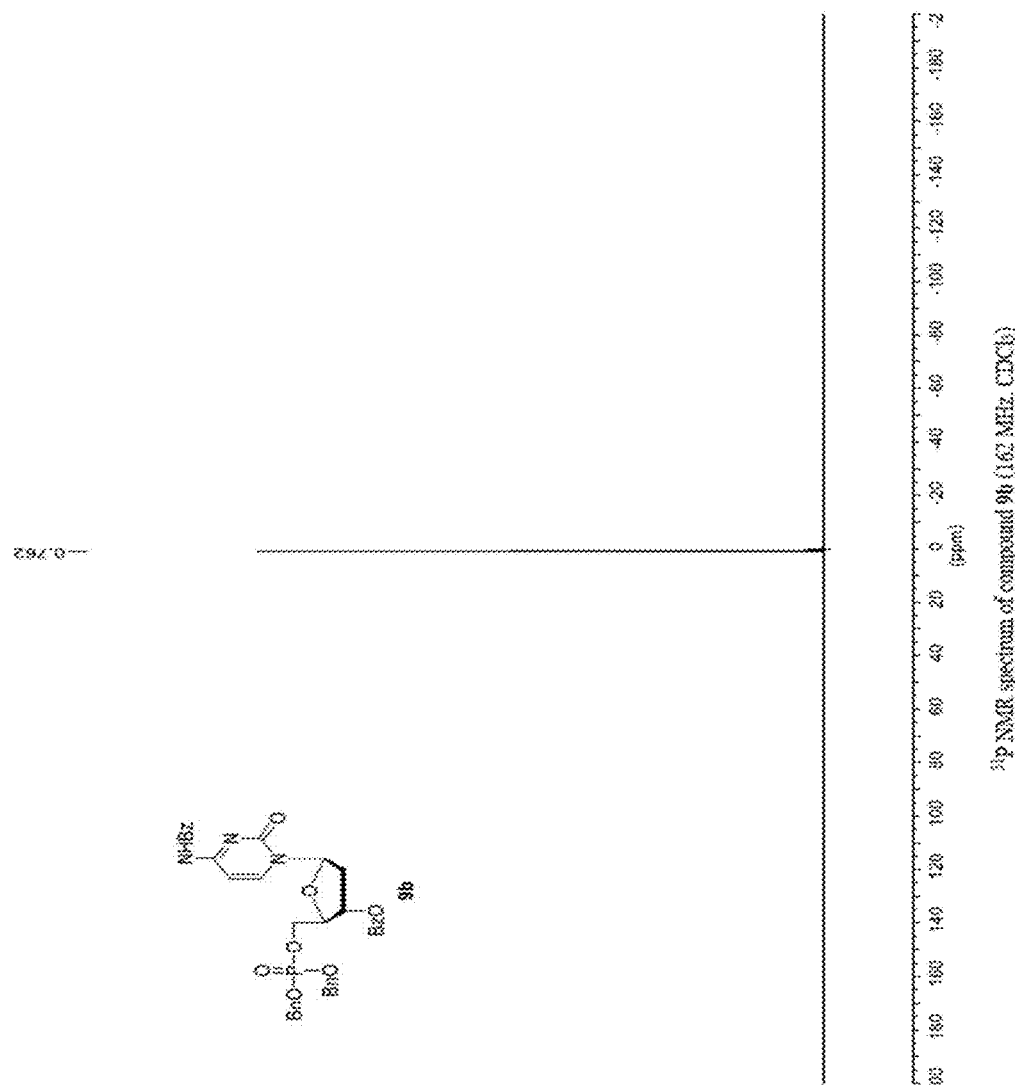
FIG. 47 depicts an $^{31}$P NMR spectrum of synthesized compound 9b.
Figure 48:
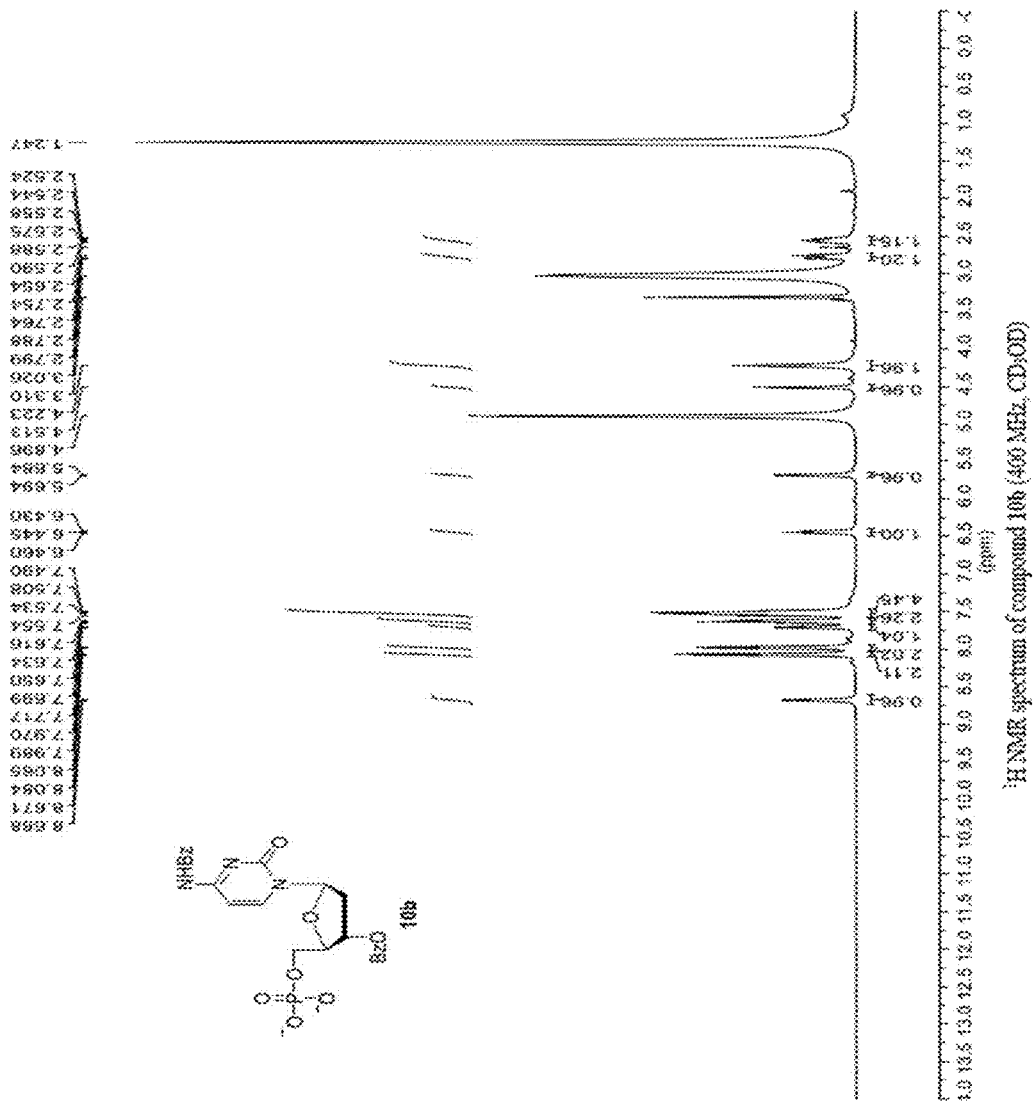
FIG. 48 depicts an $^1$H NMR spectrum of synthesized 3"-O, N4-Dibenzoyl-2'-deoxycytidine-5'-monophosphate (compound 10b).
Figure 49:
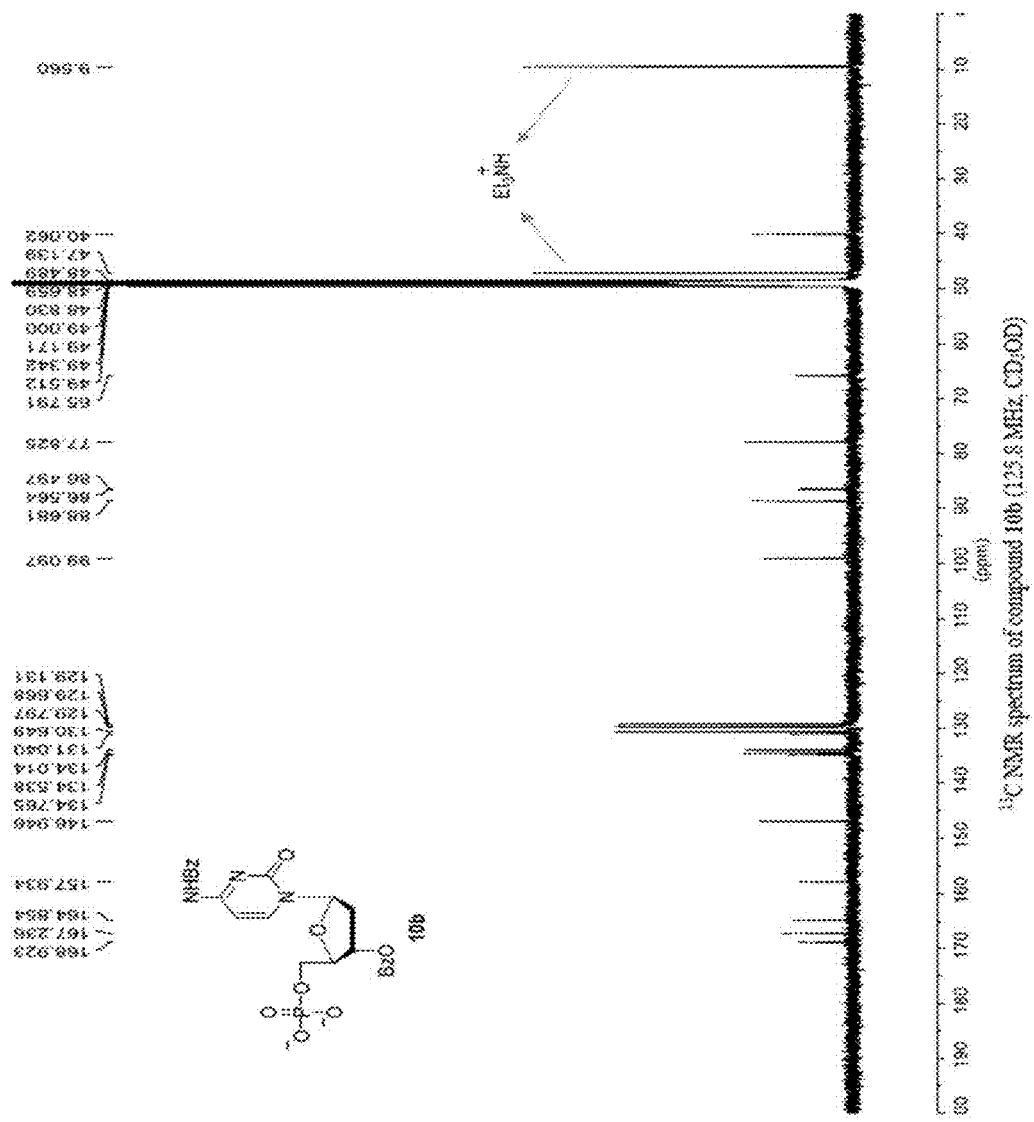
FIG. 49 depicts a $^{13}$C NMR spectrum of synthesized compound 10b.
Figure 50:
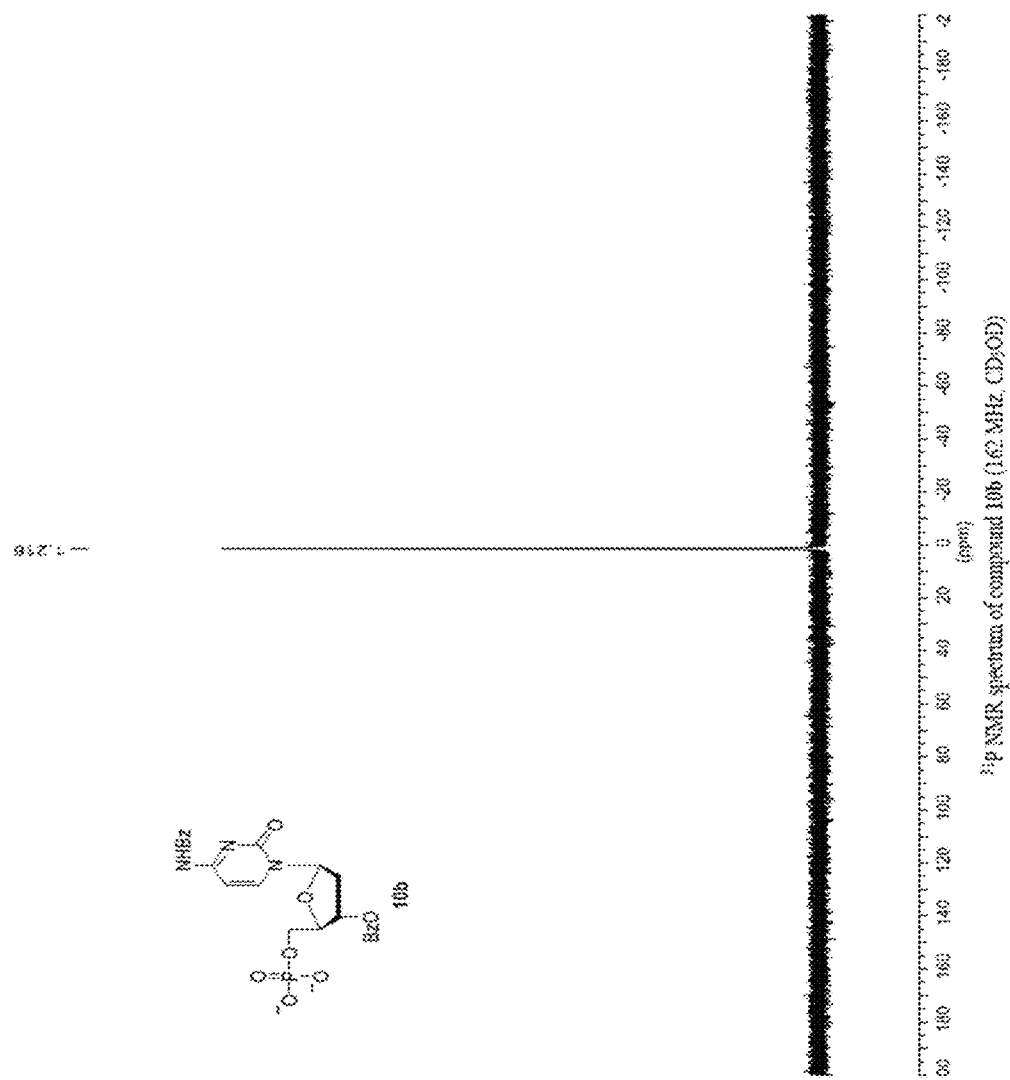
FIG. 50 depicts an $^{31}$P NMR spectrum of synthesized compound 10b.
Figure 51:
FIG. 51 depicts an $^{31}$P NMR spectrum of synthesized 3'-O, $N^4$-Dibenzoyl-2'-deoxycytidine-5'-phosphor-2-methylimidazolide (compound 11b).
Figure 52:
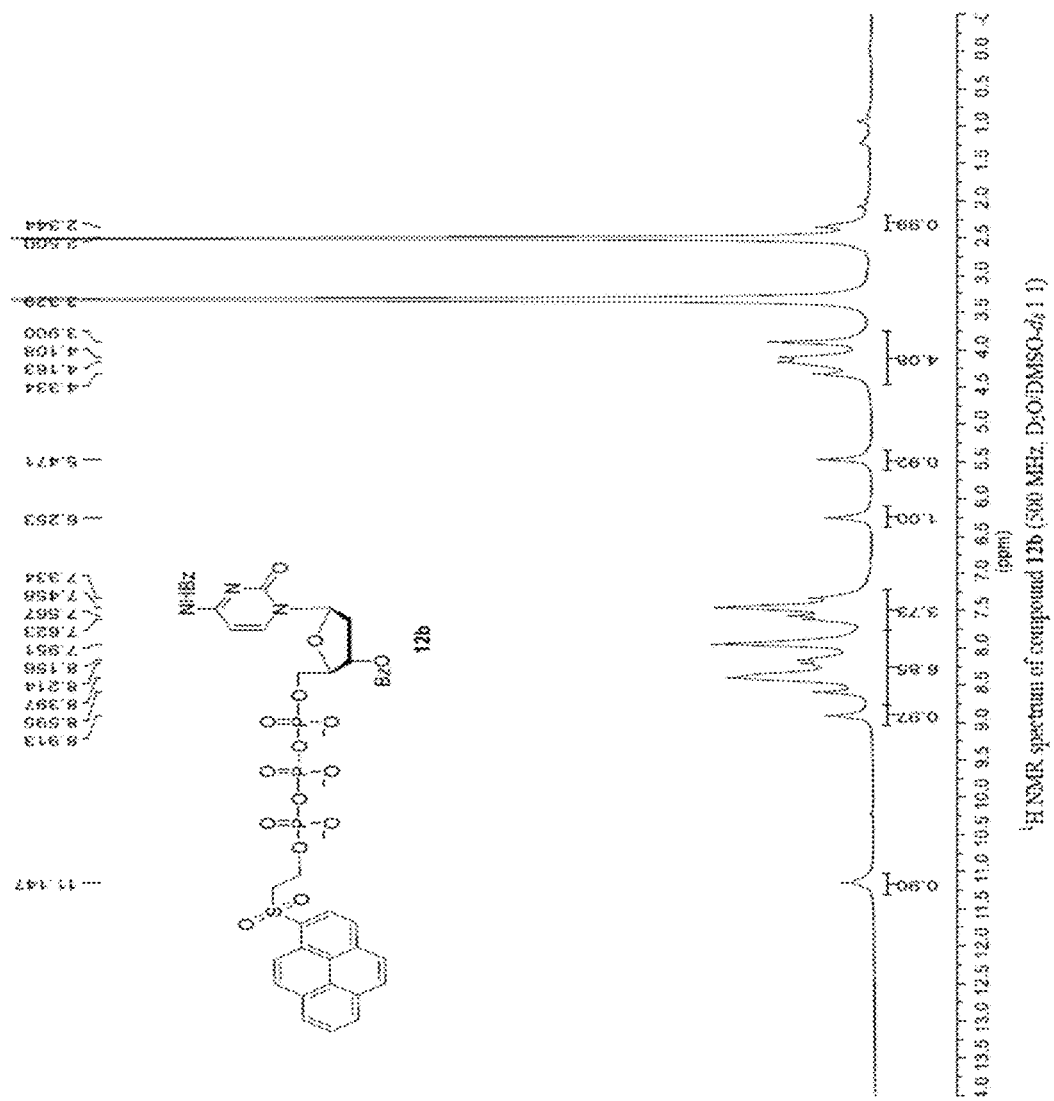
FIG. 52 depicts an $^1$H NMR spectrum of synthesized 3'-O,$N^4$-Dibenzoyl-2'-deoxycytidine-5'-(γ-(2-(pyrenesulfonyl)ethyl))triphosphate (compound 12b).
Figure 53:
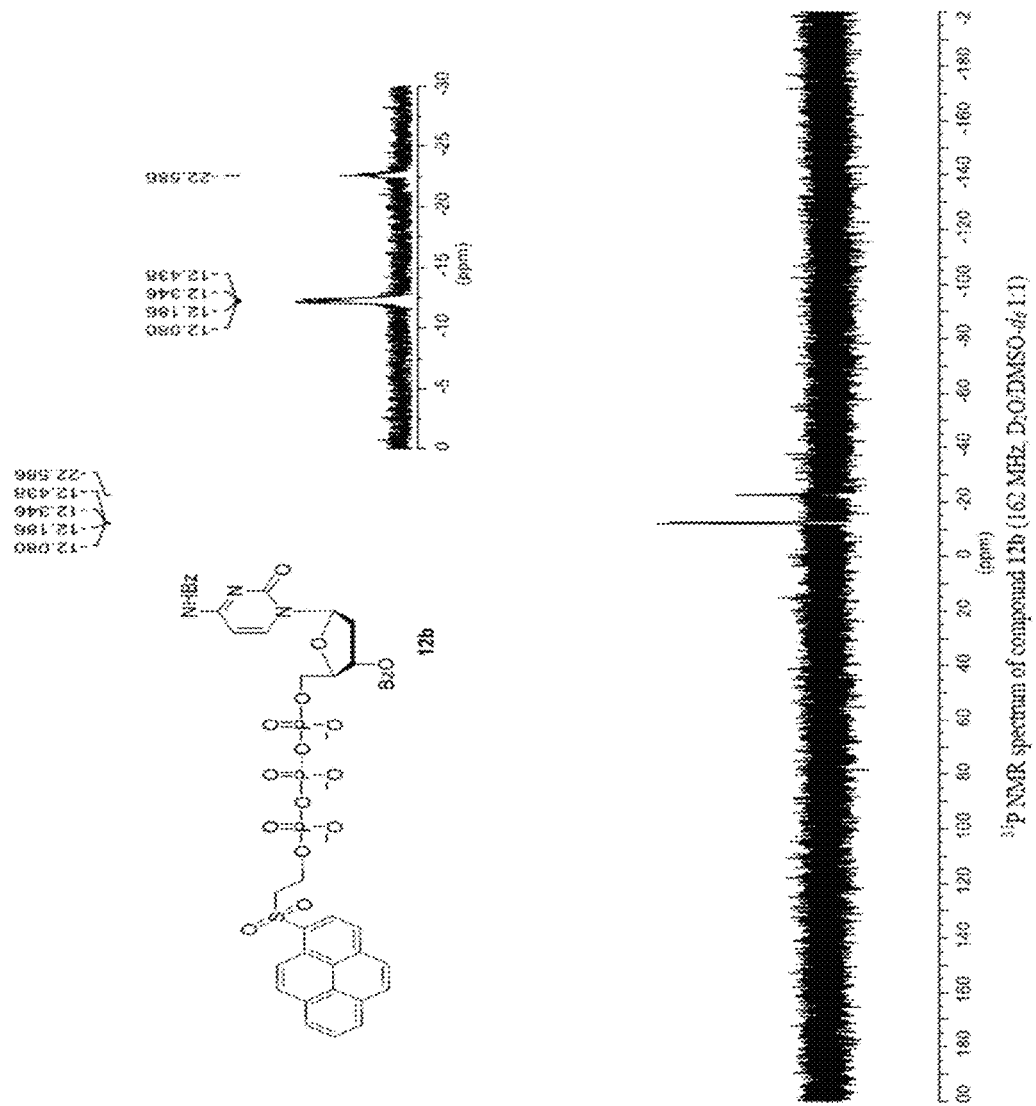
FIG. 53 depicts an $^{31}$P NMR spectrum of synthesized compound 12b.
Figure 54:
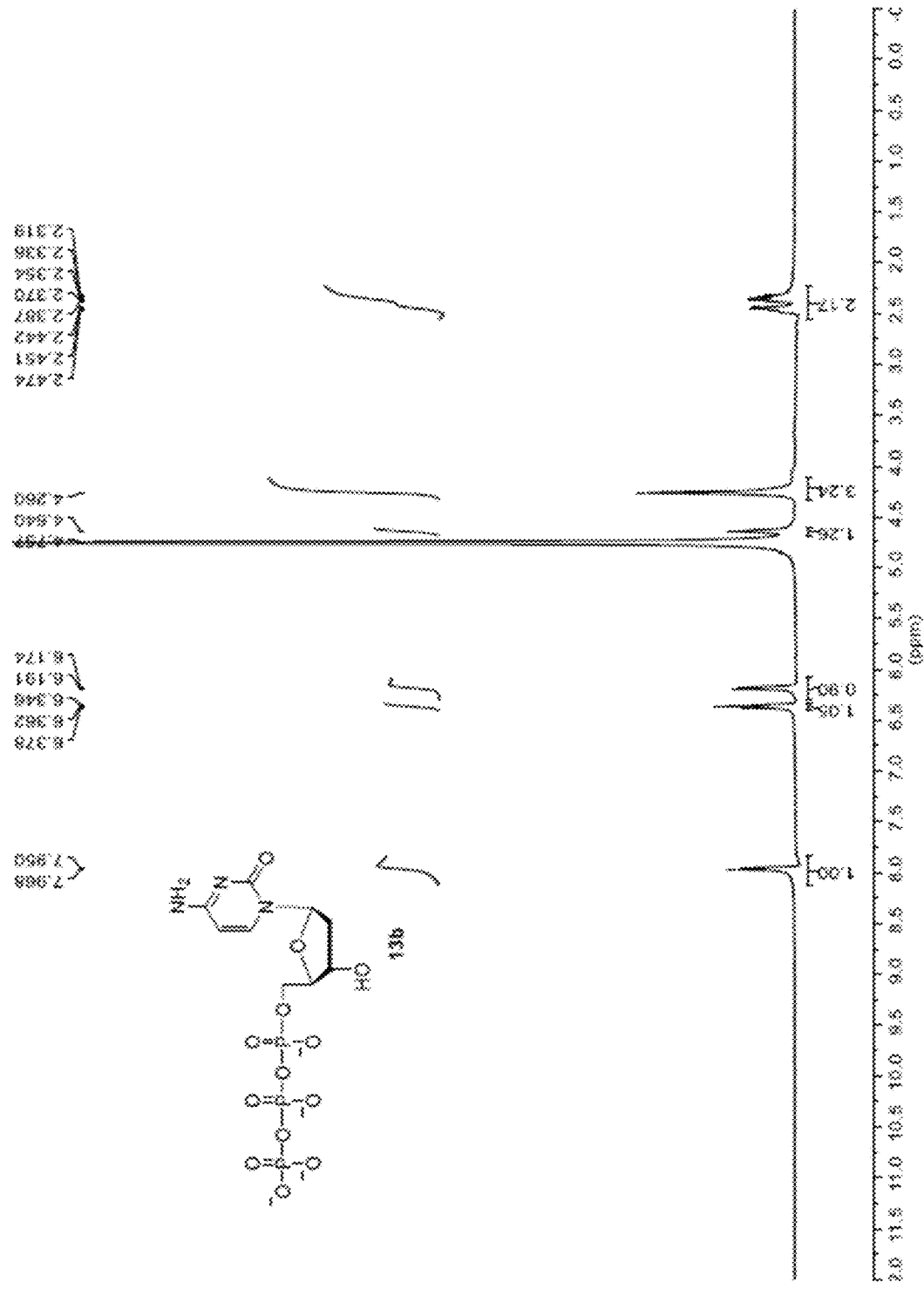
FIG. 54 depicts an $^1$H NMR spectrum of synthesized compound 13b.
Figure 55:
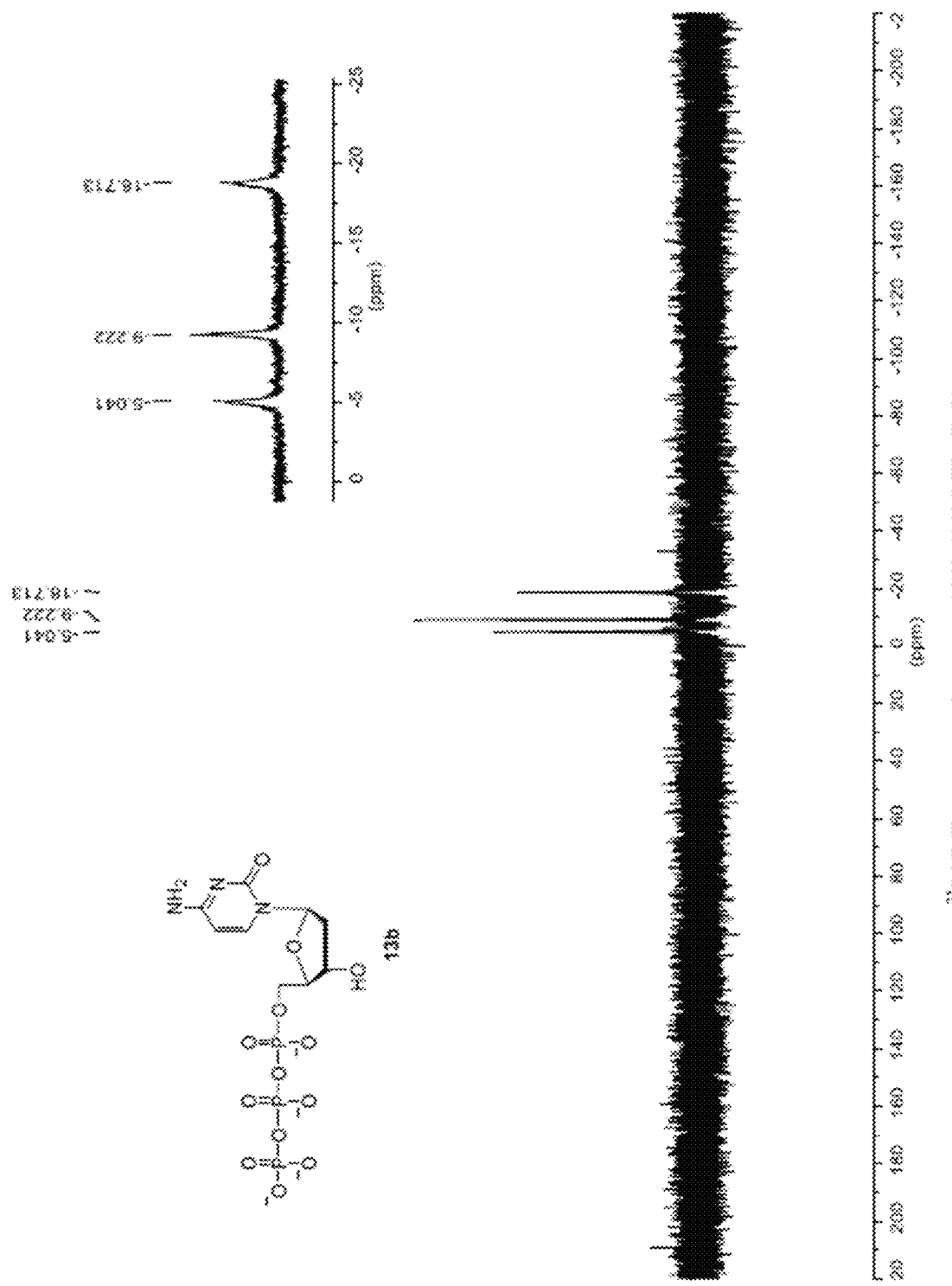
FIG. 55 depicts a $^{31}$P NMR spectrum of synthesized compound 13b.
Figure 57:
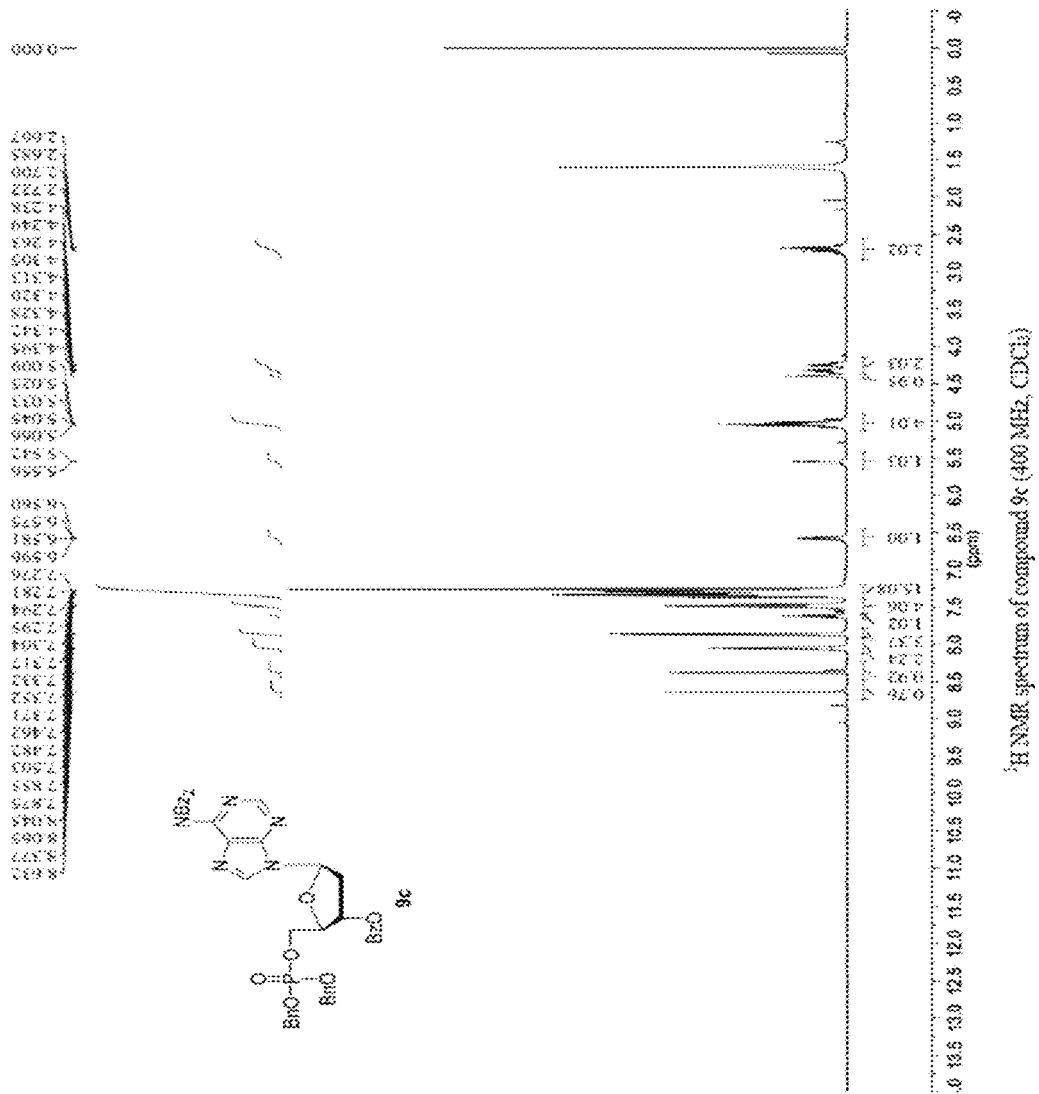
FIG. 57 depicts an $^1$H NMR spectrum of synthesized 3'-O, N$^6$, N$^6$-Tribenzoyl-2'-deoxyadenosine-5'-dibenzylmonophosphate (compound 9c).
Figure 58:
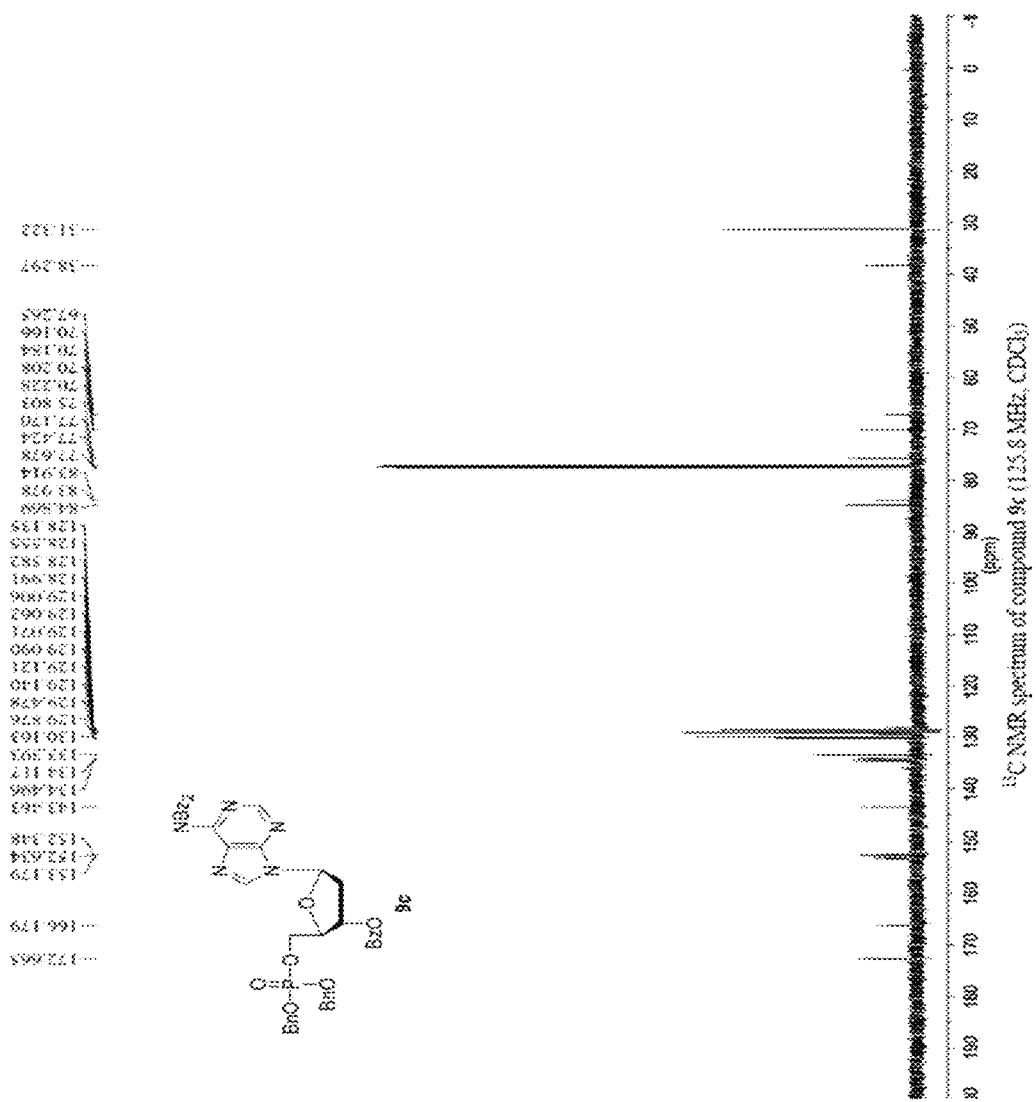
FIG. 58 depicts a $^{13}$C NMR spectrum of synthesized compound 9c.
Figure 59:
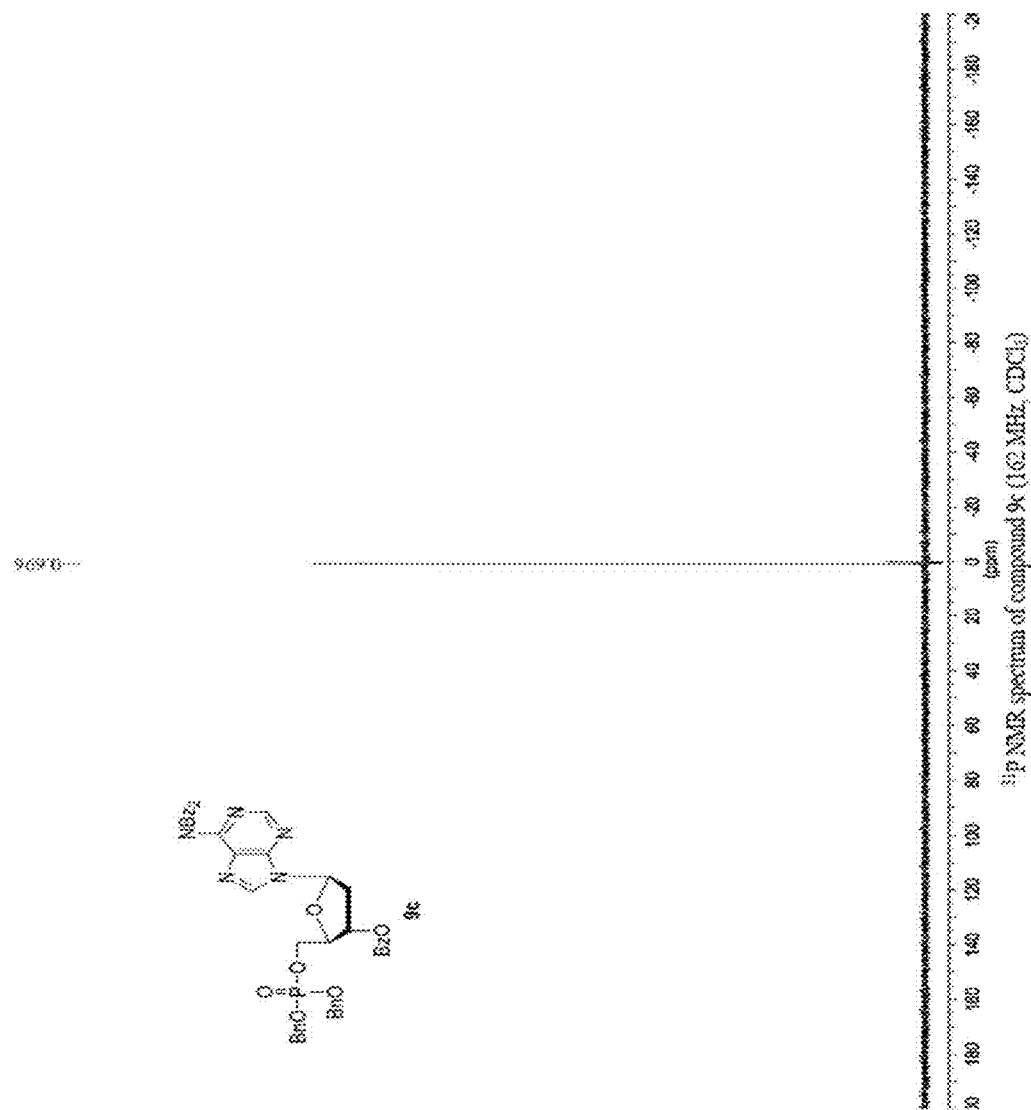
FIG. 59 depicts an $^{31}$P NMR spectrum of synthesized compound 9c.
Figure 60:
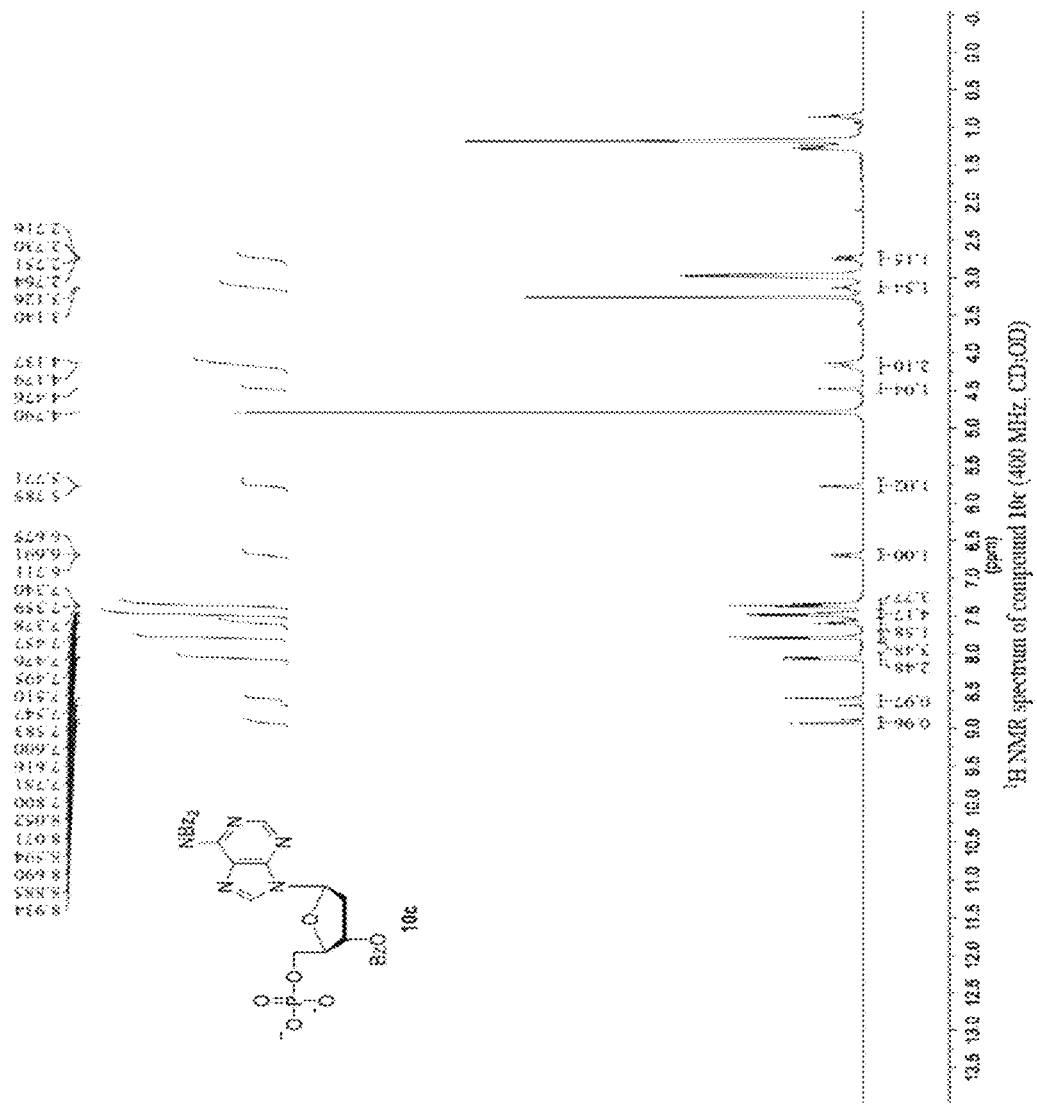
FIG. 60 depicts an $^1$H NMR spectrum of synthesized 3'-O, N$^6$, N$^6$-Tribenzoyl-2'-deoxyadenosine-5'''-monophosphate (compound 10c).
Figure 61:
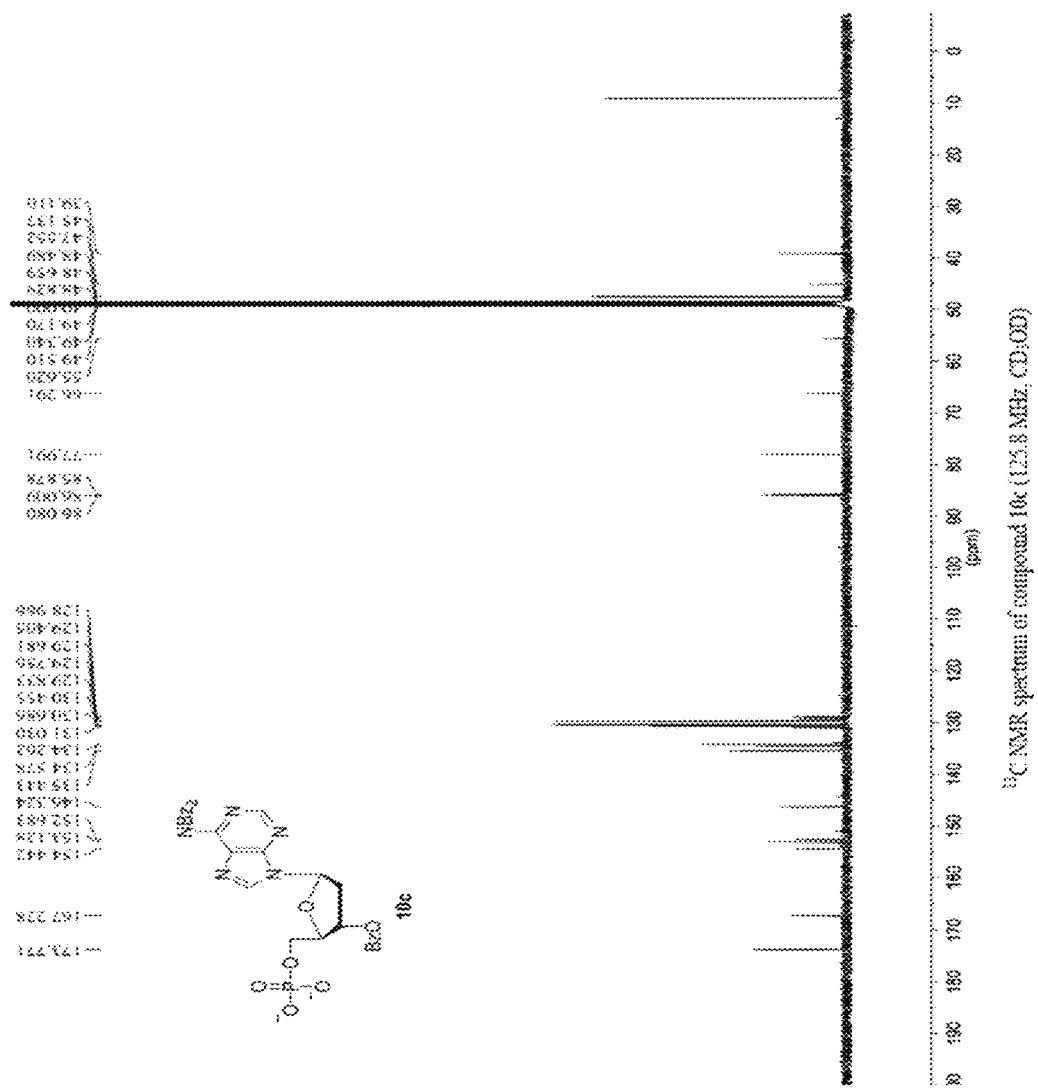
FIG. 61 depicts a $^{13}$C NMR spectrum of synthesized compound 10c.
Figure 62:
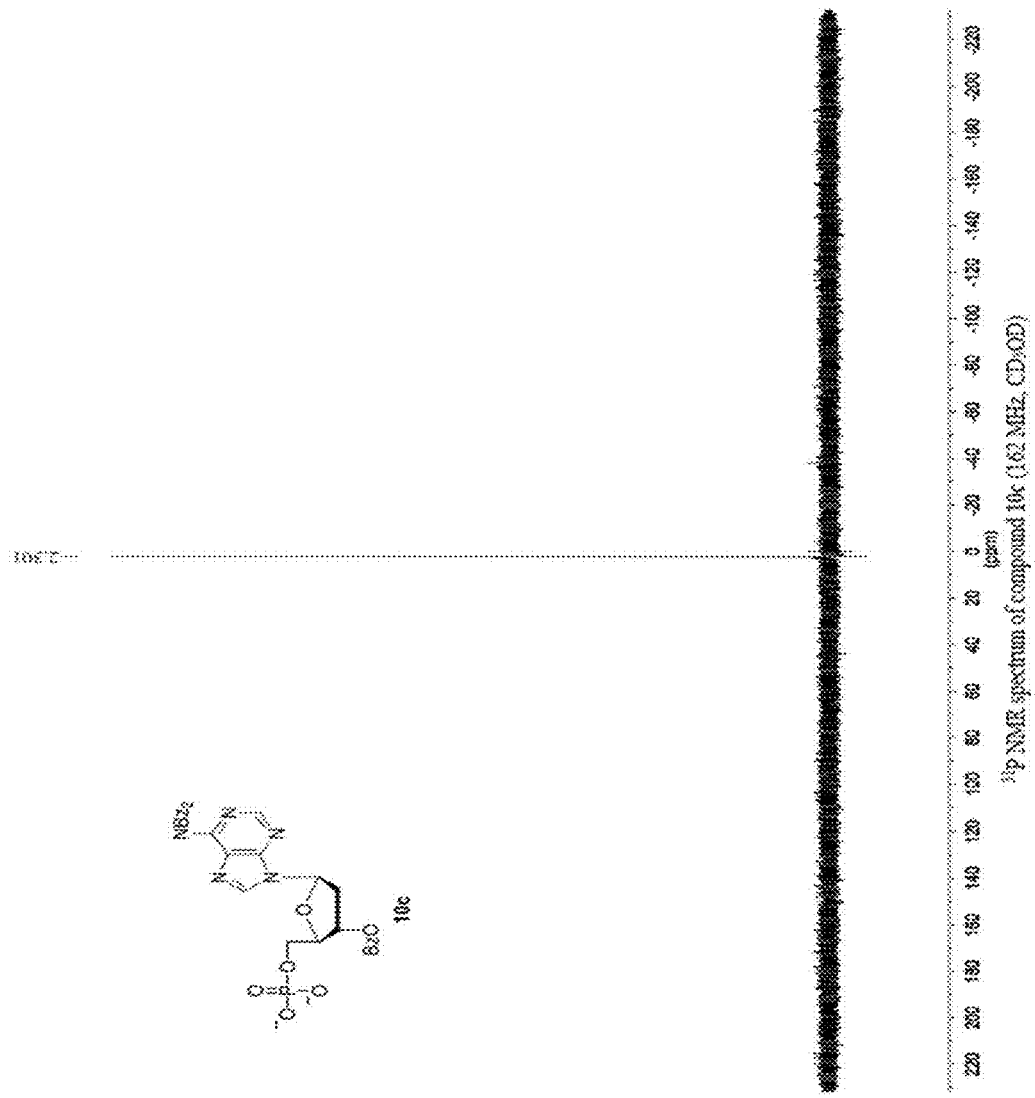
FIG. 62 depicts an $^{31}$P NMR spectrum of synthesized compound 10c.
Figure 63:
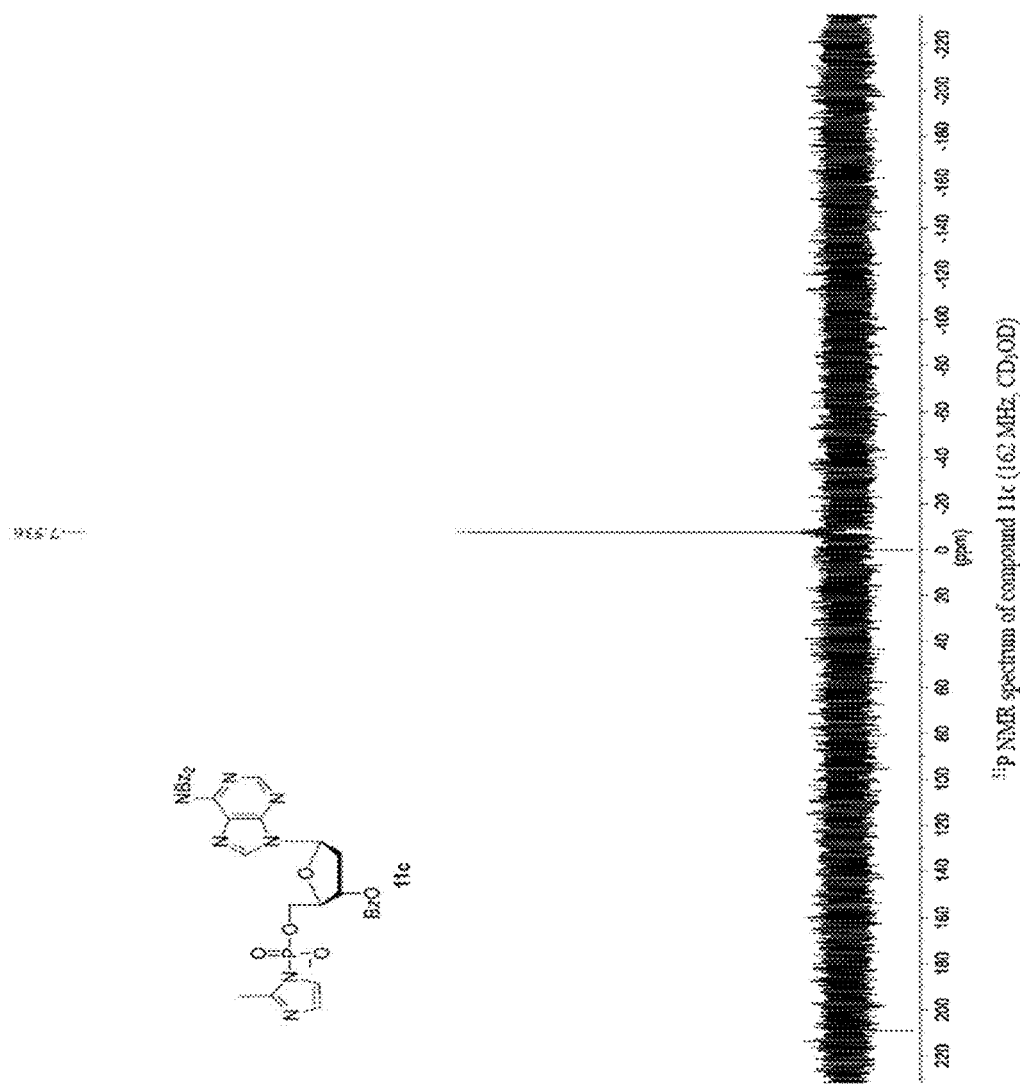
FIG. 63 depicts an $^{31}$P NMR spectrum of synthesized 3'-O, N$^6$, N$^6$-Tribenzoyl-2'-deoxyadenosine-5'-phosphor-2-methylimidazolide (compound 11c).
Figure 64:
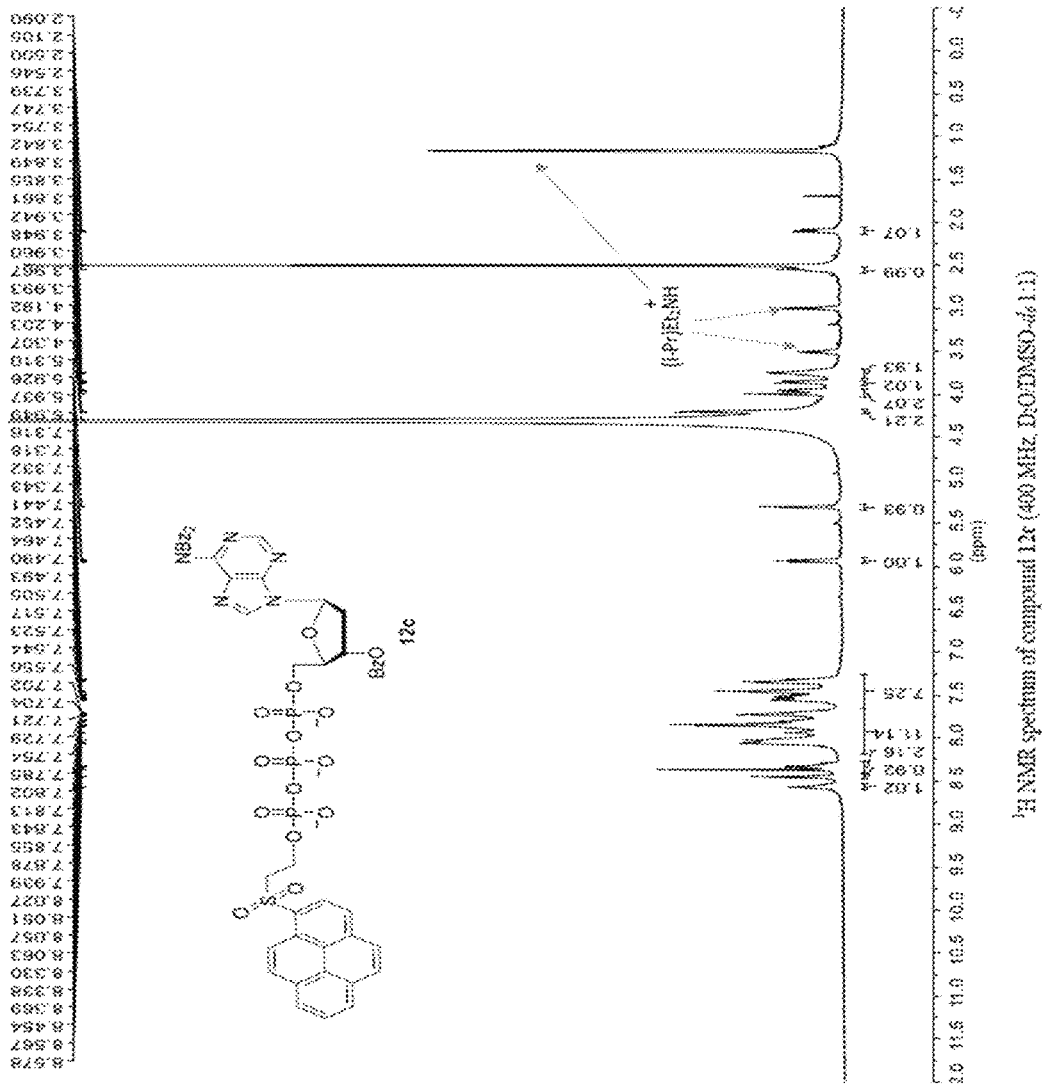
FIG. 64 depicts an NMR spectrum of synthesized 3'-O, N$^6$, N$^6$-Tribenzoyl-2'-deoxyadenosine-5'-γ-(2-(pyrenesulfonyl)ethyl]-triphosphate (compound 12c).
Figure 65:
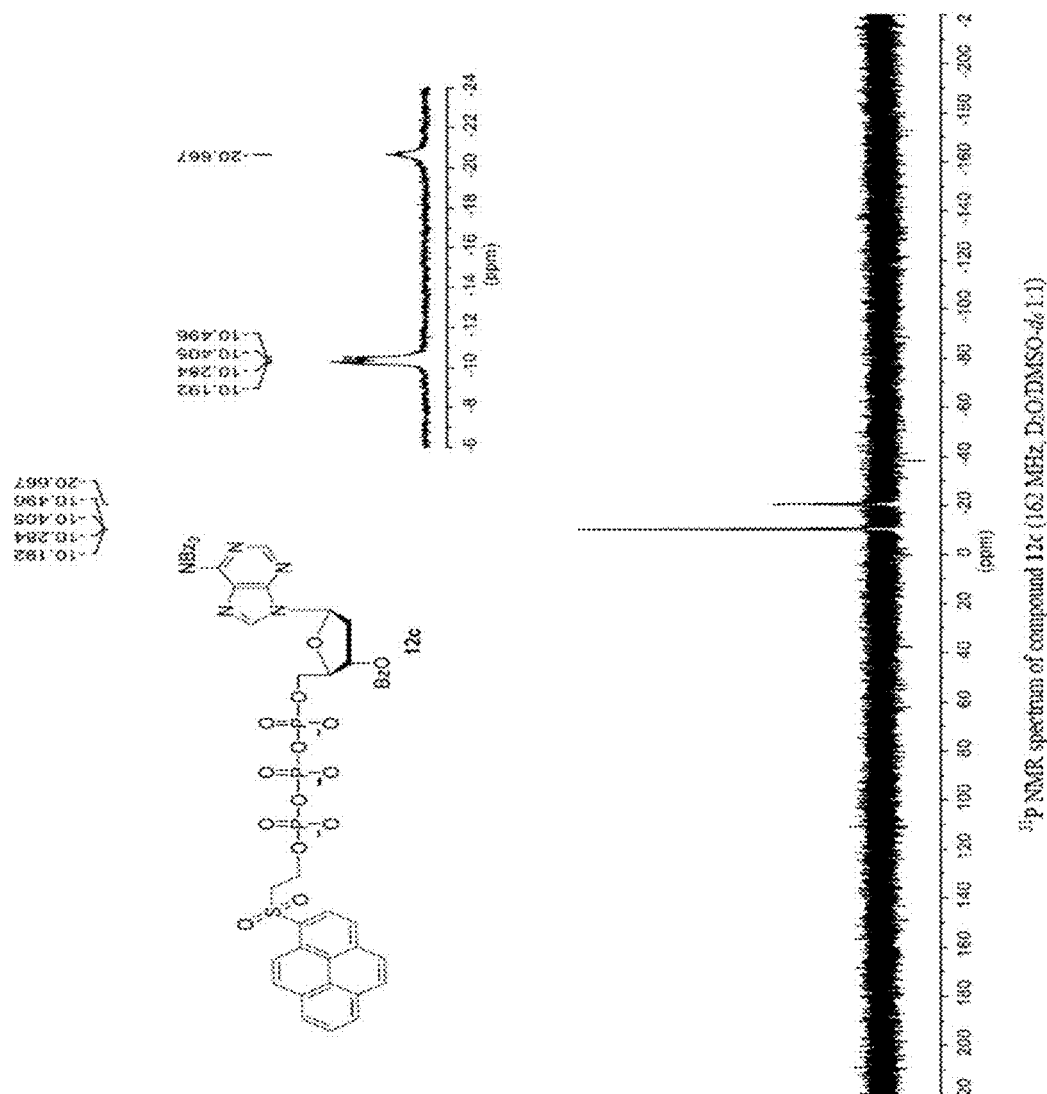
FIG. 65 depicts an $^{31}$P NMR spectrum of synthesized compound 12c.
Figure 66:
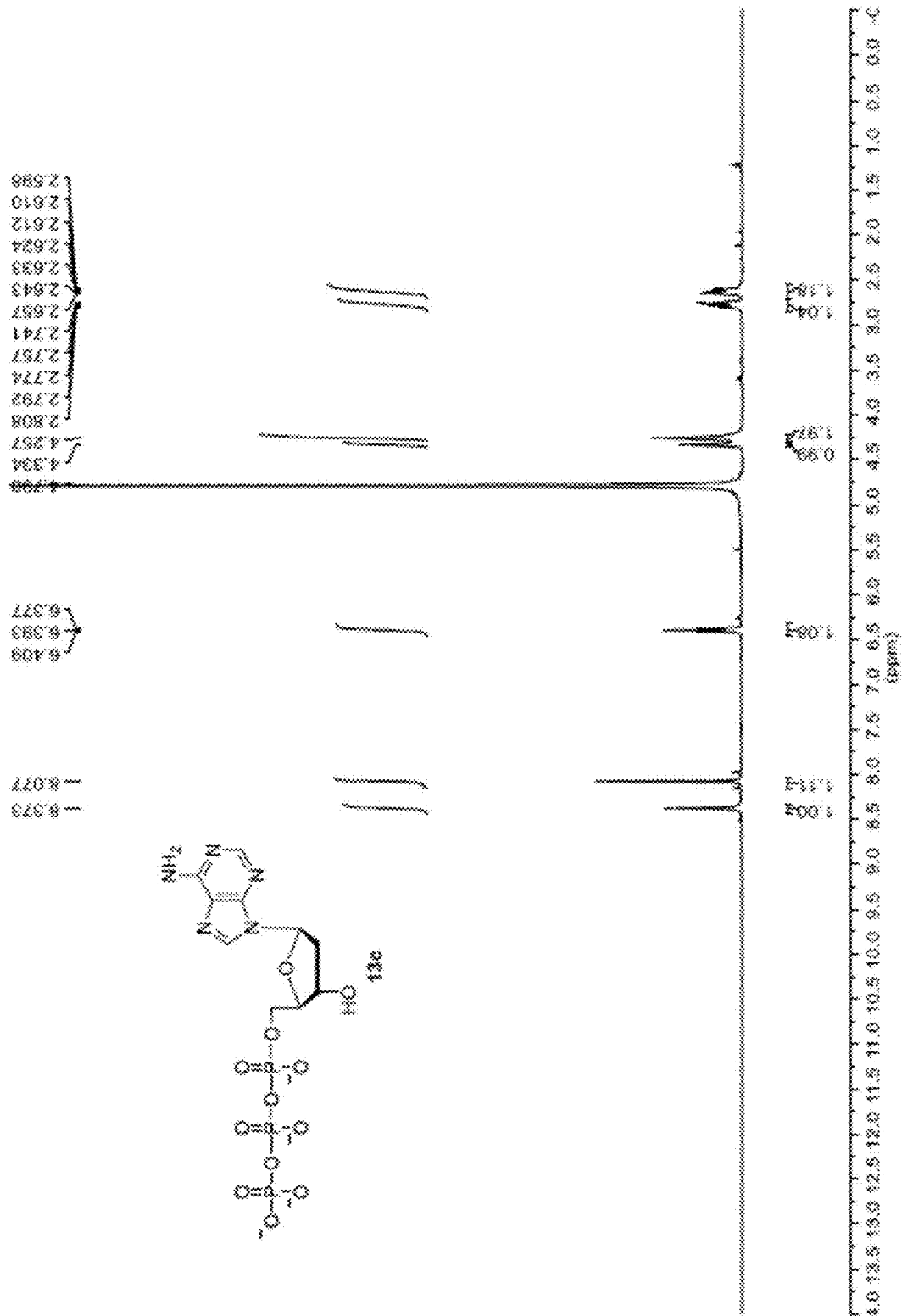
FIG. 66 depicts an $^1$H NMR spectrum of synthesized compound 13c.
Figure 67:
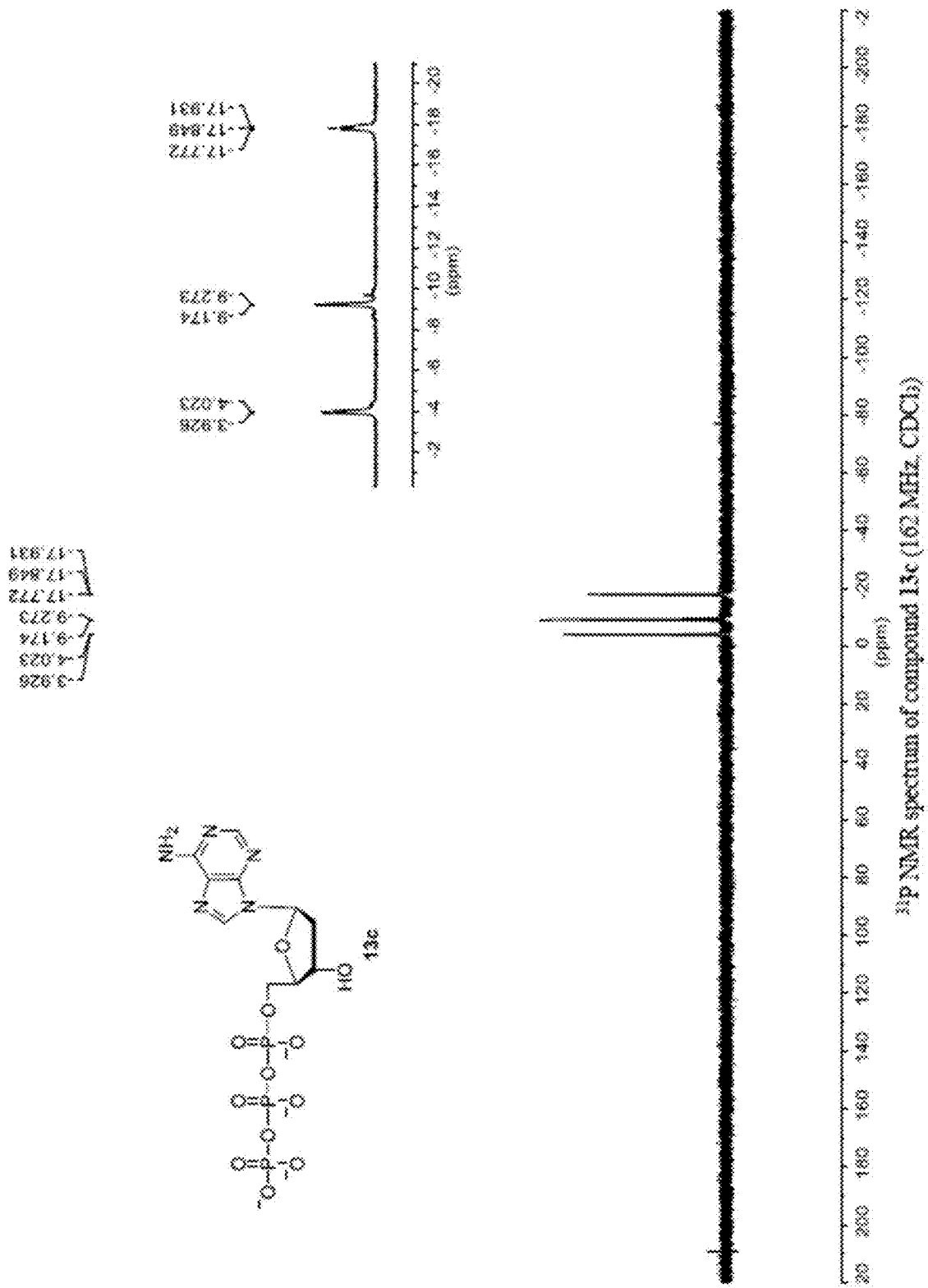
FIG. 67 depicts a $^{31}$P NMR spectrum of synthesized compound 13c.

FIG. 44 shows the synthesis scheme for 2'-deoxycytidine-5'-triphosphate (dCTP, compound 13b). FIG. 45 through FIG. 55 provide NMR spectra of the synthesized intermediates and product.

Methods used for the synthesis are now described.

3'-O, N$^4$-Dibenzoyl-2'-deoxycytidine-5'-dibenzyl-monophosphate (Compound 9b)

General procedure A with 1.04 g (2.40 mmol) of 3'-O, N$^4$-dibenzoyl-2'-deoxythymidine compound 8b, 306 mg (4.31 mmol) of tetrazole, 16 mL of anhydrous solution (MeCN; CH$_2$Cl$_2$, 1:1), 0.99 mL (3.12 mmol) of dibenzyl-N, N-diisopropylphosphoramidite for 1 hour stirring at room temperature followed by 6 mL of H$_2$O$_2$ for 1 hour oxidation reaction. Column chromatography with eluents (MeOH/CH$_2$Cl$_2$ from 0% to 12.5%) to afford the product compound 9b as a white solid; yield: 1.26 g (75.5%); TLC (MeOH/CH$_2$Cl$_2$, 1:60) $R_f$=0.32; $^1$H NMR (400 MHz, CDCl$_3$) δ 8.12 (d, 1H, J=7.6 Hz), 8.02 (d, 2H, J=7.6 Hz), 7.96 (d, 2H, J=7.6 Hz), 7.59-7.52 (m, 2H), 7.48-7.41 (m, 5H), 7.36-7.28 (m, 10H), 6.37 (dd, 1H, J=8.4, 5.6 Hz), 5.41 (d, 1H, J=6.4 Hz), 5.14-5.02 (m, 4H), 4.42-4.32 (m, 3H), 2.82 (dd, 1H, J=14.0, 5.2 Hz), 2.05-1.97 (m, 1H); $^{13}$C NMR (125.8 MHz, CDCl$_3$) δ 165.7, 162.4, 154.6, 143.8, 135.4, 135.3, 133.4, 133.1, 132.9, 129.6, 128.9, 128.7, 128.6, 128.6, 128.4, 127.9, 127.9, 127.7, 96.9, 87.0, 83.6 (d, $J_C$, P=7.8 Hz), 75.0, 69.7 (d, $J_C$, P=5.3 Hz), 66.8 (d, $J_C$, P=5.2 Hz), 38.7; $^{31}$P NMR (162 MHz, CDCl$_3$) δ 0.76; HRMS (ESI-TOF) calcd. for $C_{37}H_{34}N_3O_9PNa$ [M+Na]$^+$ 718.1931. found 718.1949.

3'-O, N$^4$-Dibenzoyl-2'-deoxycytidine-5'-monophosphate (Compound 10b)

General procedure B with 1.26 g (1.81 mmol) of compound 9b, 100 mL of MeOH, and 250 mg of 10% Pd/C for 3 h stirring. The suspension was filtered over a pad of celite, washed with 100 mL of MeOH containing 2% triethylamine four times to afford the product compound 10a as a white foam of triethylammonium salt; yield: 1.05 g (84.1%); TLC (MeOH/CH$_2$Cl$_2$, 1:10) $R_f$=0; $^1$H NMR (400 MHz, CD$_3$OD) δ 8.68 (d, 1H, J=6.8 Hz), 8.08 (d, 2H, J=7.6 Hz), 7.98 (d, 2H, J=7.6 Hz), 7.71 (d, 1H, J=7.2 Hz), 7.65-7.62 (m, 2H), 7.55-7.49 (m, 4H), 6.45 (t, 1H, J=6.0 Hz), 5.69 (d, 1H, J=4.0 Hz), 4.51 (s, 1H), 4.22 (s, 1H), 2.78 (dd, 1H, J=13.6, 4.0 Hz), 2.59-2.52 (m, 1H); $^{13}$CNMR (125.8 MHz, CD$_3$OD) δ 168.9, 167.2, 164.9, 157.9, 146.9, 134.8, 134.5, 134.0, 131.0, 130.6, 129.8, 129.7, 129.1, 99.1, 88.7, 86.5 (d, $J_C$, P=8.4

Hz), 77.8, 65.8, 40.1; $^{31}$P NMR (162 MHz, CD$_3$OD) δ 1.22; HRMS (ESI-TOF) calcd. for C$_{23}$H$_{22}$N$_3$O$_9$PNa [M+Na]$^+$ 538.0991. found 538.0984.

3'-O, N$^4$-Dibenzoyl-2'-deoxycytidine-5' phosphor-2-methylimidazolide (Compound 11b)

General procedure C with 1.05 g (1.46 mmol) of compound 10b, 7.3 mL of anhydrous DMF, 1.02 mL (7.30 mmol) of triethylamine, 252 mg (3.07 mmol) of 2-methylimidazole, 918 mg (3.5 mmol) of triphenylphosphine, 804 mg (3.65 mmol) of dipyridyl disulfide for 2 hours reaction at room temperature. First precipitation was achieved with 250 mL of diethyl ether. The product was resuspended with 10 mL of DMF and dropwise added to the solution containing 1.79 g of sodium perchlorate, 15 mL of triethylamine in 300 mL of mixing solution (ethyl acetate/ether 1.5:1) for second precipitation. The product was afforded as a white solid compound 11b; yield: 0.82 g (93.4%); $^{31}$P NMR (162 MHz, D$_2$O) δ −6.63; HRMS (ESI-TOF) calcd. for C$_{27}$H$_{25}$N$_5$O$_8$PNa$_2$ [M−H+2Na]$^+$ 624.1236. found 624.1256.

3'-O,N$^4$-Dibenzoyl-2'-deoxycytidine-5'-(γ-(2-(pyrenesulfonyl)ethyl))triphosphate (Compound 12b)

General procedure D with 0.82 g (1.36 mmol) of compound 11b, 0.77 g (1.63 mmol) of 1-(2-(pyrenesulfonyl) ethyl) pyrophosphate (compound 7) and 13.6 mL (13.6 mmol) of ZnCl$_2$ solution (1.0 M in anhydrous DMF) for 3 hours with stirring. Then crude was precipitated by dropwise adding the solution to the 300 mL of ethyl acetate with stirring for precipitation. After centrifugation, the pellet was resuspended by 20% H$_2$O/MeCN containing 2% Hunig's base and filtered by pyrex glass funnel. The filtrate was evaporated and crude product was purified by silica column chromatography with eluents 7% H$_2$O/isopropanol containing 1% diisopropylethylamine (DIPEA) and then H$_2$O in (isopropanol/MeCN 1:1) from 5% to 8% containing 1% diisopropylethylamine (DIPEA) to afford the white solid compound 12b; yield: 1.07 g (58.1%); TLC (H$_2$O/acetone 1:10 containing 2% DIPEA): Rf=0.32; 1H NMR (500 MHz, D$_2$O/DMSO-d$_6$ 1:1) δ 11.15 (s, 1H), 8.91 (s, 1H), 8.60-7.95 (m, 7H), 7.62-7.33 (m, 4H), 6.25 (s, 1H), 5.47 (s, 1H), 4.33-3.90 (m, 4H), 2.34 (s, 1H); $^{31}$P NMR (162 MHz, D$_2$O/DMSO-d$_6$ 1:1) δ −12.13 (d, 1P, J=17.2 Hz), −12.38 (d, 1P, J=14.9 Hz), −22.59 (brs, 1P); HRMS (ESI-TOF) calcd. for C$_{41}$H$_{34}$N$_3$O$_{17}$P$_3$SNa$_3$ [M−2H+3Na]$^+$ 1034.0515. found 1034.0485.

2'-deoxythymidine-5'-triphosphate (Compound 13b)

General procedure E with 1.04 g (0.79 mmol) of compound 12b in 55 mL of 33% NH$_4$OH$_{(aq)}$ for 3 hours deprotection at 37° C. and then 15 hours deprotection at room temperature. The product compound 13b was afforded as a white solid; yield: 302 mg (82.5%, C, ε$_{280}$: 13100 M$^{-1}$ cm$^{-1}$); $^1$H NMR (400 MHz, D$_2$O) δ 7.96 (d, 1H, J=7.2 Hz), 6.36 (t, 1H, J=6.4 Hz), 6.18 (t, 1H, J=6.8 Hz), 4.64 (s, 1H), 4.26 (s, 3H), 2.47-2.32 (m, 2H); $^{31}$P NMR (162 MHz, D$_2$O) δ −5.04 (brs), −9.23 (brs), −18.71 (brs).

Synthesis of 2'-deoxyadenosine-5'-triphosphate

FIG. 56 shows the synthesis scheme for 2'-deoxyadenosine-5'-triphosphate (dATP, compound 13c). FIG. 57 through FIG. 67 provide NMR spectra of the synthesized intermediates and product.

Methods used for the synthesis are now described.

3'-O, N$^6$, N$^6$-Tribenzoyl-2'-deoxyadenosine-5'-dibenzylmonophosphate (Compound 9c)

General procedure A with 1.03 g (1.83 mmol) of 3'-O, N$^6$,N$^6$-tribenzoyl-2'-deoxyadenosine compound 8c, 233 mg (3.29 mmol) of tetrazole, 12 mL of anhydrous solution (MeCN/CH$_2$Cl$_2$, 1:1), 0.75 mL (2.38 mmol) of dibenzyl-N, N-diisopropylphosphoramidite for 1 hour stirring at room temperature. Then, the reaction was added to 6 mL of H$_2$O$_2$ for 1 hour oxidation reaction. Column chromatography with eluents (EtOAc/hexane, from 33% to 66%) to afford the product compound 9c as a white foam; yield: 1.33 g (88.3%); TLC (EtOAc/hexane. 1:60) R$_f$=0.32; $^1$H NMR (400 MHz, CDCl$_3$) δ 8.63 (s, 1H), 8.38 (s, 1H), 8.06 (d, 2H, J=8.0 Hz), 7.87 (d, 3H, J=8.0 Hz), 7.64-7.61 (m, 1H), 7.50-7.46 (m, 4H), 7.37-7.28 (m, 15H), 6.60-6.56 (m, 1H), 5.55 (d, 1H, J=5.6 Hz), 5.07-5.01 (m, 4H), 4.40 (s, 1H), 4.34-4.24 (m, 2H), 2.72-2.67 (m, 2H); $^{13}$CNMR (125.8 MHz, CDCl$_3$) δ 172.7, 166.2, 153.2, 152.6, 152.3, 143.5, 134.5, 134.1, 133.4, 129.9, 129.5, 129.1, 129.1, 129.1, 129.1, 129.1, 129.0, 129.0, 128.6, 128.6, 128.1, 84.9, 83.9 (d, J$_C$, P=10.4 Hz), 75.0, 69.7 (d, J$_C$, P=5.3 Hz), 66.8 (d, J$_C$, P=5.2 Hz), 38.7; $^{31}$P NMR (162 MHz, CDCl$_3$) (50.70; HRMS (ESI-TOF) calcd. for C$_{45}$H$_{38}$N$_5$O$_9$PNa [M+Na]$^+$ 846.2305; found 846.2291.

3'-O, N$^6$. N$^6$-Tribenzoyl-2'-deoxyadenosine-5'-monophosphate (Compound 10c)

General procedure B with 1.33 g (1.62 mmol) of compound 9c, 100 mL of MeOH, and 230 mg of 10% Pd/C for 3 hours stirring. The suspension was filtered over a pad of celite, washed with 100 mL of MeOH containing 2% triethylamine four times to afford the product compound 10c as a white foam of triethylammonium salt; yield: 0.88 g (84.5%); TLC (MeOH/CH$_2$Cl$_2$ 1:10 with 1% triethylamine) R$_f$=0; $^1$H NMR (400 MHz, CD$_3$OD) δ 8.93 (s, 1H), 8.69 (s, 1H), 8.06 (d, 2H, J=7.6 Hz), 7.80-7.78 (m, 3H), 7.62-7.58 (m, 1H), 7.49-7.47 (m, 4H), 7.37-7.34 (m, 3H), 6.71 (t, 1H, J=1.6 Hz), 5.77 (d, 1H, J=5.6 Hz), 4.47 (5, 1H), 4.17-4.13 (m, 2H), 3.14-3.12 (m, 1H), 2.74 (dd, 1H, J=13.6, 5.6 Hz); $^{13}$C NMR (125.8 MHz, CD$_3$OD) 173.7, 167.2, 154.4, 153.1, 152.6, 146.3, 135.4, 134.5, 134.5, 134.2, 131.0, 130.6, 130.4, 129.8, 129.7, 129.6, 129.4, 128.9, 86.0 (d, J$_C$, P=10.4 Hz), 77.9, 66.2, 55.6, 47.5, 39.1; $^{31}$P NMR (162 MHz, CD$_3$OD) δ 2.30; HRMS (ESI-TOF) calcd. for C$_{31}$H$_{25}$N$_5$O$_9$PNa$_2$ [M−H+2Na]$^+$ 688.1185. found 688.1204.

3'-O, N$^6$, N$^6$-Tribenzoyl-2'-deoxyadenosine-5'-phosphor-2-methylimidazolide (Compound 11c)

General procedure C with 0.88 g (1.37 mmol) of compound 10c, 7.15 mL of anhydrous DMF, 1.0 mL (7.19 mmol) of triethylamine, 239 mg (2.85 mmol) of 2-methylimidazole, 760 mg (2.90 mmol) of triphenylphosphine, 642 mg (2.92 mmol) of dipyridyl disulfide for 2 hours reaction at room temperature. The crude was dropwise added to 300 mL of ether for precipitation and the solid was collected by centrifugation at 4400 rpm for 10 minutes at room temperature. The crude product was resuspended with minimal volume of CH$_2$Cl$_2$ and dropwise added to 300 mL of ether containing 1.4 g of LiClO$_4$. The precipitate was collected by centrifugation at 4400 rpm for 10 minutes at room temperature to afford the white solid compound 11c; yield: 1.08 g (97.5%);

$^{31}$P NMR (162 MHz, D$_2$O) δ 7.59; HRMS (ESI-TOF) calcd. for C$_{35}$H$_{30}$N$_7$O$_8$PNa [M+Na]$^+$ 730.1791. found 730.1799.

3'-O, N$^6$, N$^6$-Tribenzoyl-2'-deoxyadenosine-5'-γ-(2-(pyrenesulfonyl)ethyl]-triphosphate (Compound 12c)

General procedure D with 1.08 g (1.34 mmol) of compound 11c, 0.77 g (1.63 mmol) of 1-(2-(pyrenesulfonyl)ethyl)-pyrophosphate (compound 7) and 13.6 mL (13.6 mmol) of ZnCl$_2$ solution (1.0 M in anhydrous DMF) for 3 hours with stirring. After the reaction, the solution was precipitated by 300 mL of ether. After centrifugation, the pellet was resuspended by 20% H$_2$O/MeCN containing 2% Hunig's base and filtered by pyrex glass funnel. The filtrate was evaporated and the crude product was purified by silica column chromatography with eluents [(8% H$_2$O/isopropanol+1% diisopropylethylamine), then (H$_2$O/(isopropanol-MeCN 1:1) from 2% to 7% containing 1% diisopropylethylamine (DIPEA)] to afford the white solid compound 12c; yield: 928 mg (46.7%); TLC (H$_2$O/acetone 1:10 containing 2% DIPEA): Rf=0.28; $^1$H NMR (600 MHz, D$_2$O/DMSO-d$_6$ 1:1) δ 8.58-8.57 (m, 1H), 8.45 (s, 1H), 8.37-8.33 (m, 2H), 8.06-7.70 (m, 11H), 7.57-7.32 (m, 7H), 5.94 (t, 1H, J=7.2 Hz), 5.31 (s, 1H), 4.20 (d, 2H, J=6.6 Hz), 3.99-3.97 (m, 2H), 3.86-3.84 (m, 1H), 3.75-3.74 (m, 1H), 2.55 (s, 1H), 2.10 (dd, 1H, J=13.8, 4.8 Hz); $^{31}$P NMR (162 MHz, D$_2$O/DMSO-d$_6$ 1:1) δ −10.24 (d, J=14.9 Hz), −10.45 (d, J=14.7 Hz), −20.67 (brs, 1P); HRMS (ESI-TOF) calcd. for C$_{42}$H$_{34}$N$_5$O$_{16}$P$_3$SNa [M−2H+Na]$^+$ 1012.0832. found 1012.0827. During HRMS, analysis one of the two benzoyl group is removed from the exocyclic amino group.

2'-deoxyadenosine-5'-triphosphate (Compound 13c)

General procedure E with 928 mg (0.63 mmol) of compound 12c in 45 mL of 33% NH$_4$OH$_{(aq)}$ in deprotection step for 3 hours at 37° C. and then 15 hours at room temperature. The product compound 13c was afforded as a white solid; yield: 284 mg (92.6%, A, ε$_{259}$: 15200 M$^{-1}$ cm$^{-1}$); $^1$H NMR (400 MHz, D$_2$O) δ 8.37 (s, 1H), 8.08 (s, 1H), 6.39 (t, 1H, J=6.4 Hz), 4.33 (s, 1H), 4.26 (s, 2H), 2.81-2.74 (m, 1H), 2.66-2.60 (m, 1H); $^{31}$P NMR (162 MHz, D$_2$O) δ −3.97 (d, J=15.7 Hz), −9.22 (d, J=16.0 Hz), −17.85 (t, J=13.3 Hz).

Synthesis of 2'-deoxyguanosine-5'-triphosphate

Figure 68:
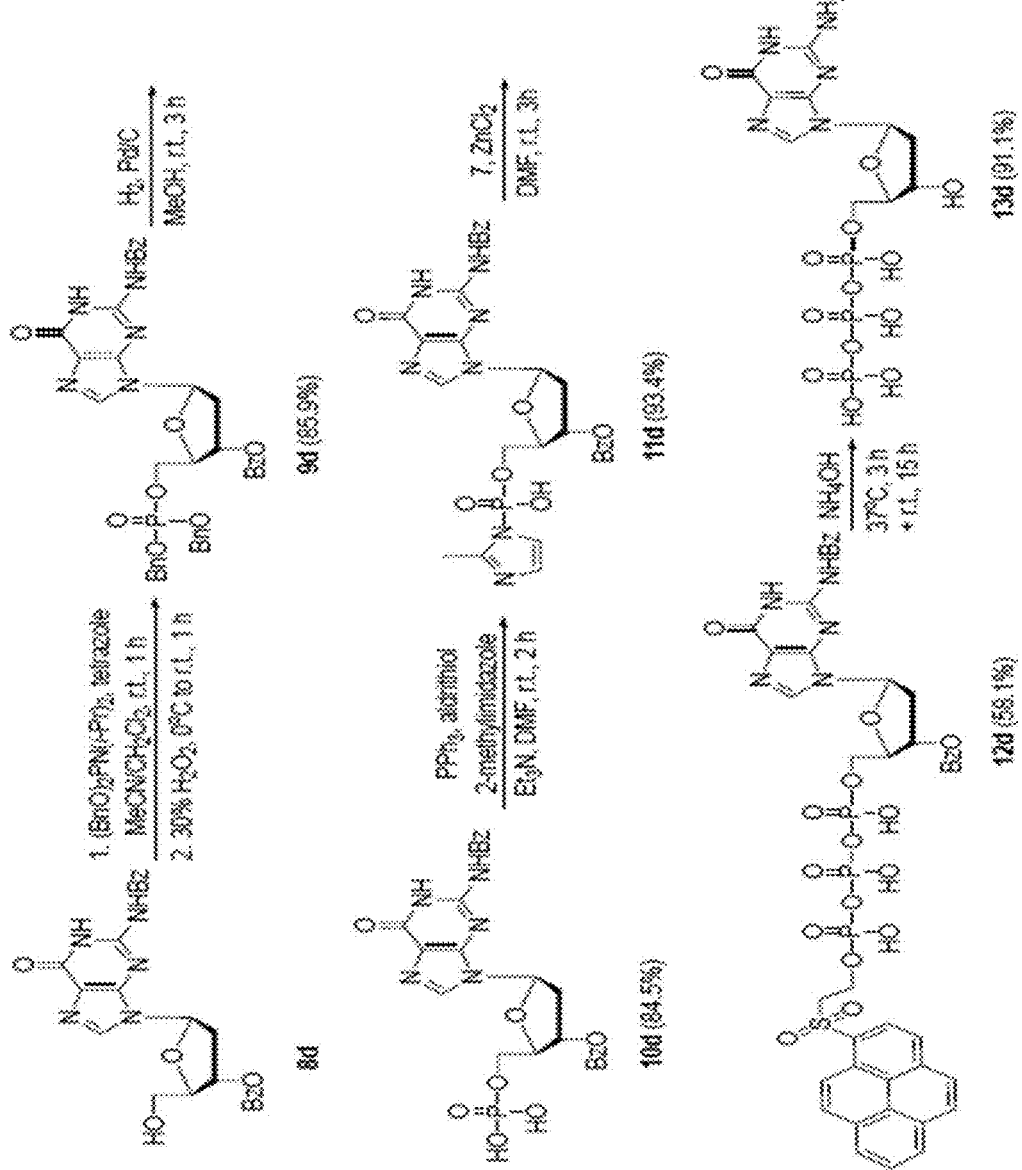
FIG. 68 depicts a synthesis scheme for 2'-deoxyguanosine-5'-triphosphate (dGTP, compound 13d).
Figure 69:
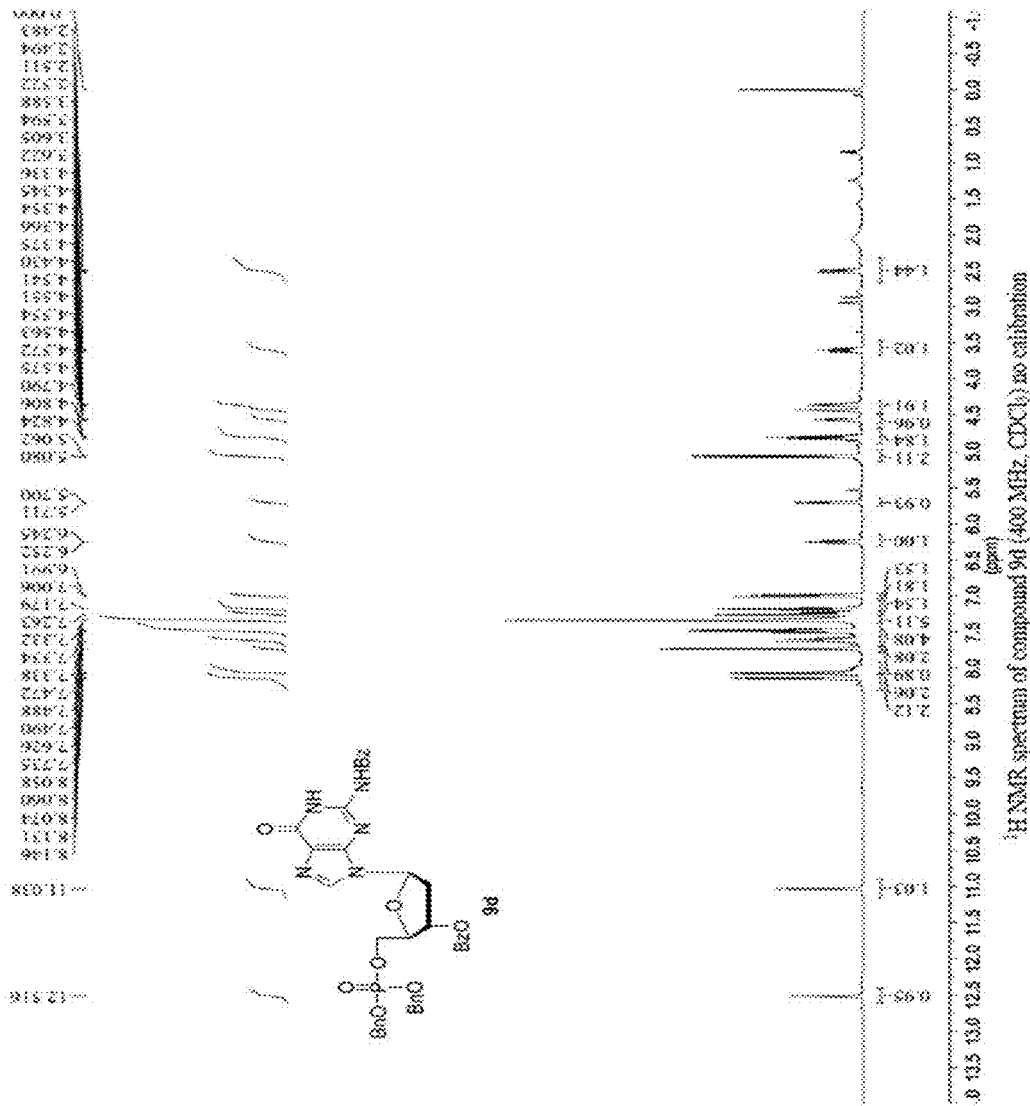
FIG. 69 depicts an $^1$H NMR spectrum of synthesized 3'-O, N2-Dibenzoyl-2'-deoxyguanosine-5'-dibenzylmonophosphate (compound 9d).
Figure 70:
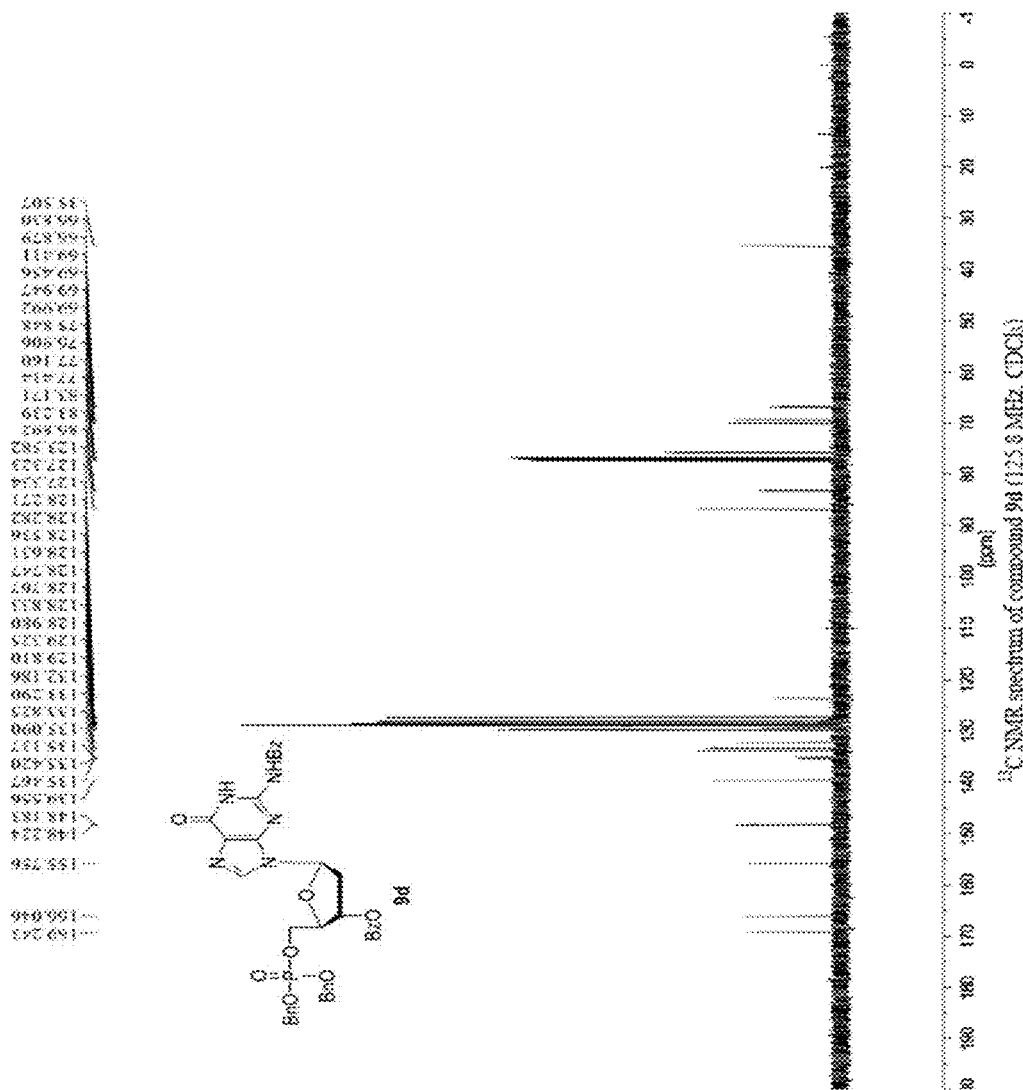
FIG. 70 depicts a $^{13}$C NMR spectrum of synthesized compound 9d.
Figure 71:
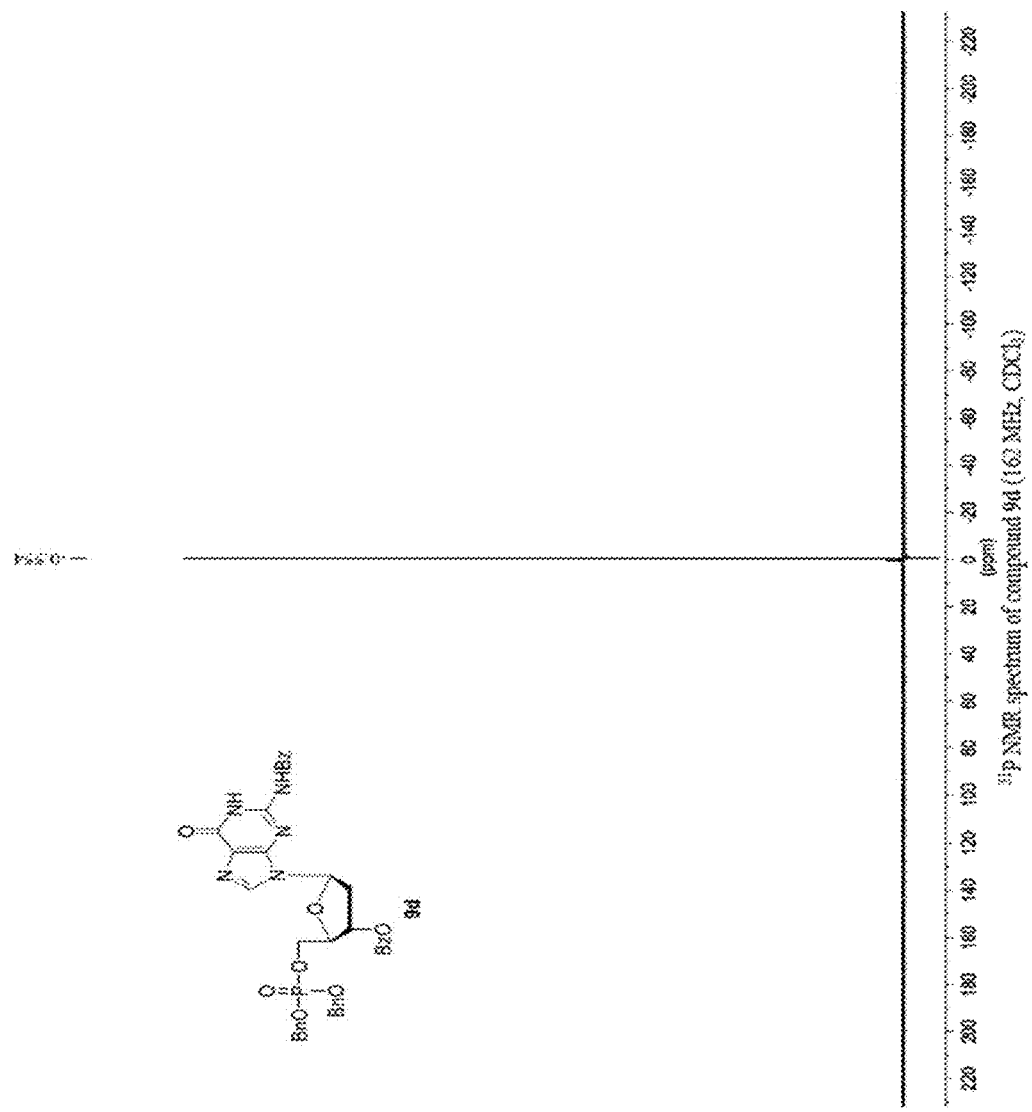
FIG. 71 depicts an $^{31}$P NMR spectrum of synthesized compound 9d.
Figure 72:
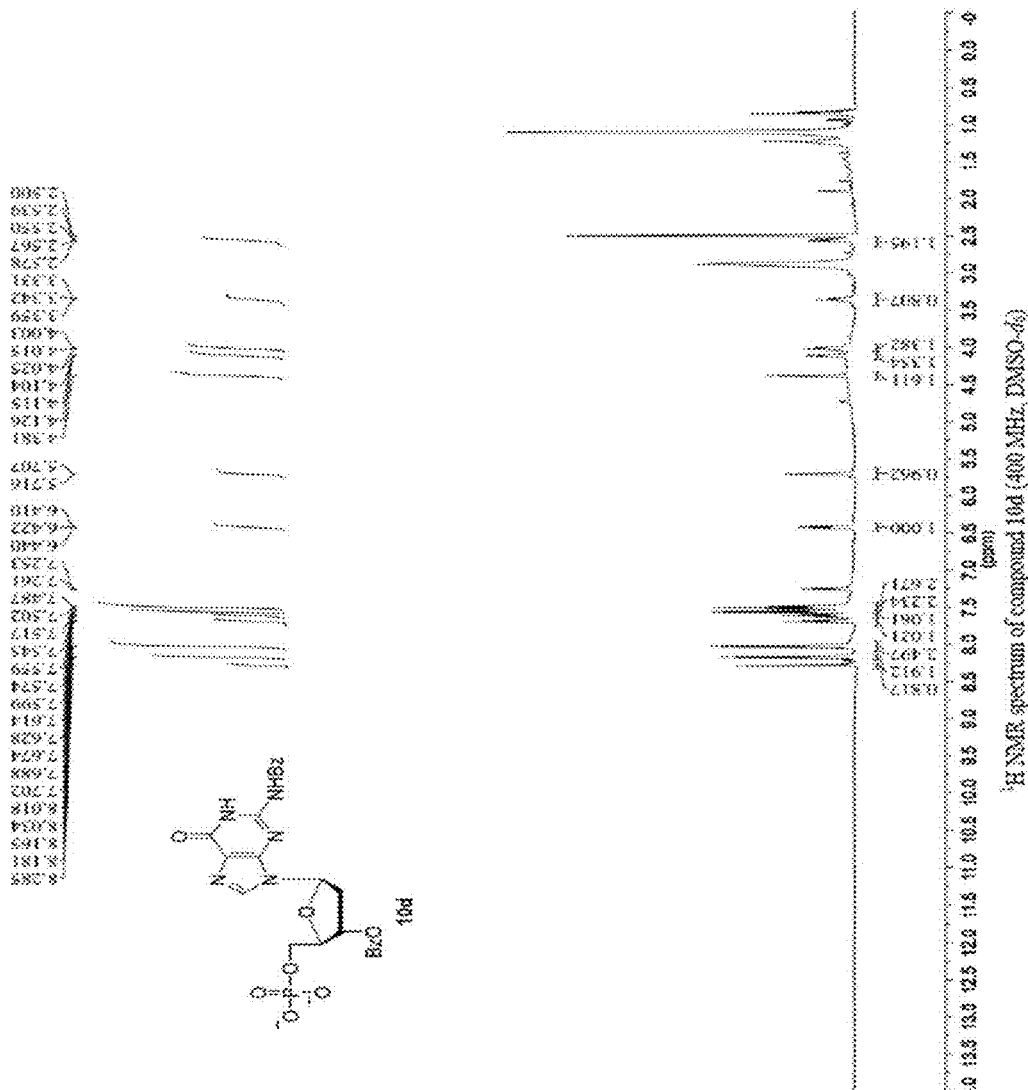
FIG. 72 depicts an $^1$H NMR spectrum of synthesized 3'-O, N2-Dibenzoyl-2'-deoxyguanosine-5'-monophosphate (compound 10d).
Figure 73:
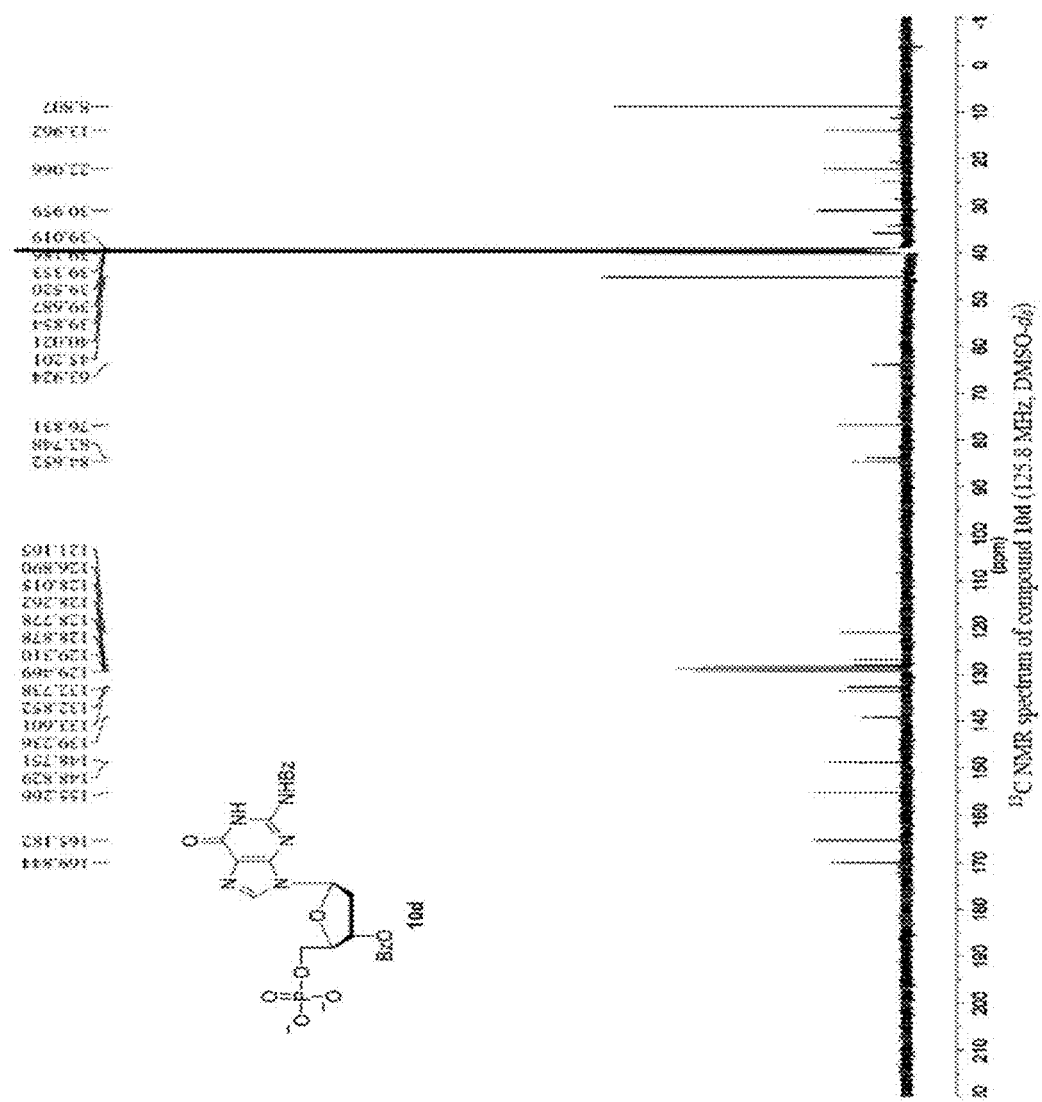
FIG. 73 depicts a $^{13}$C NMR spectrum of synthesized compound 10d.
Figure 74:
FIG. 74 depicts an $^{31}$P NMR spectrum of synthesized compound 10d.
Figure 75:
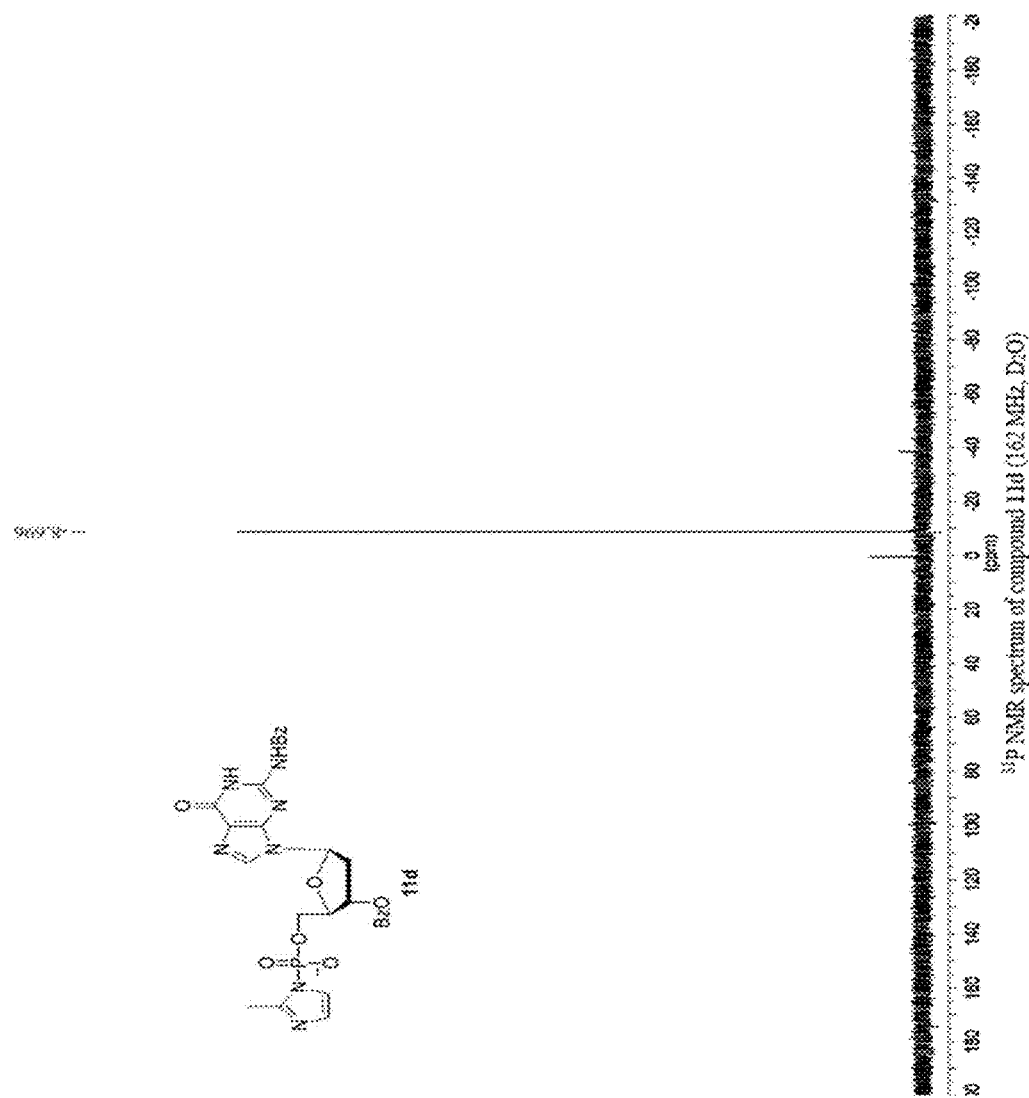
FIG. 75 depicts an $^{31}$P NMR spectrum of synthesized 3'-O, N$^2$-Dibenzoyl-2'-deoxyguanosine-5'-phosphor-2-methylimidazolide (compound 11d).
Figure 76:
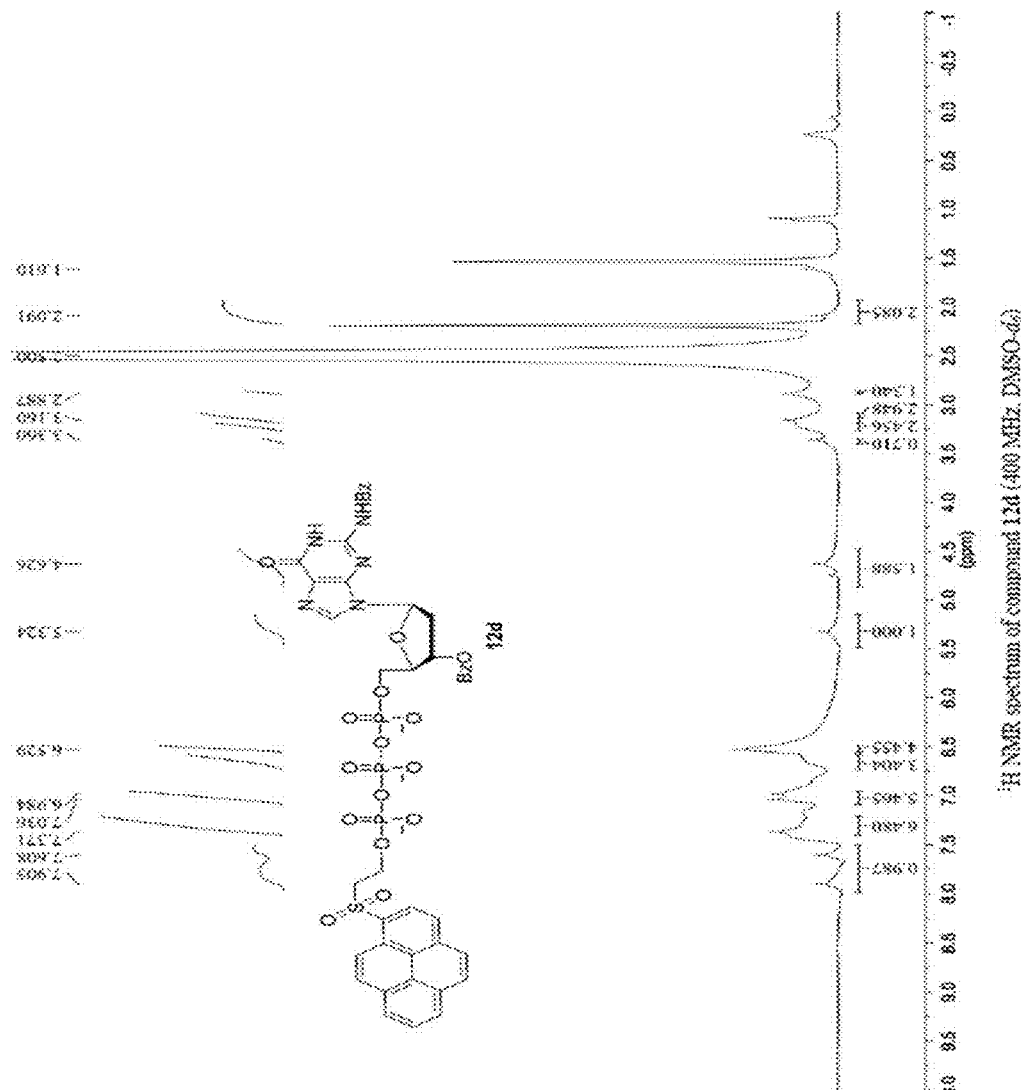
FIG. 76 depicts an $^1$H NMR spectrum of synthesized 3'-O, N$^2$-Dibenzoyl-2'-deoxyadenosine-5'-(γ(2-(pyrenesulfonyl)ethyl))-triphosphate (compound 12d)
Figure 77:
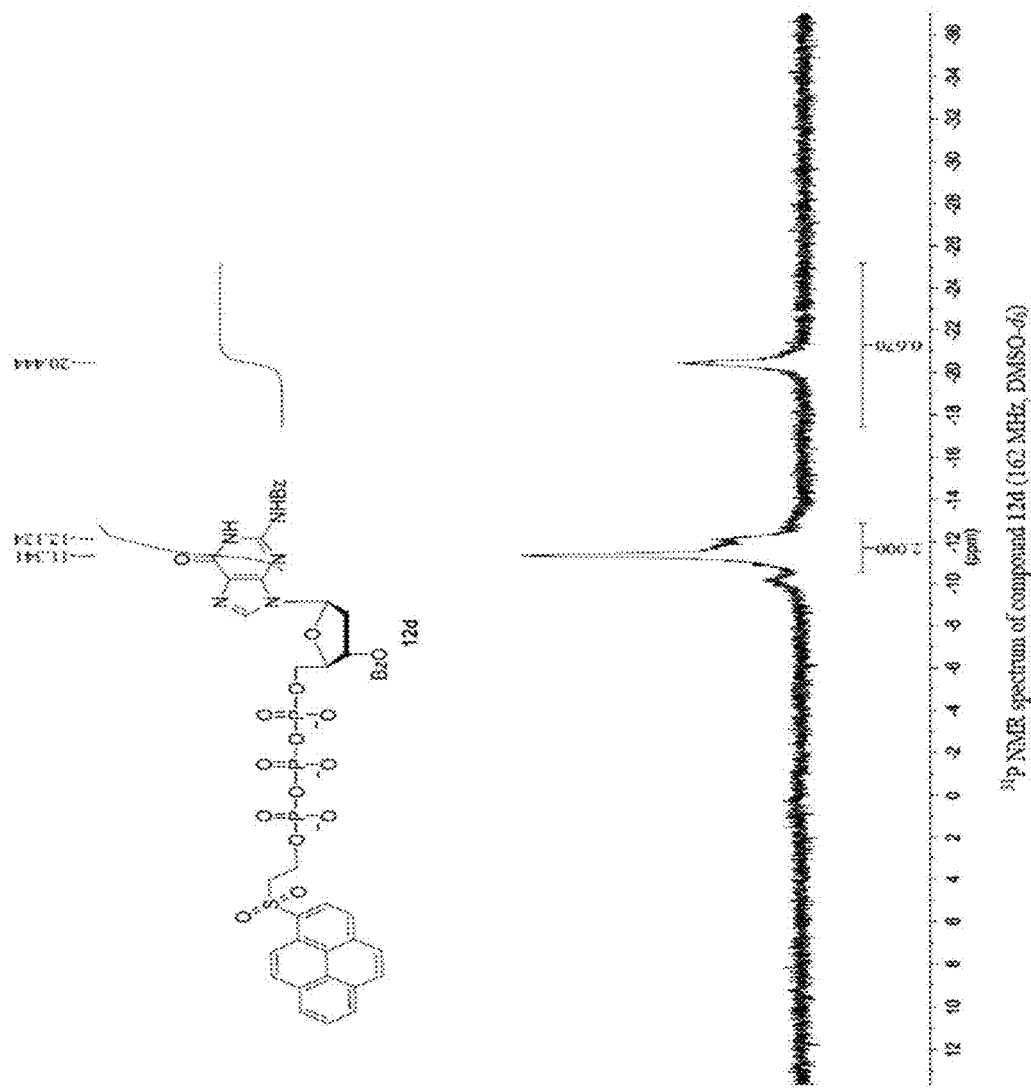
FIG. 77 depicts a MIR spectrum of synthesized compound 12d.
Figure 78:
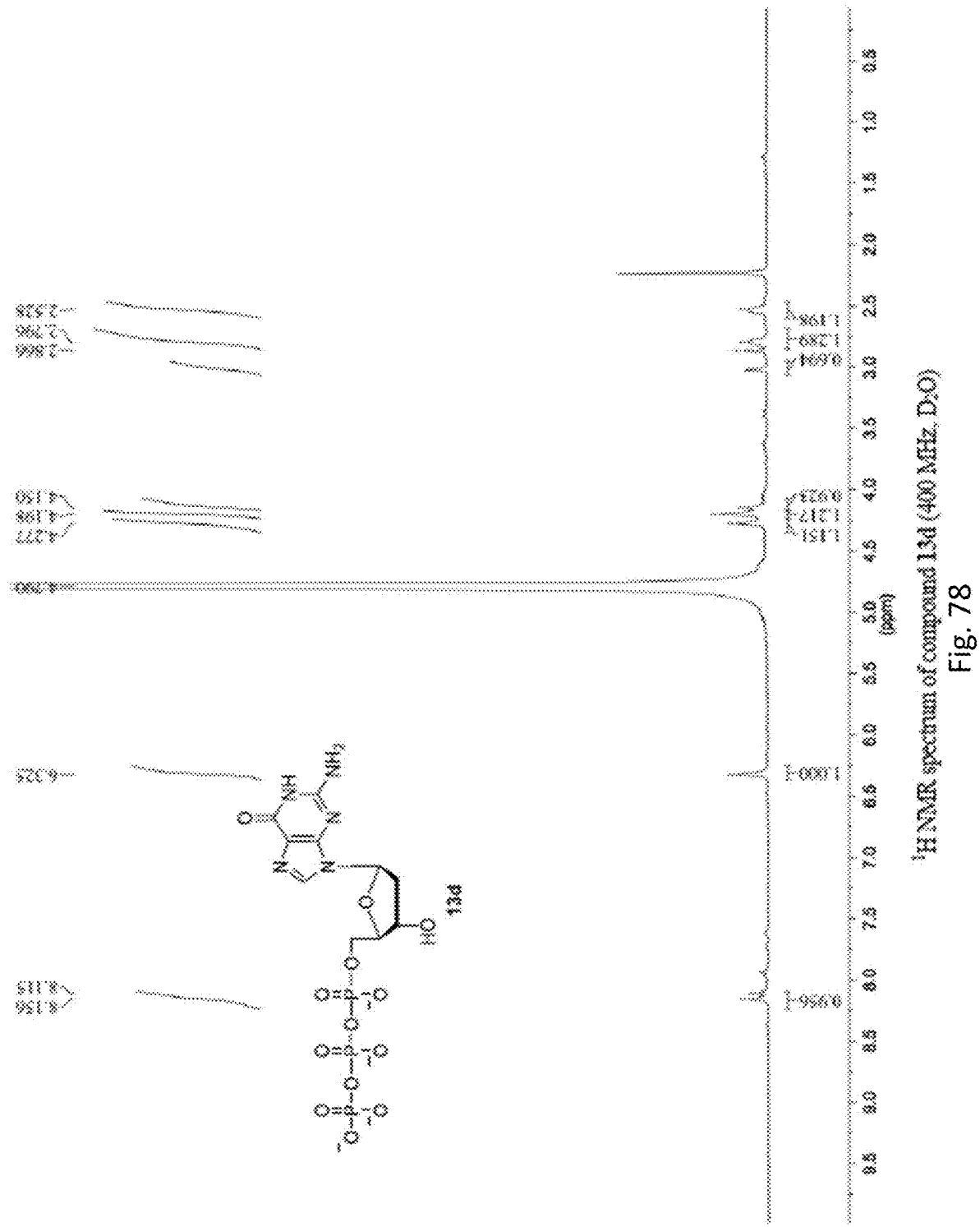
FIG. 78 depicts an $^1$H NMR spectrum of synthesized compound 13d.
Figure 79:
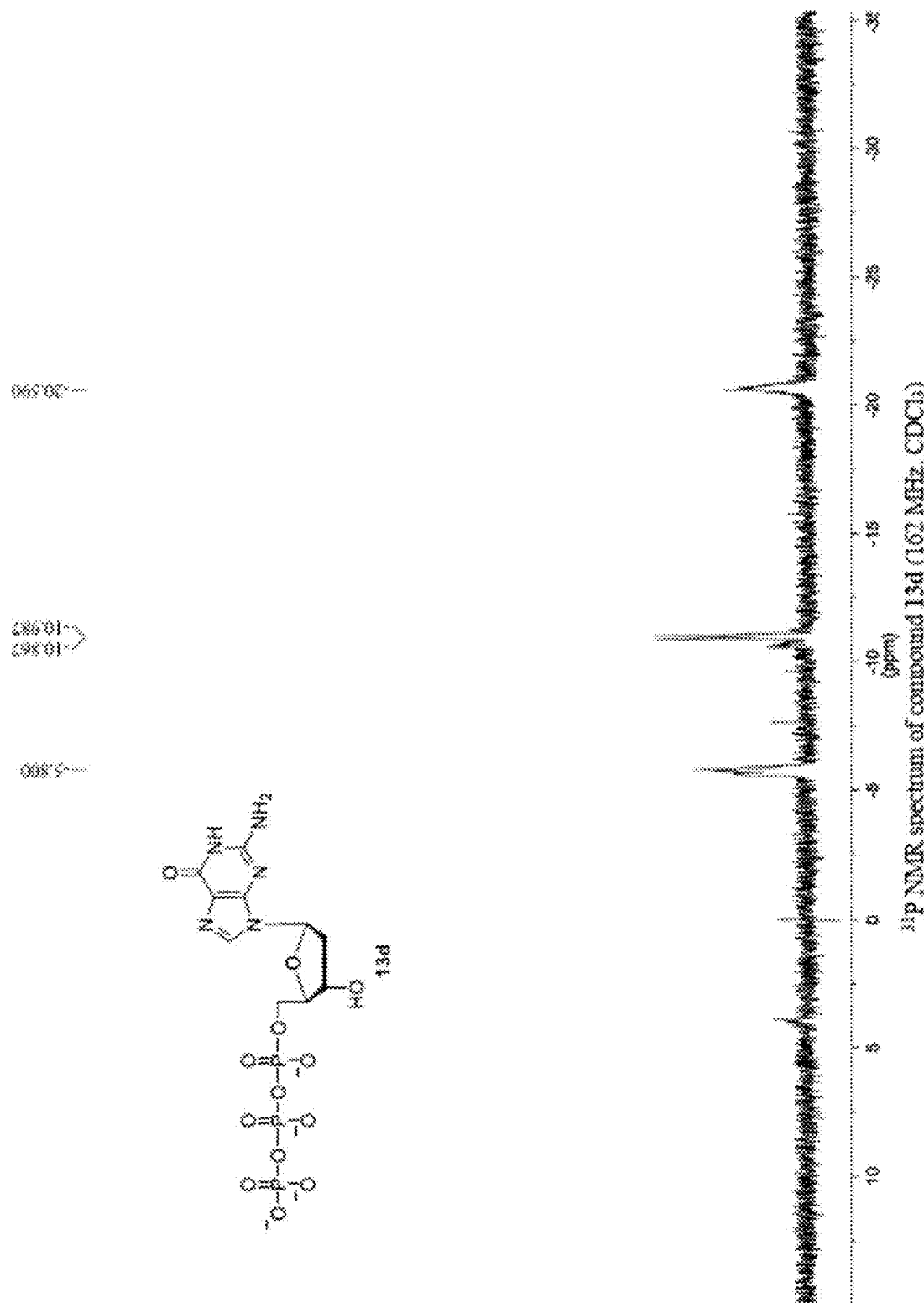
FIG. 79 depicts a $^{31}$P NMR spectrum of synthesized compound 13d.

FIG. 68 shows the synthesis scheme for 2'-deoxyguanosine-5'-triphosphate (dGTP, compound 13d). FIG. 69 through and FIG. 79 provide NMR spectra of the synthesized intermediates and product.

Methods used for the synthesis are now described.

3'-O, N$^2$-Dibenzoyl-2'-deoxyguanosine-5'-dibenzyl-monophosphate (Compound 9d)

General procedure A with 1.0 g (2.10 mmol) of 3'-O, N$^2$-dibenzoyl-2'-deoxyguanosine. 0.29 g (4.21 mmol) of tetrazole, 15 mL of anhydrous solution (MeCN/CH$_2$Cl$_2$, 1:1), 0.85 mL (2.52 mmol) of dibenzyl-N, N-diisopropylphosphoramidite for 1 hour stirring at room temperature. Then, the reaction was added to 6 mL of H$_2$O$_2$ for 1 hour oxidation reaction. Column chromatography with eluents (EtOAc/hexane, from 33% to 66%) to afford the product compound 9d as a white foam; yield: 1.35 g (85.9%); TLC (EtOAc/hexane, 1:60) R$_f$=0.32; $^1$H NMR (400 MHz, CDCl$_3$) δ 12.51 (s, 1H), 11.03 (s, 1H), 8.14 (d, 2H, J=6.0 Hz), 8.06 (d, 2H, J=16.0 Hz), 7.73 (s, 1H), 7.62-7.60 (m, 2H), 7.50-7.45 (m, 4H), 7.33 (m, 5H), 7.26-7.22 (m, 1H), 7.19-7.16 (m, 1H), 7.00 (d, 2H, J=16.0 Hz), 6.25 (dd, 1H, J=12.0, 2.8 Hz), 5.70 (d, 11-1, J=4.4 Hz), 5.08 (d, 2H, J=4.4 Hz), 4.80 (m, 2H), 4.56 (m, 1H), 4.43 (s, 1H), 4.35 (m, 1H), 3.60 (m, 1H), 2.51 (s, 1H); $^{13}$C NMR (125.8 MHz, CDCl$_3$) δ 169.2, 166.0, 155.7, 148.2, 148.1, 139.5, 135.4, 135.1, 135.0, 133.8, 133.2, 132.1, 129.8, 129.3, 128.9, 128.8, 128.7, 128.6, 128.5, 128.3, 128.2, 128.2, 127.3, 127.3, 123.5, 86.8, 83.2, 75.8, 69.9 (d, J$_C$, P=5.3 Hz), 69.4 (d, J$_C$, P=5.2 Hz), 66.8, 35.5; $^{31}$P NMR (162 MHz, CDCl$_3$) δ −0.55; HRMS (ESI-TOF) calcd. for C$_{38}$H$_{34}$N$_5$O$_9$PNa [M+Na]$^+$ 758.1992; found 758.2000.

3'-O, N$^2$-Dibenzoyl-2'-deoxyguanosine-5'-monophosphate (Compound 10d)

General procedure B with 0.88 g (1.19 mmol) of compound 9d, 10 mL of MeOH, and 250 mg of 10% Pd/C for 3 hours with stirring. The suspension was filtered over a pad of celite, washed with 100 mL of MeOH containing 2% triethylamine four times to afford the product compound 10d as a white foam of triethylammonium salt; yield: 0.72 g (84.5%); TLC (MeOH/CH$_2$Cl$_2$ 1:10 with 1% triethylamine); $^1$H NMR (400 MHz, DMSO-d$_6$) δ 8.28 (s, 1H), 8.18 (d, 2H, J=6.4 Hz), 8.03 (m, 2H), 7.70-7.62 (m, 1H), 7.61-7.59 (m, 1H), 7.57-7.54 (m, 2H), 7.51 (m, 2H), 6.44 (m, 1H), 5.71 (d, 1H, J=3.6 Hz), 4.38 (s, 1H), 4.12 (m, 1H), 4.02 (m, 1H), 3.35 (m, 1H), 2.56 (dd, 1H, J=15.6, 6.8 Hz). $^{13}$C NMR (125.8 MHz, DMSO-d$_6$) δ 169.8, 165.1, 155.2, 148.8, 139.2, 133.6, 132.8, 132.7, 129.4, 129.3, 128.8, 128.7, 128.2, 128.0, 126.8, 121.1, 84.6, 83.7, 76.8, 63.9, 30.5; $^{31}$P NMR (162 MHz, CD$_3$OD) δ −0.34; HRMS (ESI-TOF) calcd. for C$_{24}$H$_{21}$N$_5$O$_9$PNa$_2$ [M−H+2Na]$^+$ 600.0872. found 600.0865.

3'-O, N$^2$-Dibenzoyl-2'-deoxyguanosine-5'-phosphor-2-methylimidazolide (Compound 11d)

General procedure C with 0.65 g (1.17 mmol) of compound 10d, 10 mL of anhydrous DMF, 0.82 mL (7.19 mmol) of triethylamine, 240 mg (5.85 mmol) of 2-methylimidazole, 768.3 mg (2.93 mmol) of triphenylphosphine, 645.5 mg (2.93 mmol) of dipyridyl disulfide for 2 hours reaction at room temperature. First precipitation was achieved with 300 mL of diethyl ether. The product was resuspended with 15 mL of CH$_2$Cl$_2$ and dropwise added to the solution containing 1.17 g of sodium perchlorate, 15 mL of triethylamine in 300 mL of ethyl acetate for second precipitation. The product was afforded as a white solid compound 11d; yield: 0.68 g (93.4%); $^{31}$P NMR (162 MHz, D$_2$O) 6-8.70; HRMS (ESI-TOF) calcd. for C$_{28}$H$_{25}$N$_7$O$_8$PNa$_2$ [M−H+2Na]$^+$ 664.1298. found 664.1276.

3'-O, N$^2$-Dibenzoyl-2'-deoxyadenosine-5'-(γ-(2-(pyrenesulfonyl)ethyl))-triphosphate (Compound 12d)

General procedure D with 0.5 g (0.81 mmol) of compound 11d, 0.495 g (1.05 mmol) of 1-(2-(pyrenesulfonyl)ethyl)-pyrophosphate (compound 7) and 5.38 mL (8.07 mmol) of ZnCl$_2$ solution (1.5 M in anhydrous DMF) for 3 h with stirring. After the reaction, the solution was precipitated by 300 mL of ether. Silica column chromatography with eluents [(H$_2$O in isopropanol/MeCN) 1:1 from 3% to 8% containing 1% diisopropylethylamine (DIPEA)] to afford the white solid compound 12d; yield: 1.07 g (58.1%); TLC (H$_2$O/acetonitrile 1:10 containing 2% DIPEA) Rf=0.34; $^1$H NMR (400 MHz, DMSO-d$_6$) δ 7.90-7.60 (m, 1H), 7.31 (s, 6H), 7.03-6.98 (m, 5H), 6.72 (m, 3H), 6.52 (s, 4H), 5.32 (s, 1H), 4.62 (s, 1H), 3.36 (brs, 2H), 3.16 (brs, 2H), 2.87 (s, 1H), 2.09 (s, 2H); $^{31}$P NMR (162 MHz, DMSO-d$_6$) δ −11.34, −12.12, −20.44; HRMS (ESI-TOF) calcd. for C$_{42}$H$_{34}$N$_5$O$_{17}$P$_3$SNa [M−2H+Na]$^-$ 1028.0781. found 1028.0796.

2'-deoxyguanosine-5'-triphosphate (Compound 13d)

General procedure E with 800 mg (0.81 mmol) of compound 12d in 45 mL of 33% NH$_4$OH$_{(aq)}$ for 3 hours at 37° C. and then 15 hours deprotection reaction at room temperature. The product compound 13d was afforded as a white solid; yield: 372 mg (91.1%, G, ε$_{253}$: 13700 M$^{-1}$ cm$^{-1}$); $^1$H NMR (400 MHz, D$_2$O) δ 8.15 (m, 1H), 6.32 (s, 1H), 4.27 (s, 1H), 4.19 (m, 2H), 4.15 (s, 1H), 2.79 (brs, 1H), 2.52 (s, 1H); $^{31}$P NMR (162 MHz, D$_2$O) 6-5.80 (d, J=15.7 Hz), −10.86 (d, J=16.0 Hz), −20.59 (t, J=13.3 Hz).

Synthesis of 2'-deoxythymidine-3'-triphosphate

Figure 80:
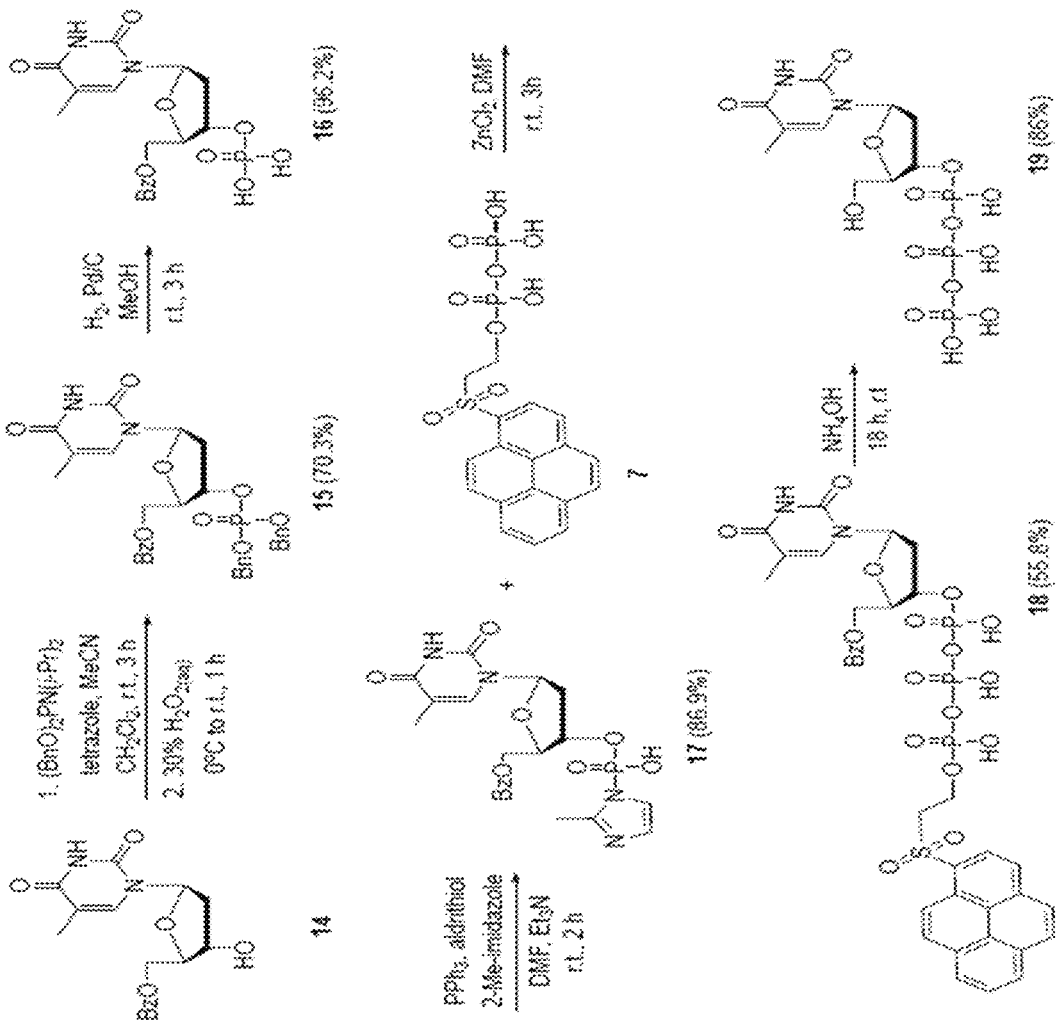
FIG. 80 depicts a synthesis scheme for 2'-deoxythymidine-3'-triphosphate (3'-TTP, compound 19).
Figure 81:
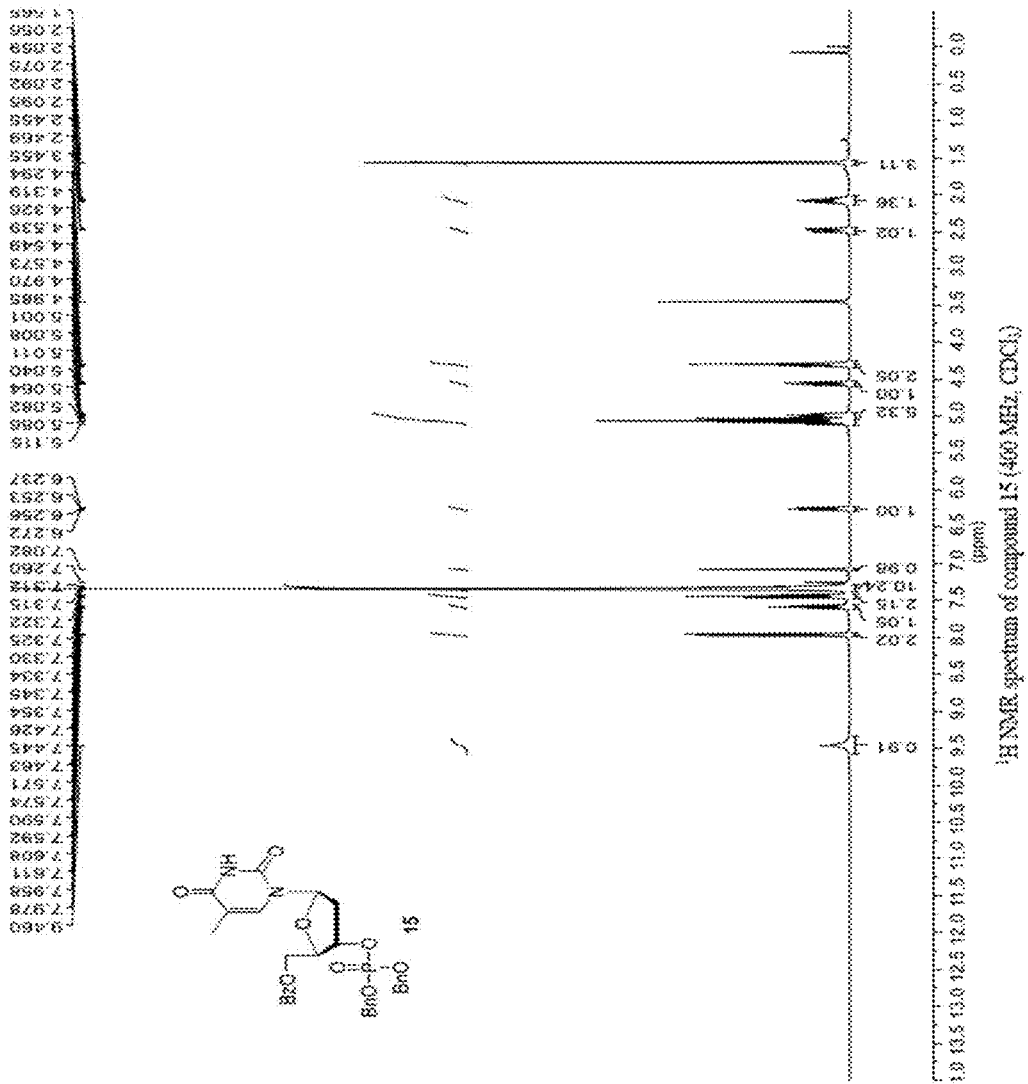
FIG. 81 depicts an $^1$H NMR spectrum of synthesized 5'-Benzoyl-2'-(compound 15).
Figure 82:
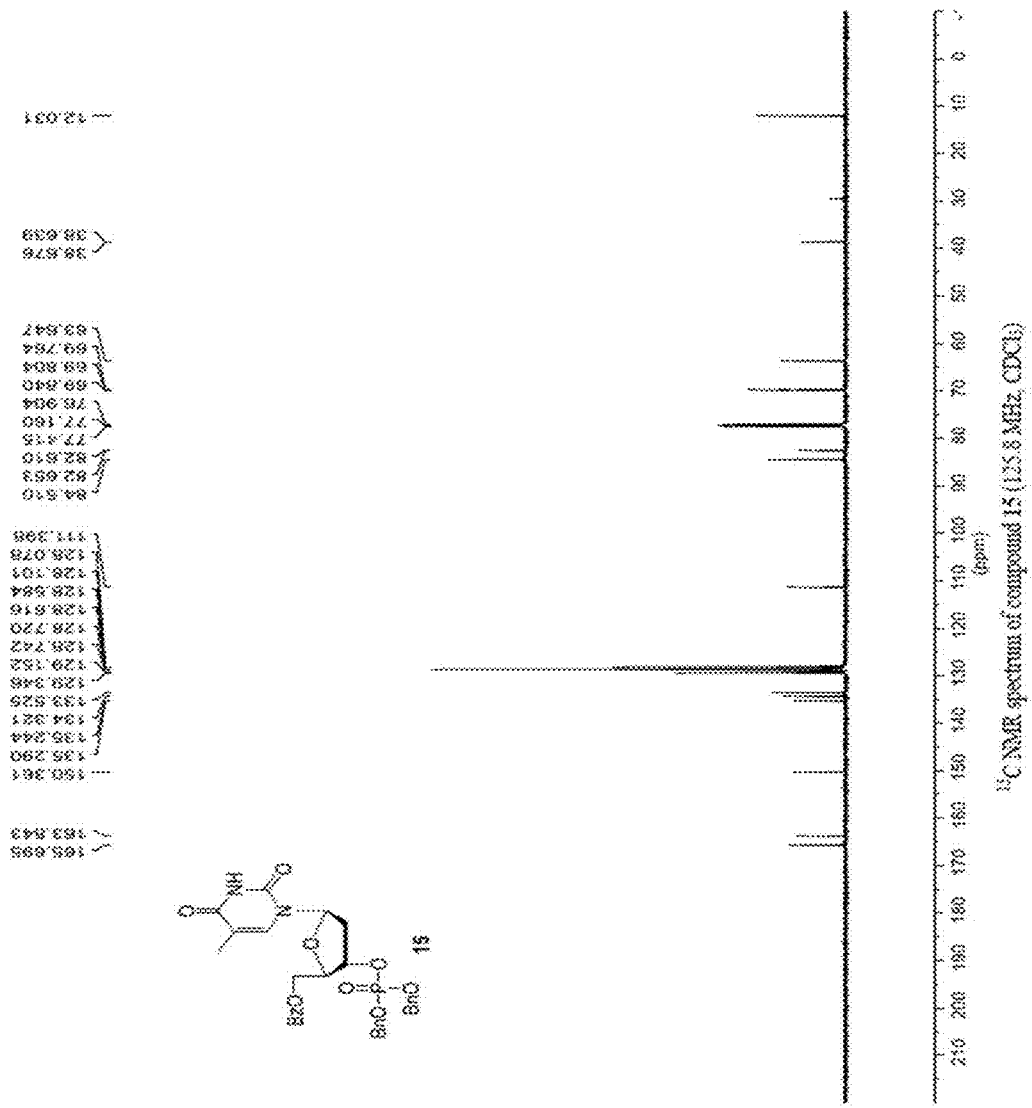
FIG. 82 depicts a $^{13}$C NMR spectrum of synthesized compound 15.
Figure 83:
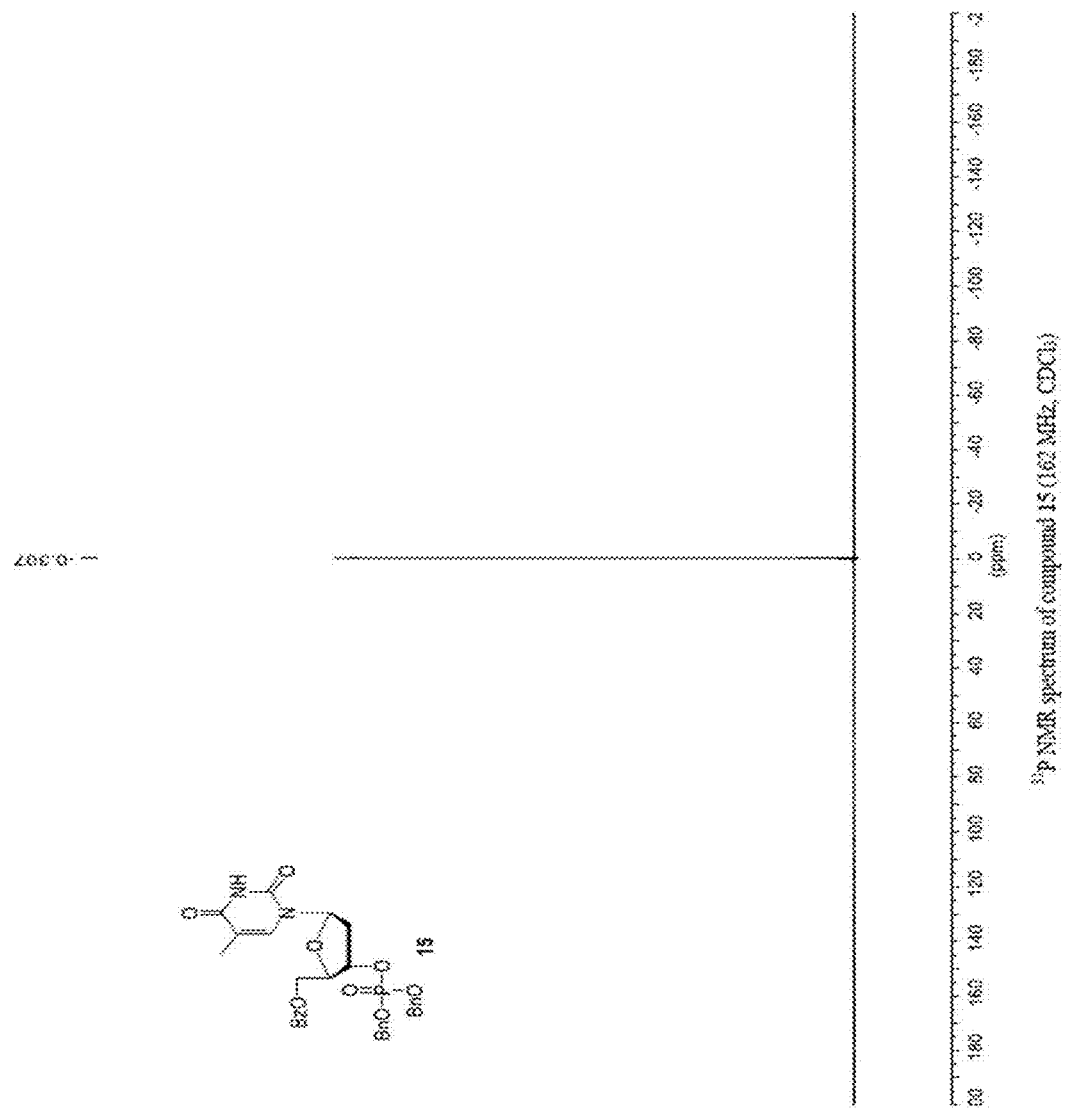
FIG. 83 depicts an $^{31}$P NMR spectrum of synthesized compound 15.
Figure 84:
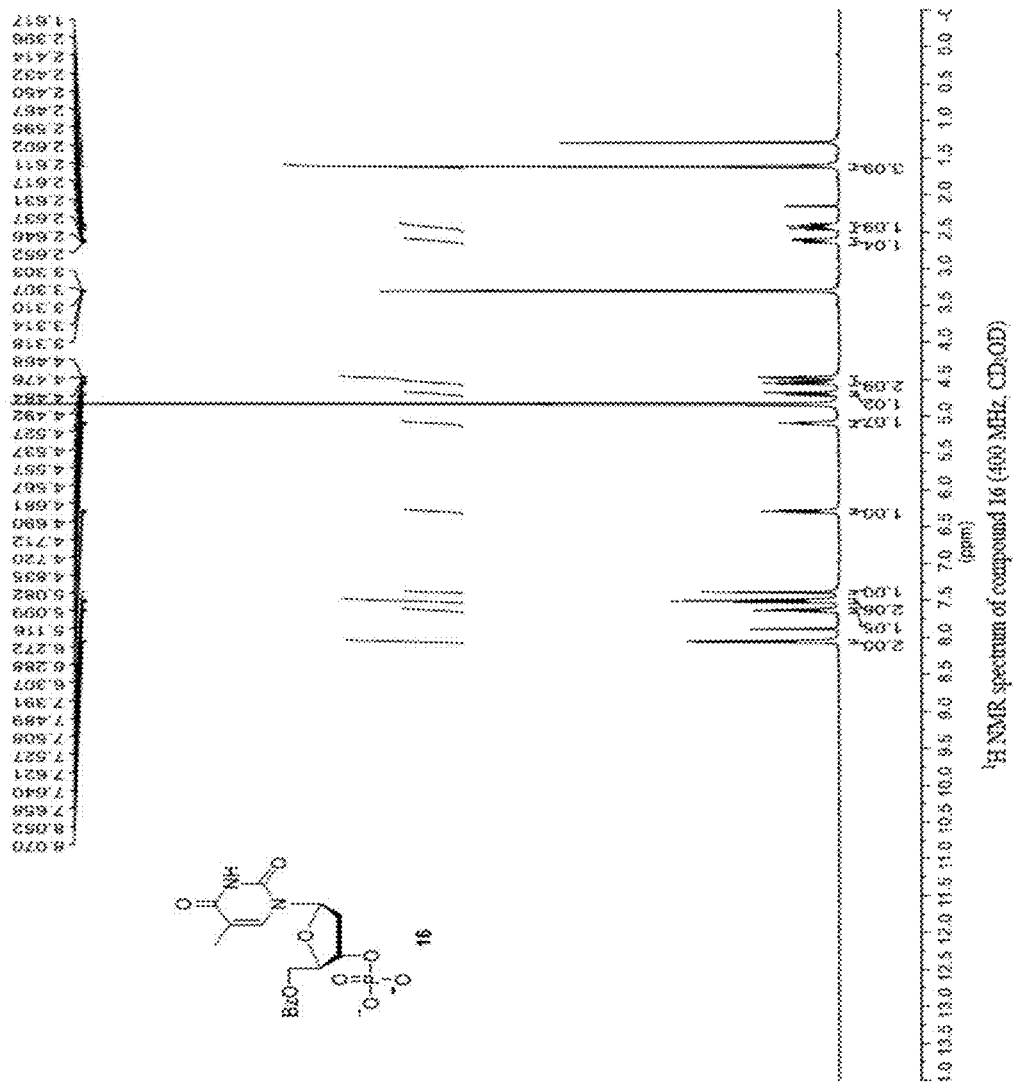
FIG. 84 depicts an $^1$H NMR spectrum of synthesized 5'-Benzoyl-2'-deoxythymidine-3'-monophosphate (compound 16).
Figure 85:
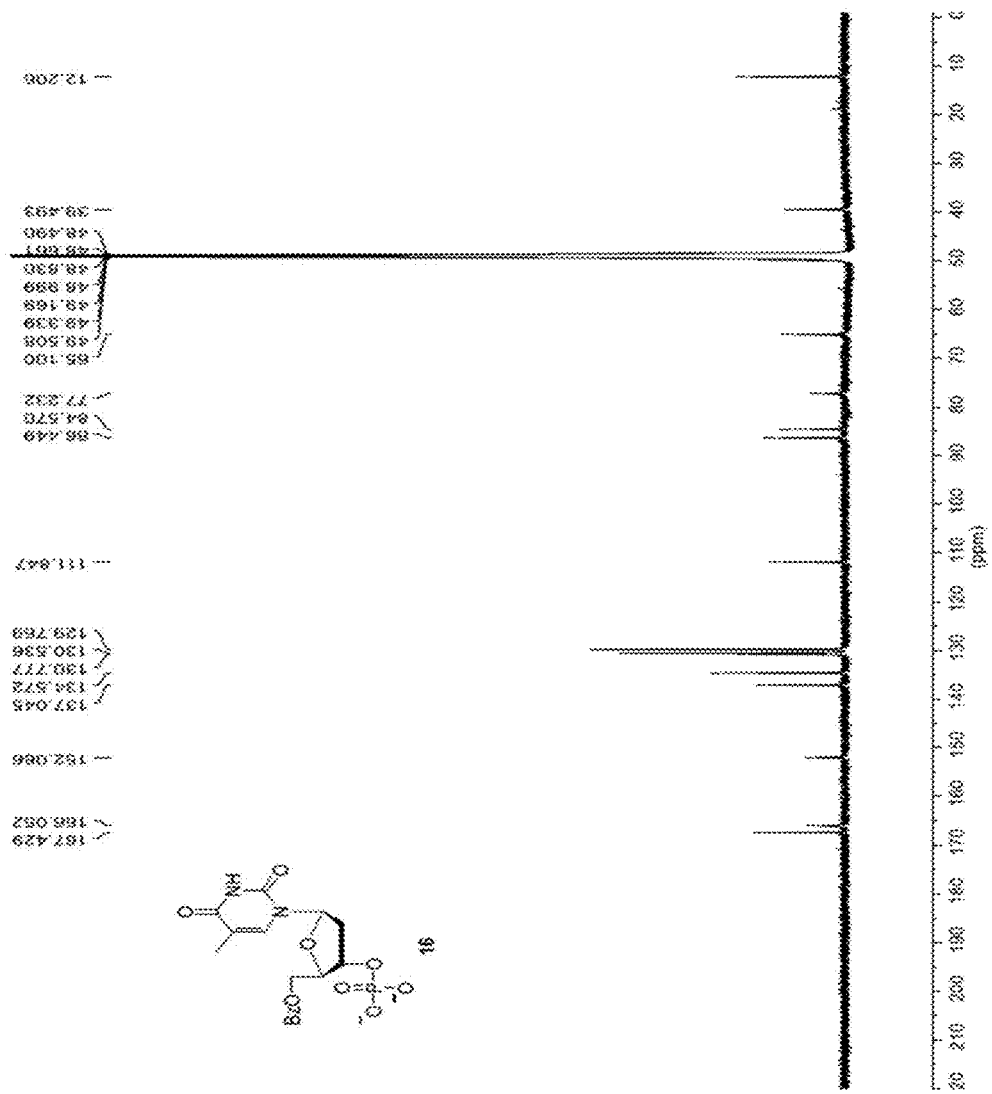
FIG. 85 depicts a $^{13}$C NMR spectrum of synthesized compound 16.
Figure 86:
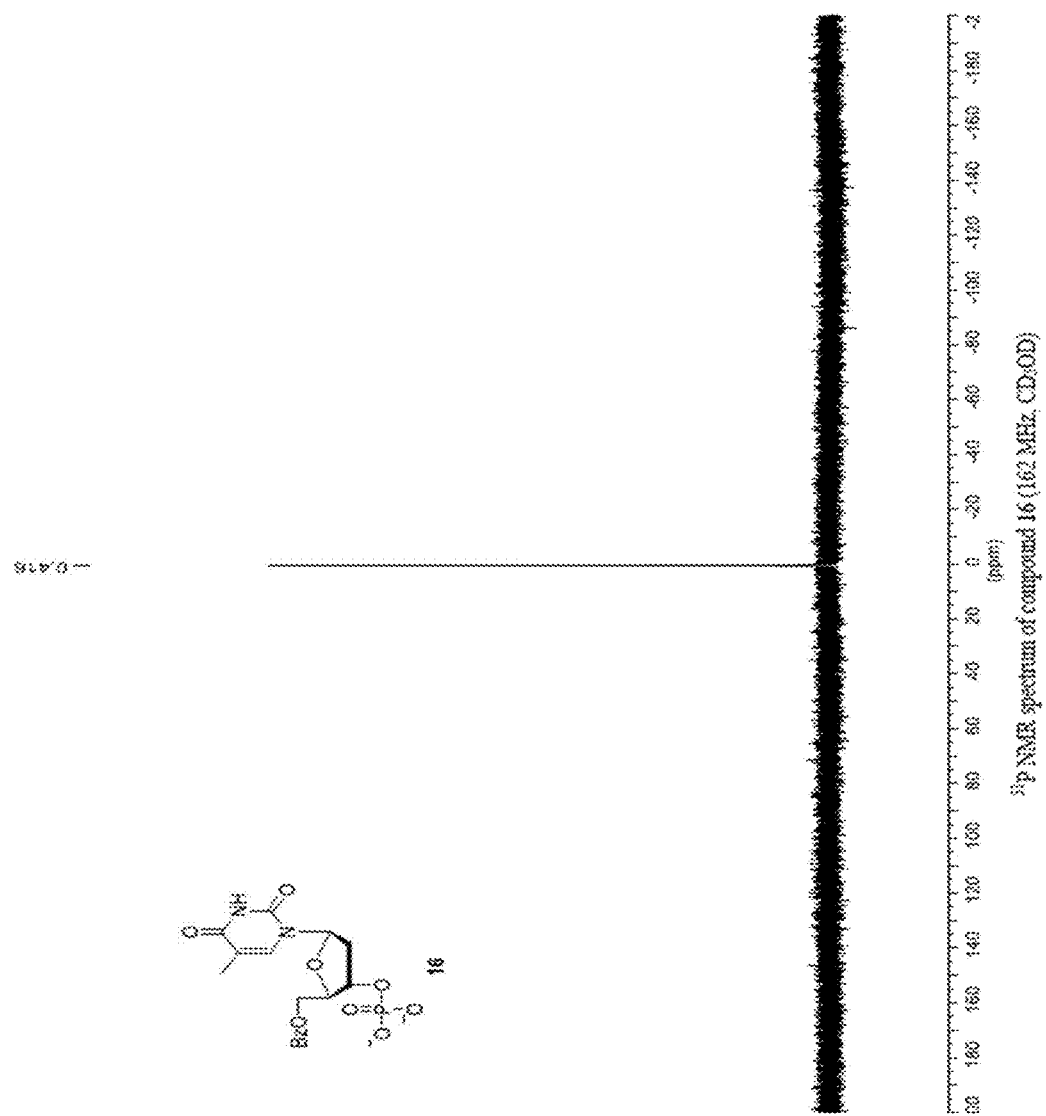
FIG. 86 depicts an $^{31}$P NMR spectrum of synthesized compound 16.
Figure 87:
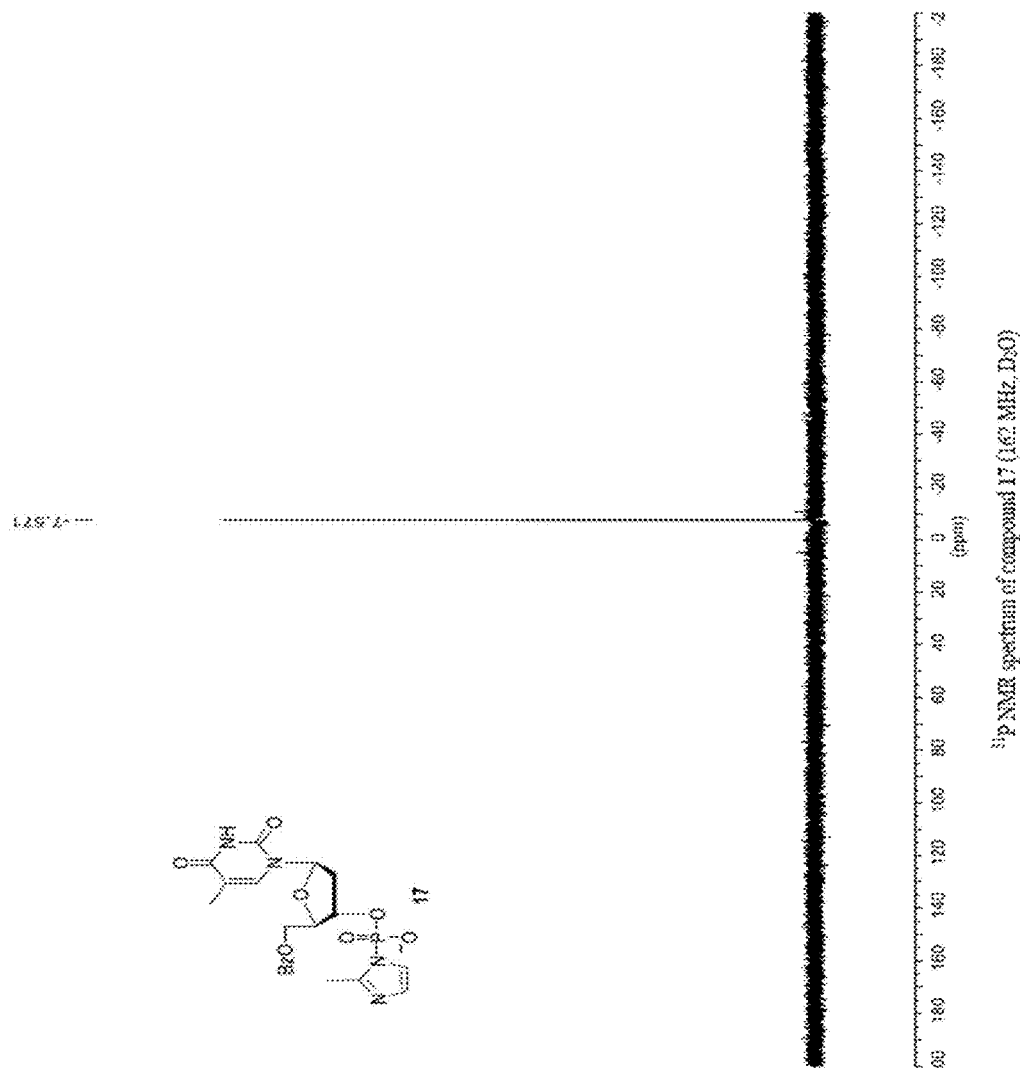
FIG. 87 depicts an $^{31}$P NMR spectrum of synthesized 5'-Benzoyl-2'-deoxythymidine-3'-phosphor-2-methylimidazolide (compound 17).
Figure 88:
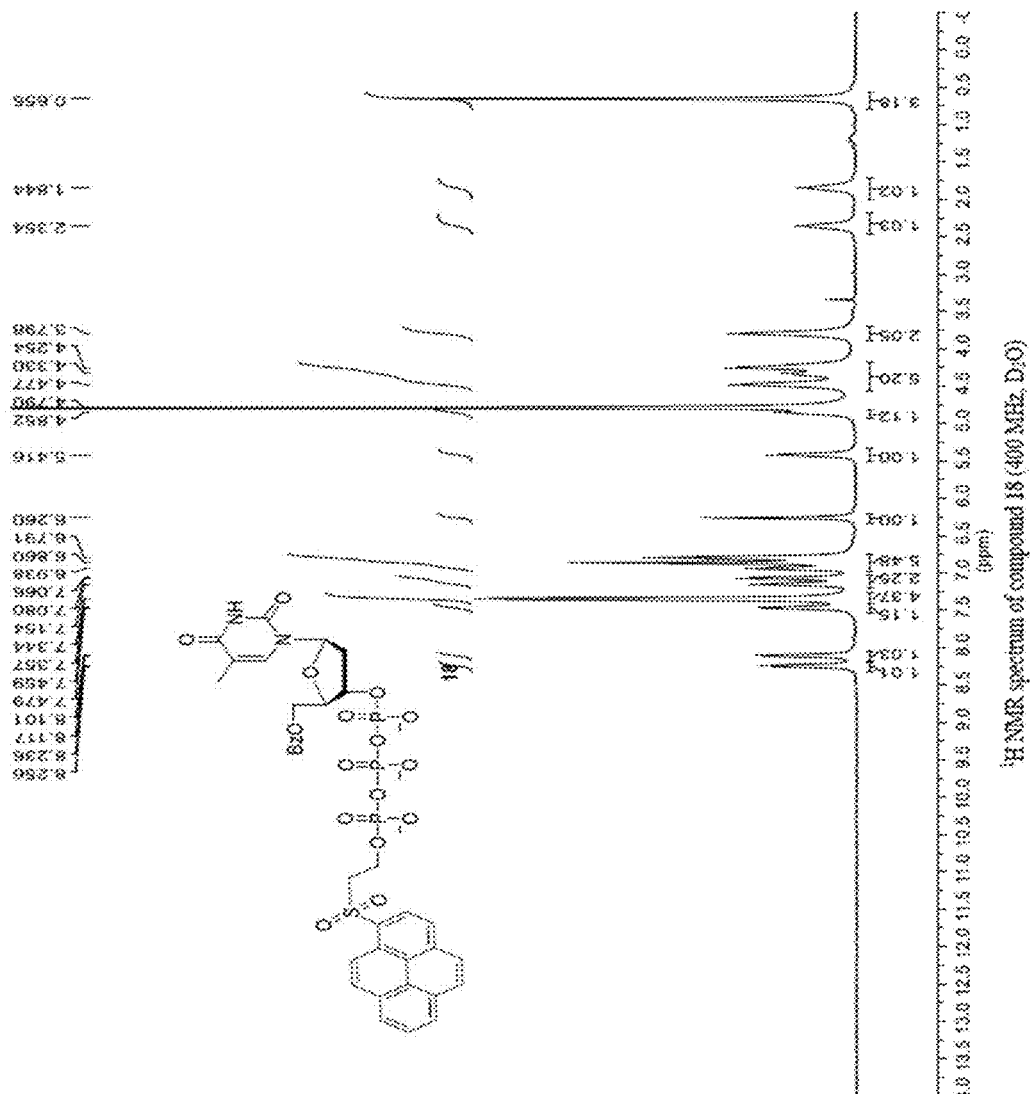
FIG. 88 depicts an $^1$H NMR spectrum of synthesized 5'-Benzoyl-2'-deoxythymidine-3'-γ-(2-(pyrenesulfonyl)ethyl)triphosphate (compound 18).
Figure 89:
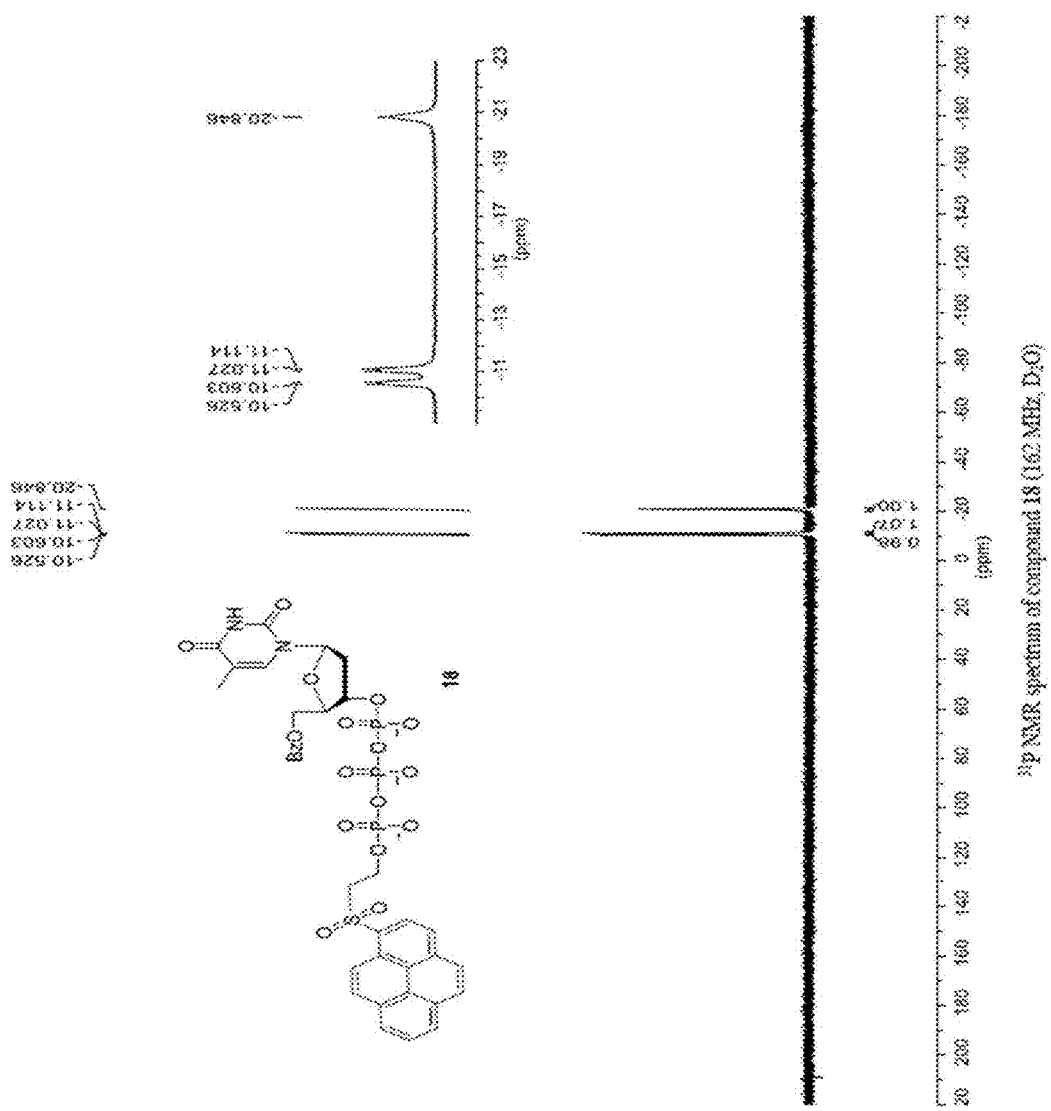
FIG. 89 depicts an $^{31}$P NMR spectrum of synthesized compound 18.
Figure 90:
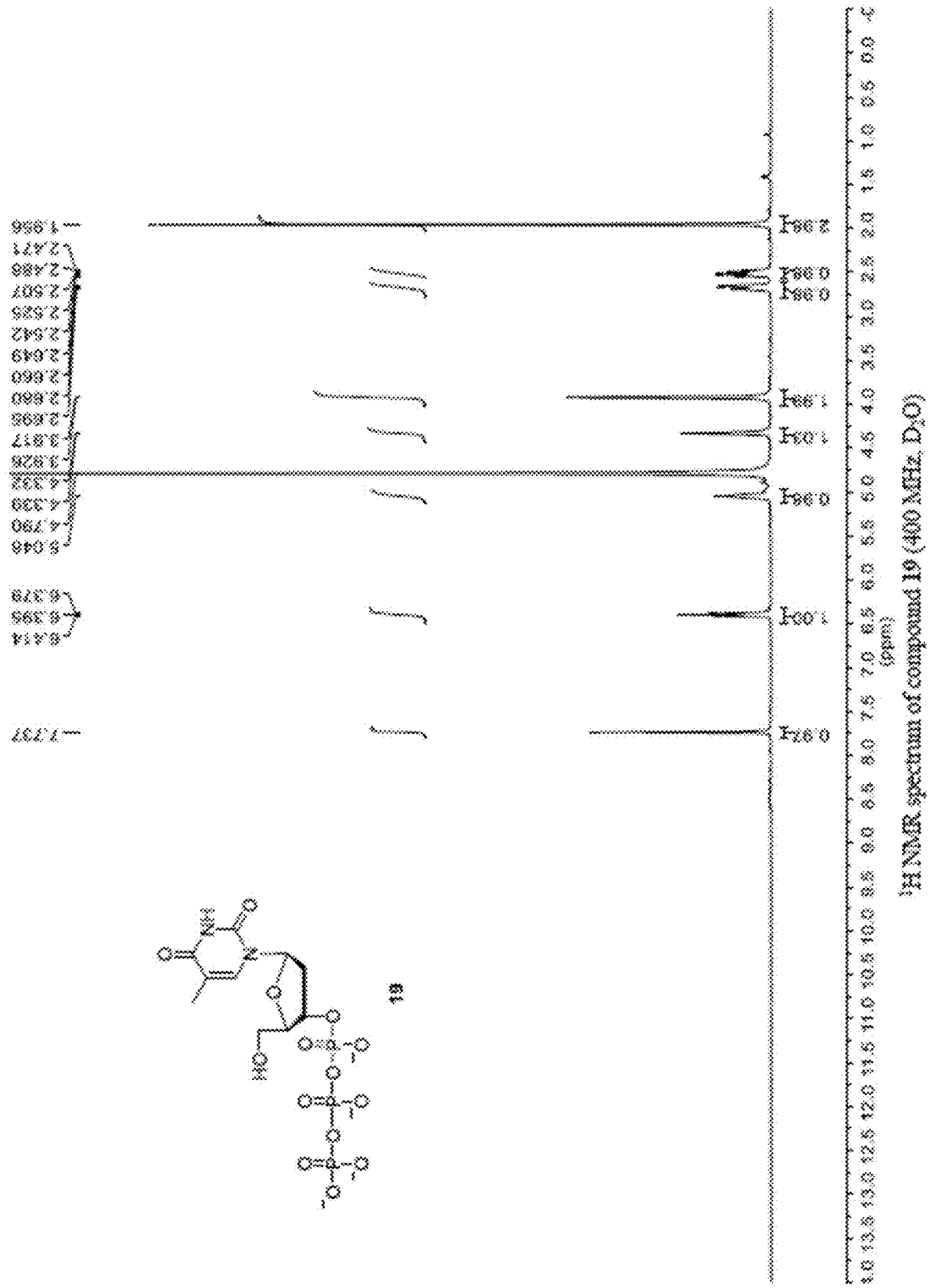
FIG. 90 depicts an $^1$H NMR spectrum of synthesized compound 19.
Figure 91:
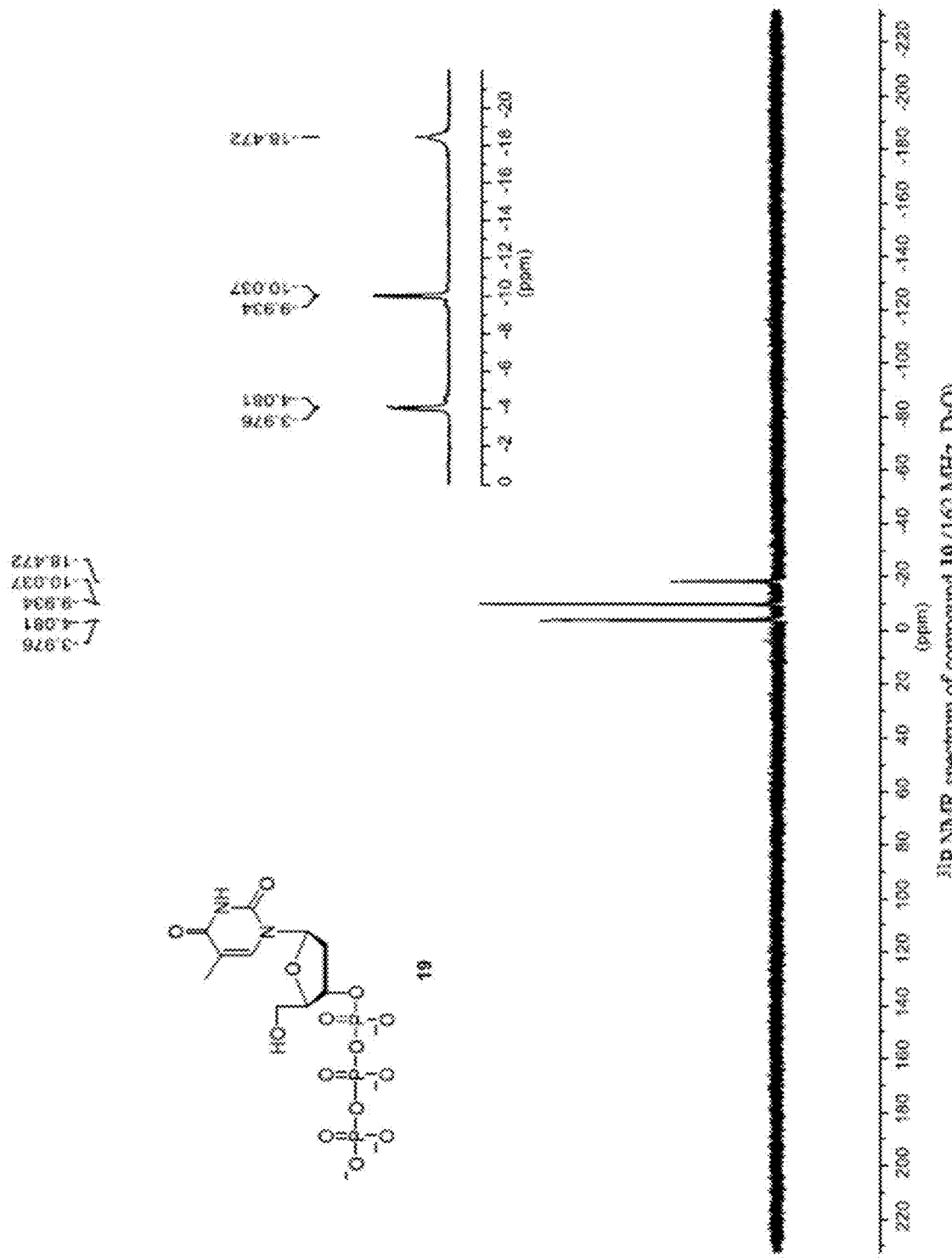
FIG. 91 depicts a $^{31}$P NMR spectrum of synthesized compound 19.

FIG. 80 shows the synthesis scheme for 2'-deoxythymidine-3'-triphosphate (3'-TTP, compound 19). FIG. 81 through FIG. 91 provide NMR spectra of the synthesized intermediates and product.

Methods used for the synthesis are now described.

5'-Benzoyl-2'-deoxythymidine-3'-dibenzylmonophosphate (Compound 15)

General procedure A with 1.04 g (3.0 mmol) of 5'-benzoyl-2'-deoxythymidine compound 14, 383 mg (5.4 mmol) of tetrazole, 30 mL of anhydrous solution (MeCN/CH$_2$Cl$_2$, 1:1), 1.23 mL (3.91 mmol) of dibenzyl-N, N-diisopropylphosphoramidite for 3 hours reaction at room temperature. Then 8 mL of 30% H$_2$O$_{2(aq)}$ for 1 hour reaction at room temperature. Column chromatography with eluents (MeOH/CH$_2$Cl$_2$, from 1% to 1.4%) to afford the product compound 15 as a white solid; yield: 1.28 g (70.3%); TLC (MeOH/CH$_2$Cl$_2$, 1:40) R$_f$=0.22; $^1$H NMR (400 MHz, CDCl$_3$) δ 9.46 (s, 1H), 7.97 (d, 2H, J=8.0 Hz), 7.61-7.57 (m, 1H), 7.45 (t, 2H, J=7.2 Hz), 7.35-7.31 (m, 10H), 7.08 (5, 1H), 6.25 (dd, 1H, J=7.6, 6.4 Hz), 5.11-4.97 (m, 5H), 4.56 (dd, 1H, J=13.2, 3.6 Hz), 4.33-4.29 (m, 2H), 2.48 (dd, 1H, J=14.4, 5.6 Hz), 2.11-2.06 (m, 1H), 1.57 (s, 3H); $^{13}$C NMR (125.8 MHz, CDCl$_3$) δ 165.7, 163.8, 150.4, 135.3, 135.2, 134.3, 133.5, 129.3, 129.2, 128.7, 128.7, 128.6, 128.6, 128.1, 128.1, 111.4, 84.5, 82.6 (d, J$_C$, P=5.4 Hz), 69.8, 69.8, 69.8, 63.6, 38.6 (d, J$_C$, P=4.7 Hz), 12.0; 31P NMR (162 MHz, CDCl$_3$) δ −0.31; HRMS (ESI-TOF) calcd. for C$_{31}$H$_{31}$N$_2$O$_9$PNa [M+Na]$^+$ 629.1665. found 629.1666.

5'-Benzoyl-2'-deoxythymidine-3'-monophosphate (Compound 16)

General procedure B with 1.28 g (2.11 mmol) of compound 15, 50 mL of MeOH, and 200 mg of 10% Pd/C for 3 hours with stirring at room temperature. The suspension was filtered over a pad of celite, washed with 100 mL of MeOH four times to afford the product, compound 16, as a white foam; yield: 0.86 g (96.2%); TLC (MeOH/CH$_2$Cl$_2$, 1:10) R$_f$=0; $^1$H NMR (400 MHz, CD$_3$OD) δ 8.06 (d, 2H, J=7.2 Hz), 7.64 (t, 1H, J=7.6 Hz), 7.51 (t, 2H, J=7.6 Hz), 7.39 (s, 1H), 6.29 (m, 1H), 5.10 (t, 1H, J=6.8 Hz), 4.70 (dd, 1H, J=12.0, 3.2 Hz), 4.57-4.47 (m, 2H), 2.63 (ddd, 1H, J=14.0, 6.0, 2.4 Hz), 2.43 (m, 1H), 1.62 (s, 3H); $^{13}$C NMR (125.8 MHz, CD$_3$OD) δ 167.4, 166.1, 152.1, 137.0, 134.6, 130.8, 130.5, 129.8, 111.8, 86.4, 84.6, 77.2, 65.1, 39.5, 12.2; $^{31}$P NMR (162 MHz, CD$_3$OD) δ 0.42; HRMS (ESI-TOF) calcd. for C$_{17}$H$_{18}$N$_2$O$_9$PNa$_2$ [M−H+2Na]$^+$ 471.0545. found 471.0551.

5'-Benzoyl-2'-deoxythymidine-3'-phosphor-2-methylimidazolide (Compound 17)

General procedure C with 0.86 g (2.0 mmol) of compound 16, 10 mL of anhydrous DMF, 1.39 mL (10.0 mmol) of triethylamine, 328 mg (4.1 mmol) of 2-methylimidazole, 1.05 g (4.0 mmol) of triphenylphosphine, 903 g (4.0 mmol) of dipyridyl disulfide. First precipitation was achieved in 250 mL of diethyl ether. The product was resuspended with 10 mL of DMF and dropwise added to the solution containing 2.0 g of sodium perchlorate, 20 mL of triethylamine in 400 mL of ethyl acetate for the second precipitation. The product was afforded as a white solid compound 17; yield: 0.89 g (86.9%); $^{31}$P NMR (162 MHz, D$_2$O) δ −7.57; HRMS (ESI-TOF) calcd. for C$_{21}$H$_{23}$N$_4$O$_8$PNa [M+Na]$^+$ 513.1151. found 513.1158.

5'-Benzoyl-2'-deoxythymidine-3'-γ-(2-(pyrenesulfonyl)ethyl)triphosphate (Compound 18)

General procedure D with 0.89 g (1.74 mmol) of compound 16, 0.89 g (1.90 mmol) of 1-(2-(pyrenesulfonyl)ethyl)) pyrophosphate (compound 7) and 11.5 mL (17.30 mmol) of ZnCl$_2$ solution (1.5 M in anhydrous DMF) for 3 hours with stirring at room temperature. The product was purified by 2.5 cm silica gel flash column with eluents [H$_2$O-isopropanol from 5% to 10% containing 1% diisopropylethylamine (DIPEA)] to afford the yellowish solid compound 18; yield: 1.23 g (55.8%); TLC (1:10 H$_2$O-acetone/2%-DIPEA): Rf=30.8; $^1$H NMR (400 MHz, D$_2$O) δ 8.25 (d, 1H, J=8.8 Hz), 8.11 (d, 1H, J=6.4 Hz), 7.47 (d, 1H, J=8.0 Hz), 7.36-7.34 (m, 4H), 7.15-7.07 (m, 2H), 6.94-6.79 (m, 5H), 6.26 (s, 1H), 5.12 (s, 1H), 4.85 (s, 1H), 4.48-4.25 (m, 5H), 3.80 (s, 2H), 2.35 (s, 1H), 1.84 (s, 1H), 0.66 (s, 3H); $^{31}$P NMR (162 MHz, D$_2$O) δ −10.56 (d, 1P, J=12.5 Hz), −11.07 (d, 1P, J=14.1 Hz), −20.85 (brs, 1P); HRMS (ESI-TOF) calcd. for C$_{35}$H$_{30}$N$_2$O$_{17}$P$_3$SNa$_4$ [M−3H+4Na]$^+$ 967.0069. found 967.0080.

2'-deoxythymidine-3'-triphosphate (Compound 19)

General procedure E with 1.23 g of compound 18, 5 mL of CH$_2$Cl$_2$ and 50 mL of 33% NH$_4$OH$_{(aq)}$ for 18 hours deprotection at room temperature. The product, compound 19, was afforded as a white solid; yield: 404 mg (86%, ε$_{267}$=9600 M$^{-1}$ cm$^{-1}$); $^1$H NMR (400 MHz, D$_2$O) δ 7.74 (s, 1H), 6.40 (t, 1H, J=7.6 Hz), 5.05 (5, 1H), 4.34 (d, 1H, J=2.8 Hz), 3.92 (d, 2H, J=3.6 Hz), 2.70-2.65 (m, 1H), 2.54-2.47 (m, 1H), 1.96 (s, 3H); $^{31}$P NMR (162 MHz, D$_2$O) δ −4.03 (d, 1P, J=17.0 Hz), −9.99 (d, 1P, J=16.7 Hz), −18.47 (brs, 1P).

Synthesis of 1-(α-L-threofuranosyl)thymidine-3'-triphosphate

Figure 92:
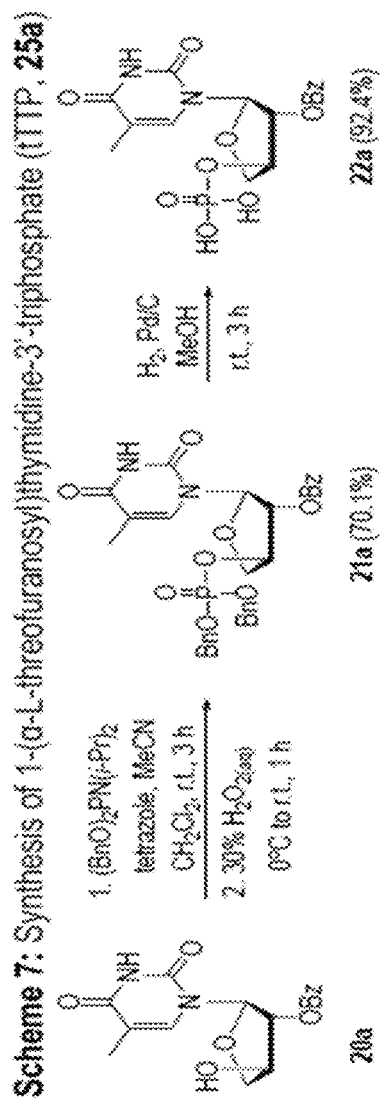
FIG. 92 depicts a synthesis scheme for 1-(α-L-threofuranosyl)thymidine-3'-triphosphate (tTTP, compound 25a)
Figure 93:
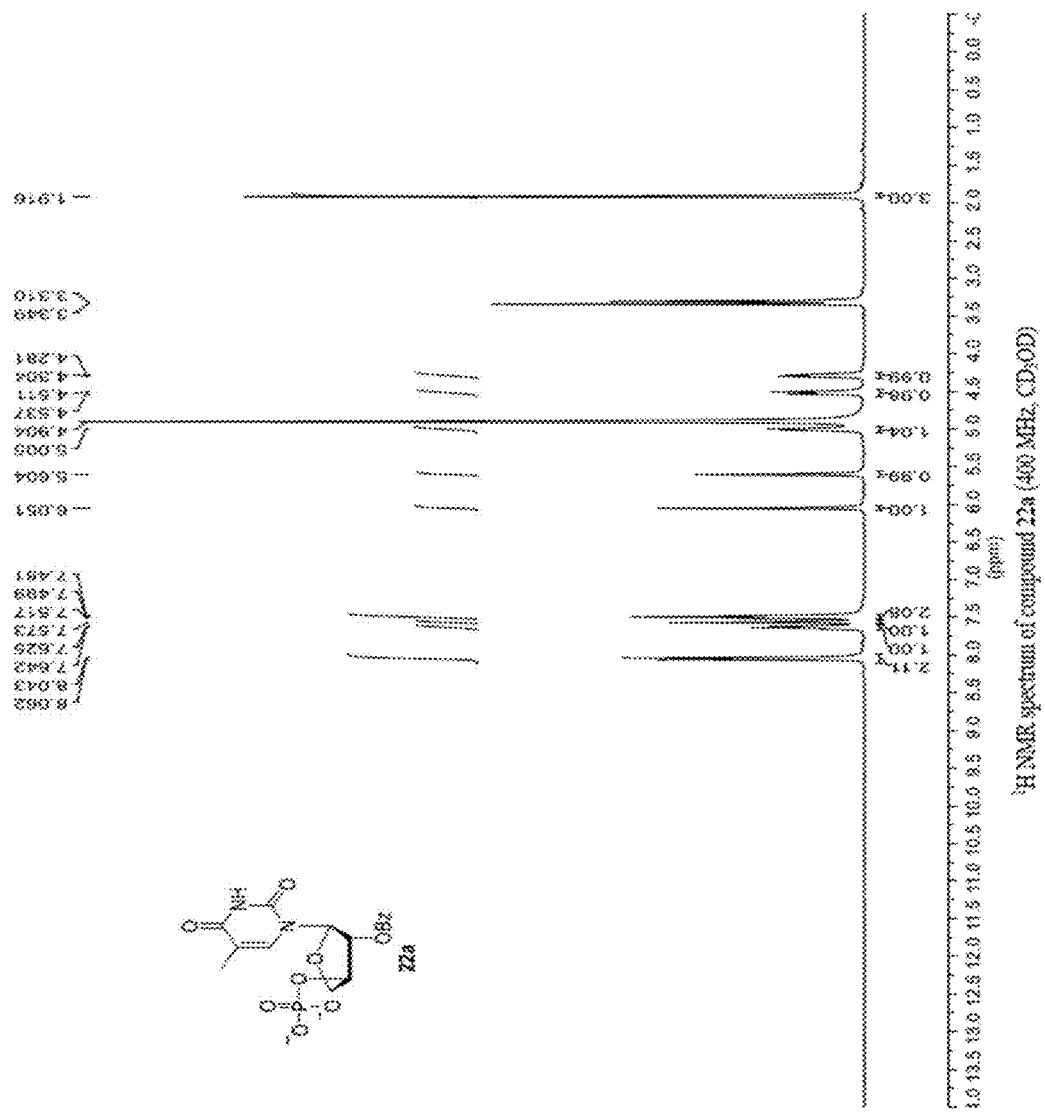
FIG. 93 depicts an $^1$H NMR spectrum of synthesized 1-(2'-O-benzoyl-α-L-threofuranosyl)thymidine-3'-monophosphate (compound 22a).
Figure 94:
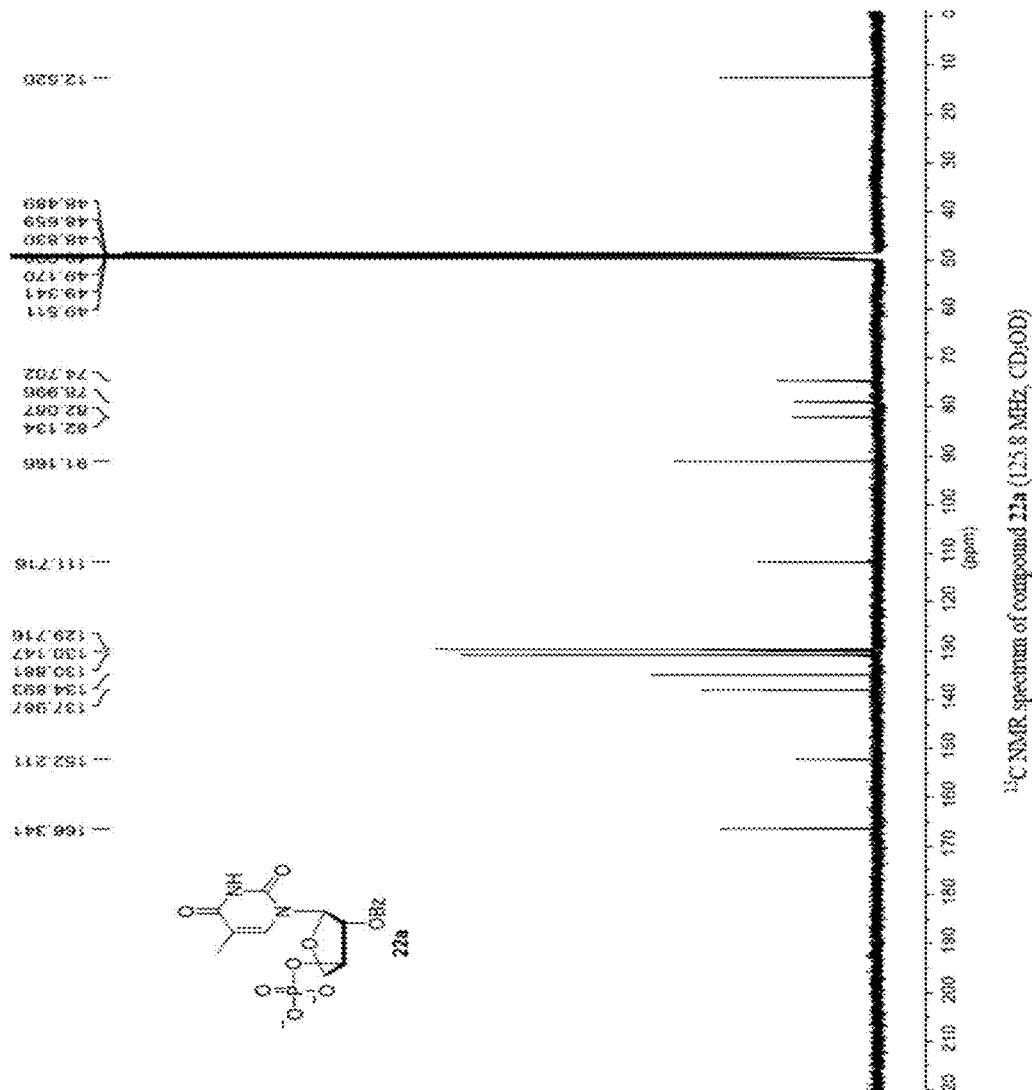
Figure 95:
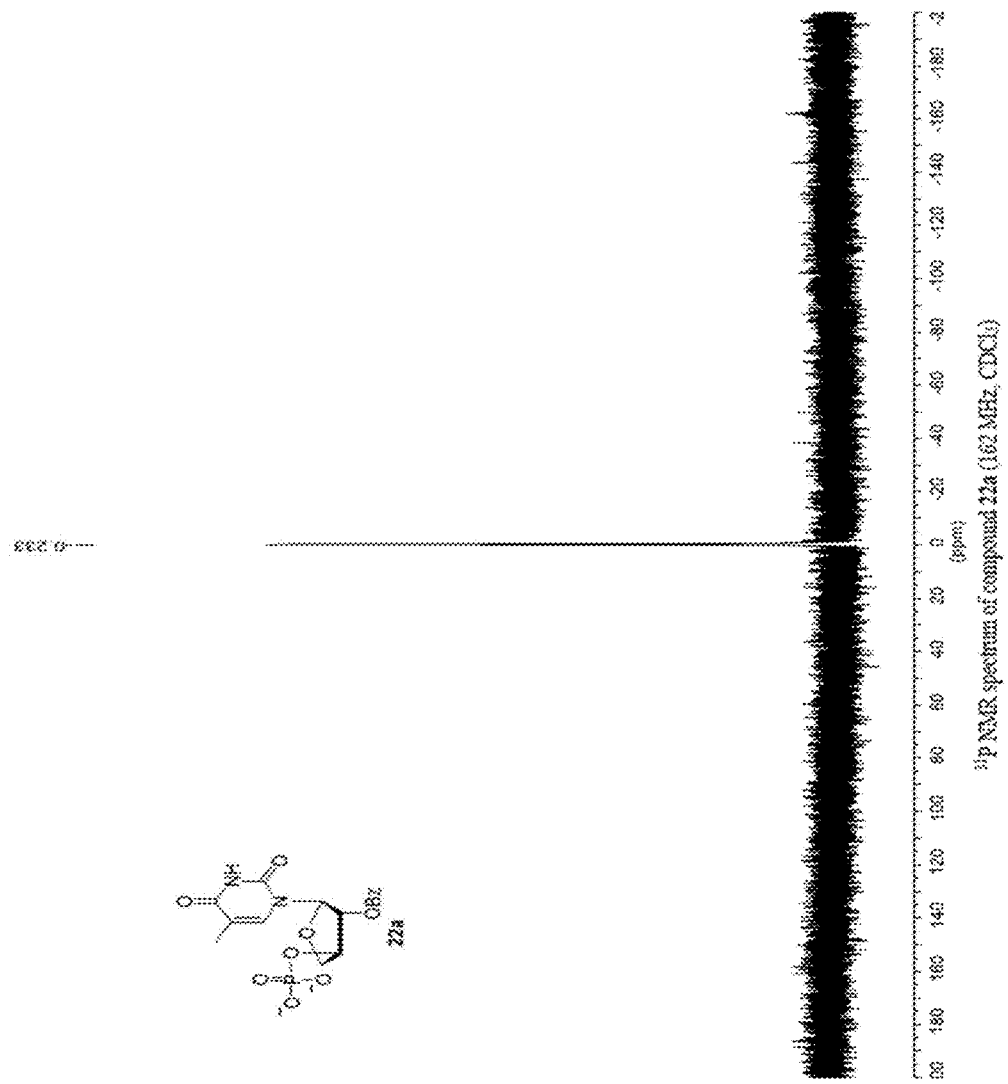
Figure 96:
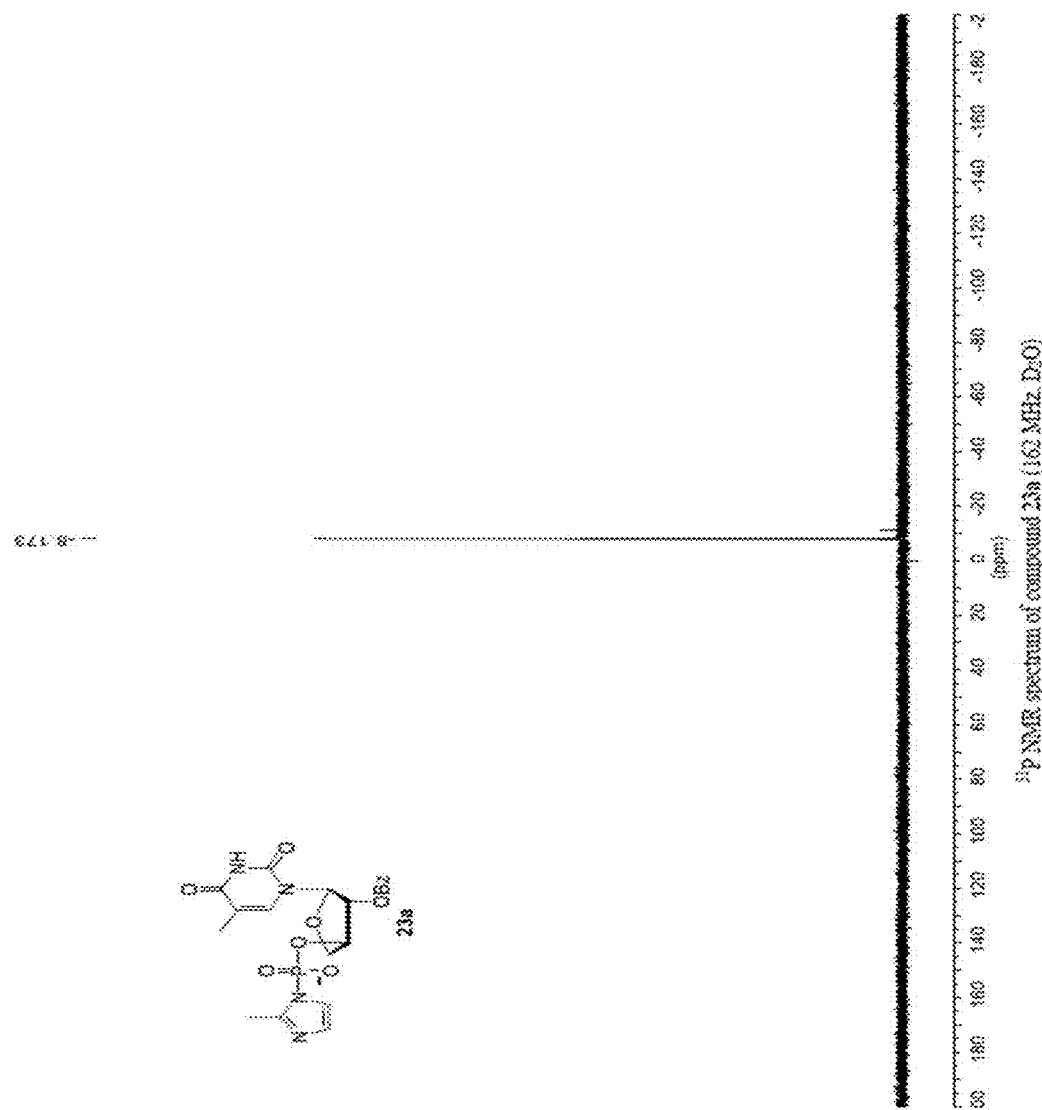
FIG. 96 depicts an $^{31}$P NMR spectrum of synthesized 1-(2'-O-benzoyl-α-L-threofuranosyl)thymidine-3'-monophosphor-2-methylimidazolide (compound 23a).
Figure 97:
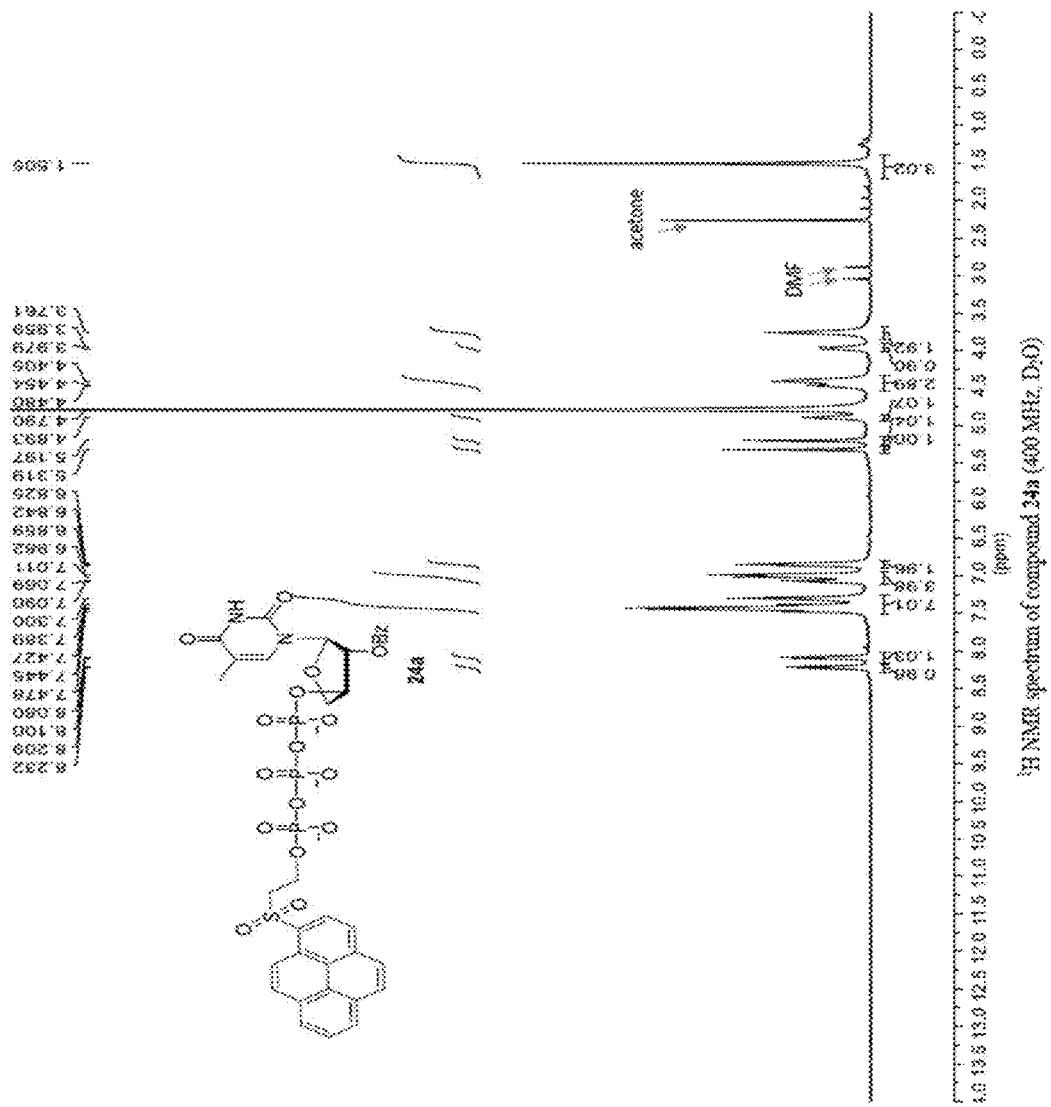
FIG. 97 depicts an $^1$H NMR spectrum of synthesized 1-(2'-O-benzoyl-α-L-threofuranosyl)thymidine-3'-(γ-(2-(pyrenesulfonyl)ethyl)) triphosphate (compound 24a).
Figure 98:
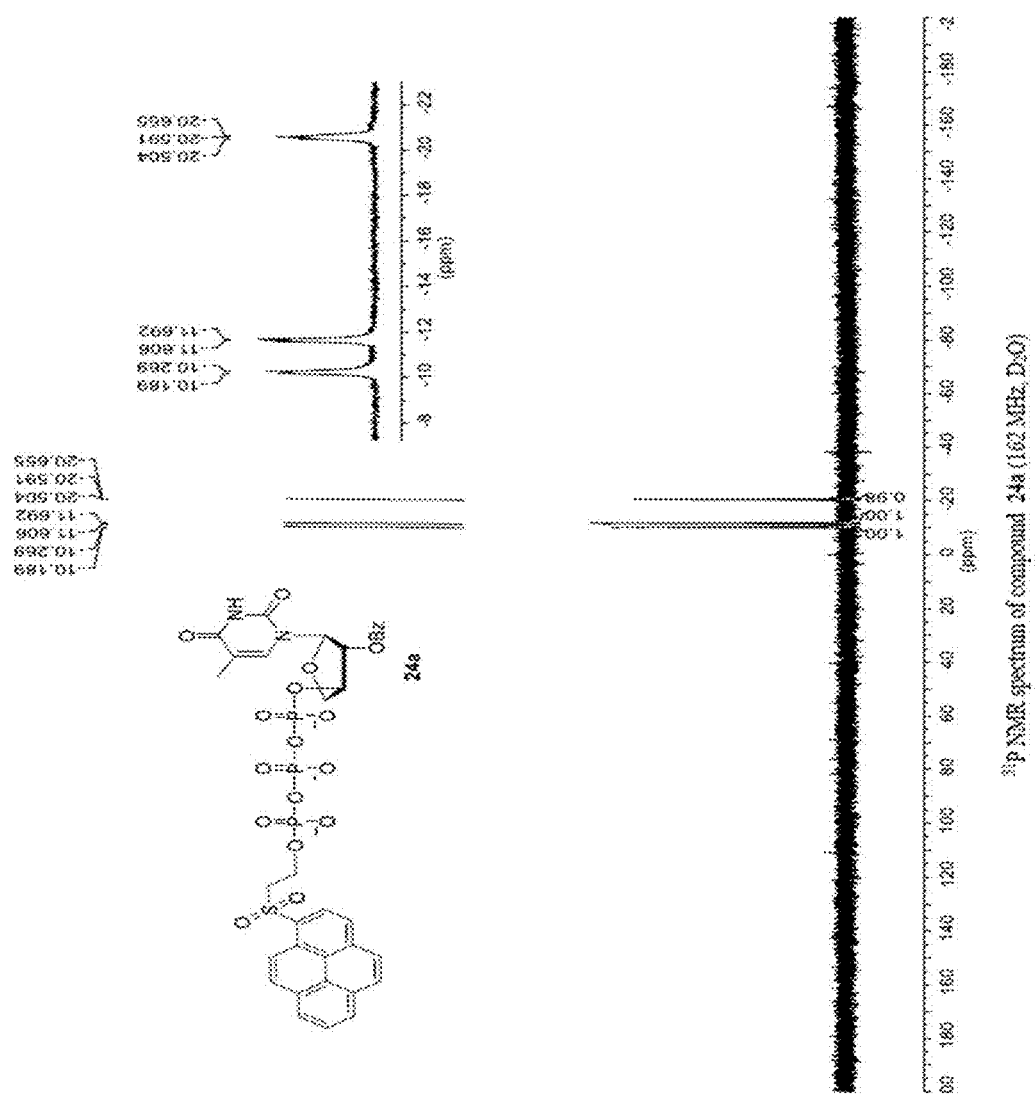
Figure 99:
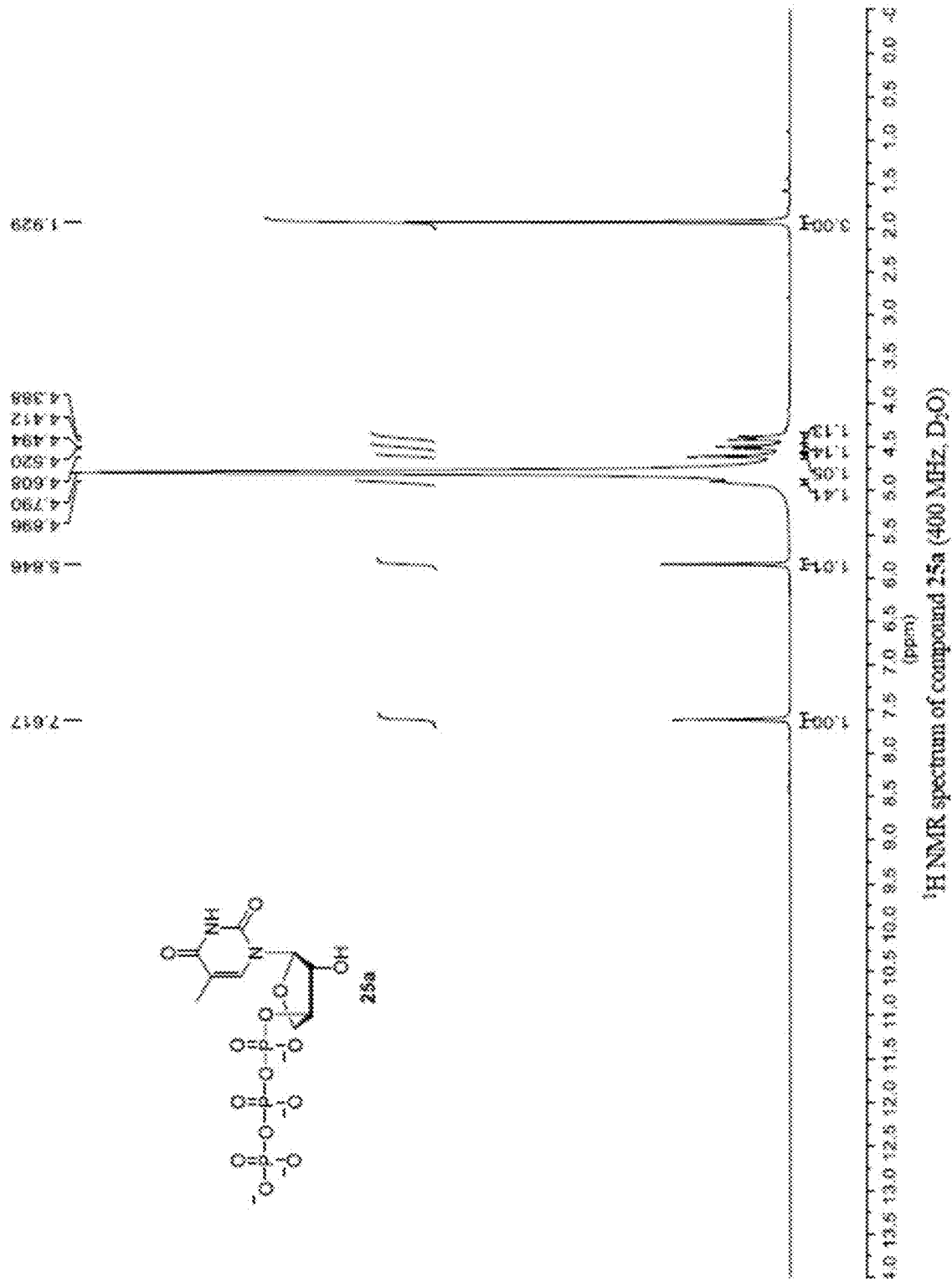
Figure 100:
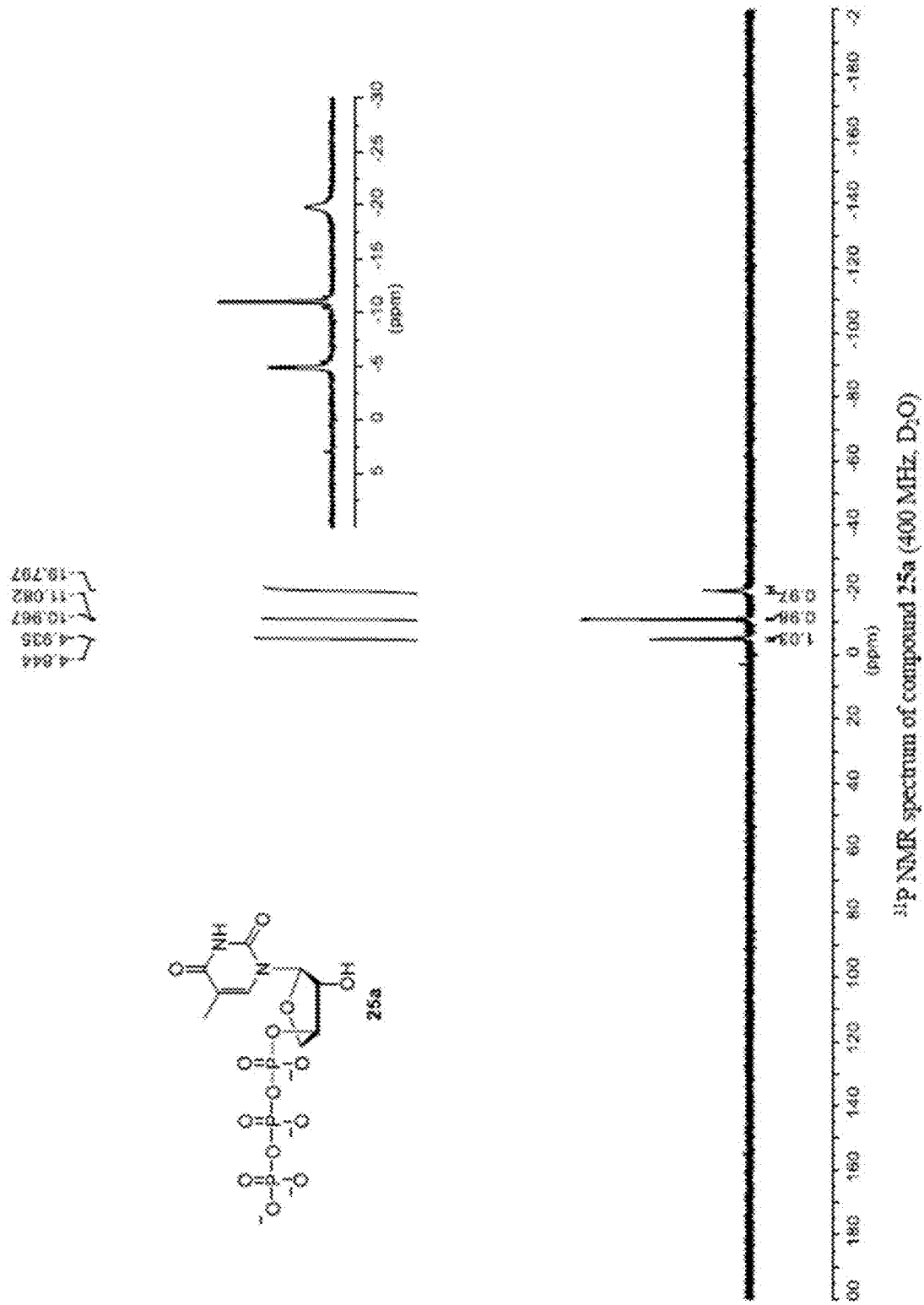

FIG. 92 shows the synthesis scheme for 1-(α-L-threofuranosyl)thymidine-3'-triphosphate (tTTP, compound 25a). FIG. 93 through FIG. 100 provide NMR spectra of the synthesized intermediates and product.

Methods used for the synthesis are now described.

1-(2'-O-benzoyl-α-L-threofuranosyl)thymidine-3'-dibenzylmonophosphate (Compound 21a)

General procedure A with 1 g (3.01 mmol) of 1-(2'-O-benzoyl-α-L-threofuranosyl)thymine, 379.7 mg (5.42 mmol) of tetrazole, 24 mL of anhydrous solution (MeCN/CH$_2$Cl$_2$, 1:1), 1.24 mL (3.91 mmol) of dibenzyl-N, N-diisopropylphosphoramidite for 3 hours stirring at room temperature and 6 mL of H$_2$O$_2$ for 1 hour oxidation reaction. Silica gel column chromatography with eluents (MeOH/CH$_2$Cl$_2$, from 0 to 2%). The product, compound 21a, was acquired as a white solid; yield: 1.25 g (70.1%). Compound 21a has been reported in Sau et al., 2017, Org. Lett. 19, 4379-4382.

1-(2'-O-benzoyl-α-L-threofuranosyl)thymidine-3'-monophosphate (Compound 22a)

General procedure B with 1.25 g (2.11 mmol) of compound 21a, 50 mL of MeOH, and 200 mg of 10% Pd/C for 3 hours stirring. The suspension was filtered over a pad of celite, washed with 100 mL of MeOH four times. The product compound 22a was afforded as a white foam; yield: 0.83 g (92.4%); TLC (MeOH/CH$_2$Cl$_2$, 1:10) R$_f$=0; $^1$H NMR (400 MHz, CD$_3$OD) δ 8.05 (d, 1H, J=7.6 Hz), 7.64 (t, 1H, J=7.2 Hz), 7.57 (s, 1H), 7.50 (t, 2H, J=7.2 Hz), 6.05 (s, 1H), 5.60 (s, 1H), 5.01 (s, 1H), 4.52 (d, 1H, J=10.4 Hz), 4.29 (d, 1H, J=9.2 Hz), 1.92 (s, 3H); $^{13}$C NMR (125.8 MHz, CD$_3$OD) δ 166.3, 152.2, 138.0, 134.9, 130.9, 130.1, 129.7, 111.7, 91.2, 82.1 (d, J$_C$, P=5.9 Hz), 79.0, 74.7, 12.5; $^{31}$P NMR (162 MHz, CDCl$_3$) δ -0.23; HRMS (ESI-TOF) calcd. for C$_{16}$H$_{17}$N$_2$O$_9$PNa [M+Na]$^+$ 435.0569. found 435.0557.

1-(2'-O-benzoyl-α-L-threofuranosyl)thymidine-3'-monophosphor-2-methylimidazolide (Compound 23a)

General procedure C with 0.83 g (2 mmol) of compound 22a, 7.0 mL of anhydrous DMF, 1.40 mL (10.1 mmol) of triethylamine, 328 mg (4 mmol) of 2 methylimidazole, 1.05 g (4 mmol) of triphenylphosphine, 0.88 g (4 mmol) of dipyridyl disulfide. First precipitation was achieved with 250 mL of diethyl ether. The product was resuspended with 15 mL of CH$_2$Cl$_2$ and dropwise added to the solution containing 2.01 g of sodium perchlorate, 10 mL of triethylamine in 300 mL of ethyl acetate for the second precipitation. The product, compound 23a, was afforded as a white solid; yield: 0.98 g (98.3%); $^{31}$P NMR (162 MHz, D$_2$O) δ -8.17; HRMS (ESI-TOF) calcd. for C$_{20}$H$_{21}$N$_4$O$_8$PNa [M+Na]$^+$ 499.0995. found 499.0992.

1-(2'-O-benzoyl-α-L-threofuranosyl)thymidine-3'-(γ-(2-(pyrenesulfonyl)ethyl)) Triphosphate (Compound 24a)

General procedure D with 0.98 g (1.97 mmol) of compound 23a, 1.11 g (2.36 mmol) of compound 7 and 13.13 mL (19.7 mmol, 1.5 M in anhydrous DMF) of ZnCl$_2$ solution for 3 hours stirring at room temperature. The product was purified by 2 cm silica gel column chromatography with eluents [H$_2$O-isopropanol from 5% to 12.5% containing 1% diisopropylethylamine (DIPEA)] to afford the white solid compound 24a; yield: 1.53 g (62.1%); TLC (1:10 H$_2$O-acetone with 2%-DIPEA): Rf=0.25; $^1$H NMR (400 MHz, D$_2$O) δ 8.22 (d, 1H, J=9.2 Hz), 8.09 (d, 1H, J=8.0 Hz), 7.48-7.30 (m, 7H), 7.09-6.98 (m, 4H), 6.84 (t, 2H, J=6.8 Hz), 5.32 (s, 1H), 5.20 (s, 1H), 4.89 (s, 1H), 4.48-4.40 (m, 3H), 3.97 (d, 1H, J=8.0 Hz), 3.76 (m, 2H), 1.50 (s, 3H); $^{31}$P NMR (162 MHz, D$_2$O) δ -10.23 (d, J=13.0 Hz), -11.65 (d, J=13.9 Hz), 20.59 (brs); HRMS (ESI-TOF) calcd. for C$_{34}$H$_{29}$N$_2$O$_{17}$P$_3$SNa$_3$ [M-2H+3Na]$^+$ 931.0093. found 931.0049.

1-(α-L-threofuranosyl)thymidine-3'-triphosphate (Compound 25a)

General procedure E with 1.53 g (1.22 mmol) of compound 24a in 50 mL of 33% NH$_4$OH$_{(aq)}$ for 18 hours deprotection at room temperature. The product, compound 25a, was afforded as a white solid; yield: 445 mg (78.9%, ε$_{267}$=9600 M$^{-1}$ cm$^{-1}$); $^1$H NMR (400 MHz, D$_2$O) δ 7.62 (s, 1H), 5.85 (s, 1H), 4.90 (s, 1H), 4.61 (s, 1H), 4.51 (d, 1H, J=10.4 Hz), 4.40 (d, 1H, J=9.2 Hz), 1.95 (s, 1H); $^{31}$P NMR (162 MHz, D$_2$O) δ -4.89 (d, J=14.7 Hz), -11.02 (d, J=18.63 Hz), -19.80 (brs).

Synthesis of 1-(α-L-threofuranosyl)cytidine-3'-triphosphate

Figure 101:
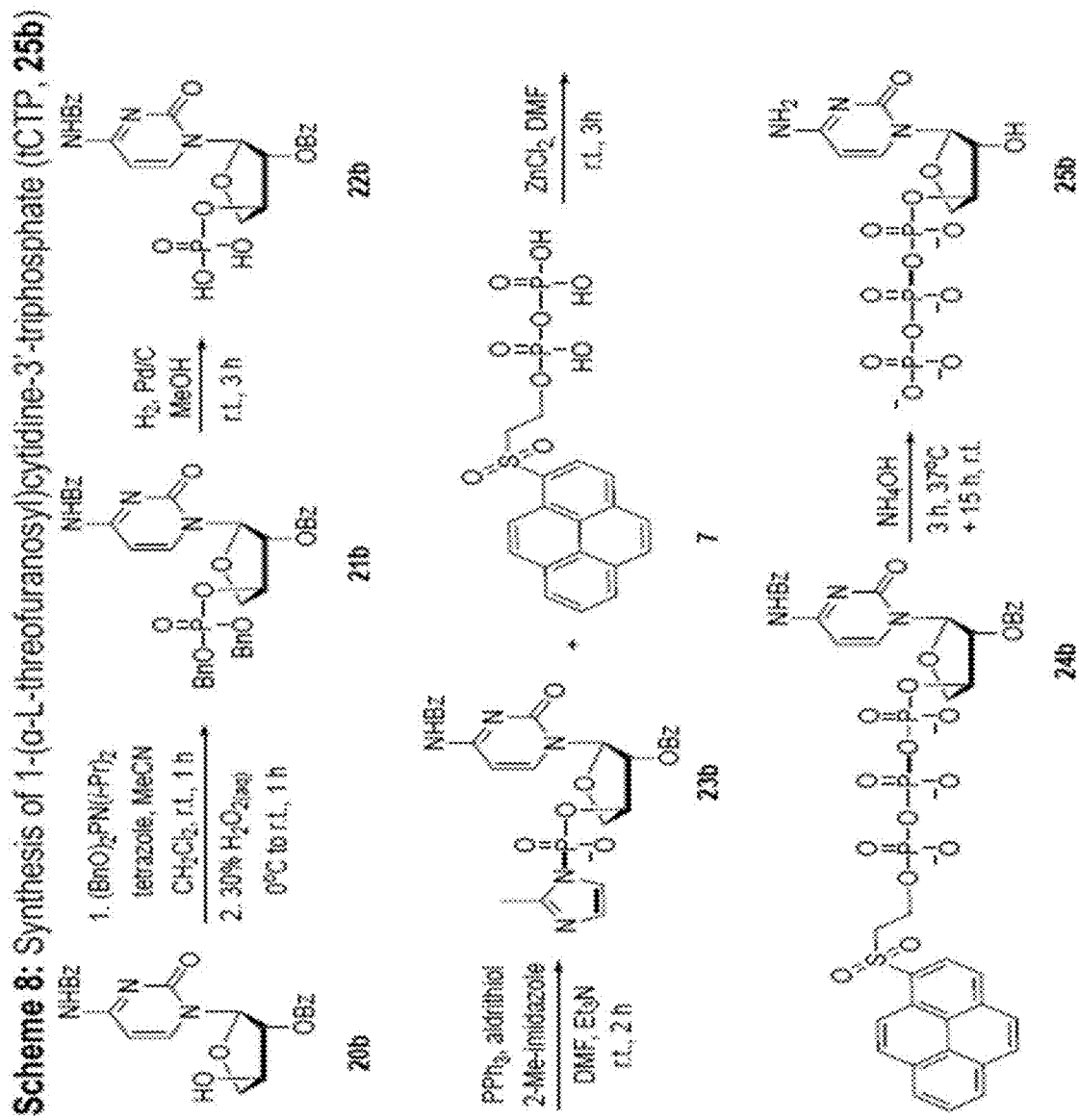
FIG. 101 depicts a synthesis scheme for 1-(α-L-threofuranosyl)cytidine-3'-triphosphate (tCTP, compound 25b).
Figure 102:
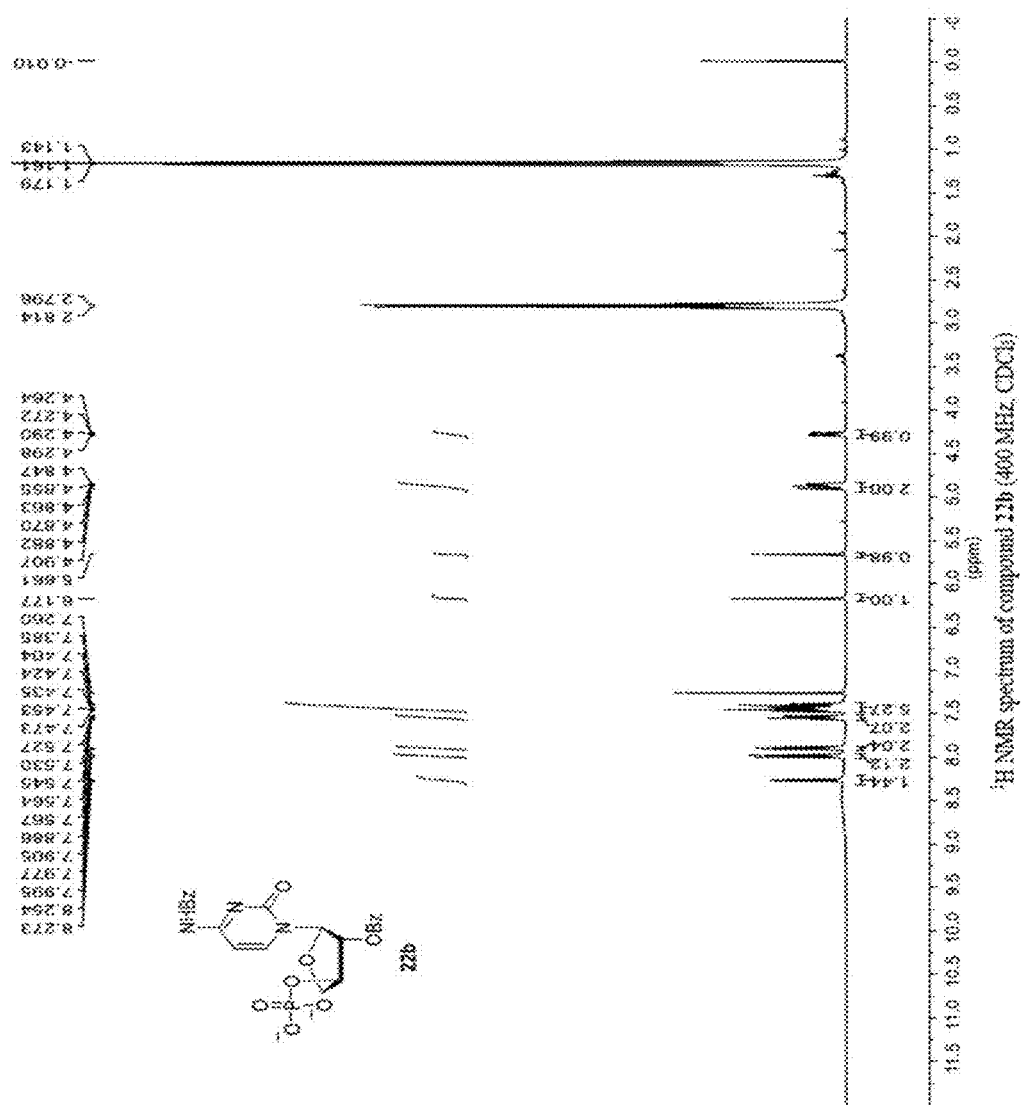
FIG. 102 depicts an $^1$H NMR spectrum of synthesized N$^4$-Benzoyl-1-(2'-O-benzoyl-α-L-threofuranosyl)cytidine-3'-monophosphate (compound 22b).
Figure 103:
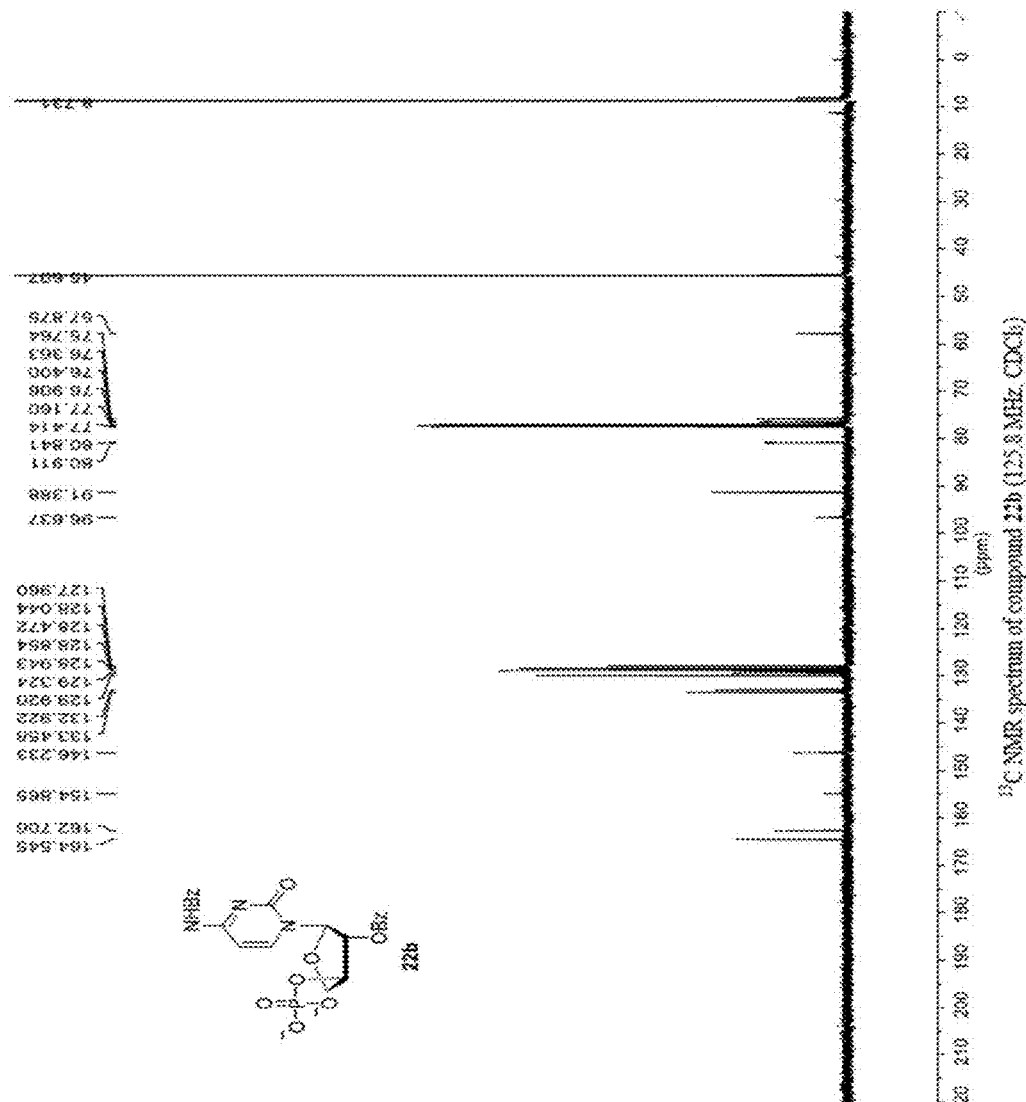
FIG. 103 depicts a $^{13}$C NMR spectrum of synthesized compound 22b.
Figure 104:
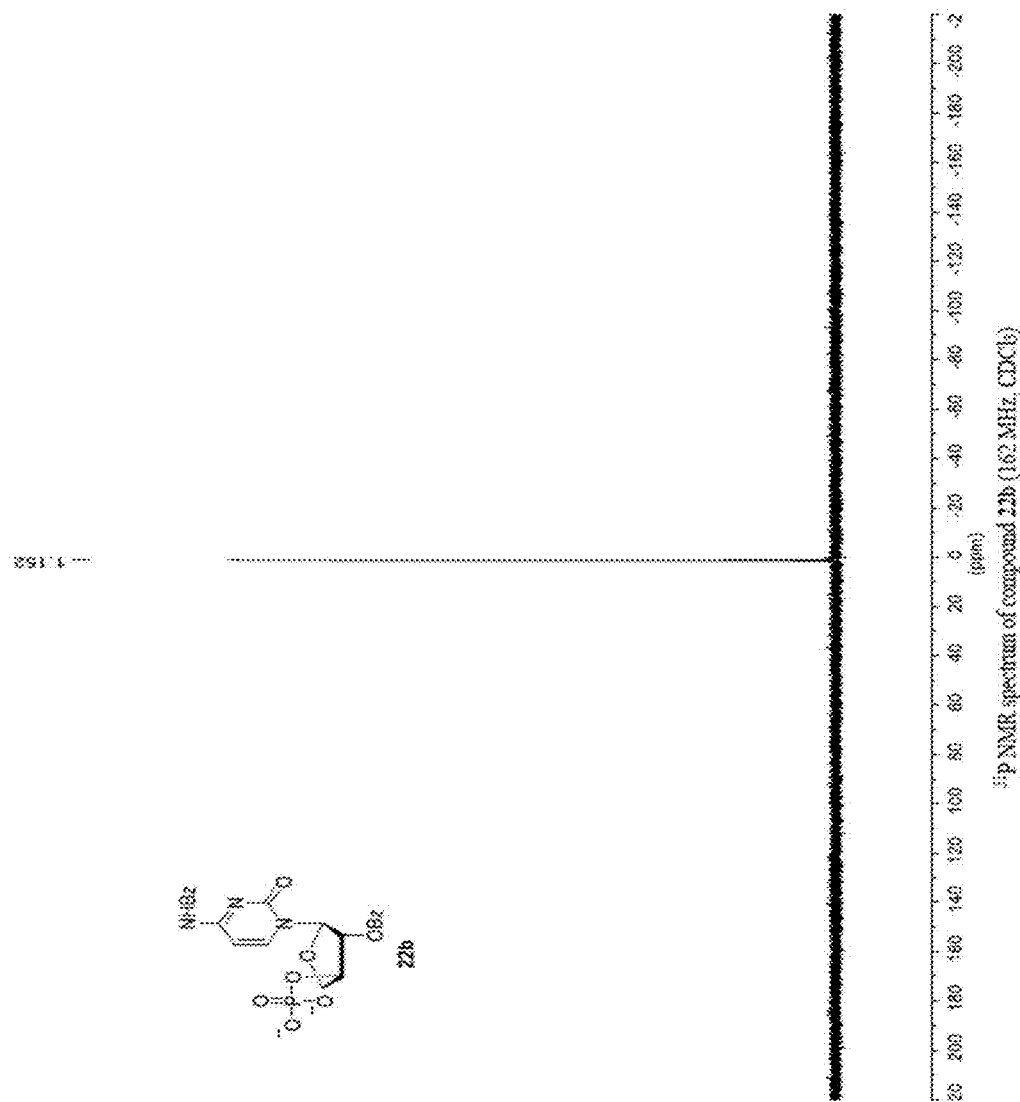
FIG. 104 depicts an $^{31}$P NMR spectrum of synthesized compound 22b.
Figure 105:
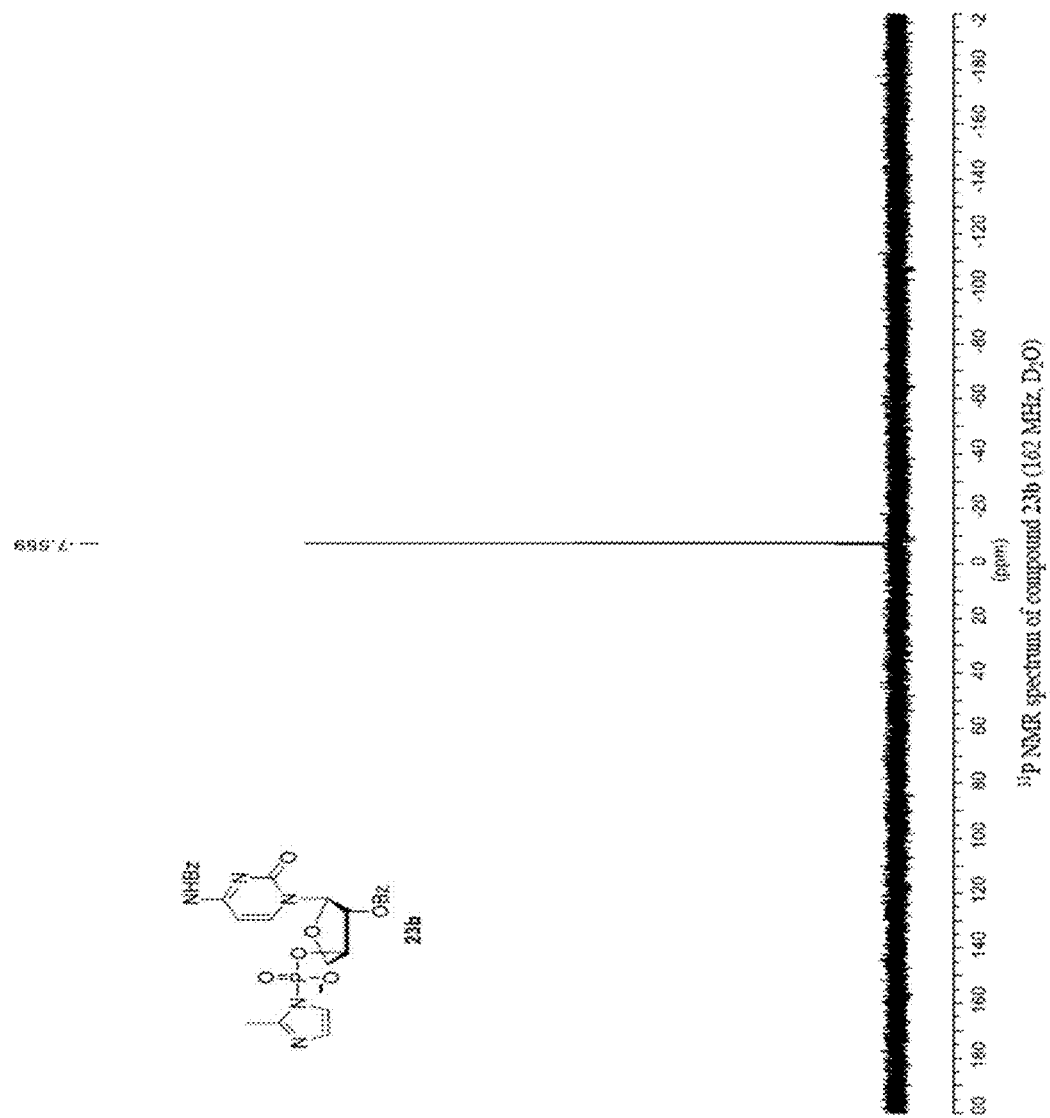
FIG. 105 depicts an $^{31}$P NMR spectrum of synthesized N$^4$-Benzoyl-1-(2'-O-benzoyl-α-L-threofuranosyl)cytidine-3'-monophosphor-2-methylimidazolide (compound 23b).
Figure 106:
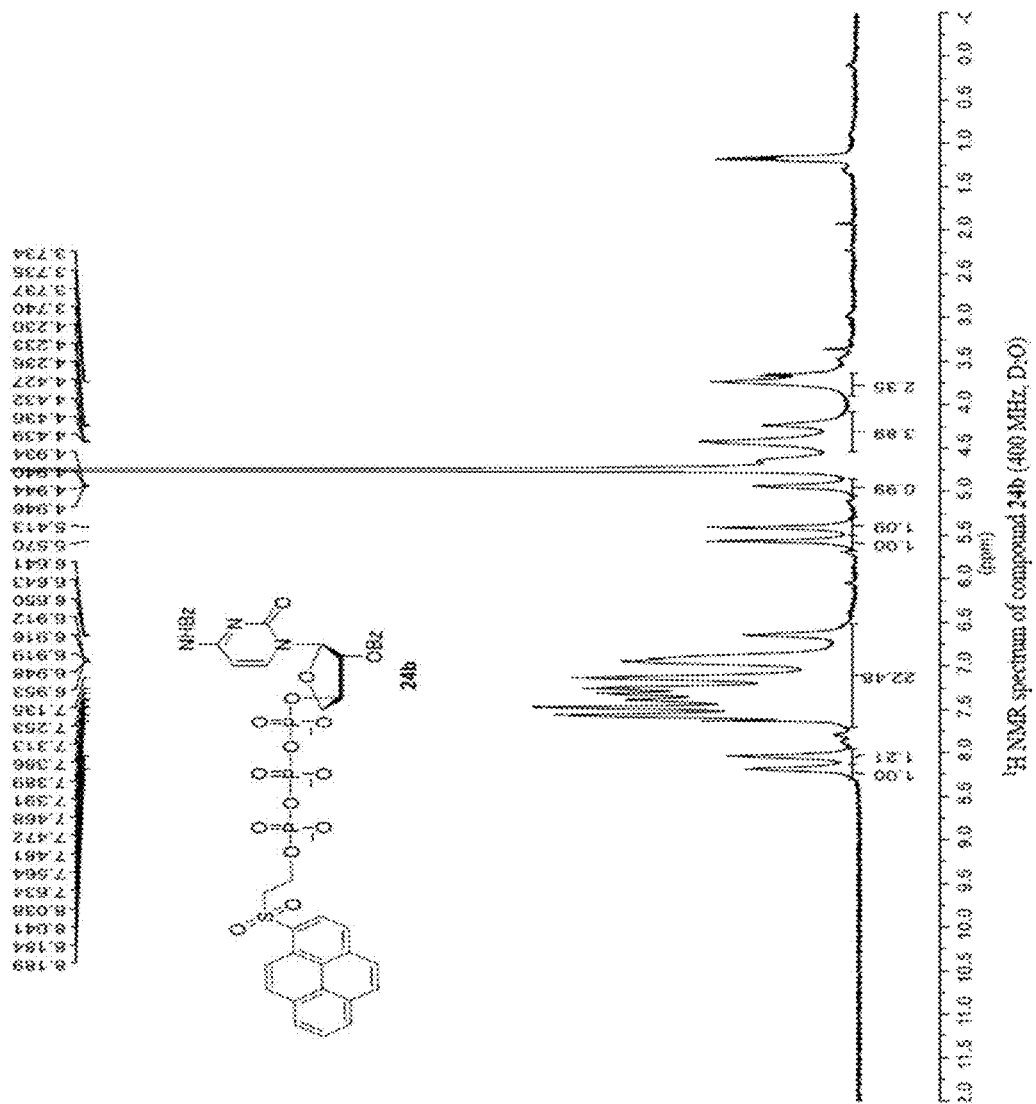
FIG. 106 depicts an $^1$H NMR spectrum of synthesized N$^4$-Benzoyl-1-(2'-O-benzoyl-α-L-threofuranosyl)cytidine-3'-(γ-(2-(pyrenesulfonyl)ethyl) triphosphate (compound 24b).
Figure 107:
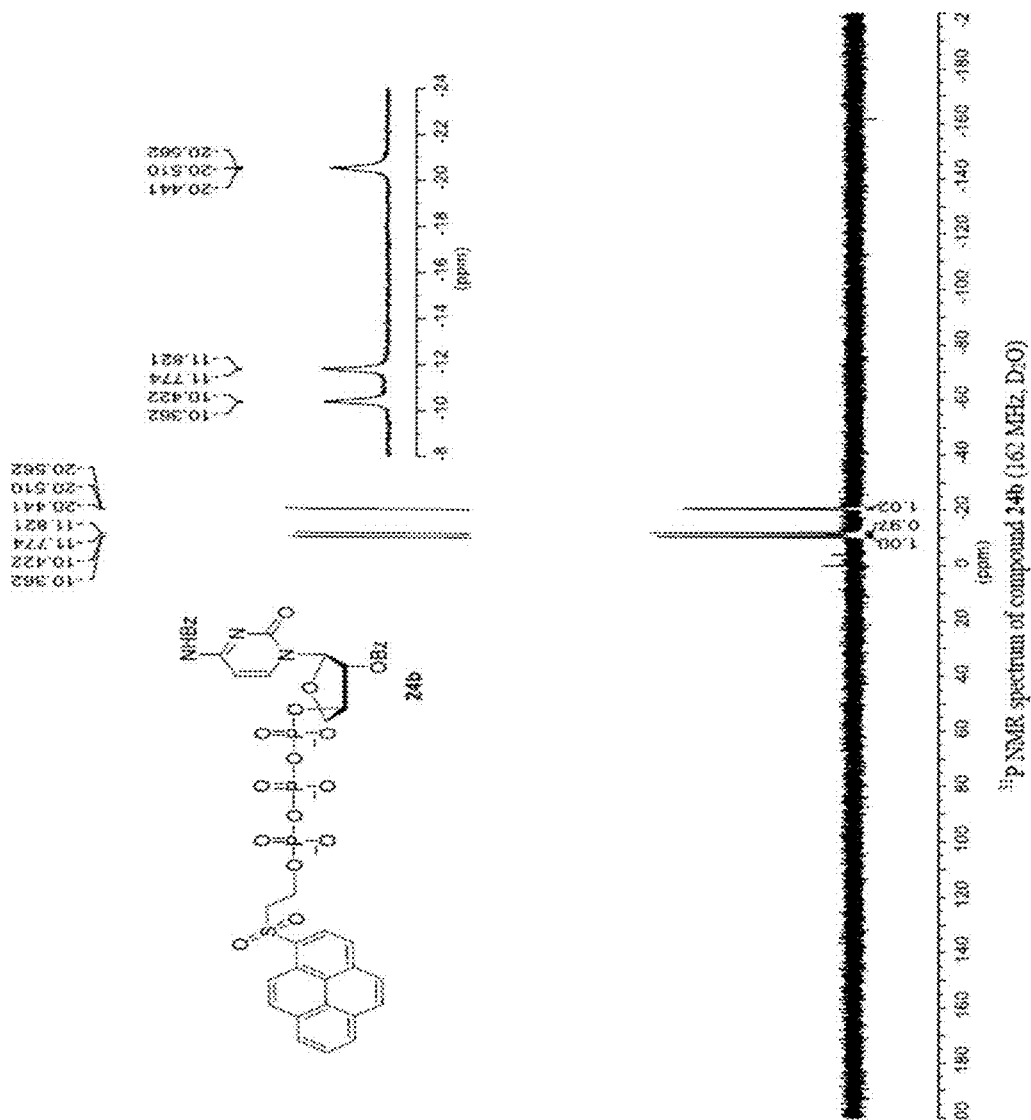
FIG. 107 depicts an $^{31}$P NMR spectrum of synthesized compound 24b.
Figure 108:
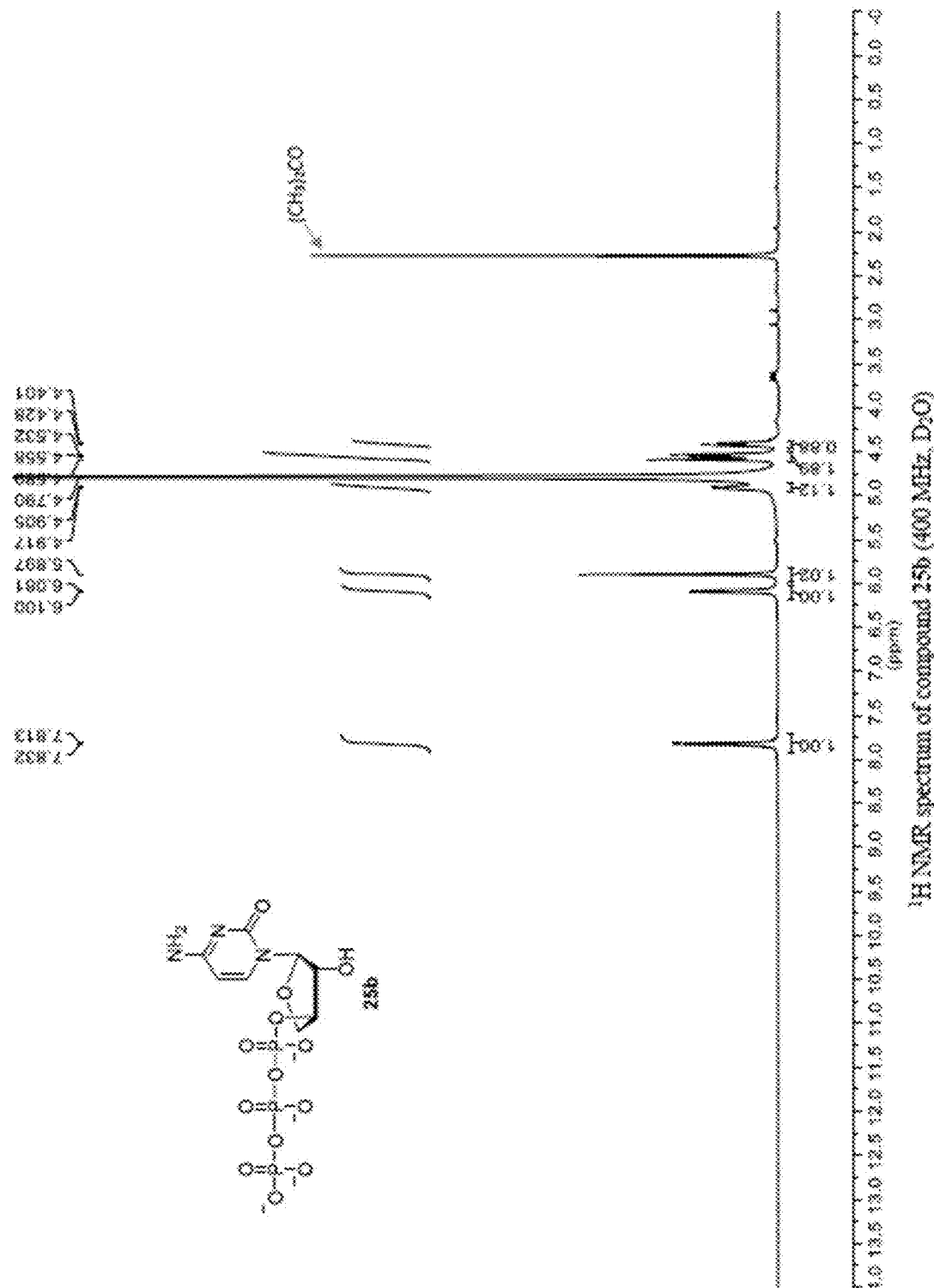
FIG. 108 depicts an $^1$H NMR spectrum of synthesized compound 25b.
Figure 109:
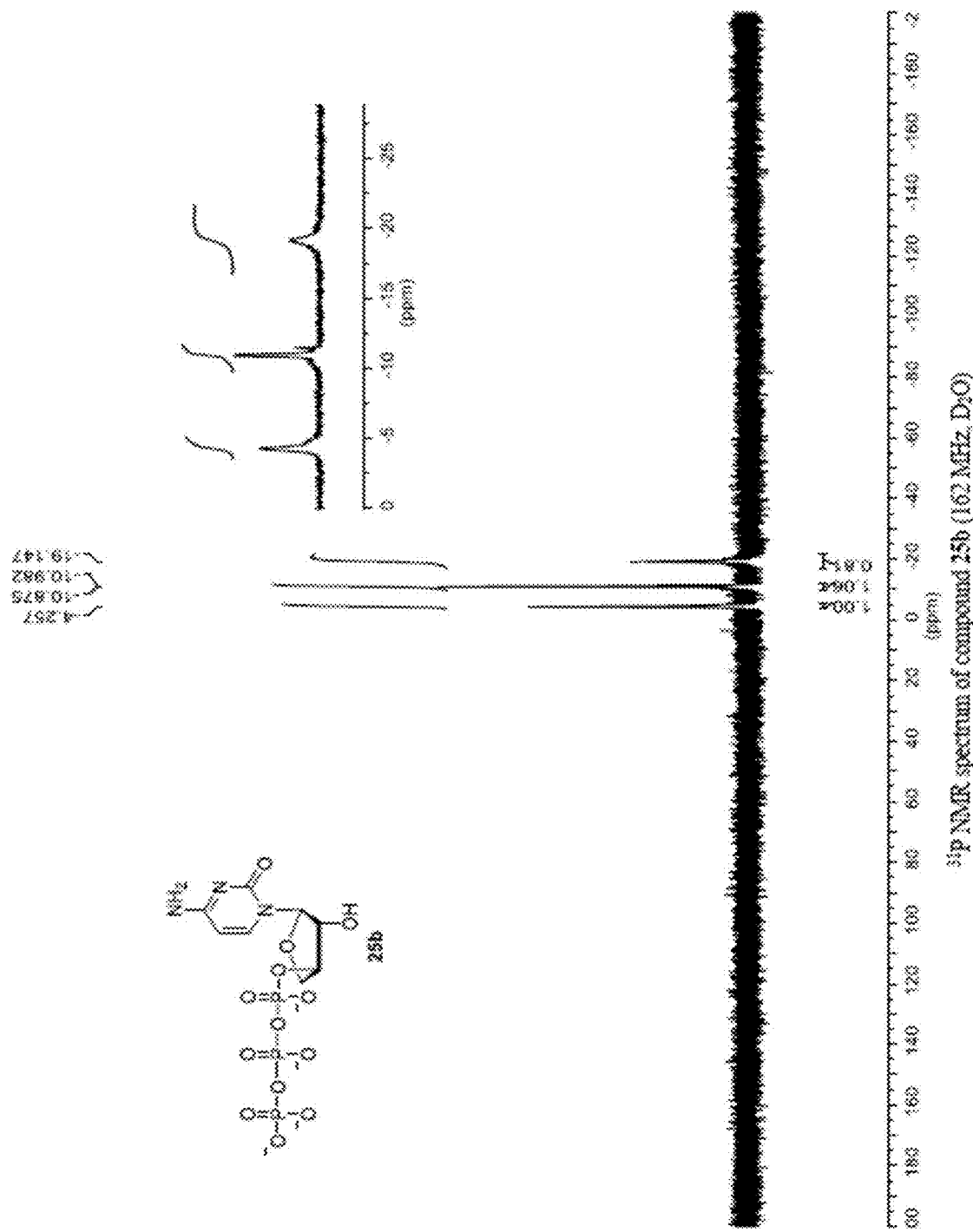
FIG. 109 depicts a $^{31}$P NMR spectrum of synthesized compound 25b.

FIG. 101 shows the synthesis scheme for 1-(α-L-threofuranosyl)cytidine-3'-triphosphate (tCTP, compound 25b). FIG. 102 through FIG. 109 provide NMR spectra of the synthesized intermediates and product.

Methods used for the synthesis are now described.

N$^4$-Benzoyl-1-(2'-O-benzoyl-α-L-threofuranosyl) cytidine-3'-dibenzylmonophosphate (Compound 21b)

Modified general procedure A with 1 g (2.37 mmol) of N$^4$-benzoyl-1-(2'-O-benzoyl-α-L-threofuranosyl)cytosine (compound 20b), 300 mg (4.27 mmol) of tetrazole, 15.8 mL of anhydrous solution (MeCN/CH$_2$Cl$_2$, 1:1), 0.98 mL (3.09 mmol) of dibenzyl-N N-diisopropylphosphoramidite for 1 hour reaction at room temperature and 5 mL of H$_2$O$_2$ for 1 hour oxidation reaction. After the reaction, the product, compound 21b, was afforded as a white solid; yield: 1.29 g (79.3%).

N$^4$-Benzoyl-1-(2'-O-benzoyl-α-L-threofuranosyl) cytidine-3'-monophosphate (Compound 22b)

General procedure B with 1.29 g (1.89 mmol) of compound 21b, 50 mL of MeOH, and 250 mg of 10% Pd/C for 5 hours stirring. The suspension was filtered over a pad of celite, washed with 100 mL of MeOH containing 2% triethylamine four times. The product, compound 22b, was afforded as a white foam of a triethylammonium salt; yield 1.23 g (92.8%); $^1$H NMR (400 MHz, CDCl$_3$) δ 8.26 (d, 1H, J=7.6 Hz), 7.99 (d, 2H, J=7.2 Hz), 7.90 (d, 2H, J=7.6 Hz), 7.57-7.53 (m, 2H), 7.47-7.39 (m, 5H), 6.18 (s, 1H), 5.66 (s, 1H), 4.91-4.85 (m, 2H), 4.28 (dd, 1H, J=10.4, 3.2 Hz); $^{13}$C NMR (125.8 MHz, CDCl$_3$) δ 164.6, 162.7, 154.9, 146.2, 133.5, 132.9, 129.9, 129.3, 128.9, 128.9, 128.5, 128.0, 128.0, 96.6, 91.4, 80.9 (d, J$_C$, P=6.5 Hz), 76.4 (d, J$_C$, P=4.7 Hz), 57.9; $^{31}$P NMR (162 MHz, CDCl$_3$) δ -1.15; HRMS (ESI-TOF) calcd. for C$_{20}$H$_{20}$N$_3$O$_9$PNa$_3$ [M-2H+3Na]$^+$ 546.0630. found 546.0640.

N$^4$Benzoyl-1-(2'-O-benzoyl-α-L-threofuranosyl) cytidine-3'-monophosphor-2-methylimidazolide (Compound 23b)

General procedure C with 1.02 g (1.75 mmol) of compound 22b, 4.3 mL of anhydrous DMF, 0.87 mL (6.4 mmol)

of triethylamine, 287 mg (3.5 mmol) of 2-methylimidazole, 0.94 g (3.6 mmol) of triphenylphosphine, 0.79 g (3.6 mmol) of dipyridyl disulfide for 2 hours stirring at room temperature. First precipitation was achieved with 200 mL of diethyl ether. The product was resuspended with 15 mL of $CH_2Cl_2$ and dropwise added to the solution containing 2.04 g of sodium perchlorate, 10 mL of triethylamine in 300 mL of ethyl acetate for the second precipitation. The product, compound 23b, was afforded as a white solid; yield: 0.94 g (91.5%); $^{31}P$ NMR (162 MHz, $D_2O$) δ −7.56; HRMS (ESI-TOF) calcd. for $C_{26}H_{24}N_5O_8PNa$ $[M+Na]^+$ 588.1260. found 588.1246.

$N^4$-Benzoyl-1-(2'-O-benzoyl-α-L-threofuranosyl)cytidine-3'-(γ-(2-(pyrenesulfonyl)ethyl) triphosphate (Compound 24b)

General procedure D with 0.94 g (1.6 mmol) of compound 23b, 0.9 g (1.92 mmol) of compound 7 and 10.67 mL (16 mmol, 1.5 M in anhydrous DMF) of $ZnCl_2$ solution for 5 hours stirring at room temperature. The product was purified by silica gel chromatography with eluents [(6% $H_2O$/isopropanol containing 1% DIPEA) and then (5% to 10% of $H_2O$/(isopropanol-MeCN 1:1)) containing 1% diisopropylethylamine (DIPEA) to afford the white solid compound 24b; yield: 1.43 g (66.7%); TLC (1:10 $H_2O$-acetone with 2%-DIPEA) Rf=0.25; $^1H$ NMR (400 MHz, $D_2O$) (S 8.18 (s, 1H), 8.04 (s, 1H), 7.63-7.25 (m, 13H), 7.14 (s, 3H), 6.95-6.91 (m, 4H), 6.64 (s, 1H), 5.57 (s, 1H), 5.41 (s, 1H), 4.94 (s, 1H), 4.63 (s, 1H), 4.44 (s, 2H), 4.23 (s, 1H), 3.74-3.63 (m, 2H); $^{31}P$ NMR (162 MHz, $D_2O$) δ −10.23 (d, J=13.0 Hz), −11.65 (d, J=13.9 Hz), −20.59 (brs); HRMS (ESI-TOF) calcd. for $C_{40}H_{32}N_3O_{17}P_3SNa$ $[M+Na]^+$ 974.0563. found 974.0620.

1-(α-L-threofuranosyl)cytidine-3'-triphosphate (Compound 25b)

General procedure E with 1.43 g (1.07 mmol) of compound 24b in 50 mL of 33% $NH_4OH_{(aq)}$ for 3 hours at 37° C. and then 15 hours deprotection reaction at room temperature. The product, compound 25b, was afforded as a white solid; yield: 412 mg (85.8%, C280=13100 $M^{-1}$ $cm^{-1}$); $^1H$ NMR (400 MHz, $D_2O$) δ 7.82 (d, 1H, J=7.6 Hz), 6.09 (d, 1H, J=7.6 Hz), 5.90 (s, 1H), 4.91 (d, 1H, J=4.8 Hz), 4.58-4.53 (m, 2H), 4.42 (d, 1H, J=6.8 Hz); $^{31}P$ NMR (162 MHz, $D_2O$) δ −4.26 (brs), −10.93 (d, J=17.3 Hz), −19.15 (brs).

Synthesis of 9-(α-L-threofuranosyl)adenosine-3'-triphosphate

Figure 110:
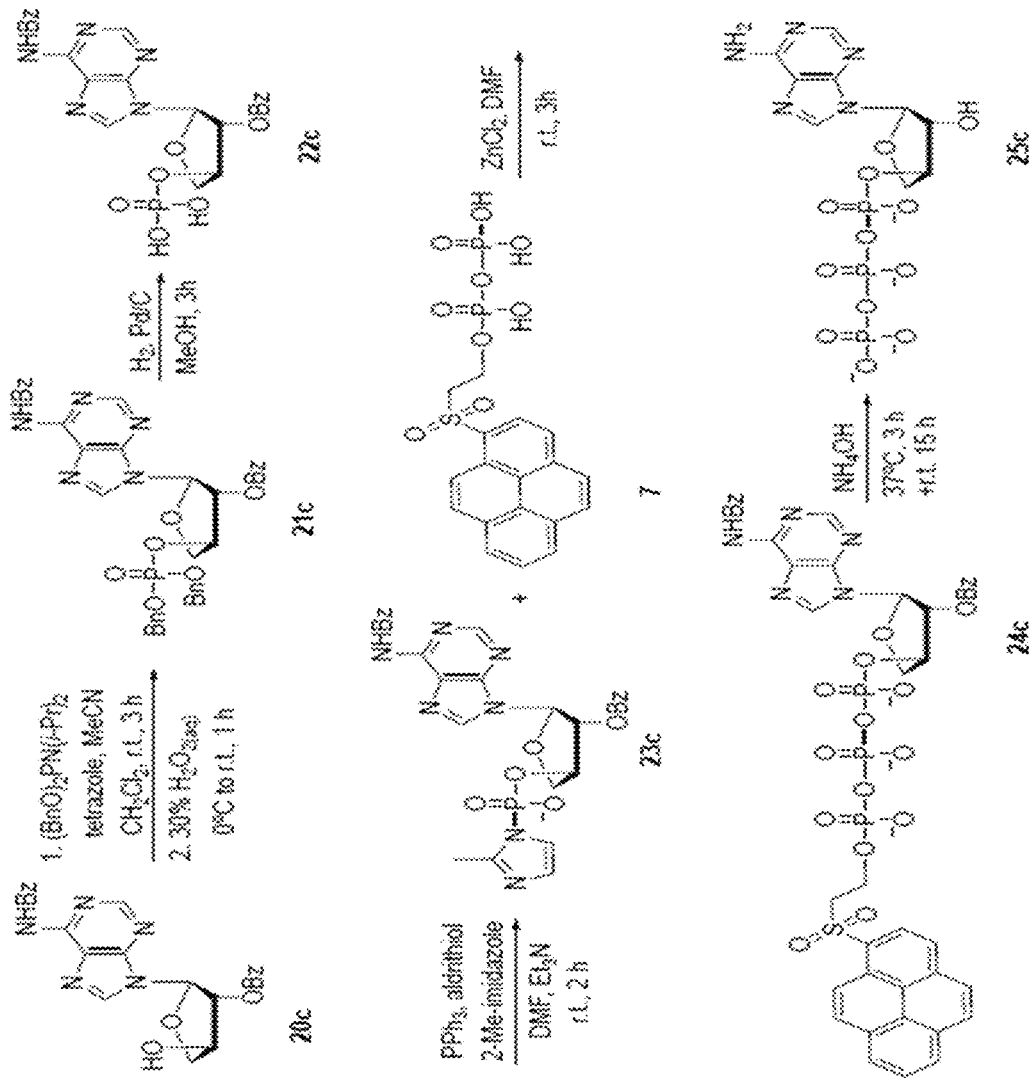
FIG. 110 depicts a synthesis scheme for 9-(α-L-threofuranosyl)adenosine-3'-triphosphate (tATP, compound 25c).
Figure 111:
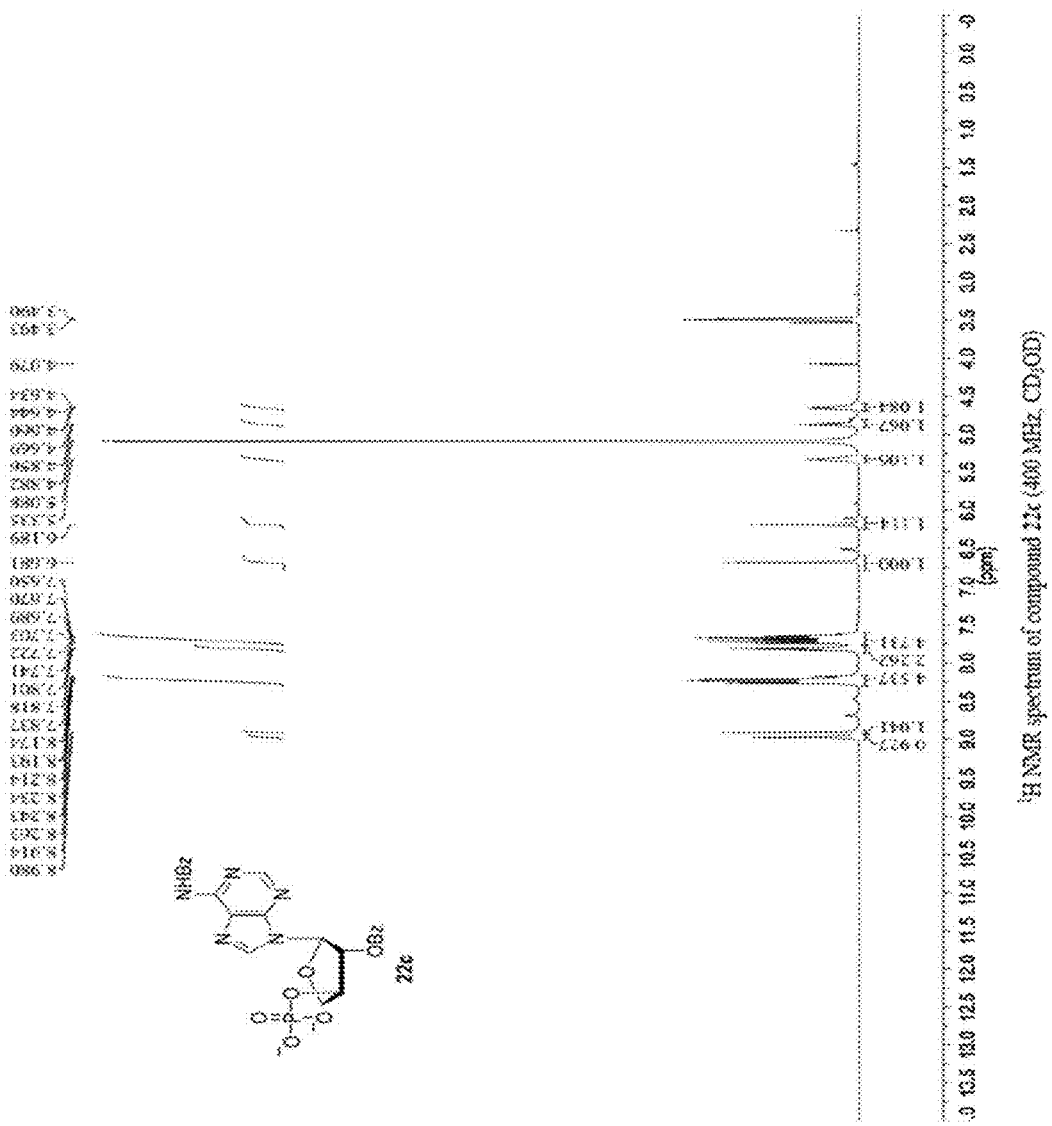
FIG. 111 depicts an $^1$H NMR spectrum of synthesized V-Benzoyl-9-(2'-O-benzoyl-α-L-threofuranosyl)adenosine-3'-monophosphate (compound 22c)
Figure 112:
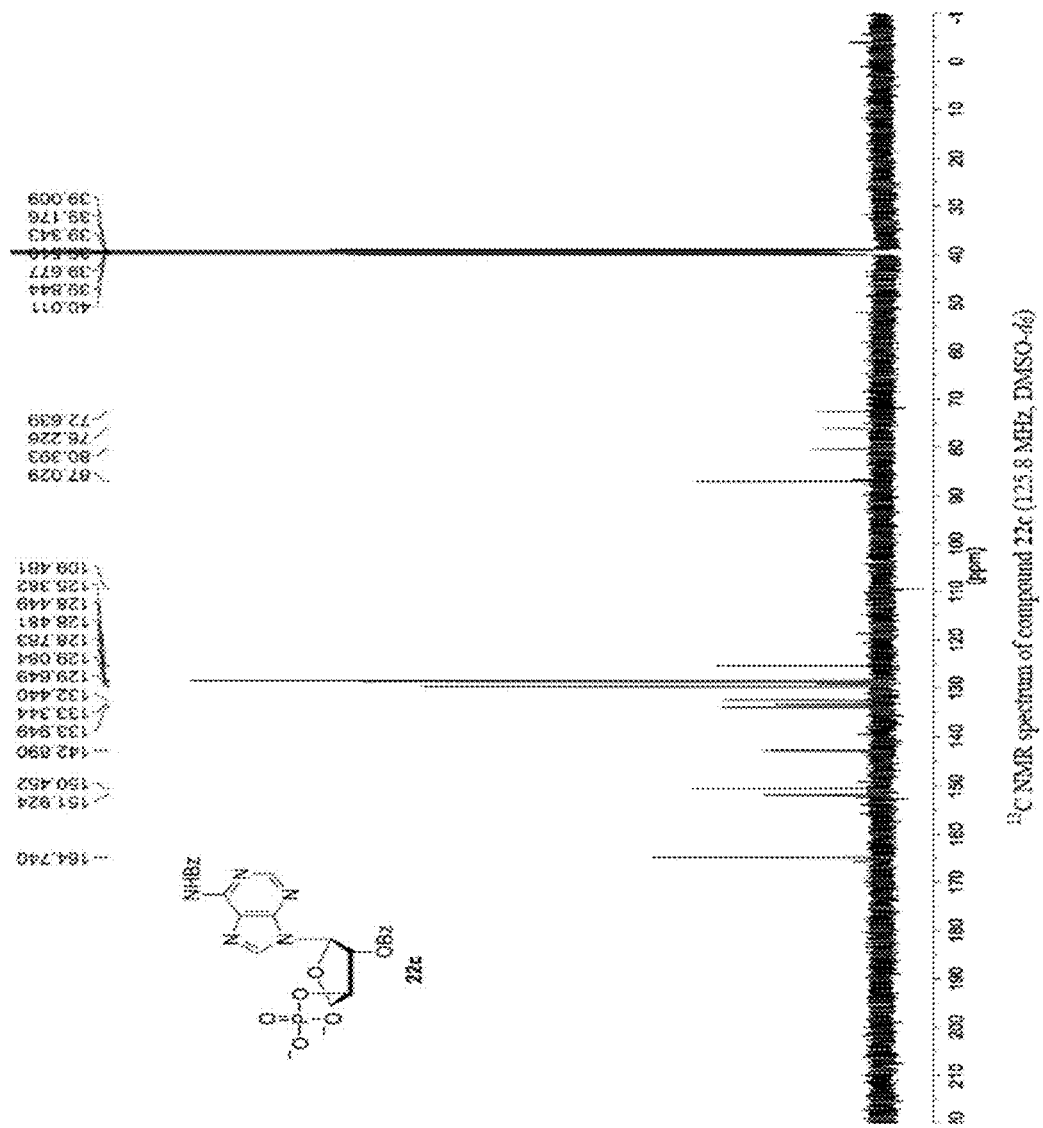
FIG. 112 depicts a $^{13}$C NMR spectrum of synthesized compound 22c.
Figure 113:
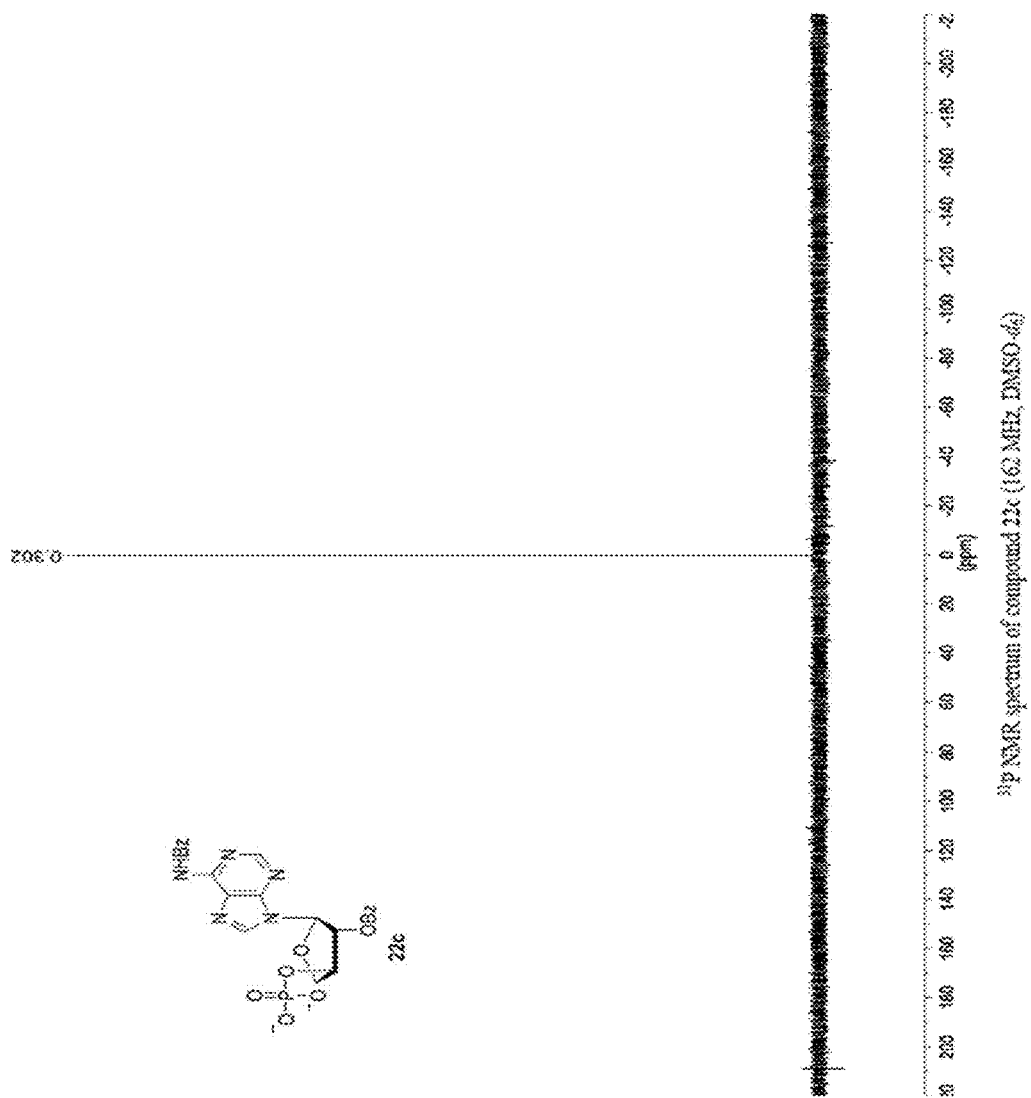
FIG. 113 depicts an $^{31}$P NMR spectrum of synthesized compound 22c.
Figure 114:
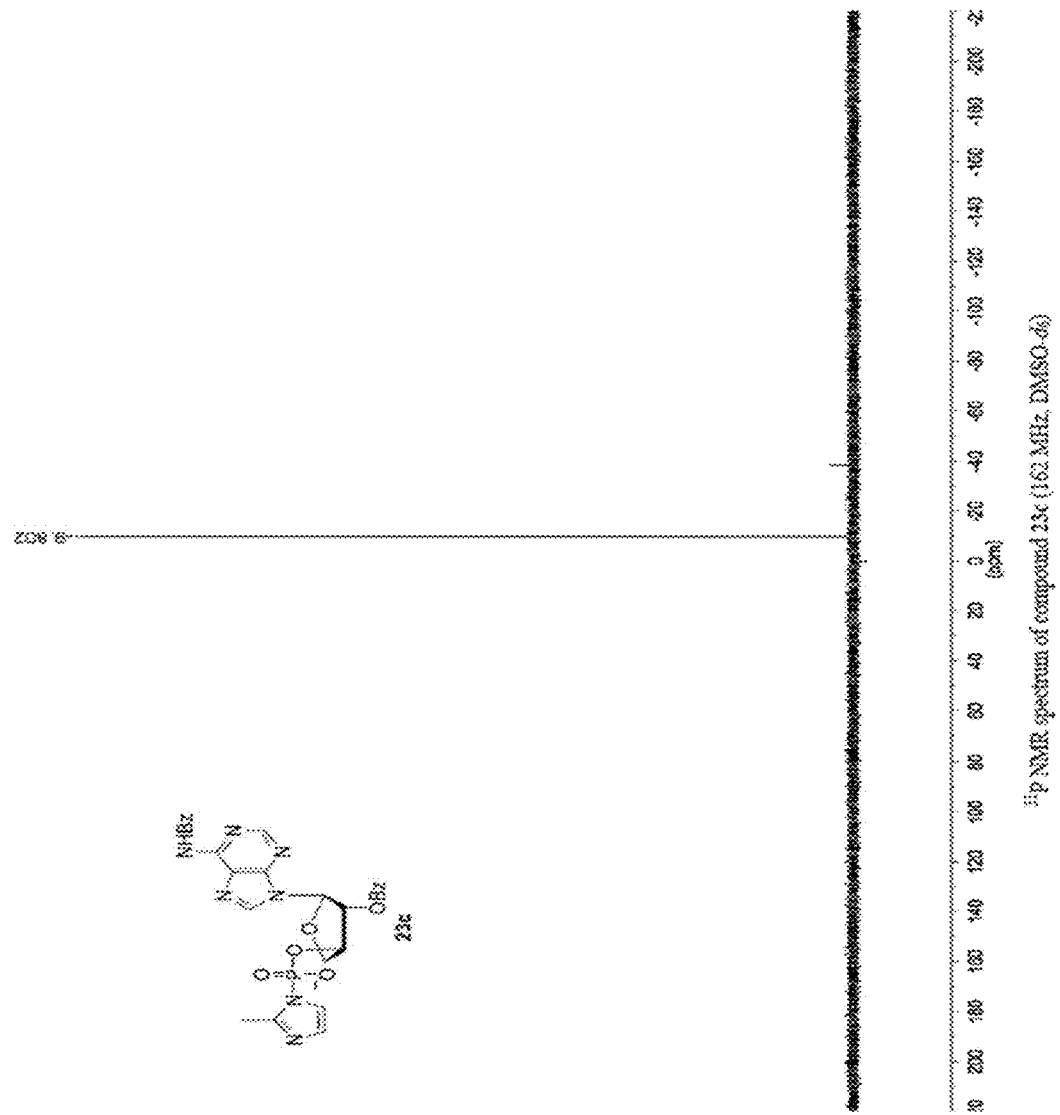
FIG. 114 depicts an $^{31}$P NMR spectrum of synthesized N$^6$-Benzoyl-9-(2'-O-benzoyl-α-L-threofuranosyl)adenosine-3'-monophosphor-2-methylimidazolide (compound 23c).
Figure 115:
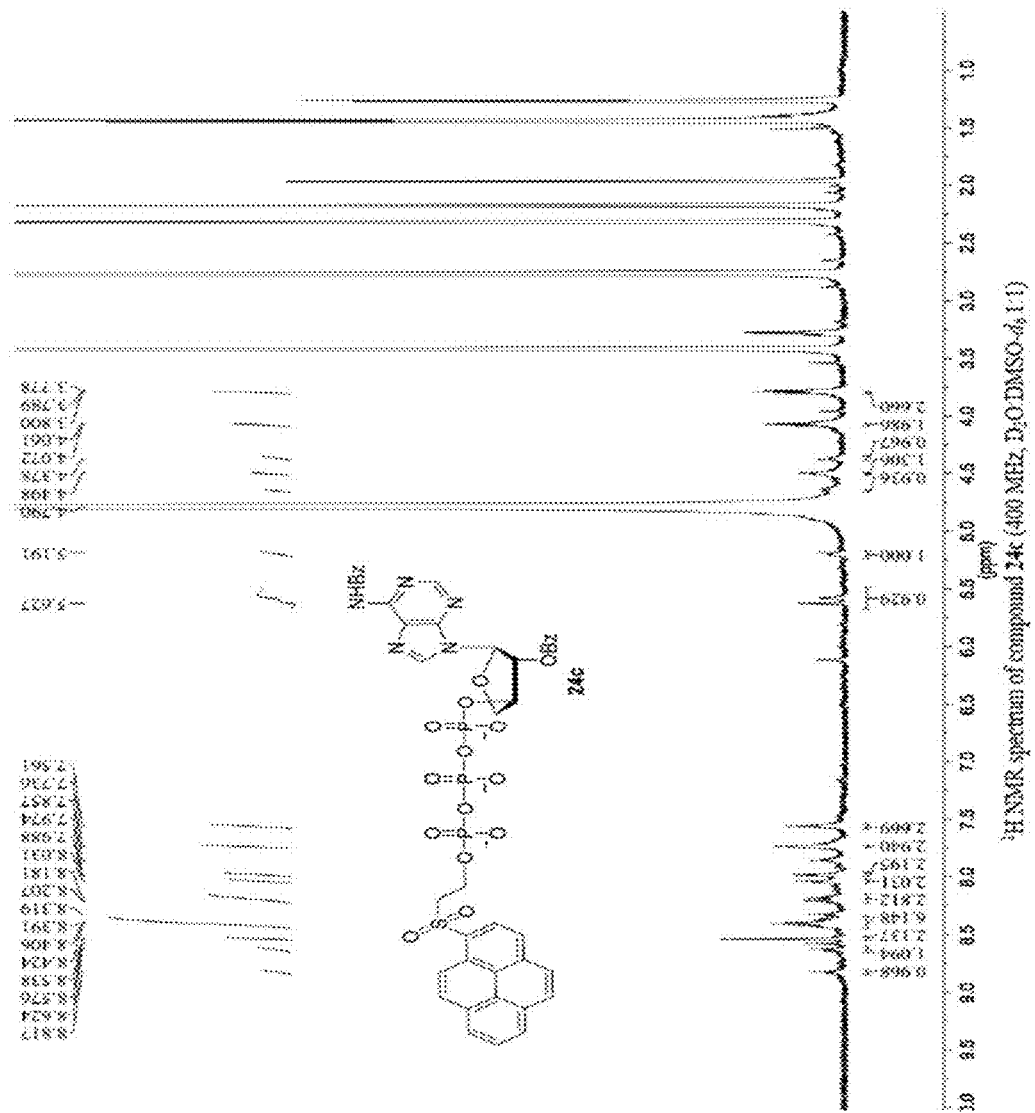
FIG. 115 depicts an $^1$H NMR spectrum of synthesized N$^6$-Benzoyl-9-(2'-O-benzoyl-α-L-threofuranosyl)adenosine-3'-γ-[2-(pyrenesulphonyl)ethyl]triphosphate (compound 24c).
Figure 116:
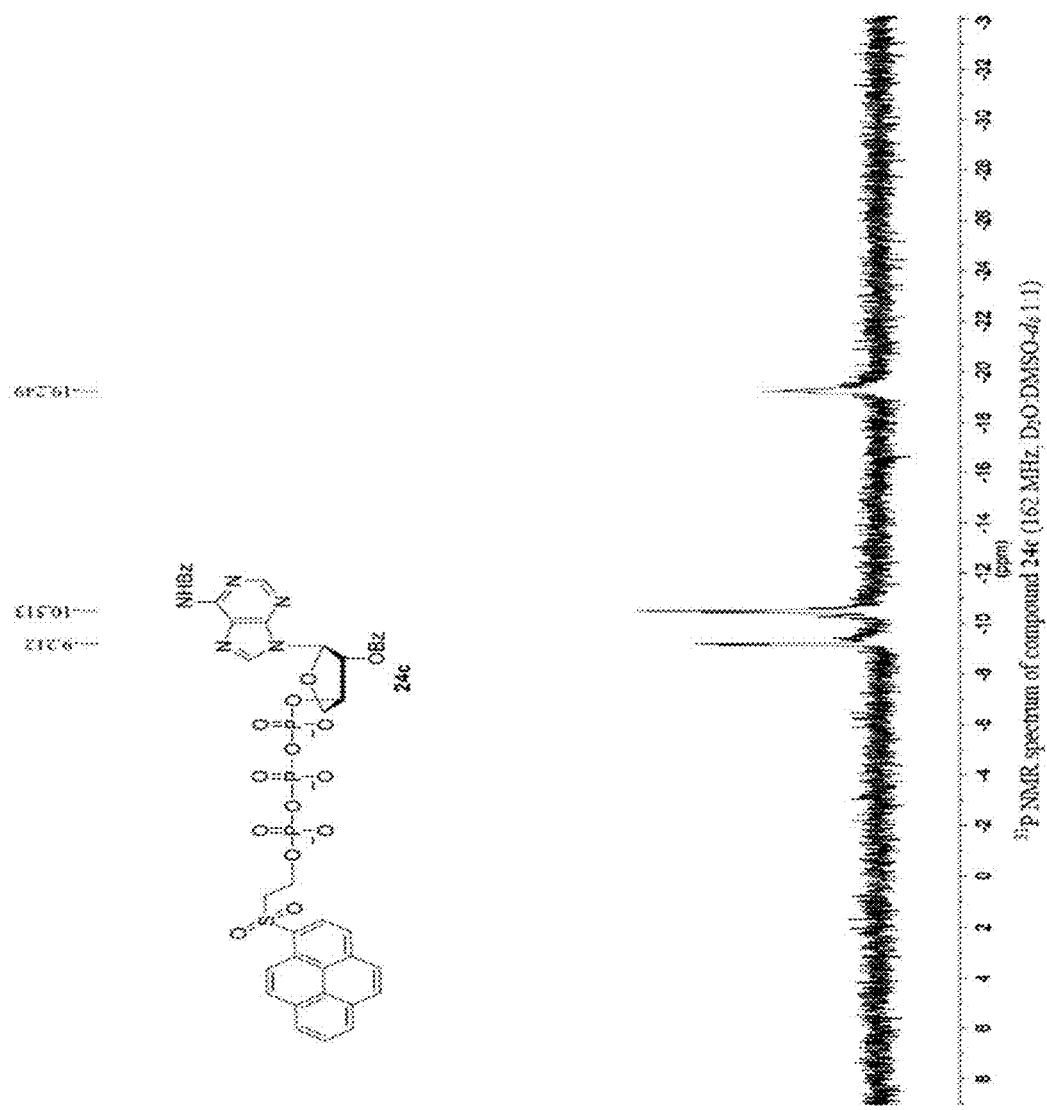
FIG. 116 depicts an $^{31}$P NMR spectrum of synthesized compound 24c.
Figure 117:
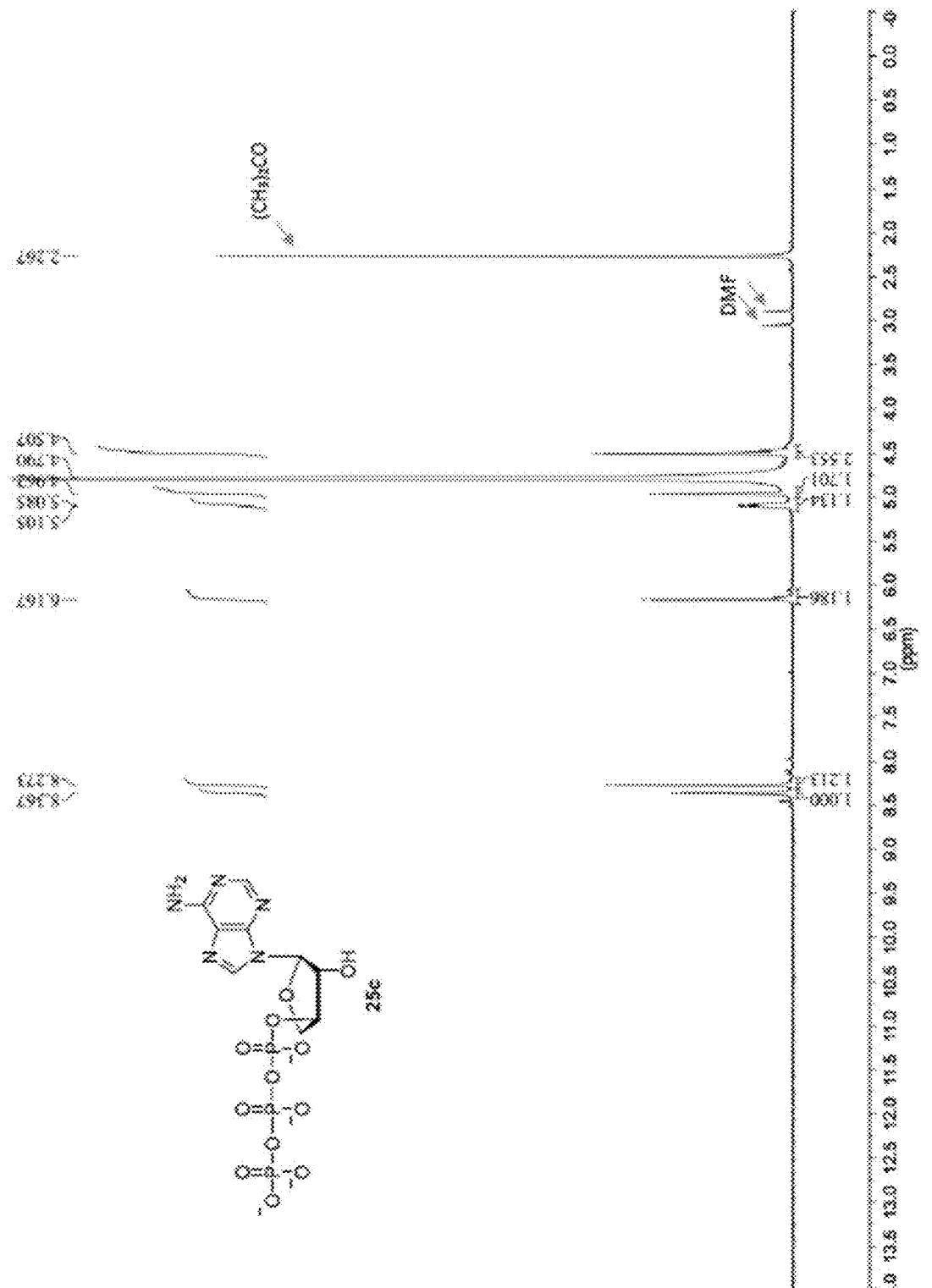
FIG. 117 depicts an $^1$H NMR spectrum of synthesized compound 25c.
Figure 118:
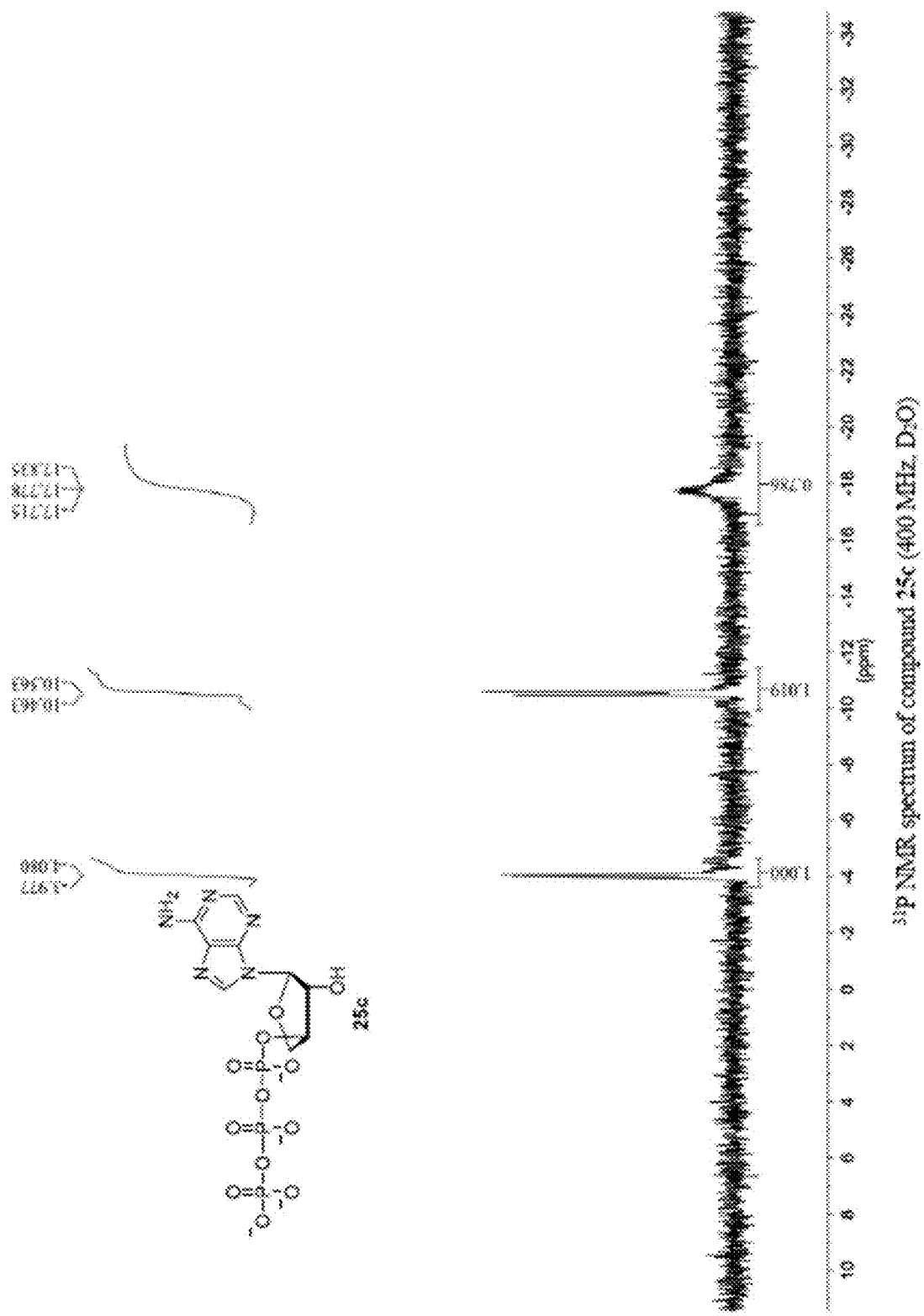
FIG. 118 depicts a $^{31}$P NMR spectrum of synthesized compound 25c.

FIG. 110 shows the synthesis scheme for 9-(α-L-threofuranosyl)adenosine-3'-triphosphate (tATP, compound 25c). FIG. 111 through FIG. 118 provide NMR spectra of the synthesized intermediates and product.

Methods used for the synthesis are now described.

$N^6$-Benzoyl-9-(2'-O-benzoyl-α-L-threofuranosyl)adenosine-3'-dibenzyl Monophosphate (Compound 210

General procedure A with 1.007 g (2.26 mmol) of $N^6$-benzoyl-9-(2'-O-benzoyl-α-L-threofuranosyl)adenine (compound 20c), 316 mg (4.52 mmol) of tetrazole, 15 mL of anhydrous solution (MeCN/$CH_2Cl_2$, 1:1), 0.91 mL (2.71 mmol) of dibenzyl-N, N-diisopropylphosphoramidite for 3 hours reaction at room temperature and 5 mL of $H_2O_2$ for 1 hour oxidation reaction. The product, compound 21c, was afford as a white solid; yield: 1.41 g (88.4%).

$N^6$-Benzoyl-9-(2'-O-benzoyl-α-L-threofuranosyl)adenosine-3'-monophosphate (Compound 22c)

General procedure B with 1.3 g (1.84 mmol) of compound 21c, 10 mL of MeOH, and 400 mg of 10% Pd/C for 12 hours with stirring. The suspension was filtered over a pad of celite, washed with 100 mL of MeOH four times. The product, compound 22c, was afford as a white solid; yield: 943 mg (97.4%); $^1H$ NMR (400 MHz, $CD_3OD$): δ 8.98 (s, 1H), 8.91 (s, 1H), 8.26-8.17 (m, 4H), 7.83-7.80 (m, 2H), 7.74-7.65 (m, 4H), 6.68 (s, 1H), 6.18 (s, 1H), 5.33 (s, 1H), 4.88-4.85 (m, 1H), 4.66 (dd, 1H, J=14, 6.4 Hz). $^{13}C$ NMR (125.8 MHz, DMSO-$d_6$): δ 164.7, 151.9, 150.4, 142.8, 133.9, 133.3, 132.4, 129.6, 129.0, 128.7, 128.4, 128.4, 125.3, 109.4, 87.0, 80.3, 76.2, 72.6; $^{31}P$ NMR (162 MHz, DMSO-$d_6$): 0.30; HRMS (ESI-TOF) calcd. for $C_{23}H_{21}N_5O_8P$ $[M+H]^+$ 526.1128. found 526.1118.

$N^6$—Benzoyl-9-(2'-O-benzoyl-α-L-threofuranosyl)adenosine-3'-monophosphor-2-methylimidazolide (Compound 23c)

General procedure C with 0.93 g (1.58 mmol) of compound 22c, 12 mL of anhydrous DMF, 1.1 mL (7.89 mmol) of triethylamine, 284 mg (3.94 mmol) of 2 methylimidazole, 1.03 g (3.94 mmol) of triphenylphosphine, 0.87 g (3.95 mmol) of dipyridyl disulfide. First precipitation was achieved with 150 mL of diethyl ether. The product was resuspended with 5 mL of $CH_2Cl_2$ and dropwise added to the solution containing 1.5 g of sodium perchlorate, 6 mL of triethylamine in 150 mL of ethyl acetate for the second precipitation. The product afford as a white solid compound 23c; yield: 0.89 g (93.02%); $^{31}P$ NMR (162 MHz, DMSO-$d_6$): −9.80; HRMS (ESI-TOF) calcd. for $C_{27}H_{24}N_7O_7PNa$ $[M+Na]^+$ 612.1373. found 612.1345.

$N^6$-Benzoyl-9-(2'-O-benzoyl-α-L-threofuranosyl)adenosine-3'-γ-[2-(pyrenesulphonyl)ethyl]triphosphate (Compound 2401

General procedure D with 0.6 g (1.02 mmol) of compound 23c, 0.52 g (mmol) of compound 7 and 7 mL (10.17 mmol, 1.5 M in anhydrous DMF) of $ZnCl_2$ solution for 3 hours stirring at room temperature. The product was purified by silica gel chromatography with eluents [MeOH—$CHCl_3$ from 5% to 12% containing 1% diisopropylethylamine (DIPEA)] to afford the white solid compound 24c; yield 0.64 g (63.1%); TLC (1:10 $H_2O$-acetone with 2%-DIPEA) Rf=0.31; $^1H$ NMR (400 MHz, $D_2O$) δ 9.50 (s, 1H), 9.18-7.56 (m, 7H), 7.51-7.46 (m, 6H), 7.35-7.09 (m, 9H), 6.19 (m, 1H), 5.72 (m, 1H), 4.72-4.52 (m, 1H), 3.48 (s, 2H), 2.99 (d, 2H, J=12 Hz); $^{31}P$ NMR (162 MHz, $D_2O$) δ −9.21 (d, J=12.9 Hz), −10.51 (d, J=13.0 Hz), −19.24 (brs); HRMS (ESI-TOF) calcd. for $C_{41}H_{32}N_5O_{16}P_3SNa$ $[M-2H+Na]^+$ 998.0676. found 998.0667.

9-(α-L-threofuranosyl)adenosine-3'-triphosphate (Compound 25c)

General procedure E with 0.5 g (0.51 mmol) of compound 24c, 35 mL of 33% $NH_4OH_{(aq)}$ for 3 hours deprotection at 37° C., and then 15 hours deprotection reaction at room temperature. The product compound 25c was afforded as a white solid; yield: 0.21 g (86.2%, $\varepsilon_{280}$=15200 $M^{-1}$ $cm^{-1}$); $^1$H NMR (400 MHz, $D_2O$) δ 8.36 (s, 1H), 8.27 (s, 1H), 6.16 (s, 1H), 5.09 (d, 1H, J=8.0 Hz), 4.96 (s, 1H), 4.50 (s, 2H); $^{31}$P NMR (162 MHz, $D_2O$) δ −4.02 (d, J=16.6 Hz), −10.51 (d, J=16.2 Hz), −17.77 (brs).

Synthesis of 9-(α-L-threofuranosyl)guanosine-3'-triphosphate

Figure 119:
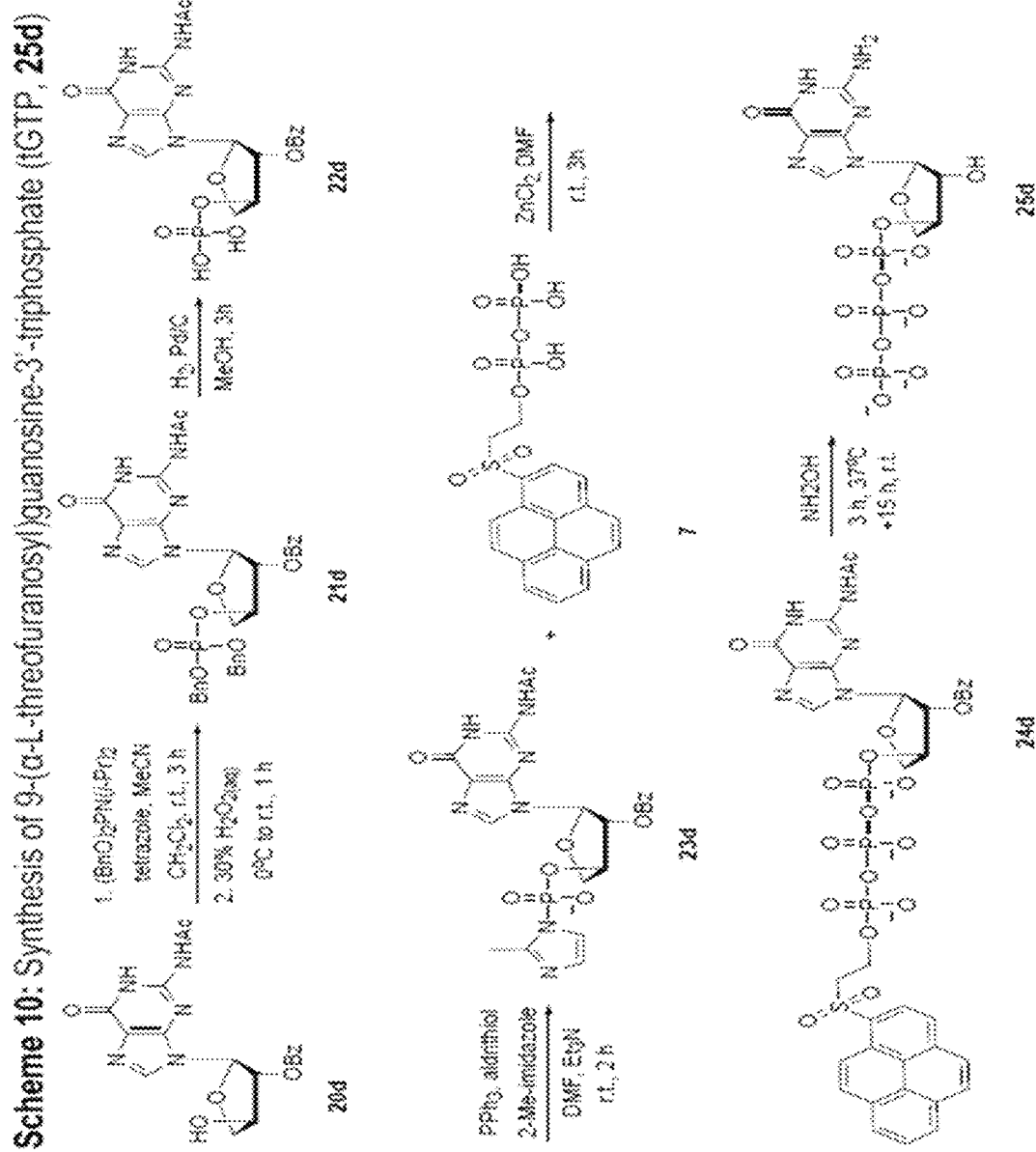
FIG. 119 depicts a synthesis scheme for 9-(α-L-threofuranosyl)guanosine-3'-triphosphate (tGTP, compound 25d).
Figure 120:
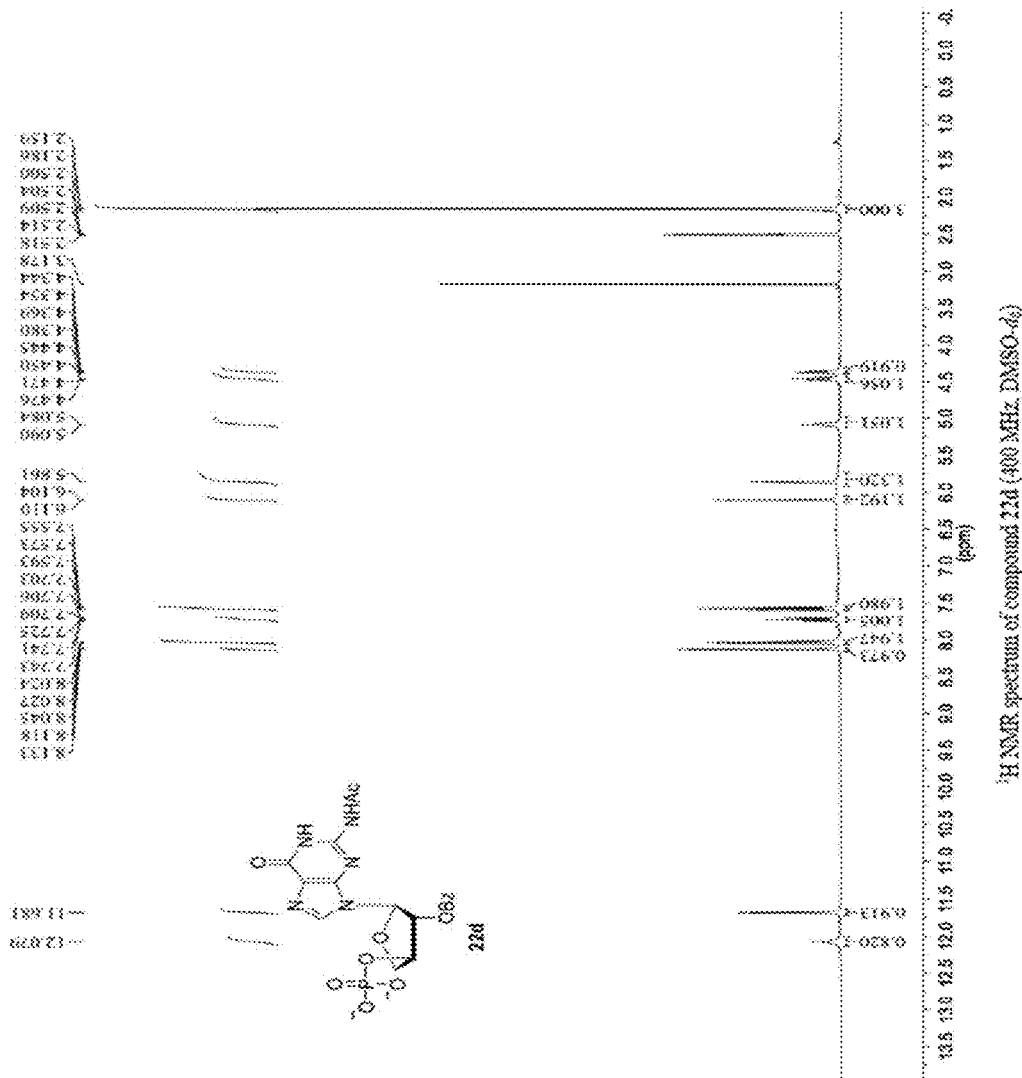
FIG. 120 depicts an $^1$H NMR spectrum of synthesized N$^2$-Acetyl-9-(2'-O-benzoyl-α-L-threofuranosyl)guanosine-3'-monophosphate (compound 22d).
Figure 121:
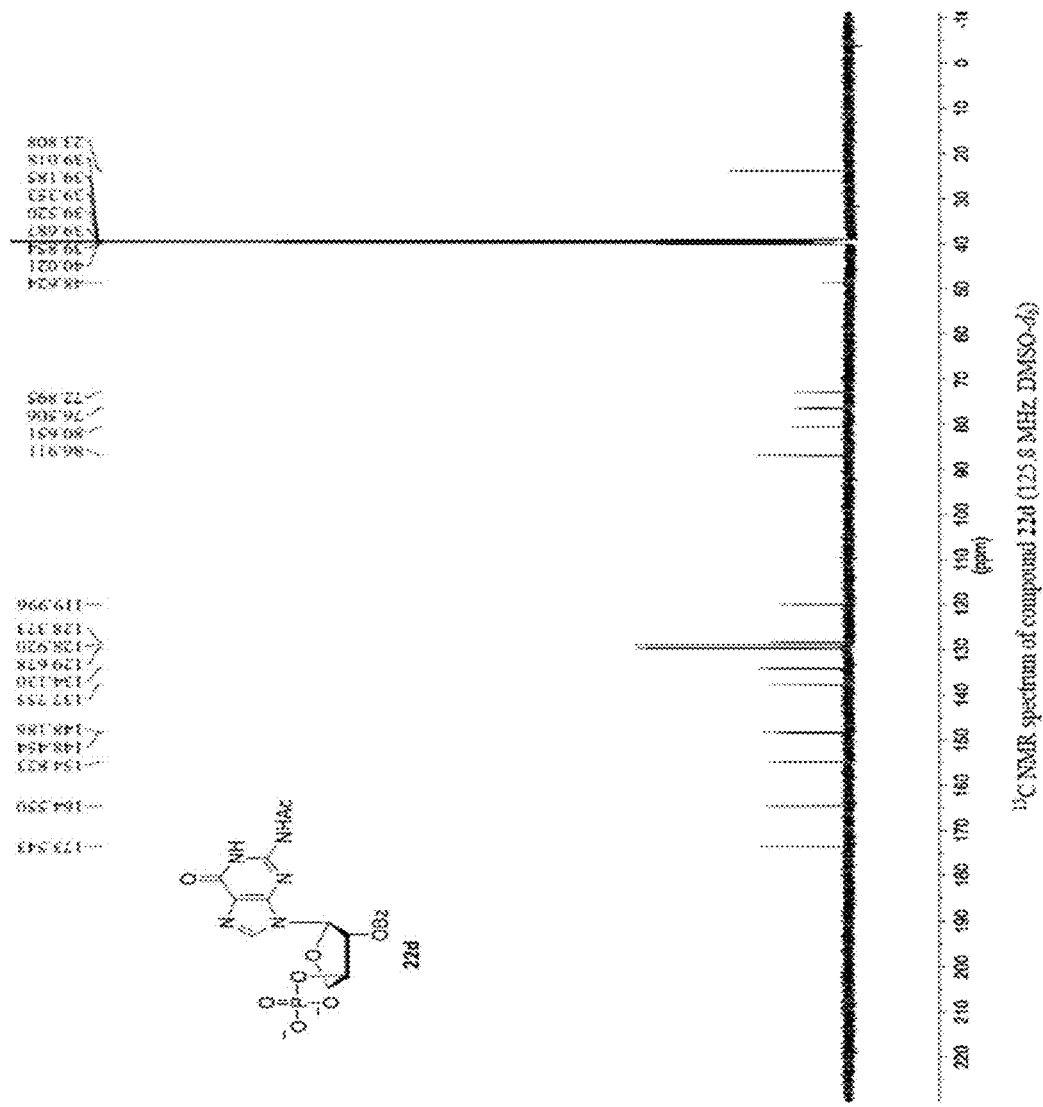
FIG. 121 depicts a $^{13}$C NMR spectrum of synthesized compound 22d.
Figure 122:
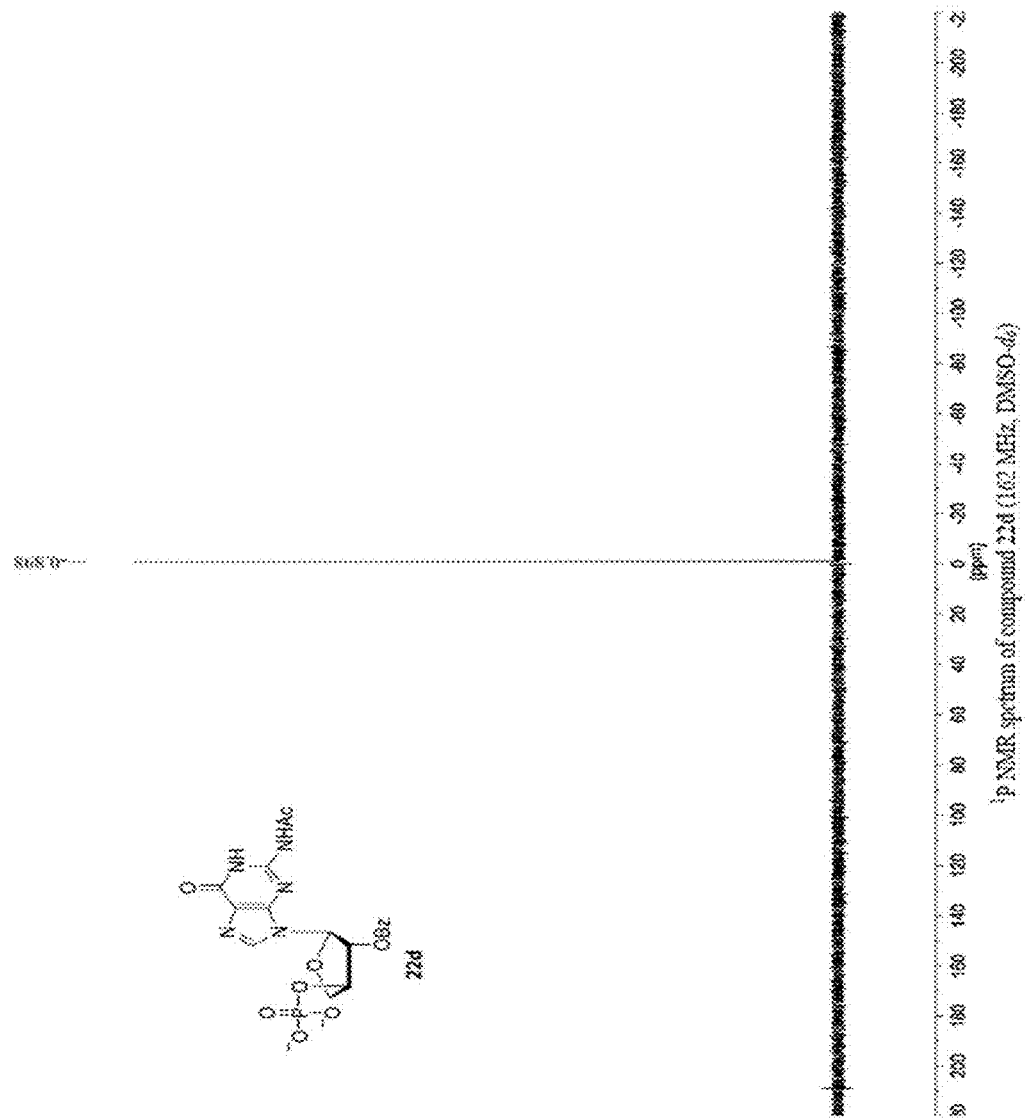
FIG. 122 depicts an $^{31}$P NMR spectrum of synthesized compound 22d.
Figure 123:
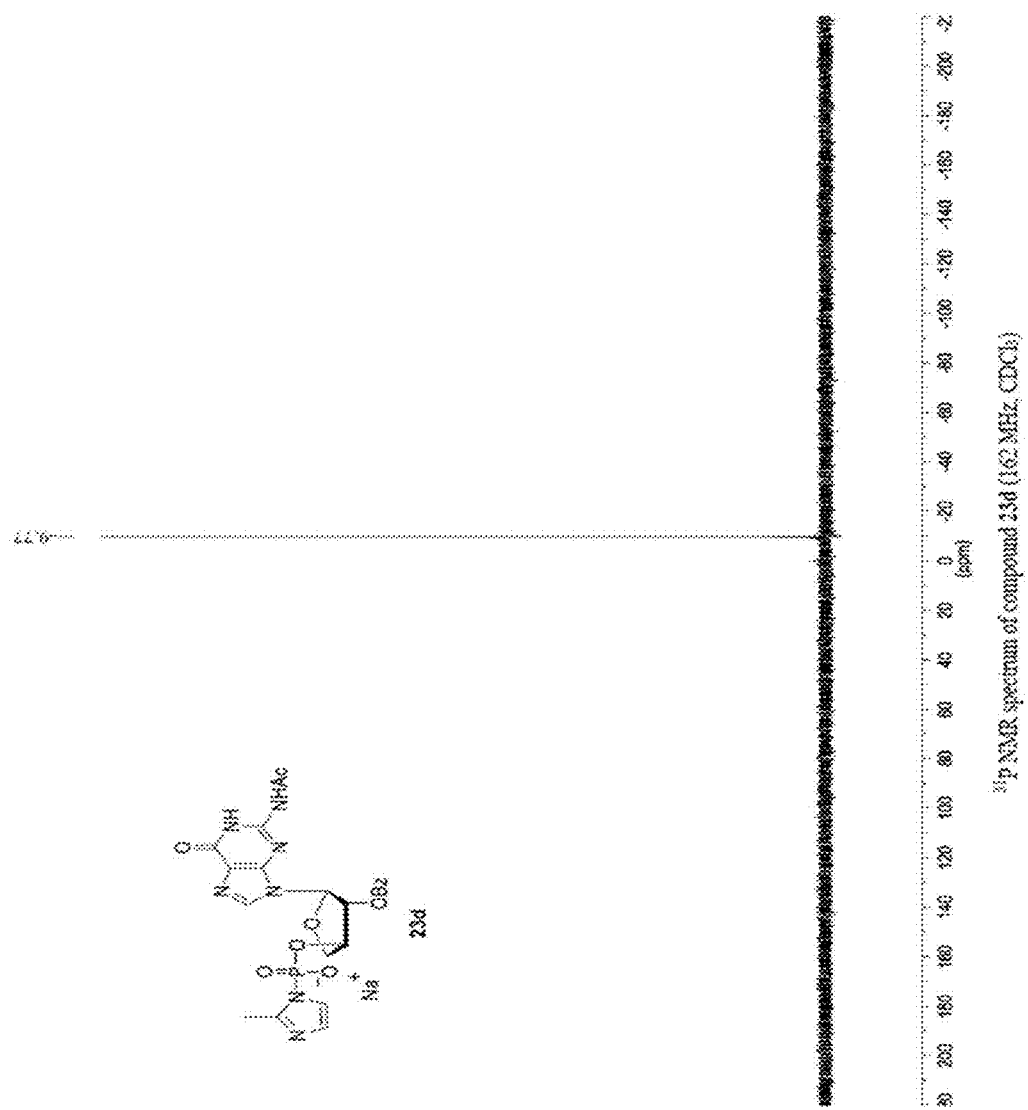

FIG. 119 shows the synthesis scheme for 9-(α-L-threofuranosyl)guanosine-3'-triphosphate (tGTP, compound 25d). FIG. 120 through FIG. 127 provide NMR spectra of the synthesized intermediates and product.

Methods used for the synthesis are now described.

$N^2$-Acetyl-9-(2'-O-benzoyl-α-L-threofuranosyl) guanosine-3'-dibenzylmonophosphate (Compound 21d)

General procedure A with 1 g (1.68 mmol) of $N^2$-acetyl-9-(2'-O-benzoyl-α-L-threofuranosyl)guanine (compound 20d), 212 mg (3.03 mmol) of tetrazole, 12 mL of anhydrous solution (MeCN/$CH_2Cl_2$, 1:1), 735 mL (2.19 mmol) of dibenzyl-N, N-diisopropylphosphoramidite for 3 hours reaction at room temperature and 6 mL of $H_2O$, for 1 hour oxidation. Column chromatography with eluents (EtOAc/Hexane, 50%; then EtOAc/$CH_2Cl_2$, from 16% to 25%) to afford the product compound 21d as a white solid; yield: 1.14 g (79.4%). TLC (EtOAc/$CH_2Cl_2$, 1:4) Rf=0.44; Compound 20d has been reported in Sau et al., 2016, J. Org. Chem. 81, 2302-2307. Compound 21d has been reported in Sau et al., 2017, Org. Lett. 19, 4379-4382.

$N^2$-Acetyl-9-(2'-O-benzoyl-α-L-threofuranosyl) guanosine-3'-monophosphate (Compound 22d)

General procedure B with 1.63 g (2.47 mmol) of compound 21d, 15 mL of MeOH, and 600 mg of 10% Pd/C for 3 hours stirring. The suspension was filtered over a pad of celite, washed with 100 mL of MeOH four times. The product compound 22d was afford as a white solid; yield; 1.04 g (87.7%). $^1$H NMR (400 MHz, DMSO-$d_6$): δ 12.1 (s, 1H), 11.68 (s, 1H), 8.13 (s, 1H), 8.04-8.02 (m, 2H), 7.74-7.70 (m, 1H), 7.59-7.55 (m, 2H), 6.11 (d, 1H, J=4 Hz), 5.86 (s, 1H), 5.09 (d, 1H, J=2.4 Hz) 4.47-4.45 (m, 1H), 4.38-4.34 (m, 1H), 2.15 (s, 3H); $^{13}$C NMR (125.8 MHz, DMSO-$d_6$): 173.5, 164.5, 154.8, 148.4, 148.1, 137.7, 134.1, 129.6, 128.9, 128.3, 119.9, 86.9, 80.6, 76.5, 72.8, 48.6, 23.8; $^{31}$P NMR (162 MHz, DMSO-$d_6$): −0.89; HRMS (ESI-TOF) calcd. for $C_{18}H_{18}N_5O_9PNa$ [M+Na]$^+$ 502.0740. found 502.0727.

$N^2$-Acetyl-9-(2'-O-benzoyl-α-L-threofuranosyl) guanosine-3'-monophosphor-2-methylimidazolide (Compound 23d)

General procedure C with 0.94 g (1.97 mmol) of compound 22d, 12 mL of anhydrous DMF, 1.3 mL (9.86 mmol) of triethylamine, 355 mg (4.93 mmol) of 2-methylimidazole, 1.29 g (4.93 mmol) of triphenylphosphine, 1.086 g (4.93 mmol) of dipyridyl disulfide. First precipitation was achieved with 150 mL of diethyl ether. The product was resuspended with 5 mL of $CH_2Cl_2$ and dropwise added to the solution containing 1.5 g of sodium perchlorate, 6 mL of trimethylamine in 150 mL of ethyl acetate for the second precipitation. The product afford as a white solid compound 23d; yield: 0.88 g (82.1%); $^{31}$P NMR (162 MHz, DMSO-$d_6$): −9.77; HRMS (ESI-TOF) calcd. for $C_{22}H_{22}N_7O_8PNa$ [M+Na]$^+$ 566.1165. found 566.1163.

$N^2$-Acetyl-9-(2'-O-benzoyl-α-L-threofuranosyl) guanosine-3'-(γ-(2-(pyrenesulfonyl)ethyl))triphosphate (Compound 24d)

General procedure D with 0.5 g (0.92 mmol) of compound 23d, 0.56 g (1.20 mmol) of 7 and 10 mL (9.2 mmol, 1.5 M in anhydrous DMF) of $ZnCl_2$ solution for 3 hours stirring at room temperature. The product was purified by silica gel chromatography with eluents [($H_2O$ isopropanol from 5% to 10% then $H_2O$/(isopropanol-MeCN 1:1) containing 1% diisopropylethylamine (DIPEA)] to afford the white solid compound 24d; yield: 0.74 g (80.9%); TLC (1:10 $H_2O$-acetonitrile with 2% DIPEA) Rf=0.31; $^1$H NMR (400 MHz, $D_2O$) δ 12.00 (m, 1H), 8.96 (d, 1H, J=8.4 Hz), 8.65 (d, 1H, J=8.2 Hz), 8.48-8.42 (m, 3H), 8.39-8.30 (m, 1H), 8.28 (s, 1H), 8.19-8.11 (m, 2H), 7.99-7.97 (m, 1H), 7.51 (brs, 2H), 7.25 (s, 2H), 7.13 (s, 2H), 7.01 (s, 1H), 6.01 (s, 1H), 5.85 (s, 1H), 5.09 (s, 1H), 4.63 (s, 1H), 4.19 (s, 2H), 3.90 (d, 2H, J=5.6 Hz), 3.07 (s, 2H), 1.93 (s, 3H); $^{31}$P NMR (162 MHz, $D_2O$) δ −12.87 (brs, 2P), −20.71 (brs, 1P); HRMS (ESI-TOF) calcd. for $C_{36}H_{30}N_5O_{17}P_3SNa$ [M−2H+Na]$^+$ 952.0473. found 952.0466.

9-(α-L-threofuranosyl)guanosine-3'-triphosphate (Compound 25d)

General procedure E with 0.55 g of compound 24c, 50 mL of 33% $NH_4OH_{(aq)}$ for 3 hours deprotection at 37° C. and then 15 hours at room temperature. The product was afforded as a white solid; yield: 0.24 g (87.2%, $\varepsilon_{253}$=13700 $M^{-1}$ $cm^{-1}$); $^1$H NMR (400 MHz, $D_2O$) δ 7.84 (m, 1H), 6.06 (d, 1H, J=7.2 Hz), 5.84 (1H), 4.53 (d, 1H, J=8 Hz), 4.41 (m, 1H), 4.31 (s, 2H), 3.35 (m, 2H), 2.96 (m, 1H); $^{31}$P NMR (162 MHz, $D_2O$) δ −9.75 (d, J=20.4 Hz), −11.27 (d, J=20.4 Hz), −22.16 (d, J=16.2 Hz).

Synthesis of L-2'-deoxythymidine-5'-triphosphate

FIG. 128 shows the synthesis scheme for L-2'-deoxythymidine-5'-triphosphate (L-dTTP, compound 31). FIG. 129 through FIG. 139 provide NMR spectra of the synthesized intermediates and product.

Methods used for the synthesis are now described.

3'-Benzoyl-2'-deoxy-L-thymidine-5'-dibenzylmonophosphate (Compound 27)

General procedure A with 200 mg (0.58 mmol) of compound 26, 72.9 mg (1.18 mmol) of tetrazole, 12 mL of anhydrous solution (MeCN/$CH_2Cl_2$, 1:1), 260 μL (0.75 mmol) of dibenzyl-N, N-diisopropylphosphoramidite for 3 hours reaction at room temperature. Then 2 mL of 30% $H_2O_{2(aq)}$ for 1 hour oxidation reaction at room temperature. Column chromatography with eluents (MeOH/$CH_2Cl_2$, from 1% to 1.4%) to afford the product compound 27 as a white solid; yield: 0.32 g (68.2%); TLC (MeOH/$CH_2Cl_2$, 1:40) $R_f$=0.23; $^1$H NMR (400 MHz, $CD_3OD$) δ 7.96 (d, 2H, J=7.6 Hz), 7.55-7.52 (m, 1H), 7.41-7.38 (m, 3H), 7.31-7.25 (m, 10H), 6.30 (dd, 1H, J=14.4, 2.4 Hz), 5.35 (d, 1H, J=6.8 Hz), 5.06-5.03 (m, 4H), 4.31-4.28 (m, 2H), 4.24 (brs, 1H), 2.42 (dd, J=19.2, 8.4 Hz), 2.21-2.14 (m, 1H), 1.72 (s, 3H); $^{13}$CNMR (125.8 MHz, $CD_3OD$) δ 167.9, 166.7, 152.9, 137.8, 137.7, 137.7, 137.7, 137.6, 135.4, 131.5, 131.3, 130.6, 130.5, 130.5, 130.0, 130.0, 112.9, 87.0, 84.7 (d, $J_C$, P=6.5 Hz), 76.9, 71.8 (t, $J_C$, P=4.5 Hz), 69.4 (d, $J_C$, P=4.6 Hz), 38.6, 13.4 (d, $J_C$, P=2.7 Hz); $^{31}$P NMR (162 MHz, CD$_3$OD) 0.19; HRMS (ESI-TOF) calcd. for C$_{31}$H$_{31}$N$_2$O$_9$PNa [M+Na]$^+$ 629.1665. found 629.1685.

3'-Benzoyl-2'-deoxy-L-thymidine-5'-monophosphate (Compound 28)

General procedure B with 300 mg (0.49 mmol) of compound 27, 15 mL of MeOH, and 80 mg of 10% Pd/C for 3 hours stirring at room temperature. The suspension was filtered over a pad of celite, and washed with 60 mL of MeOH containing 2% triethylamine four times to afford the product compound 28 as a white foam of triethylammonium salt; yield: 190 mg (91.3%); TLC (MeOH/CH$_2$Cl$_2$, 1:10 with 1% triethylamine) R$_f$=0; $^1$H NMR (400 MHz, CD$_3$OD) δ 8.05-7.89 (m, 3H), 7.64-7.50 (m, 3H), 6.47 (s, 1H), 5.66 (s, 1H), 4.40 (brs, 2H), 3.33-3.26 (m, 2H), 2.53 (5, 2H), 1.96 (s, 3H); $^{13}$C NMR (125.8 MHz, CD$_3$OD) S 168.1, 167.3, 153.4, 138.9, 135.3, 131.8, 131.4, 130.5, 113.2, 86.9, 86.3, 78.8, 67.0, 48.2, 39.3, 13.4; $^{31}$P NMR (162 MHz, CD$_3$OD) δ 1.02; HRMS (ESI-TOF) calcd. for C$_{10}$H$_{14}$N$_2$O$_8$P [M–H]$^-$ 321.0488. found 321.0493.

3'-Benzoyl-2'-deoxy-L-thymidine-5'-phosphor-2-methylimidazolide (Compound 29)

General procedure C with 180 mg (0.42 mmol) of compound 28, 8 mL of anhydrous DMF, 300 μL (2.1 mmol) of triethylamine, 86 mg (1.05 mmol) of 2-methylimidazole, 275 mg (1.05 mmol) of triphenylphosphine, 242 mg (1.05 mmol) of dipyridyl disulfide for 2 hours reaction at room temperature. First precipitation was achieved with 50 mL of diethyl ether. The product was resuspended with 10 mL of DMF and dropwise added to the solution containing 700 mg of sodium perchlorate, 15 mL of triethylamine in 100 mL of ethyl acetate for the second precipitation. The product was afforded as a white solid compound 29; yield: 145 mg (96.9%); $^{31}$P NMR (162 MHz, CD$_3$OD) δ –7.85; HRMS (ESI-TOF) C$_{21}$H$_{23}$N$_4$O$_8$PNa [M+Na]$^+$513.1151. found 513.1146.

3'-Benzoyl-2'-deoxy-L-thymidine-5'-(γ-(2-(pyrenesulfonyl)ethyl))triphosphate (Compound 30)

General procedure D with 170 mg (0.44 mmol) of compound 29, 248 mg (0.53 mmol) of 2-(pyrenesulfonyl)ethyl]-pyrophosphate (compound 7) and 3 mL (4.40 mmol) of ZnCl$_2$ solution (1.5 M in anhydrous DMF) for 3 hours stirring. After the reaction, the solution was precipitated by 150 mL of ether. Silica column chromatography with eluents (H$_2$O/(isopropanol-MeCN 1:1) from 2% to 7% containing 1% diisopropylethylamine (DIPEA) to afford the white solid compound 30; yield: 150 mg (46.7%); TLC (H$_2$O/isopropanol 1:10 containing 2% DIPEA): Rf=0.35; $^1$H NMR (400 MHz, DMSO-d$_6$+D$_2$O (1:2)) δ: 8.99 (brs, 1H), 8.65 (d, 1H, J=8 Hz), 8.32-8.21 (m, 5H), 8.15-8.09 (m, 2H), 7.98-7.87 (m, 2H), 7.70 (s, 1H), 7.56-7.55 (m, 1H), 7.41 (s, 1H), 6.22 (t, 1H, J=4 Hz), 5.10 (s, 1H), 4.35 (s, 2H), 4.22 (s, 1H), 4.11 (s, 1H), 3.92 (t, 2H, J=4 Hz), 2.33 (s, 1H), 1.88 (s, 1H); $^{31}$P NMR (162 MHz, DMSO-d$_6$+D$_2$O (1:2)) δ–10.99 (brs, 1P), –11.26 (brs, 1P) –20.94 (brs, 1P); HRMS (ESI-TOF) calcd. for C$_{35}$H$_{31}$N$_2$O$_{17}$P$_3$SNa [M–2H+Na]$^-$ 899.0459. found 899.0454.

"L-2"-deoxythymidine-5'-triphosphate (Compound 31)

General procedure E with 20 mg (0.04 mmol) of compound 30.10 mL of 33% NH$_4$OH$_{(aq)}$ for 15 hours stirring at room temperature. The product, compound 31, was afforded as a white solid; yield: 8 mg (83.2%); $^1$H NMR (400 MHz, D$_2$O) δ 7.84 (s, 1H), 6.28 (t, 1H, J=6.0 Hz), 5.17 (s, 1H), 4.54 (s, 1H), 4.15 (d, 1H, J=10.4 Hz), 2.83-2.77 (m, 1H), 2.49 (s, 1H), 2.45 (s, 2H), 2.00 (s, 3H); $^{31}$P NMR (162 MHz, D$_2$O) δ –4.38 (d, J=16.2 Hz), –10.65 (d, J=16.2 Hz), –19.74 (brs).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound having the structure of formula (1):

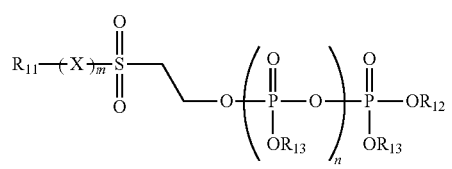

wherein:

m is an integer from 0 to 5;

n is an integer from 0 to 5;

X is selected from the group consisting of O and $CH_2$;

$R_{11}$ is selected from the group consisting of a heteroaryl,

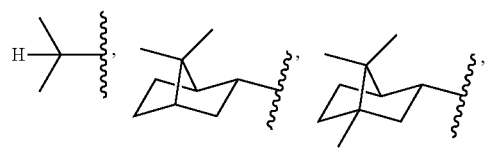

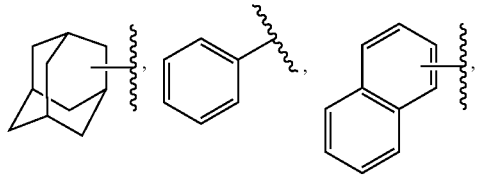

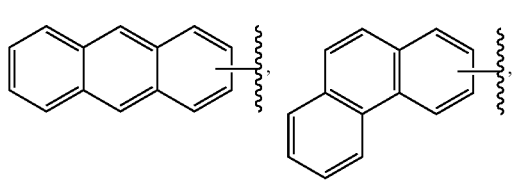

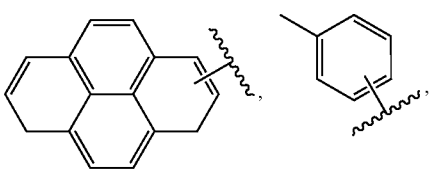

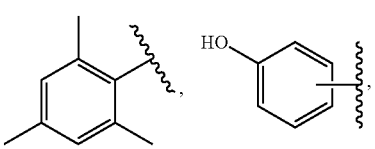

101

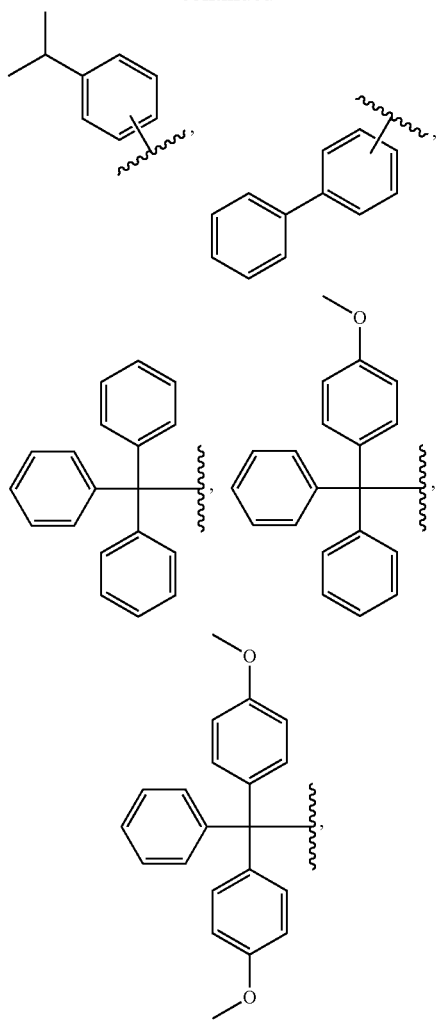

an alkenyl, an alkynyl, an alkyl-aryl, an aryl-alkyl, and a silyl group wherein $R_{11}$ is optionally substituted;

$R_{12}$ is hydrogen, null, a substituted tetahydrofuranyl group, or an alkyl-substituted tetahydrofuranyl group; and each occurrence of $R_{13}$ is independently hydrogen or null.

2. The compound of claim 1, wherein $R_{11}$ is substituted with a group selected from the group consisting of alkyl, alkenyl, alkynyl, aryl, cycloalkyl, heteroaryl, halogen, —CN, —$OR_{14}$, and —$N(R_{14})_2$, wherein each occurrence of $R_{14}$ is independently selected from the group consisting of hydrogen, alkyl, alkenyl, alkynyl, aryl, cycloalkyl, heteroaryl, and halogen.

3. The compound of claim 1, wherein $R_{11}$ is selected from the group consisting of:

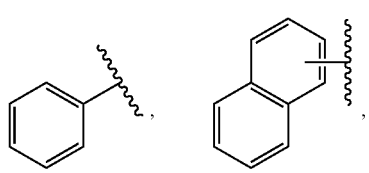

102

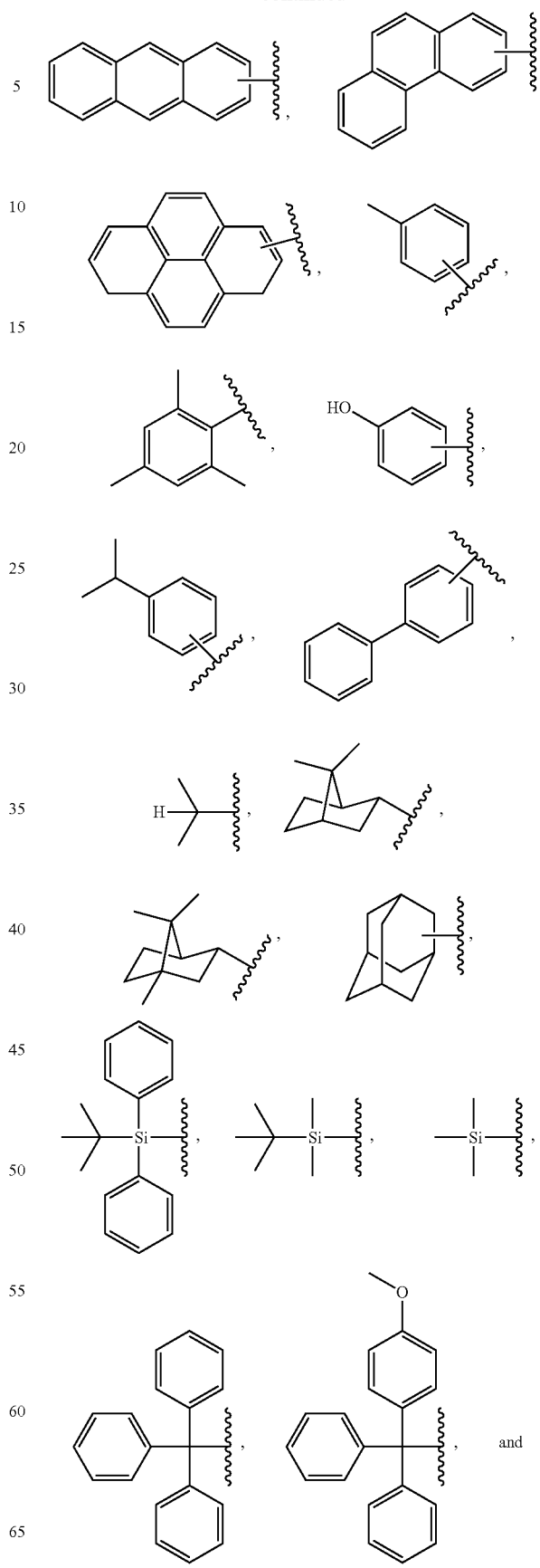

and

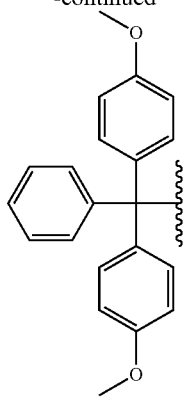

4. A compound having the structure selected from the group consisting of formulae (1a)-(1e):

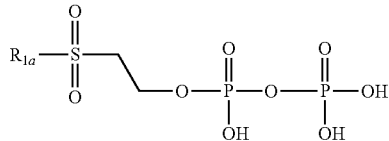
(1a)

wherein $R_{1a}$ is selected from the group consisting of an aryl, a heteroaryl,

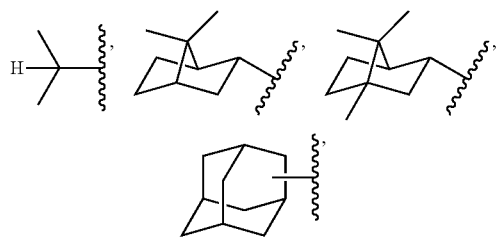

an alkenyl, an alkynyl, an alkyl-aryl, and an aryl-alkyl; and wherein $R_{1a}$ is optionally substituted;

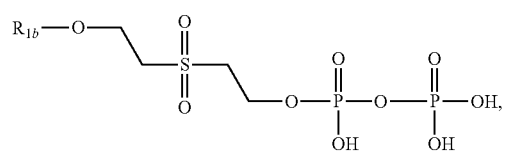
(1b)

wherein $R_{1b}$ is a hydroxy protecting group;

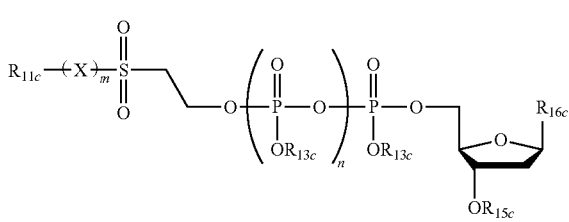
(1c)

wherein m is an integer from 0 to 5;
n is an integer from 0 to 5;
X is selected from the group consisting of O and $CH_2$;
$R_{11c}$ is selected from the group consisting of an aryl, a heteroaryl, an alkyl, a cycloalkyl, an alkenyl, an alkynyl, an alkyl-aryl, an aryl-alkyl, and a silyl group;
each occurrence of $R_{13c}$ is independently selected from the group consisting of hydrogen and null;
$R_{15c}$ is selected from the group consisting of hydrogen, aryl, and heteroaryl; and
$R_{16c}$ is a nitrogenous base, wherein the nitrogenous base is a natural nitrogenous base or artificial nitrogenous base;

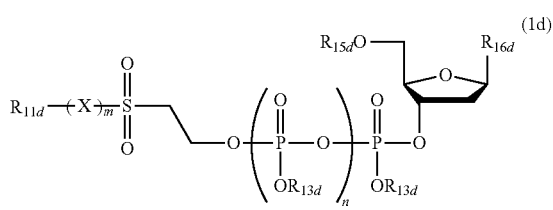
(1d)

wherein m is an integer from 0 to 5;
n is an integer from 0 to 5;
X is selected from the group consisting of O and $CH_2$;
$R_{11d}$ is selected from the group consisting of an aryl, a heteroaryl, an alkyl, a cycloalkyl, an alkenyl, an alkynyl, an alkyl-aryl, an aryl-alkyl, and a silyl group;
each occurrence of $R_{13d}$ is independently selected from the group consisting of hydrogen and null;
$R_{15d}$ is selected from the group consisting of hydrogen, aryl, and heteroaryl; and
$R_{16d}$ is a nitrogenous base, wherein the nitrogenous base is a natural nitrogenous base or artificial nitrogenous base; and

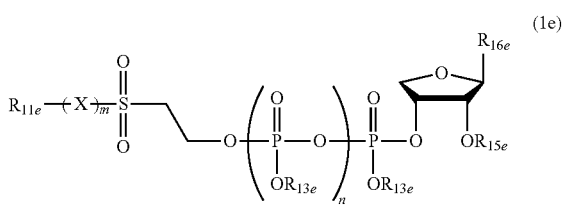
(1e)

wherein m is an integer from 0 to 5;
n is an integer from 0 to 5;
X is selected from the group consisting of O and $CH_2$;
$R_{11c}$ is selected from the group consisting of an aryl, a heteroaryl, an alkyl, a cycloalkyl, an alkenyl, an alkynyl, an alkyl-aryl, an aryl-alkyl, and a silyl group;
each occurrence of $R_{13e}$ is independently selected from the group consisting of hydrogen and null;
$R_{15e}$ is selected from the group consisting of hydrogen, aryl, acetyl, and heteroaryl; and
$R_{16e}$ is a nitrogenous base, wherein the nitrogenous base is a natural nitrogenous base or artificial nitrogenous base.

5. The compound of claim 4, wherein $R_{1a}$ is substituted with a group selected from the group consisting of alkyl, alkenyl, alkynyl, aryl, cycloalkyl, heteroaryl, halogen, —CN, —$OR_{11a}$, and —$N(R_{11a})_2$, wherein each occurrence of $R_{11a}$ is independently selected from the group consisting of hydrogen, alkyl, alkenyl, alkynyl, aryl, cycloalkyl, heteroaryl, and halogen.

6. The compound of claim 4, wherein $R_{1a}$ is selected from the group consisting of:
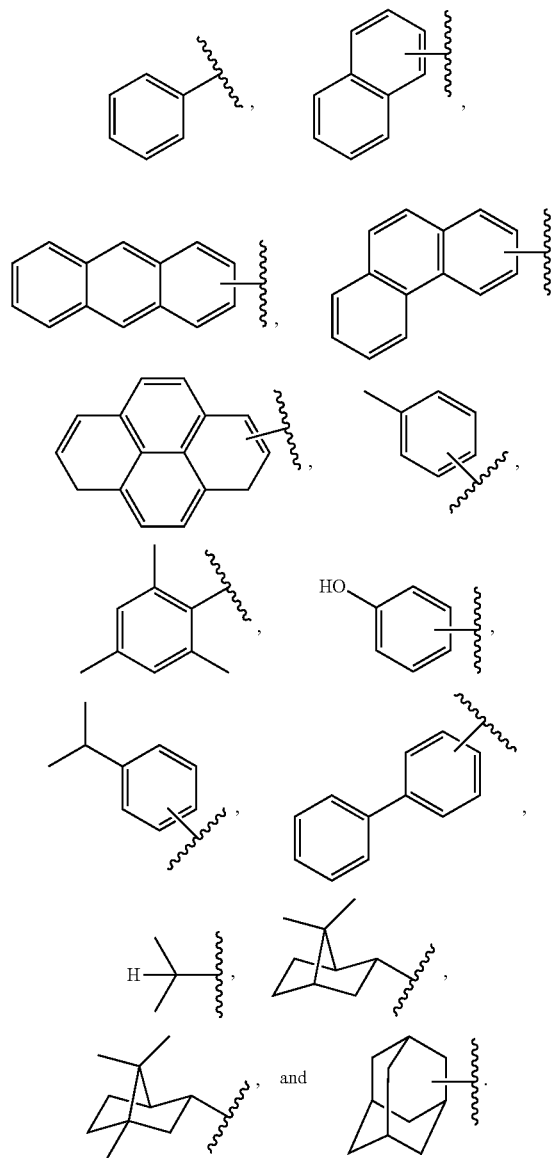
7. The compound of claim 4, wherein the compound of formula (1a) is selected from the group consisting of:
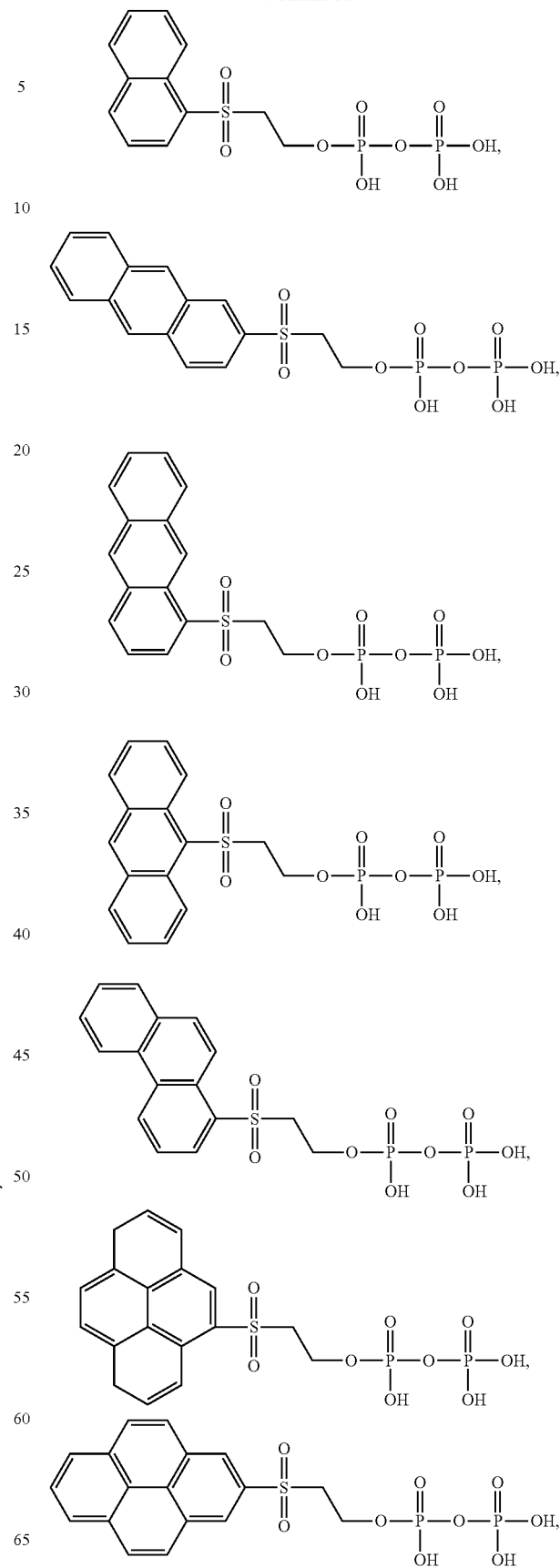

107
-continued
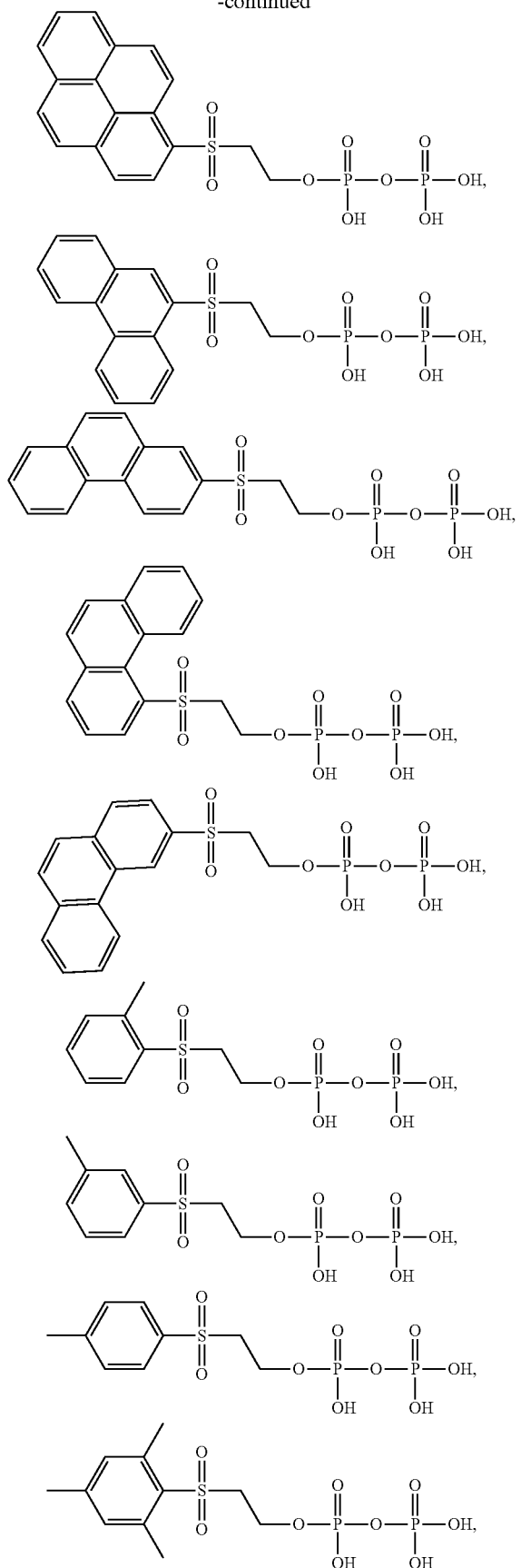
108
-continued
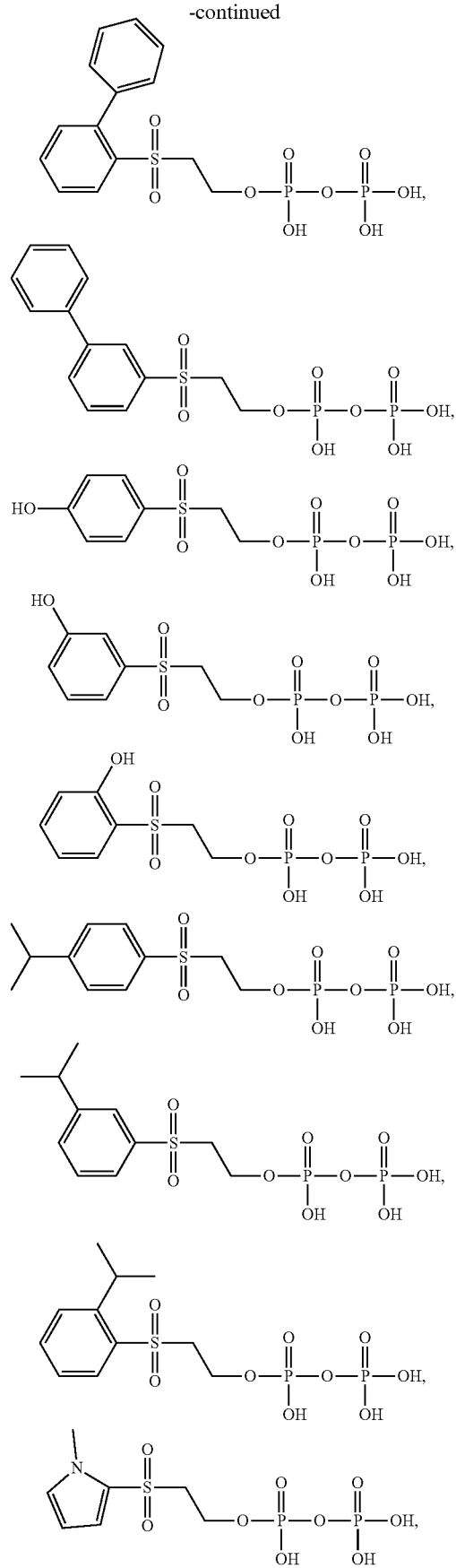

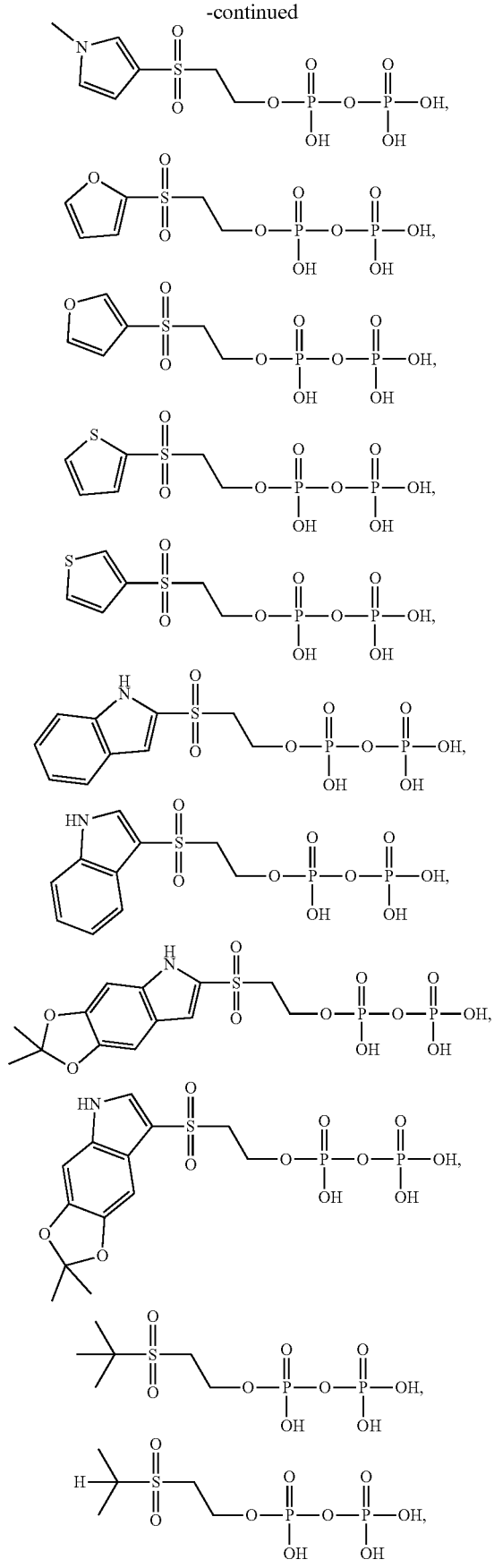

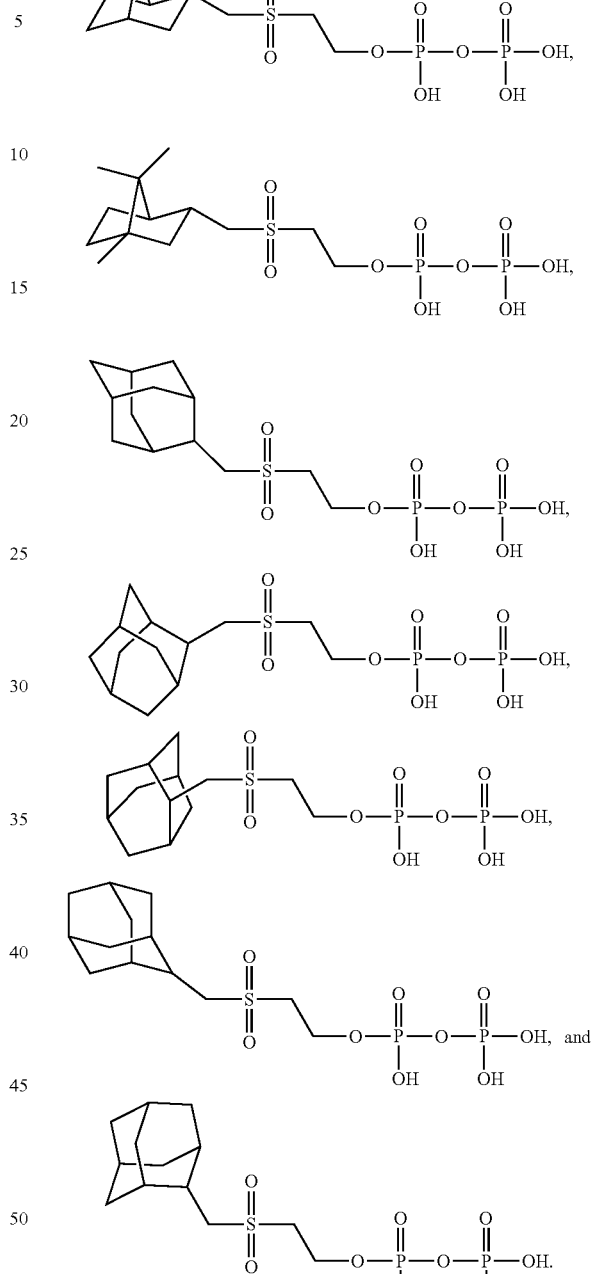

8. The compound of claim 4, wherein $R_{1b}$ is selected from the group consisting of an aryl, a heteroaryl, an alkyl, a cycloalkyl, an alkenyl, an alkynyl, an alkyl-aryl, and an aryl-alkyl; and wherein $R_{1b}$ is optionally substituted.

9. The compound of claim 8, wherein $R_{1b}$ is substituted with a group selected from the group consisting of alkyl, alkenyl, alkynyl, aryl, cycloalkyl, heteroaryl, halogen, —CN, —$OR_{11b}$, and —$N(R_{11b})_2$, wherein each occurrence of $R_{11b}$ is independently selected from the group consisting of hydrogen, alkyl, alkenyl, alkynyl, aryl, cycloalkyl, heteroaryl, and halogen.

10. The compound of claim 4, wherein $R_{1b}$ is selected from the group consisting of
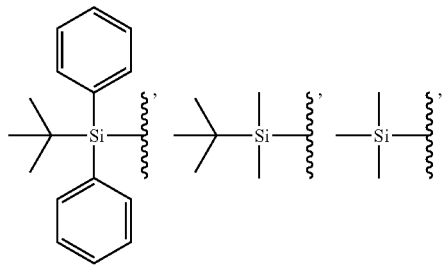
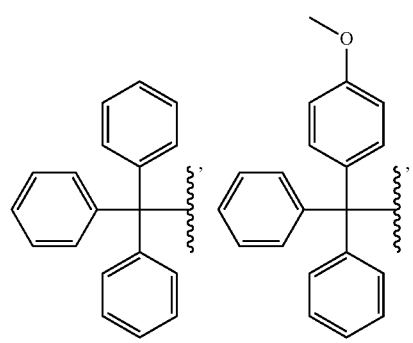
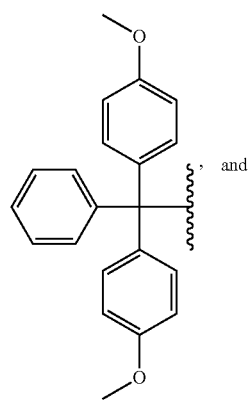, and
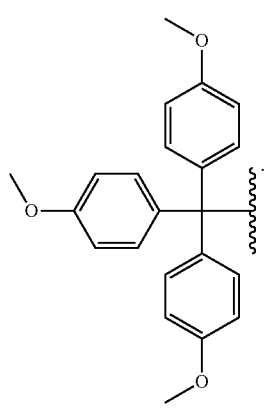
11. The compound of claim 4, wherein the compound of formula (1b) is selected from the group consisting of:
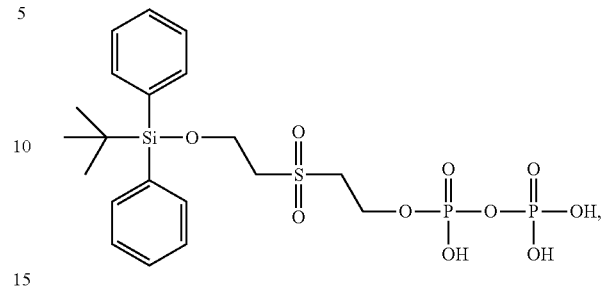
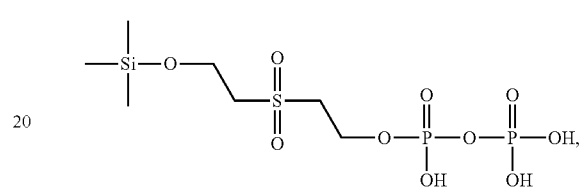
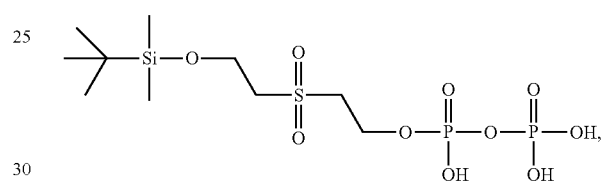
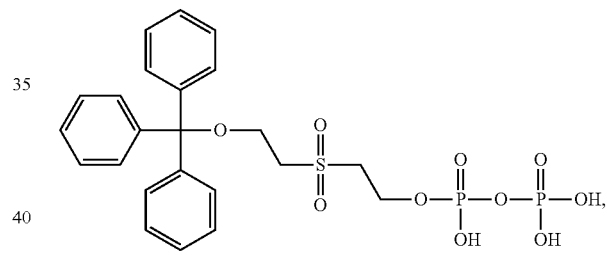
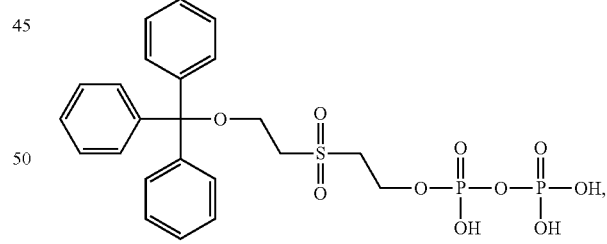
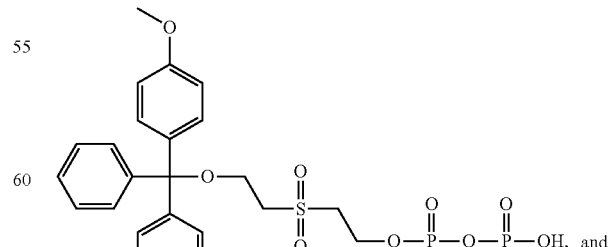

-continued

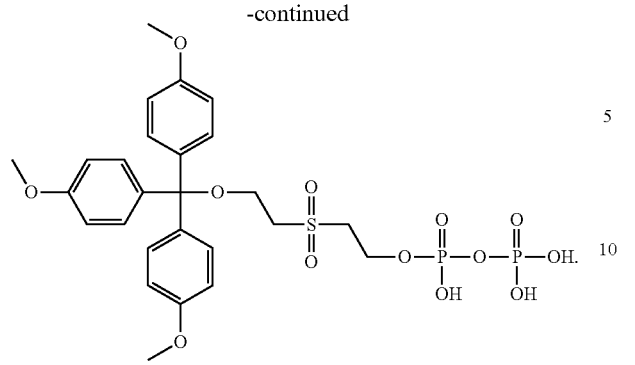

12. A composition comprising an organic molecule comprising a phosphate moiety selected from the group consisting of formulae (2)-(4):

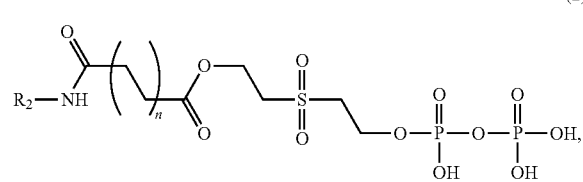

(2)

wherein n is an integer from 1 to 10, and wherein $R_2$ is a support;

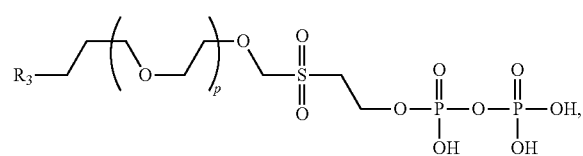

(3)

wherein p is an integer from 0 to 10, and wherein $R_3$ is a support;

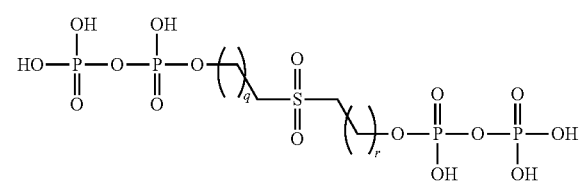

(4)

wherein q is an integer from 0 to 10, and wherein r is an integer from 0 to 10; and

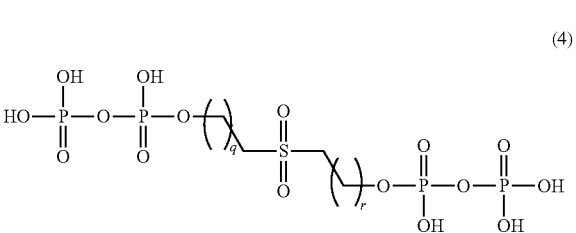

(4)

wherein q is an integer from 0 to 10, and wherein r is an integer from 0 to 10.

13. The composition of claim 12, wherein q is 1.
14. The composition of claim 12, wherein r is 1.
15. The composition of claim 12, wherein the compound of formula (4) is

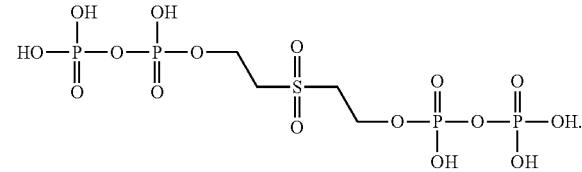 [SMILES: O=P(O)(O)OP(=O)(O)OCCS(=O)(=O)CCOP(=O)(O)OP(=O)(O)O]

16. The composition of claim 12, wherein the composition is a pharmaceutical composition.
17. A method of treating a disease of disorder in a subject in need thereof, the method comprising administering to the subject a composition of claim 16.
18. A composition comprising at least one compound of claim 1.
19. The composition of claim 18, wherein the composition is a pharmaceutical composition.
20. A method of treating a disease of disorder in a subject in need thereof, the method comprising administering to the subject a composition of claim 19.
21. A composition comprising at least one compound of claim 4.
22. The composition of claim 21, wherein the composition is a pharmaceutical composition.
23. A method of treating a disease of disorder in a subject in need thereof, the method comprising administering to the subject a composition of claim 22.

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 1
caaccggtcc ccacgttgcc                                                 20

<210> SEQ ID NO 2
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 2
aacggctggg agaacctggt tctcaatgta                                      30
```

```
<210> SEQ ID NO 3
<211> LENGTH: 200
<212> TYPE: DNA
<213> ORGANISM: Artificial Sequence
<220> FEATURE:
<223> OTHER INFORMATION: Chemically Synthesized

<400> SEQUENCE: 3
caaccggtcc ccacgttgcc gttgccaaga ggttggccgc gagaggagtc aaaatacgcc        60
ctggaacggt gataagctac atcgtgctca agggctctgg gaggataggc gacagggcga       120
taccgttcga cgagttcgac ccgacgaagc acaagtacga cgccgagtac tacattgaga       180
accaggttct cccagccgtt                                                   200

<210> SEQ ID NO 4
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 4
gtccccttgg ggataccacc                                                    20

<210> SEQ ID NO 5
<211> LENGTH: 60
<212> TYPE: DNA
<213> ORGANISM: Artificial Sequence
<220> FEATURE:
<223> OTHER INFORMATION: Chemically Synthesized

<400> SEQUENCE: 5
atcgagtaca gtcagatcga tatgatctat atattaatta ggtggtatcc ccaaggggac        60
```